(12) United States Patent
El-Ahmad et al.

(10) Patent No.: US 10,253,043 B2
(45) Date of Patent: Apr. 9, 2019

(54) 2,3-DIHYDRO-1H-IMIDAZO{1,2-A} PYRIMIDIN-5-ONE AND THIS 1,2,3,4-TETRAHYDROPYRIMIDO{1,2-A}PYRIMIDIN-6-ONE DERIVATIVES COMPRISING A SUBSTITUTED MORPHOLINE, PREPARATION THEREOF AND PHARMACEUTICAL USE THEREOF

(71) Applicant: SANOFI, Paris (FR)

(72) Inventors: Youssef El-Ahmad, Paris (FR); Bruno Filoche-Romme, Paris (FR); Jean-Philippe Letallec, Paris (FR); Gilbert Marciniak, Paris (FR); Baptiste Ronan, Paris (FR); Bertrand Vivet, Paris (FR); Maurice Brollo, Paris (FR)

(73) Assignee: SANOFI, Paris (FR)

( * ) Notice: Subject to any disclaimer, the term of this patent is extended or adjusted under 35 U.S.C. 154(b) by 14 days.

(21) Appl. No.: 14/409,964

(22) PCT Filed: Jun. 21, 2013

(86) PCT No.: PCT/IB2013/055099
§ 371 (c)(1),
(2) Date: Dec. 19, 2014

(87) PCT Pub. No.: WO2013/190510
PCT Pub. Date: Dec. 27, 2013

(65) Prior Publication Data
US 2015/0148328 A1 May 28, 2015

(30) Foreign Application Priority Data
Jun. 22, 2012 (FR) ...................................... 12 55917

(51) Int. Cl.
*C07D 519/00* (2006.01)
*C07D 233/46* (2006.01)
(Continued)

(52) U.S. Cl.
CPC ........ *C07D 519/00* (2013.01); *A61K 31/5377* (2013.01); *A61K 31/5386* (2013.01);
(Continued)

(58) Field of Classification Search
CPC .. C07D 519/00; C07D 233/46; C07D 239/14; C07D 239/70; C07D 295/04; C07D 471/04; C07D 487/04
See application file for complete search history.

(56) References Cited

U.S. PATENT DOCUMENTS 8,846,670 B2 * 9/2014 Bacque ................ C07D 239/06
514/233.2
9,321,790 B2 * 4/2016 El-Ahmad ........... A61K 31/519
(Continued)

FOREIGN PATENT DOCUMENTS

EP 1340761 A1 9/2003
EP 1454909 A1 9/2004
(Continued)

OTHER PUBLICATIONS

Cancer and Metastasis Reviews (1998), 17(1), 91-106.*
(Continued)

*Primary Examiner* — Rebecca L Anderson
(74) *Attorney, Agent, or Firm* — McDonnell Boehnen Hulbert & Berghoff LLP

(57) ABSTRACT

The invention relates to the novel products of formula (I) with p, q=0, 1 or 2; R1=phenyl, pyridyl; —(CH$_2$)$_m$—Ra; alkylene; cycloalkyl; heterocycloalkyl; alkyl; —SO$_2$—Rb; —CO—Re; m=1 or 2; Ra=aryl, heteroaryl, —CO-cycloalkyl, —CO-heterocycloalkyl, —CO—Rb, —C(Rb) =N—ORc, —CO 2 Rd, —CONRxRy; Rb=alkyl, aryl, heteroaryl; Rc=H, alkyl; Rd=alkyl, cycloalkyl; Re=alkyl, cycloalkyl, aryl, heteroaryl; NRxRy with Rx,Ry=H, alkyl, cycloalkyl, alkoxy, phenyl, or form with N a ring with optionally O, N; R2, R3=H, alkyl, CF 3, or form with C a ring with optionally O, S and N; R4=H, F, Cl, CH$_3$ or CN; the morpholine is substituted with Me, and optionally substituted with F, OH; or is (Formula 1a) and the isomer of configuration R,R (Formula 1b) these products being in all the isomer forms and the salts, as medicaments, in particular as anticancer medicaments.

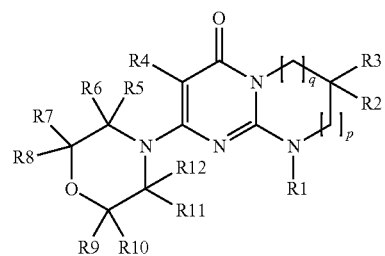

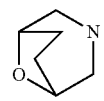

formula 1a

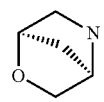

formula 1b

14 Claims, No Drawings

(51) Int. Cl.

| | | |
|---|---|---|
| C07D 239/14 | (2006.01) | |
| C07D 239/70 | (2006.01) | |
| C07D 471/04 | (2006.01) | |
| C07D 487/04 | (2006.01) | |
| C07D 295/04 | (2006.01) | |
| A61K 31/5377 | (2006.01) | |
| A61K 31/5386 | (2006.01) | |
| A61K 31/55 | (2006.01) | |
| A61K 45/06 | (2006.01) | |

(52) U.S. Cl.
CPC ............ A61K 31/55 (2013.01); A61K 45/06 (2013.01); C07D 233/46 (2013.01); C07D 239/14 (2013.01); C07D 239/70 (2013.01); C07D 295/04 (2013.01); C07D 471/04 (2013.01); C07D 487/04 (2013.01)

(56) References Cited

U.S. PATENT DOCUMENTS

| | | |
|---|---|---|
| 2012/0142679 A1 | 6/2012 | Brolio et al. |
| 2012/0208810 A1 | 8/2012 | Bacque et al. |
| 2013/0289031 A1 | 10/2013 | Arigon et al. |

FOREIGN PATENT DOCUMENTS

| | | |
|---|---|---|
| EP | 1460076 A1 | 9/2004 |
| FR | 2378792 A1 | 8/1978 |
| WO | 2002/018386 A1 | 3/2002 |
| WO | 2003/024949 A1 | 3/2003 |
| WO | 2003/027116 A2 | 4/2003 |
| WO | 2003/072579 A1 | 9/2003 |
| WO | 2005/058908 A1 | 6/2005 |
| WO | 2006/109081 A1 | 10/2006 |
| WO | 2006/109084 A1 | 10/2006 |
| WO | 2006/126010 A2 | 11/2006 |
| WO | 2007/097981 A2 | 8/2007 |
| WO | 2008/064244 A2 | 5/2008 |
| WO | 2008/148074 A2 | 12/2008 |
| WO | 2011/001112 A1 | 1/2011 |
| WO | 2011/001113 A1 | 1/2011 |
| WO | 2011/001113 A2 | 1/2011 |
| WO | 2012/085244 A1 | 6/2012 |
| WO | 2013/190123 A1 | 12/2013 |

OTHER PUBLICATIONS

Science (1999), vol. 286, 531-537.*
Bi et al. "Proliferative Defect and Embryonic Lethality in Mice Homozygous for a Deletion in the p110a Subunit of Phosphoinositide 3-Kinase", J. Biol. Chem., 274: 10963-10968 (1999).
Bi et al. "Early embryonic lethality in mice deficient in the pll013 catalytic subunit of PI 3-kinase", Mammalian Genome, 13: 169-172 (2002).
Brigaud et al. "Concise Synthesis of Enantiopure a-Trifluoromethyl Alanines, Diamines, and Amino Alcohols via the Strecker-type Reaction", Journal of Organic Chemistry, 71(18): 7075-7078 (2006).
Cully et al. "Beyond PTEN mutations: the PI3K pathway as an integrator of multiple inputs during tumorigenesis", Nature Rev., 6: 184-192 (2006).
Doerig et al. "Antimalarial drug discovery: targeting protein kinases", Expert Opinion Ther. Targets, 11: 279-290 (2007).
El-Sayed et al. "Nonsteroidal antiinflammatory agents—Part 1: Antiinflammatory, analgesic and antipyretic activity of some new 1-(pyrimidin-2-yl)-3-pyrazolin-5ones and 2-(pyrimidin-2-yl)-1,2,4,5,6,7-hexahydro-3H-indazol-3-ones", Eur. J. Med. Chem., 33(5): 349-361 (1998).
Engelman et al. "The evolution of phosphatidylinositol 3-kinases as regulators of growth and metabolism", Nature Rev. Genetics, 7: 606-619 (2006).
Ihle et al. "Take your PIK: phosphatidylinositol 3-kinase inhibitors race through the clinic and toward cancer therapy", Current Opinion in Drug Discovery & Development, 13: 41-49 (2010).
Ihle et al. "Take your PIK: phosphatidylinositol 3-kinase inhibitors race through the clinic and toward cancer therapy", Mol Cancer Ther., 8: 1-9 (2009).
Okkenhaug et al. "Impaired B and T Cell Antigen Receptor Signaling in p1108 PI 3-Kinase Mutant Mice", Science 297: 1031-1034 (2002).
Ting et al. "Substituted 1,3-Dihydro-2H-pyrrolo[2,3-b]pyridin-2-oneass Potential Antiinflammatory Agents", J. Med. Chem., 33(10): 2697-2706 (1990).
Vaid et al. "PfPI3K, a phosphatidylinositol-3 kinase from Plasmodium falciparum, is exported to the host erythrocyte and is involved in hemoglobin trafficking", Blood 115: 2500-2507 (2010).
Ward et al. "Protein kinases of the human malaria parasite Plasmodium falciparum: the kinome of a divergent eukaryote", BMC Genomics 5: 79 (2004).
Yamashita et al. "Synthetic Communications: An International Journal for Rapid Communication of Synthetic Organic Chemistry", Syn. Commun., 34(5): 795-803 (2004).
Zhou et al. "Deletion of PIK3C3/Vps34 in sensory neurons causes rapid neurodegeneration by disrupting the endosomal but not the autophagic pathway", PNAS, 107: 9424-9429 (2010).
Tanis et al. "Solvent and in situ catalyst preparation impacts upon Noyori reductions of aryl-chloromethyl ketones: application to syntheses of chiral 2-amino-1-aryl-ethanols", Tet. Asymmetry 17: 2154-2182 (2006).
International Search Report for International Patent Application No. PCT/EP2013/063065 dated Jul. 24, 2013 (dated Aug. 5, 2013), pp. 1-8.
Ulmann, "Ueber eine neue Bildungsweise von Diphenylaminderivaten", Chem. Berichte, 36, 2389 (1903).
Lin, Hong et al. "Synthesis and structure—activity relationships of imidazo[1,2-a]pyrimidin-5(1H)-ones as a novel series of beta isoform selective phosphatidylinositol 3-kinase inhibitors," Bioorganic & Medicinal Chemistry Letters 22 (2012) 2230-2234.
Johnson et al. "Gene silencing reveals a specific function of hVps34 phosphatidylinositol 3-kinase in late versus early endosomes". Journal of Cell Science 119, 1219-1232 (2006).
Jaber et al. "Class III PI3K Vps34 plays an essential role in autophagy and in heart and liver function." PNAS 109 (6), 2003-2008 (2012).
Apel et al. "Blocked Autophagy Sensitizes Resistant Carcinoma Cells to Radiation Therapy." Cancer Res 68 (5), 1485-1494 (2008).
Zhou et al. "Replication of the Association of a MET Variant with Autism in a Chinese Han Population." PLoS ONE 6(11): e27428 (2011).
Yoon et al. "Class III PI-3-kinase activates phospholipase D in an amino acid-sensing mTORC1 pathway." J. Cell Biol. vol. 195 No. 3 435-447 (2011).
Yang et al. "Eaten alive: a history of macroautophagy." Nat Cell Biol. 12(9), 814-822 (2010).
Tooze et al. "The origin of the autophagosomal membrane." Nature Cell Biology 12 (9), 831-835 (2010).
Vergne et al. "The role of PI3P phosphatases in the regulation of autophagy." FEBS Letters 584, 1313-1318 (2010).
Taguchi-Atarashi et al. "Modulation of Local PtdIns3P Levels by the PI Phosphatase MTMR3 Regulates Constitutive Autophagy." Traffic 11, 468-478 (2010).
Janku et al. "Autophagy as a target for anticancer therapy." Nat. Rev. Clin. Oncol. 8, 528-539 (2011).
Mosesson et al. "Derailed endocytosis: an emerging feature of cancer." Nature Reviews Cancer 8, 835-850 (2008).
Jaber et al. "Class III PI3K Vps34 plays an essential role in autophagy and in heart and liver function." PNAS Early Edition, 1-6 (2011).
Fan et al. "Akt and Autophagy Cooperate to Promote Survival of Drug-Resistant Glioma." Sci Signal., 3(147), ra81 (2010).
Sagona et al. "PtdIns(3)P controls cytokinesis through KIF13A-mediated recruitment of FYVE-CENT to the midbody." Nature Cell Biology, 12(4), 362-373 (2010).

(56) References Cited

OTHER PUBLICATIONS

Aliabiev et al. "A Convenient Synthesis of Novel Substituted Isoxazolo[5,4-d]Pyrimidines." Letters in Organic Chemistry, 4, 273-280 (2007).

Yamashita et al. "Improved Procedures for Preparation of Racemic Capreomycidine." Synthetic Communications, 34(5), 795-803 (2004).

Mitsunobu, Oyo. "The Use of Diethyl Azodicarboxylate and Triphenylphosphine in Synthesis and Transformation of Natural Products." Synthesis, 1981(1), 1-28 (1981).

Paal et al. "Zur Kenntniss der Chlor- und Brom-Diphenacyle." Chem. Ber., 36, 2386-2404 (1903).

Li et al. "Inhibition of autophagy augments 5-fluorouracil chemotherapy in human colon cancer in vitro and in vivo model." European Journal of Cancer, 46, 1900-1909 (2010).

Li et al. "The EGFR antibody cetuximab induces autophagy in cancer cells by downregulating HIF-1α and Bcl-2 and activating the beclin-1/hVps34 complex." Cancer Res., 70(14), 5942-5952 (2010).

Wu et al. "Autophagy Blockade Sensitizes Prostate Cancer Cells towards Src Family Kinase Inhibitors." Genes & Cancer, 1(1) 40-49 (2010).

Samaddar et al. "A role for macroautophagy in protection against 4-hydroxytamoxifen-induced cell death and the development of antiestrogen resistance." Mol Cancer Ther, 7(9), 2977-2987 (2008).

Raben et al. "Suppression of autophagy permits successful enzyme replacement therapy in a lysosomal storage disorder—murine Pompe disease." Autophagy, 6(8), 1078-1089 (2010).

Mizushima et al. "Autophagy fights disease through cellular self-digestion." Nature, 451(7182), 1069-1075 (2008).

Hoang et al. "Effect of autophagy on multiple myeloma cell viability." Mol Cancer Ther, 8(7), 1974-84 (2009).

Levine et al. "Autophagy in the Pathogenesis of Disease." Cell, 132(1), 27-42 (2008).

Carew et al. "Targeting autophagy augments the anticancer activity of the histone deacetylase inhibitor SAHAto overcome Bcr-Abl-mediated drug resistance." Blood, 110, 313-322 (2007).

Vazquez-Martin et al. "Autophagy Facilitates the Development of Breast Cancer Resistance to the Anti-HER2 Monoclonal Antibody Trastuzumab." PLoS ONE, 4(7), e6251 (2009).

Huguenot et al. "Concise Synthesis of Enantiopure r-Trifluoromethyl Alanines, Diamines, and Amino Alcohols via the Strecker-type Reaction." J. Org. Chem., 71, 7075-7078 (2006).

Gupta et al. "Autophagy inhibition and antimalarials promote cell death in gastrointestinal stromal tumor (GIST)." PNAS, 107(32), 14333-14338 (2010).

Badawey et al. "Nonsteroidal antiinflammatory agents—Part 1: Antiinflammatory, analgesic and antipyretic activity of some new 1-(pyrimidin-2-yl)-3-pyrazolin-5-ones and 2-(pyrimidin-2-yl)-I,2,4,5,6,7-hexahydro-3H-indazol-3-ones." Eul: J. Med. Chem., 33, 349-361 (1998).

Vanhaesebroeck et al. "The emerging mechanisms of isoform-specific PI3K signalling." Nature Reviews Molecular Cell Biology, 11, 329-341 (2010).

Wee, Susan, el al., "PTEN-deficient cancers depend on PIK3CB", PNAS, 105(35):13057-13062 (2008).

International Search Report issued in International Patent Application No. PCT/FR2010/051374, dated Jan. 5, 2011.

International Preliminary Report on Patentability issued in International Patent Application No. PCT/IB2013/055099, dated Dec. 23, 2014.

* cited by examiner

2,3-DIHYDRO-1H-IMIDAZO{1,2-A}PYRIMIDIN-5-ONE AND THIS 1,2,3,4-TETRAHYDROPYRIMIDO{1,2-A}PYRIMIDIN-6-ONE DERIVATIVES COMPRISING A SUBSTITUTED MORPHOLINE, PREPARATION THEREOF AND PHARMACEUTICAL USE THEREOF

This application is a national stage application under 35 U.S.C. § 371 of International Application No. PCT/IB2013/055099, filed Jun. 21, 2013, which claims priority to French Patent Application No. 1255917, filed Jun. 22, 2012.

The present invention relates to novel 2,3-dihydro-1H-imidazo{1,2-a}pyrimidin-5-one and 1,2,3,4-tetrahydropyrimido{1,2-a}pyrimidin-6-one chemical compounds comprising a substituted morpholine, to pyrimidinone derivatives, to the process for preparing same, to the novel intermediates obtained, to the use thereof as medicaments, to the pharmaceutical compositions containing them and to the novel use of such derivatives.

The present invention thus also relates to the use of said derivatives for preparing a medicament intended for treating humans.

More particularly, the invention relates to novel pyrimidinone derivatives and to the pharmaceutical use thereof for preventing and treating conditions capable of being modulated by inhibiting the Vps34/PIK3C3 pathway. Vps34/PIK3C3 is a key contributor in autophagy. Vps34/PIK3C3 is also involved in phenomena of vesicular trafficking such as endocytosis and phagocytosis (B. Vanhaesebroeck et al. Nat Rev Mol Cell Biol 2010). Vps34 also has a role in the signalling of the mTOR protein (X. Zhou et al. Plos One 2011, N. Jaber et al. PNAS 2011, M S Yoon et al. J Cell Biol 2011). Finally, Vps34 has been shown to be involved in cell proliferation (E E Johnson et al. J Cell Science 2005, X. Zhou et al. Plos One 2011, N. Jaber et al. PNAS 2012).

Inhibition and regulation of the Vps34/PIK3C3 pathway constitutes in particular a new mechanism of action for treating a large number of cancer diseases including solid and liquid tumours.

Role of the Vps34/PIK3C3 pathway

The Vps34/PIK3C3 signalling pathway is a complex network which regulates multiple cell functions summarised under the name vesicular trafficking (B. Vanhaesebroeck et al. Nat Rev Mol Cell Biol 2010). This signalling pathway is an important target in the treatment of cancer, since vesicular trafficking phenomena such as autophagy, endocytosis and phagocytosis are modified in human tumours (F. Janku et al. Nat Rev Clinical Oncol 2011, Y. Mosesson Nat Rev Cancer 2008).

The class III PI3K lipid kinase (Vps34/PIK3C3) forms a heterodimer with the Vps15 protein. Vps15 is a protein which is myristoylated, thus enabling the Vps34/Vps15 complex to be anchored in membranes. This heterodimer is found in various multiprotein complexes, thus underlining its various biological functions (B. Vanhaesebroeck et al. Nat Rev Mol Cell Biol 2010). Vps34/PIK3C3 phosphorylates phosphatidylinositol (PI) on the position 3 of the inositol, so as to give phosphatidylinositol 3 phosphate (PI3P). PI3P is a secondary messenger. Myotubularin (MTM) phosphatase lipids dephosphorylate PI3P on position 3. Among the 16 MTMs described, the MTMR3, 6, 7 and 14 (JUMPY) proteins are thought to be involved in the inhibition of autophagosome formation and therefore of autophagy (I. Vergne FEBS Lett 2010, N. Taguchi-Atarashi et al. Traffic 2010).

Role of Vps34/PIK3C3 in autophagy

The PI3P formed by Vps34/PIK3C3 is a key secondary messenger in autophagosome formation by the recruitment of proteins such as WIPI, DFCP1 and Alfy (S. Tooze et al, Nat Cell Biol 2010). The autophagosomes formed will then fuse with lysosomes, making it possible to degrade constituents of the cytoplasm (organelles, long-lived proteins, etc.) (Z Yang et al. Nat Cell Biol 2010).

Autophagy is a mechanism of cell survival which enables the cell to survive in a situation of stress, for instance faced with a metabolic stress. In the case of cancer, autophagy is implicated in the resistance of tumour cells faced with environmental stresses, such as: hypoxia, oxidative stresses, nutrient deficiency, but also faced with therapeutic stresses: treatments with anticancer agents, ionizing radiation. Furthermore, this signalling pathway is a major factor of resistance to chemotherapy, to radiotherapy and to targeted therapies such as inhibitors of EGFR, HER2 or Bcr-Abl for example (QW. Fan et al., Since signaling 2010, A. Gupta et al. PNAS 2010, X Li et al. Cancer Res 2010, A Vazquez-Martin et al. PLos One 2009, Z. Wu et al. Genes Cancer 2010).

Role of Vps34/PIK3C3 in endocytosis

At the endosome level, PI3P makes it possible to recruit molecules bearing FYVE (Fab1 YOTB, Vac1 and EEA1) or PX (Phox-homology) motifs, such as EEA1, HRS or SNXs, thus resulting in the fusion of endocytic vesicles. The Vps34/PIK3C3 protein has been described as being involved in the endosomal trafficking of certain transmembrane receptors such as receptor tyrosine kinases (EGF receptor, PDGF receptor) or the transferrin receptor, for example (B. Vanhaesebroeck et al. Nat Rev Mol Cell Biol 2010). Finally, Vps34, via the regulation of endosomes, has been shown to participate in the cytokinesis phenomenon during cell division (AP Sagona et al. Nat Cell Biol 2010).

Role of Vps34/PIK3C3 in phagocytosis

PI3P is also generated at the membranes of phagosomes. The role of the Vps34/PIK3C3 protein does not appear to be involved in phagosome membrane initiation, but in phagosome maturation. Finally, the PI3P formed by the Vps34/PIK3C3 protein is thought to be involved in the activation of NADPH oxidase at the phagosome level (B. Vanhaesebroeck et al. Nat Rev Mol Cell Biol 2010).

Kinase-inhibiting morpholinopyrimidinone derivatives are known to those skilled in the art.

Application WO2008/148074 describes products which have an mTOR-inhibiting activity. These products are pyrido[1,2-a]pyrimidin-4-ones which differ from the products of the present invention owing to their entirely aromatic nature and to their substitutions.

Application WO2008/064244 describes the application of the PI3Kβ-inhibiting products TGX-221 and TGX-155 which are of use in the treatment of cancer, and in particular in breast cancer. These products are pyrido[1,2-a]pyrimidin-4-ones previously described in applications WO2004/016607 and WO2001/053266, which differ from the products of the present invention owing to their entirely aromatic nature and to their substitutions.

Applications WO2006/109081, WO2006/109084 and WO2006/126010 describe DNA-PK-inhibiting products which are of use in the treatment of ATM deficient cancers. These products are pyrido[1,2-a]pyrimidin-4-ones which differ from the products of the present invention owing to their entirely aromatic nature and to their substitutions.

Application WO2003/024949 describes DNA-PK-inhibiting products which are of use in the treatment of ATM deficient cancers. These products are pyrido[1,2-a]pyrimidin-4-ones which differ from the products of the present invention owing to their entirely aromatic nature and to their substitutions.

The subject of the present invention is the products of formula (I):

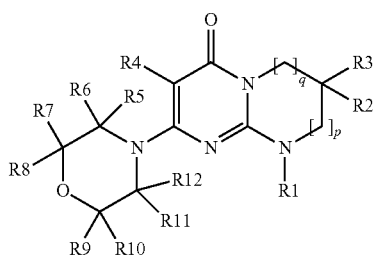

in which:
p and q are the integers 0 or 1 or 2 such that, if p=0, then q=1 or 2 and, if p=1 or 2, then q=0;
R1 is chosen from the following values a) to e):
a) R1 is a phenyl or pyridyl radical optionally substituted with one or more radicals, which may be identical or different, chosen from halogen atoms and cycloalkyl, alkyl and alkoxy radicals, the latter alkyl and alkoxy radicals being themselves optionally substituted with one or more fluorine atoms;
b) R1 is a —(CH$_2$)$_m$—Ra radical with m being the integer 1 or 2 and Ra an optionally substituted aryl or heteroaryl radical, or a —CO-cycloalkyl, —CO— heterocycloalkyl, —CO—Rb, —C(Rb)=N—ORc, —CO2Rd or —CON-RxRy radical;
c) R1 is an alkylene radical; cycloalkyl radical; heterocycloalkyl radical; or an alkyl radical optionally substituted with one or more radicals, which may be identical or different, chosen from fluorine atoms and hydroxyl, cycloalkyl, heterocycloalkyl, phenyl, pyridine and alkoxy radicals, the latter phenyl, pyridine and alkoxy radicals being themselves optionally substituted with one or more fluorine atoms;
d) R1 is an —SO$_2$—Rb radical;
e) R1 is a —CO—Re radical;
Rb is an optionally substituted alkyl, cycloalkyl, aryl or heteroaryl radical;
Rc is a hydrogen atom or an alkyl radical;
Rd is an alkyl or cycloalkyl radical;
Re is an optionally substituted alkyl, cycloalkyle, heterocycloalkyl, aryl or heteroaryl radical;
NRxRy being such that Rx and Ry, which may be identical or different, are chosen from a hydrogen atom and alkyl, cycloalkyl, alkoxy and phenyl radicals; or Rx and Ry form, with the nitrogen atom to which they are bonded, a cyclic radical containing from 3 to 7 ring members and optionally one or more other heteroatoms chosen from O, NH and N-alkyl;
R2 and R3, which may be identical or different, are chosen from a hydrogen atom and an alkyl radical optionally substituted with one or more fluorine atoms, it being understood that R2 and R3 are not both CF$_3$ and R2 and R3 are not both hydrogen; or else R2 and R3 form, together with the carbon atom to which they are bonded, a cyclic radical containing from 3 to 6 ring members and optionally one or more other heteroatoms chosen from O, S and —NRz, this cyclic radical being optionally substituted with one or more radicals, which may be identical or different, chosen from halogen atoms and oxo, Rz, —ORz and —NRzRz' radicals; with Rz and Rz', which may be identical or different, being a hydrogen atom or an alkyl, cycloalkyl or heterocycloalkyl radical;

R4 is a hydrogen atom, a fluorine or chlorine atom, a methyl radical or a CN radical;

the morpholine residue is substituted with the radicals R5 to R12, which may be identical or different, chosen from a hydrogen atom and methyl and ethyl radicals optionally substituted with a fluorine atom or a hydroxyl radical, it being understood that, either at least one of R5 to R12 is not a hydrogen atom, or this morpholine residue contains a bridge defined as follows: R7 or R8 can form an ethylene bridge with R9 or R10, or else R7 or R8 can form a methylene bridge of absolute configuration R,R with R11 or R12, or else R5 or R6 can form a methylene bridge of absolute configuration R,R with R9 or R10 so as to give the following radicals:

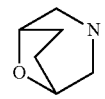

and the isomer of configuration R,R

the aryl and heteroaryl radicals that Ra, Rb and Re may represent, and also the alkyl radicals that Rb and Re may represent, being optionally substituted with one or more radicals, which may be identical or different, chosen from halogen atoms and cycloalkyl, heterocycloalkyl, heteroaryl and alkoxy radicals, the latter heteroaryl and alkoxy radicals being themselves optionally substituted with one or more radicals, which may be identical or different, chosen from fluorine atoms and hydroxyl, alkyl and alkoxy radicals;

the aryl and heteroaryl radicals that Ra, Rb and Re may represent being, in addition, optionally substituted with one or more alkyl radicals themselves optionally substituted with one or more radicals, which may be identical or different, chosen from fluorine atoms and hydroxyl and alkoxy radicals;

all the cycloalkyl radicals being optionally substituted with one or more radicals, which may be identical or different, chosen from a fluorine atom and alkyl radicals themselves optionally substituted with one or more fluorine atoms;

all the heterocycloalkyl radicals being optionally substituted with one or more radicals, which may be identical or different, chosen from a fluorine atom and alkyl radicals themselves optionally substituted with one or more fluorine atoms;

all the heterocycloalkyl radicals being, in addition, optionally substituted with a CO$_2$alk radical, where appropriate on a nitrogen atom;

all the alkyl (alk), alkylene and alkoxy radicals above being linear or branched and containing at most 7 carbon atoms, it being understood that one or more of the hydrogen atoms of said products of formula (I) can be a deuterium atom;

it being understood that, when p=0 and one of R2 and R3 is an alkyl radical and the other an alkyl radical substituted with one or more fluorine atoms, then R1 is not a phenyl or pyridyl radical as defined in a) above, said products of formula (I) being in any of the possible racemic, enantiomeric and diastereoisomeric isomer forms, and also the addition salts with inorganic and organic acids or with inorganic and organic bases of said products of formula (I).

Thus, in the products of formula (I) as defined above, R2 and R3, which may be identical or different, are such that R2 is a hydrogen atom or an alkyl radical optionally substituted with one or more fluorine atoms and R3 is an alkyl radical optionally substituted with one or more fluorine atoms, it being understood that R2 and R3 are not both $CF_3$; or else R2 and R3 form, together with the carbon atom to which they are bonded, a cyclic radical as defined above.

A subject of the present invention is the products of formula (I) as defined above, in which the morpholine residue is chosen from the following radicals:

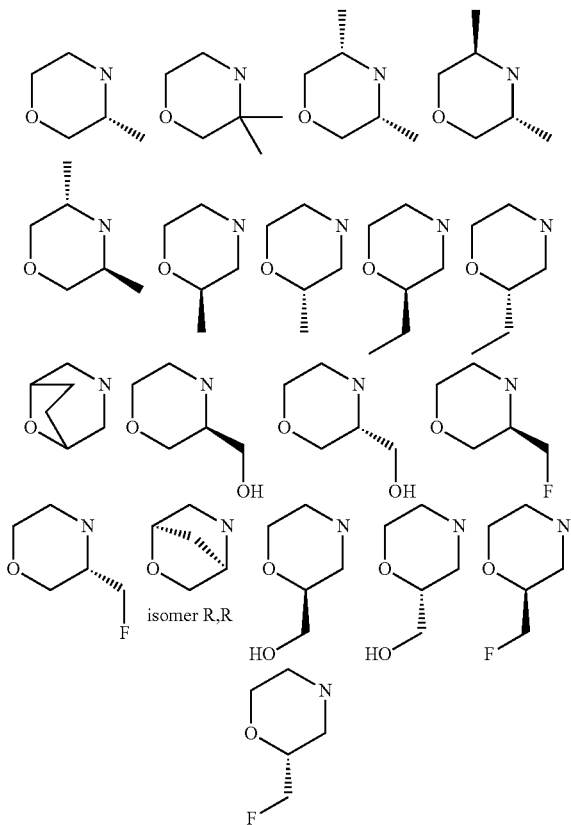

the radicals p, q, R1, R2, R3 and R4 having the meanings indicated above, said products of formula (I) being in any of the possible racemic, enantiomeric and diastereoisomeric isomer forms, and also the addition salts with inorganic and organic acids or with inorganic and organic bases of said products of formula (I).

A subject of the present invention is thus the products of formula (I) as defined above, in which p is the integer 0 and q is the integer 2 or else p is the integer 2 and q is the integer 0;

the radicals R1, R2, R3 and R4 and the morpholine residue having the meanings indicated above, said products of formula (I) being in any of the possible racemic, enantiomeric and diastereoisomeric isomer forms, and also the addition salts with inorganic and organic acids or with inorganic and organic bases of said products of formula (I).

A subject of the present invention is thus the products of formula (I) as defined above, in which p is the integer 0 and q is the integer 1 or else p is the integer 1 and q is the integer 0;

the radicals R1, R2, R3 and R4 and the morpholine residue having the meanings indicated above, said products of formula (I) being in any of the possible racemic, enantiomeric and diastereoisomeric isomer forms, and also the addition salts with inorganic and organic acids or with inorganic and organic bases of said products of formula (I).

In the products of formula (I) according to the present invention, the term alkyl (or alk) radical denotes linear and branched radicals containing from 1 to 10 carbon atoms, such as: methyl, ethyl, propyl, isopropyl, butyl, isobutyl, sec-butyl, tert-butyl, pentyl, isopentyl, hexyl, isohexyl and also heptyl, octyl, nonyl and decyl, and also the linear or branched positional isomers thereof: preference is given to the alkyl radicals containing from 1 to 6 carbon atoms and more particularly the alkyl radicals containing from 1 to 4 carbon atoms of the list above;

the term alkenyl radical denotes linear and branched radicals containing from 2 to 10 carbon atoms, chosen from the alkyl radicals defined above containing one or more double bonds, such as allyl, but-3-enyl or pent-4-enyl, and also the linear or branched positional isomers thereof: preference is given to the allyl and but-3-enyl radicals;

the term alkoxy radical denotes the linear and branched radicals, containing from 1 to 10 carbon atoms, methoxy, ethoxy, propoxy, isopropoxy, linear, secondary or tertiary butoxy, pentoxy or hexoxy, and also the linear or branched positional isomers thereof: preference is given to the alkoxy radicals containing from 1 to 4 carbon atoms of the list above;

the term alkythio or —S(O)x alkyl denotes the linear, and where appropriate branched, radicals in which the alkyl residue has the definition indicated above for the alkyl radical; —S(O)x alkyl thus in particular represents —S(O)x methyl, —S(O)x ethyl, —S(O)x propyl, —S(O)x isopropyl, linear, secondary or tertiary —S(O)x butyl, —S(O)x pentyl or —S(O)x hexyl and also the linear or branched positional isomers thereof: preference is given to the —S(O)x alkyl radicals containing from 1 to 4 carbon atoms of the list above;

the term halogen atom denotes chlorine, bromine, iodine or fluorine atoms and preferably the chlorine, bromine or fluorine atom;

the term cycloalkyl radical denotes a saturated carbocyclic radical containing from 3 to 10 carbon atoms, and thus denotes in particular the cyclopropyl, cyclobutyl, cyclopentyl and cyclohexyl radicals and quite particularly the cyclopropyl, cyclopentyl and cyclohexyl radicals;

in the —O-cycloalkyl radical, the cycloalkyl radical is as defined above;

the term heterocycloalkyl radical thus denotes a monocyclic or bicyclic carbocyclic radical containing from 3 to 10 ring members, interrupted by one or more heteroatoms, which may be identical or different, chosen from oxygen, nitrogen or sulfur atoms: mention may, for example, be made of morpholinyl, thiomorpholinyl, homomorpholinyl, aziridyl, azetidyl, piperazinyl, piperidyl, homopiperazinyl, pyrrolidinyl, imidazolidinyl, pyrazolidinyl, tetrahydrofuryl, tetrahydrothienyl, tetrahydropyran, oxodihydropyridazinyl, or else oxetanyl radicals, all these radicals being optionally substituted; mention may in particular be made of morpholinyl, thiomorpholinyl, homomorpholinyl, piperazinyl, piperidyl, homopiperazinyl or else pyrrolidinyl radicals;

the terms aryl and heteroaryl denote monocyclic or bicyclic, respectively, carbocyclic and heterocyclic, unsaturated or partially unsaturated radicals containing at most 12 ring members, which can optionally contain a —C(O) ring member, the heterocyclic radicals containing one or more heteroatoms, which may be identical or different, chosen from O, N or S with N, where appropriate, optionally substituted;

the term aryl radical thus denotes monocyclic or bicyclic radicals containing from 6 to 12 ring members, such as, for example, phenyl, naphthyl, biphenyl, indenyl, fluorenyl and anthracenyl radicals, more particularly phenyl and naphthyl radicals and even more particularly the phenyl radical. It may be noted that a carbocyclic radical containing a —C(O) ring member is, for example, the tetralone radical;

the term heteroaryl radical thus denotes monocyclic or bicyclic radicals containing from 5 to 12 ring members: monocyclic heteroaryl radicals such as, for example, the radicals: thienyl such as 2-thienyl and 3-thienyl, furyl such as 2-furyl or 3-furyl, pyrannyl, pyrrolyl, pyrrolinyl, pyrazolinyl, imidazolyl, pyrazolyl, pyridyl such as 2-pyridyl, 3-pyridyl and 4-pyridyl, pyrazinyl, pyrimidinyl, pyridazinyl, oxazolyl, thiazolyl, isothiazolyl, diazolyl, thiadiazolyl, triazolyl, thiatriazolyl, oxadiazolyl, isoxazolyl such as 3- or 4-isoxazolyl, furazanyl, free or salified tetrazolyl, all these radicals being optionally substituted, among which are more particularly the radicals: thienyl such as 2-thienyl and 3-thienyl, thiazolyl, furyl such as 2-furyl, pyrrolyl, pyrrolinyl, pyrazolinyl, imidazolyl, pyrazolyl, oxazolyl, isoxazolyl, pyridyl, pyridazinyl, these radicals being optionally substituted; bicyclic heteroaryl radicals such as, for example, the radicals: benzothienyl (benzothiophene) such as 3-benzothienyl, benzothiazolyl, quinolyl, isoquinolyl, dihydroquinolyl, quinolone, tetralone, adamentyl, benzofuryl, isobenzofuryl, dihydrobenzofuran, ethylenedioxyphenyl, thianthrenyl, benzopyrrolyl, benzimidazolyl, imidazopyridine, benzoxazinyl, benzoxazolyl, thionaphthyl, indolyl, dihydroindolyl, azaindolyl, indazolyl, purinyl, thienopyrazolyl, tetrahydroindazolyl, tetrahydroquinolyl, tetrahydroisoquinolyl, tetrahydrocyclopentapyrazolyl, dihydrofuropyrazolyl, dihydropyrrolopyridyl, tetrahydropyrrolopyrazolyl, oxotetrahydropyrrolopyrazolyl, tetrahydropyranopyrazolyl, tetrahydropyridinopyrazolyl or oxodihydropyridinopyrazolyl, all these radicals being optionally substituted.

As examples of heteroaryl or bicyclic radicals, mention may be made more particularly of pyrimidinyl, pyridyl, pyrrolyl, azaindolyl, indazolyl or pyrazolyl, benzothiazolyl or benzimidazolyl radicals optionally substituted with one or more substituents, which may be identical or different, as indicated above.

The carboxy radical(s) of the products of formula (I) may be salified or esterified with the various groups known to those skilled in the art, among which mention may be made, for example, of:

among the salification compounds, inorganic bases such as, for example, an equivalent of sodium, of potassium, of lithium, of calcium, of magnesium or of ammonium, or organic bases such as, for example, methylamine, propylamine, trimethylamine, diethylamine, triethylamine, N,N-dimethylethanolamine, tris(hydroxymethyl)aminomethane, ethanolamine, pyridine, picoline, dicyclohexylamine, morpholine, benzylamine, procaine, lysine, arginine, histidine or N-methylglucamine, among the esterification compounds, the alkyl radicals for forming alkoxycarbonyl groups, such as, for example, methoxycarbonyl, ethoxycarbonyl, tert-butoxycarbonyl or benzyloxycarbonyl, it being possible for these alkyl radicals to be substituted with radicals chosen, for example, from halogen atoms, and hydroxyl, alkoxy, acyl, acyloxy, alkylthio, amino or aryl radicals, for instance in the chloromethyl, hydroxypropyl, methoxymethyl, propionyloxymethyl, methylthiomethyl, dimethylaminoethyl, benzyl or phenethyl groups.

The compounds of formula (I) can exist in the salt form, such salts being part of the invention; these salts can be prepared with pharmaceutically acceptable acids or bases (P. Stahl, C. Wermuth; Handbook of pharmaceutical salts; Wiley Ed.), but other salts, obtained, for example, for the purification or isolation of the compounds of formula (I), are part of the invention.

The compounds of formula (I) can comprise one or more asymmetric centres. They can therefore exist in the form of enantiomers or diastereoisomers. These enantiomers, diastereoisomers and also mixtures thereof, including racemic mixtures, are part of the invention.

It may be recalled that the stereoisomerism can be defined in its broad sense as the isomerism of compounds having the same structural formula, but the various groups of which are arranged differently in space, such as, in particular, in monosubstituted cyclohexanes, the substituent of which can be in the axial or equatorial position, and the various possible rotational conformations of ethane derivatives. However, there is another type of stereoisomerism, owing to the different spatial arrangements of substituents attached either on double bonds or on rings, which is often referred to as geometric isomerism or cis-trans isomerism. The term stereoisomers is used in the present application in its broadest sense and therefore relates to all of the compounds indicated above.

In the products of formula (I) according to the present invention, when R1 is an optionally substituted phenyl or pyridyl radical, then in particular R1 is a phenyl or pyridyl radical optionally substituted with one or more radicals, which may be identical or different, chosen from fluorine and chlorine atoms and cycloalkyl, alkyl and alkoxy radicals, the latter alkyl and alkoxy radicals being themselves optionally substituted with one or more fluorine atoms, the other substituents R2, R3, R4, R5, R6, R7, R8, R9, R10, R11, R12, p and q of said products of formula (I) having the meanings indicated above.

In the products of formula (I) according to the present invention, when R1 is a —$(CH_2)_m$—Ra radical, then m is the integer 1 or 2 and in particular Ra is a radical —CO—Rb; —C(cycloalkyl)=N—ORc; $CO_2Rd$; —CONRxRy; a —CO-cyclopropyl, —CO-cyclobutyl, —CO-cyclopentyl or —CO-cyclohexyl radical, all optionally substituted with one or more alkyl radicals; a —CO-morpholine, —CO— piperidyl, —CO-tetrahydrofuran, —CO-tetrahydropyran or —CO-pyrrolidine radical, all optionally substituted with one or more alkyl radicals or a $CO_2$alk radical, where appropriate on a nitrogen atom; or else a phenyl, pyridine, oxazole, isoxazole, oxadiazole, pyrazole, thiophene, thiazole, thiadiazole, pyridazine, benzimidazole, imidazopyridine or triazole radical, all optionally substituted with one or more radicals, which may be identical or different, chosen from fluorine and chlorine halogen atoms and cycloalkyl, heterocycloalkyl, heteroaryl, alkyl and alkoxy radicals, the latter heteroaryl, alkyl and alkoxy radicals being themselves optionally substituted with one or more radicals, which may be identical or different, chosen from fluorine atoms and hydroxyl, alkyl and alkoxy radicals;

Rb is an alkyl, phenyl, pyridyl, thiazole, isoxazole, oxazole or oxadiazole radical, all optionally substituted with one or more radicals, which may be identical or different, chosen from fluorine and chlorine halogen atoms and cycloalkyl, heterocycloalkyl, phenyl, heteroaryl, alkyl and alkoxy radicals, the latter phenyl, heteroaryl, alkyl and alkoxy radicals being themselves optionally substituted with one or more radicals, which may be identical or different, chosen from fluorine atoms and hydroxyl, alkyl and alkoxy radicals;

Rc is in particular a hydrogen atom or an alkyl radical;

Rd is an alkyl or cycloalkyl radical; and NRxRy being as defined above or hereinafter;

the other substituents R2, R3, R4, R5, R6, R7, R8, R9, R10, R11, R12, p and q of said products of formula (I) having the meanings indicated above.

In the products of formula (I) according to the present invention, when NRxRy forms a ring as defined above, such an aminated ring can be chosen in particular from piperidyl, morpholinyl, homomorpholinyl, azetidine, oxaazaspiro[3.3]heptane, isoxazolidine, {1,2}oxazinane, pyrrolidinyl, pyrazolidinyl, pyrazolinyl, azepinyl, piperazinyl or homopiperazinyl radicals, these radicals being themselves optionally substituted as indicated above or hereinafter.

More particularly, when NRxRy forms a ring as defined above, such an aminated ring can be chosen in particular from piperidyl, morpholinyl, azetidine, oxaazaspiro[3.3]heptane, isoxazolidine or {1,2}oxazinane radicals.

In the products of formula (I) according to the present invention, when R1 is the SO$_2$Rb radical, then R1 is in particular the —SO$_2$-phenyl radical optionally substituted with an alkyl radical or a halogen atom, the other substituents R2, R3, R4, R5, R6, R7, R8, R9, R10, R11, R12, p and q of said products of formula (I) having the meanings indicated above.

In the products of formula (I) according to the present invention, when R1 is an alkyl radical, then in particular R1 is an alkyl radical optionally substituted with one or more radicals, which may be identical or different, chosen from fluorine atoms and hydroxyl, cyclopropyl, cyclobutyl, cyclopentyl, cyclohexyl, oxetane, tetrahydrofuran, tetrahydropyran, alkoxy, phenyl and pyridine radicals, the latter three radicals all being optionally substituted with one or more fluorine atoms, the other substituents R2, R3, R4, R5, R6, R7, R8, R9, R10, R11, R12, p and q of said products of formula (I) having the meanings indicated above.

In the products of formula (I) according to the present invention, when R1 is a cycloalkyl radical, then R1 is in particular a cyclobutyl, cyclopentyl or cyclohexyl radical, the other substituents R2, R3, R4, R5, R6, R7, R8, R9, R10, R11, R12, p and q of said products of formula (I) having the meanings indicated above.

In the products of formula (I) according to the present invention, when R1 is a heterocycloalkyl radical, then R1 is in particular an oxetane, tetrahydrofuran or tetrahydropyran radical, the other substituents R2, R3, R4, R5, R6, R7, R8, R9, R10, R11, R12, p and q of said products of formula (I) having the meanings indicated above.

In the products of formula (I) according to the present invention, in particular R2 and R3 may be such that R2 is a hydrogen atom and R3 is the trifluoromethyl radical CF$_3$, the other substituents R1, R4, R5, R6, R7, R8, R9, R10, R11, R12, p and q of said products of formula (I) having the meanings indicated above.

In the products of formula (I) according to the present invention, in particular R2 and R3 may be such that R2 is a methyl radical and R3 is the trifluoromethyl radical CF$_3$, the other substituents R1, R4, R5, R6, R7, R8, R9, R10, R11, R12, p and q of said products of formula (I) having the meanings indicated above.

In the products of formula (I) according to the present invention, in particular R2 and R3 may be such that R2 and R3 are both a methyl radical, the other substituents R1, R4, R5, R6, R7, R8, R9, R10, R11, R12, p and q of said products of formula (I) having the meanings indicated above.

In the products of formula (I) according to the present invention, one or more of the hydrogen atoms that R4, R5, R6, R7, R8, R9, R10, R11 and R12 of said products of formula (I) may represent can be a deuterium atom.

In the products of formula (I) according to the present invention, the cyclic radical that R2 and R3 may optionally form with the carbon atom to which they are bonded, as defined above, can thus be a carbocyclic (spirocycloalkyl) radical such as the spirocyclopropyl, cyclobutyl, cyclopentyl or cyclohexyl radical, or else be a heterocyclic radical such as, for example, the oxetane radical, all these radicals being optionally substituted as defined above.

In the products of formula (I) according to the present invention, when NRxRy forms a ring as defined above, such an aminated ring can be chosen in particular from pyrrolidinyl, pyrazolidinyl, pyrazolinyl, piperidyl, azepinyl, morpholinyl, homomorpholinyl, piperazinyl or homopiperazinyl radicals, these radicals being themselves optionally substituted as indicated above or hereinafter.

A subject of the present invention is the products of formula (I) as defined above, in which:

p and q are the integers 0 or 1 or 2 such that, if p=0, then q=1 or 2 and, if p=1 or 2, then q=0;

R1 is a phenyl or pyridyl radical optionally substituted with one or more radicals, which may be identical or different, chosen from fluorine and chlorine atoms and cycloalkyl, alkyl and alkoxy radicals, the latter alkyl and alkoxy radicals being themselves optionally substituted with one or more fluorine atoms; a —(CH$_2$)$_m$—Ra radical; an —SO$_2$-phenyl radical optionally substituted with an alkyl radical; a —CO-alkyl radical; an alkylene radical; or an alkyl radical optionally substituted with one or more radicals, which may be identical or different, chosen from fluorine atoms and hydroxyl, cyclopropyl, cyclobutyl, cyclopentyl, cyclohexyl, oxetane, tetrahydrofuran, tetrahydropyran, alkoxy, phenyl and pyridine radicals, the latter three radicals all being optionally substituted with one or more fluorine atoms;

m is the integer 1 or 2;

Ra is a radical —CO—Rb; —C(cycloalkyl)=N—ORc; CO$_2$Rd; —CONRxRy; a —CO-cyclopropyl, —CO-cyclobutyl, —CO-cyclopentyl or —CO-cyclohexyl radical, all optionally substituted with one or more alkyl radicals; a —CO-morpholine, —CO— piperidyl, —CO-tetrahydrofuran, —CO-tetrahydropyran or —CO-pyrrolidine radical, all optionally substituted with one or more alkyl radicals or a CO$_2$alk radical, where appropriate on a nitrogen atom; or else a phenyl, pyridine, oxazole, isoxazole, oxadiazole, pyrazole, thiophene, thiazole, thiadiazole, pyridazine, benzimidazole, imidazopyridine or triazole radical, all optionally substituted with one or more radicals, which may be identical or different, chosen from fluorine and chlorine halogen atoms and cycloalkyl, heterocycloalkyl, heteroaryl, alkyl and alkoxy radicals, the latter heteroaryl, alkyl and alkoxy radicals being themselves optionally substituted with one or more radicals, which may be identical or different, chosen from fluorine atoms and hydroxyl, alkyl and alkoxy radicals;

Rb is an alkyl, phenyl, pyridyl, thiazole, isoxazole, oxazole or oxadiazole radical, all optionally substituted with one or more radicals, which may be identical or different, chosen from fluorine and chlorine halogen atoms and cycloalkyl, heterocycloalkyl, phenyl, heteroaryl, alkyl and alkoxy radicals, the latter phenyl, heteroaryl, heterocyloalkyl, alkyl and alkoxy radicals being themselves optionally substituted with one or more radicals, which may be identical or different, chosen from fluorine atoms and hydroxyl, alkyl and alkoxy radicals;

Rc is in particular a hydrogen atom or an alkyl radical;

Rd is an alkyl or cycloalkyl radical;

NRxRy are such that Rx and Ry, which may be identical or different, are a hydrogen atom or an alkyl, alkoxy or phenyl radical or else together form a piperidyl, morpholinyl, azetidine, oxaazaspiro[3.3]heptane, isoxazolidine or {1,2}oxazinane radical;

R2 and R3 are such that:

either R2 is a hydrogen atom and R3 is the trifluoromethyl radical $CF_3$;

or R2 is a methyl radical and R3 is the trifluoromethyl radical $CF_3$;

or R2 and R3 are both a methyl radical;

R4 is a hydrogen atom, a fluorine or chlorine atom, a methyl radical or a CN radical;

the morpholine residue is chosen from the following radicals:

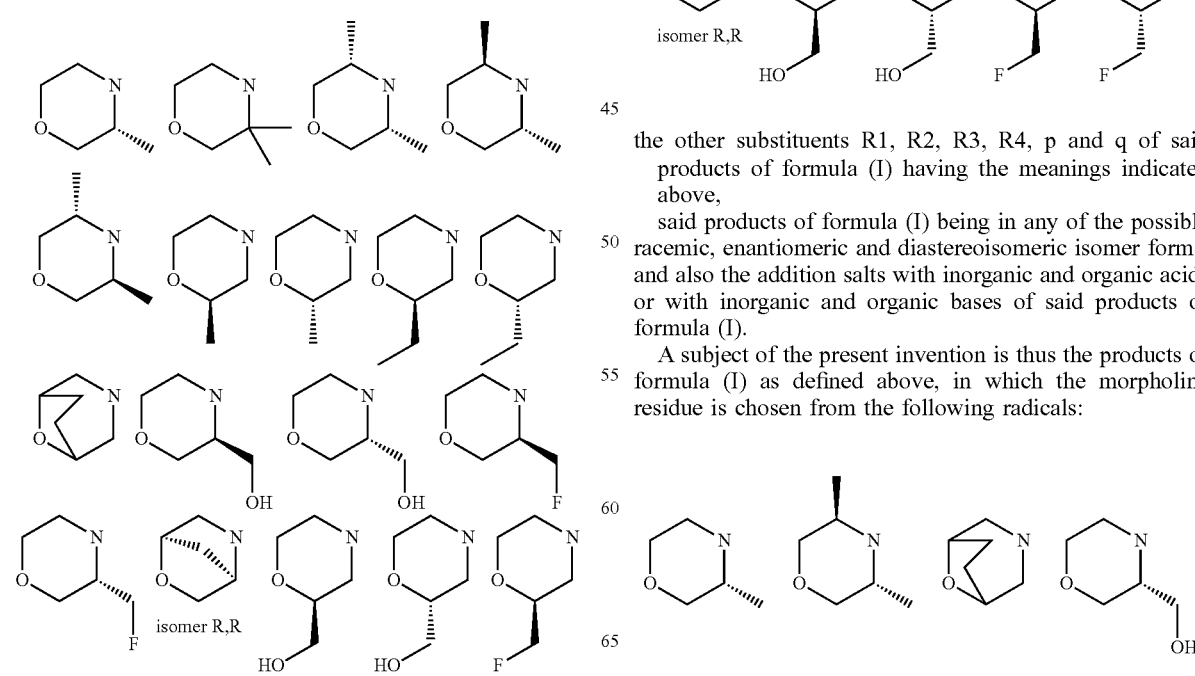

-continued

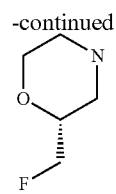

said products of formula (I) being in any of the possible racemic, enantiomeric and diastereoisomeric isomer forms, and also the addition salts with inorganic and organic acids or with inorganic and organic bases of said products of formula (I).

A subject of the present invention is thus the products of formula (I) as defined above, in which the morpholine residue is chosen from the following radicals:

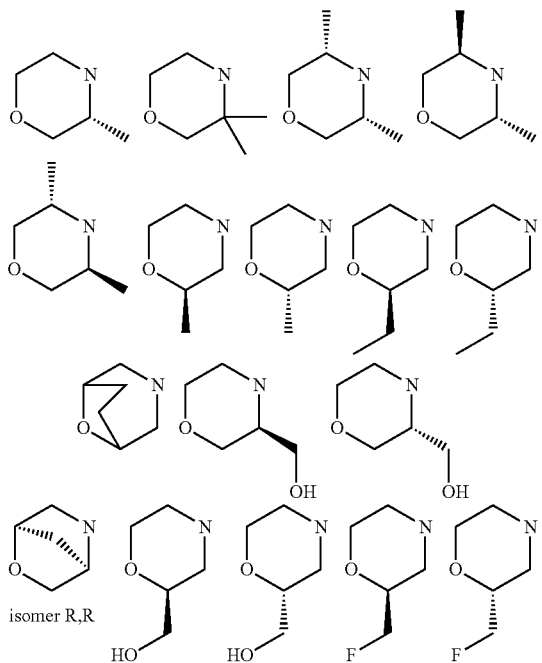

isomer R,R the other substituents R1, R2, R3, R4, p and q of said products of formula (I) having the meanings indicated above, said products of formula (I) being in any of the possible racemic, enantiomeric and diastereoisomeric isomer forms, and also the addition salts with inorganic and organic acids or with inorganic and organic bases of said products of formula (I).

A subject of the present invention is thus the products of formula (I) as defined above, in which the morpholine residue is chosen from the following radicals:

the other substituents R1, R2, R3, R4, p and q of said products of formula (I) having the meanings indicated above, said products of formula (I) being in any of the possible racemic, enantiomeric and diastereoisomeric isomer forms, and also the addition salts with inorganic and organic acids or with inorganic and organic bases of said products of formula (I).

In the products of formula (I) according to the present invention, Rb can in particular be one of the following radicals as defined above: alkyl, such as, for example, methyl, ethyl or isopropyl; phenyl, pyridyl, thiazole, isoxazole, oxazole and oxadiazole; all optionally substituted with one or more radicals, which may be identical or different, chosen from fluorine and chlorine halogen atoms and cyclopropyl, cyclobutyl, cyclopentyl and cyclohexyl, piperidyl, morpholinyle, phenyl, pyridyl, alkyl and alkoxy radicals, the latter phenyl, pyridyl, alkyl and alkoxy radicals being themselves optionally substituted with one or more radicals, which may be identical or different, chosen from fluorine atoms and hydroxyl, alkyl and alkoxy radicals.

In particular, Rd can be an alkyl or cyclopentyl radical.

In the products of formula (I) according to the present invention, R4 can be a hydrogen atom or a fluorine atom.

In the products of formula (I) according to the present invention, when R1 is a —($CH_2$)$_m$—Ra radical with m being the integer 1 or 2 and Ra being —CO -cycloalkyl or —CO-heterocycloalkyl, then these cycloalkyl and heterocycloalkyl radicals are chosen, for example, from cyclopropyl, cyclopentyl, cyclohexyl, morpholinyl, piperidyl, tetrahydrofuran, tetrahydropyran and pyrrolidine radicals, all optionally substituted with one or more alkyl radicals and, in addition, optionally with $CO_2$alk on the nitrogen of the pyrrolidine.

In the products of formula (I) according to the present invention, when R1 is a —($CH_2$)$_m$—Ra radical with m being the integer 1 or 2 and Ra being —CO—Rb, then Rb can be, for example, an alkyl radical such as, in particular, methyl, ethyl, propyl, butyl or pentyl, all linear or branched, such as, for example isopropyl, tert-butyl, linear or branched butyl, linear or branched pentyl, which are optionally substituted as indicated above.

A subject of the present invention is most particularly the products of formula (I) as defined above, corresponding to the following formulae:

(S)-2-((R)-3-Methylmorpholin-4-yl)-9-(5-methyl-[1,2,4]oxadiazol-3-ylmethyl)-8-trifluoromethyl-6,7,8,9-tetrahydropyrimido[1,2-a]pyrimidin-4-one (S)-2-((R)-3-Methylmorpholin-4-yl)-9-(3-methyl-2-oxobutyl)-8-trifluoromethyl-6,7,8,9-tetrahydropyrimido[1,2-a]pyrimidin-4-one (S)-3-Fluoro-2-((R)-3-methylmorpholin-4-yl)-9-(3-methyl-2-oxobutyl)-8-trifluoromethyl-6,7,8,9-tetrahydropyrimido[1,2-a]pyrimidin-4-one (S)-3-Fluoro-9-(2-fluoropyridin-4-ylmethyl)-2-((R)-3-methylmorpholin-4-yl)-8-trifluoromethyl-6,7,8,9-tetrahydropyrimido[1,2-a]pyrimidin-4-one (S)-9-(2-Cyclopropyl-2-oxoethyl)-3-fluoro-2-((R)-3-methylmorpholin-4-yl)-8-trifluoromethyl-6,7,8,9-tetrahydropyrimido[1,2-a]pyrimidin-4-one (S)-3-Fluoro-2-((R)-3-methylmorpholin-4-yl)-9-(2-oxopropyl)-8-trifluoromethyl-6,7,8,9-tetrahydropyrimido[1,2-a]pyrimidin-4-one (S)-3-Fluoro-9-((S)-2-hydroxypropyl)-2-((R)-3-methylmorpholin-4-yl)-8-trifluoromethyl-6,7,8,9-tetrahydropyrimido[1,2-a]pyrimidin-4-one (S)-2-((3R,5R)-3,5-Dimethylmorpholin-4-yl)-9-isoxazol-5-ylmethyl-8-trifluoromethyl-6,7,8,9-tetrahydropyrimido[1,2-a]pyrimidin-4-one (S)-9-[2-(2-Chloropyridin-4-yl)-2-oxoethyl]-2-((R)-3-methylmorpholin-4-yl)-8-trifluoromethyl-6,7,8,9-tetrahydropyrimido[1,2-a]pyrimidin-4-one (S)-2-((R)-3-Methylmorpholin-4-yl)-9-(2-oxo-2-pyridin-3-ylethyl)-8-trifluoromethyl-6,7,8,9-tetrahydropyrimido[1,2-a]pyrimidin-4-one (S)-9-(3-Methylisoxazol-4-ylmethyl)-2-((R)-3-methylmorpholin-4-yl)-8-trifluoromethyl-6,7,8,9-tetrahydropyrimido[1,2-a]pyrimidin-4-one (R)-2-((R)-3-Methylmorpholin-4-yl)-9-oxazol-2-ylmethyl-6-trifluoromethyl-6,7,8,9-tetrahydropyrimido[1,2-a]pyrimidin-4-one

[(S)-8-((R)-3-Methylmorpholin-4-yl)-6-oxo-2-trifluoromethyl-3,4-dihydro-2H,6H-pyrimido[1,2-a]pyrimidin-1-yl] acetic acid ethyl ester (S)-3-Fluoro-2-((R)-3-methylmorpholin-4-yl)-9-(5-methyl-[1,2,4]oxadiazol-3-ylmethyl)-8-trifluoromethyl-6,7,8,9-tetrahydropyrimido[1,2-a]pyrimidin-4-one (S)-2-((R)-3-Methylmorpholin-4-yl)-9-(2-oxobutyl)-8-trifluoromethyl-6,7,8,9-tetrahydropyrimido[1,2-a]pyrimidin-4-one (S)-2-((R)-3-Methylmorpholin-4-yl)-9-(3-methyl-[1,2,4]oxadiazol-5-ylmethyl)-8-trifluoromethyl-6,7,8,9-tetrahydropyrimido[1,2-a]pyrimidin-4-one (S)-3-Fluoro-2-((R)-3-methylmorpholin-4-yl)-9-[2-oxo-2-(tetrahydropyran-4-yl)ethyl]-8-trifluoromethyl-6,7,8,9-tetrahydropyrimido[1,2-a]pyrimidin-4-one (S)-3-Fluoro-2-((R)-3-methylmorpholin-4-yl)-9-(3-methyl-[1,2,4]oxadiazol-5-ylmethyl)-8-trifluoromethyl-6,7,8,9-tetrahydropyrimido[1,2-a]pyrimidin-4-one (S)-3-Fluoro-9-(2-methoxyethyl)-2-((R)-3-methylmorpholin-4-yl)-8-trifluoromethyl-6,7,8,9-tetrahydropyrimido[1,2-a]pyrimidin-4-one (R)-3-Fluoro-2-((R)-3-methylmorpholin-4-yl)-9-(5-methyl-[1,2,4]oxadiazol-3-ylmethyl)-6-trifluoromethyl-6,7,8,9-tetrahydropyrimido[1,2-a]pyrimidin-4-one (S)-3-Fluoro-2-((R)-3-methylmorpholin-4-yl)-9-(2-oxobutyl)-8-trifluoromethyl-6,7,8,9-tetrahydropyrimido[1,2-a]pyrimidin-4-one 2-[(S)-7-Fluoro-8-((R)-3-methylmorpholin-4-yl)-6-oxo-2-trifluoromethyl-3,4-dihydro-2H,6H-pyrimido[1,2-a]pyrimidin-1-yl]-N-methoxy-N-methylacetamide (S)-9-(6-Fluoropyridin-3-ylmethyl)-2-((R)-3-methylmorpholin-4-yl)-8-trifluoromethyl-6,7,8,9-tetrahydropyrimido[1,2-a]pyrimidin-4-one (S)-9-[2-(2-Fluoropyridin-4-yl)-2-oxoethyl]-2-((R)-3-methylmorpholin-4-yl)-8-trifluoromethyl-6,7,8,9-tetrahydropyrimido[1,2-a]pyrimidin-4-one (R)-2-((R)-3-Methylmorpholin-4-yl)-9-(2-oxobutyl)-6-trifluoromethyl-6,7,8,9-tetrahydropyrimido[1,2-a]pyrimidin-4-one (R)-2-((R)-3-Methylmorpholin-4-yl)-9-(5-methyl-[1,2,4]oxadiazol-3-ylmethyl)-6-trifluoromethyl-6,7,8,9-tetrahydropyrimido[1,2-a]pyrimidin-4-one (R)-3-Fluoro-2-((R)-3-methylmorpholin-4-yl)-6-trifluoromethyl-9-(3-trifluoromethyl-[1,2,4]oxadiazol-5-ylmethyl)-6,7,8,9-tetrahydropyrimido[1,2-a]pyrimidin-4-one (R)-3-Fluoro-2-((R)-3-methylmorpholin-4-yl)-9-(2-oxobutyl)-6-trifluoromethyl-6,7,8,9-tetrahydropyrimido[1,2-a]pyrimidin-4-one (S)-6-Fluoro-2-methyl-7-((R)-3-methylmorpholin-4-yl)-1-(5-methyl-[1,2,4]oxadiazol-3-ylmethyl)-2-trifluoromethyl-2,3-dihydro-1H-imidazo[1,2-a]pyrimidin-5-one (S)-1-(2-Cyclopropyl-2-oxoethyl)-2-methyl-7-((R)-3-methylmorpholin-4-yl)-2-trifluoromethyl-2,3-dihydro-1H-imidazo[1,2-a]pyrimidin-5-one (S)-9-(1-Difluoromethyl-1H-pyrazol-3-ylmethyl)-2-((R)-3-methylmorpholin-4-yl)-8-trifluoromethyl-6,7,8,9-tetrahydropyrimido[1,2-a]pyrimidin-4-one (S)-9-Isoxazol-3-ylmethyl-2-((R)-3-methylmorpholin-4-yl)-8-trifluoromethyl-6,7,8,9-tetrahydropyrimido[1,2-a]pyrimidin-4-one (S)-9-(2-Chlorothiazol-5-ylmethyl)-2-((R)-3-methylmorpholin-4-yl)-8-trifluoromethyl-6,7,8,9-tetrahydropyrimido[1,2-a]pyrimidin-4-one (S)-9-(6-Chloropyridin-3-ylmethyl)-2-((R)-3-methylmorpholin-4-yl)-8-trifluoromethyl-6,7,8,9-tetrahydropyrimido[1,2-a]pyrimidin-4-one (S)-9-Isoxazol-5-ylmethyl-2-((R)-3-methylmorpholin-4-yl)-8-trifluoromethyl-6,7,8,9-tetrahydropyrimido[1,2-a]pyrimidin-4-one (S)-9-(2-Difluoromethyl-2H-pyrazol-3-ylmethyl)-2-((R)-3-methylmorpholin-4-yl)-8-trifluoromethyl-6,7,8,9-tetrahydropyrimido[1,2-a]pyrimidin-4-one (S)-3-Fluoro-2-((R)-3-methylmorpholin-4-yl)-9-(2-oxo-2-pyridin-2-ylethyl)-8-trifluoromethyl-6,7,8,9-tetrahydropyrimido[1,2-a]pyrimidin-4-one (S)-9-(2-Fluoro-2-phenylethyl)-2-((R)-3-methylmorpholin-4-yl)-8-trifluoromethyl-6,7,8,9-tetrahydropyrimido[1,2-a]pyrimidin-4-one, single stereoisomer (S)-3-Fluoro-9-(2-methoxypyridin-4-yl)-2-((R)-3-methylmorpholin-4-yl)-8-trifluoromethyl-6,7,8,9-tetrahydropyrimido[1,2-a]pyrimidin-4-one (S)-9-(2-Chloropyridin-4-ylmethyl)-3-fluoro-2-((R)-3-methylmorpholin-4-yl)-8-trifluoromethyl-6,7,8,9-tetrahydropyrimido[1,2-a]pyrimidin-4-one (S)-3-Fluoro-2-((R)-3-methylmorpholin-4-yl)-9-oxazol-2-ylmethyl-8-trifluoromethyl-6,7,8,9-tetrahydropyrimido[1,2-a]pyrimidin-4-one (S)-9-(6-Cyclopropylpyridin-3-yl)-3-fluoro-2-((R)-3-methylmorpholin-4-yl)-8-trifluoromethyl-6,7,8,9-tetrahydropyrimido[1,2-a]pyrimidin-4-one (S)-3-Fluoro-2-((R)-3-methylmorpholin-4-yl)-9-oxazol-4-ylmethyl-8-trifluoromethyl-6,7,8,9-tetrahydropyrimido[1,2-a]pyrimidin-4-one (S)-9-(2-Chloropyridin-4-yl)-3-fluoro-2-((R)-3-methylmorpholin-4-yl)-8-trifluoromethyl-6,7,8,9-tetrahydropyrimido[1,2-a]pyrimidin-4-one (S)-3-Fluoro-9-isoxazol-5-ylmethyl-2-((R)-3-methylmorpholin-4-yl)-8-trifluoromethyl-6,7,8,9-tetrahydropyrimido[1,2-a]pyrimidin-4-one (S)-3-Fluoro-2-((R)-3-methylmorpholin-4-yl)-9-pyridin-3-yl-8-trifluoromethyl-6,7,8,9-tetrahydropyrimido[1,2-a]pyrimidin-4-one (S)-3-Fluoro-2-((R)-3-methylmorpholin-4-yl)-9-[2-(2,2,2-trifluoroethoxy)-ethyl]-8-trifluoromethyl-6,7,8,9-tetrahydropyrimido[1,2-a]pyrimidin-4-one (S)-3-Fluoro-9-(2-hydroxy-2-methylpropyl)-2-((R)-3-methylmorpholin-4-yl)-8-trifluoromethyl-6,7,8,9-tetrahydropyrimido[1,2-a]pyrimidin-4-one (S)-3-Fluoro-2-((R)-3-methylmorpholin-4-yl)-9-(2-oxo-2-pyridin-3-ylethyl)-8-trifluoromethyl-6,7,8,9-tetrahydropyrimido[1,2-a]pyrimidin-4-one (S)-3-Fluoro-9-(6-fluoropyridin-3-ylmethyl)-2-((R)-3-methylmorpholin-4-yl)-8-trifluoromethyl-6,7,8,9-tetrahydropyrimido[1,2-a]pyrimidin-4-one (S)-9-(6-Chloropyridin-3-ylmethyl)-3-fluoro-2-((R)-3-methylmorpholin-4-yl)-8-trifluoromethyl-6,7,8,9-tetrahydropyrimido[1,2-a]pyrimidin-4-one (S)-9-(6-Difluoromethylpyridin-3-yl)-3-fluoro-2-((R)-3-methylmorpholin-4-yl)-8-trifluoromethyl-6,7,8,9-tetrahydropyrimido[1,2-a]pyrimidin-4-one (S)-9-(5-tert-Butyl-[1,2,4]oxadiazol-3-ylmethyl)-3-fluoro-2-((R)-3-methylmorpholin-4-yl)-8-trifluoromethyl-6,7,8,9-tetrahydropyrimido[1,2-a]pyrimidin-4-one (S)-3-Fluoro-2-((R)-3-methylmorpholin-4-yl)-9-pyridin-4-yl-8-trifluoromethyl-6,7,8,9-tetrahydropyrimido[1,2-a]pyrimidin-4-one (S)-3-Fluoro-9-(5-fluoropyridin-2-ylmethyl)-2-((R)-3-methylmorpholin-4-yl)-8-trifluoromethyl-6,7,8,9-tetrahydropyrimido[1,2-a]pyrimidin-4-one (S)-3-Fluoro-9-(5-fluoropyridin-3-ylmethyl)-2-((R)-3-methylmorpholin-4-yl)-8-trifluoromethyl-6,7,8,9-tetrahydropyrimido[1,2-a]pyrimidin-4-one (S)-3-Fluoro-9-(2-fluoropyridin-3-ylmethyl)-2-((R)-3-methylmorpholin-4-yl)-8-trifluoromethyl-6,7,8,9-tetrahydropyrimido[1,2-a]pyrimidin-4-one (S)-3-Fluoro-9-[2-(3-fluoropyridin-2-yl)-2-oxoethyl]-2-((R)-3-methylmorpholin-4-yl)-8-trifluoromethyl-6,7,8,9-tetrahydropyrimido[1,2-a]pyrimidin-4-one (S)-9-[2-(3-Fluoropyridin-2-yl)-2-oxoethyl]-2-((R)-3-methylmorpholin-4-yl)-8-trifluoromethyl-6,7,8,9-tetrahydropyrimido[1,2-a]pyrimidin-4-one (S)-9-[2-(2-Methoxypyridin-4-yl)-2-oxoethyl]-2-((R)-3-methylmorpholin-4-yl)-8-trifluoromethyl-6,7,8,9-tetrahydropyrimido[1,2-a]pyrimidin-4-one (S)-3-Fluoro-9-(3-methylisoxazol-4-ylmethyl)-2-((R)-3-methylmorpholin-4-yl)-8-trifluoromethyl-6,7,8,9-tetrahydropyrimido[1,2-a]pyrimidin-4-one (S)-9-[2-(6-Fluoropyridin-2-yl)-2-oxoethyl]-2-((R)-3-methylmorpholin-4-yl)-8-trifluoromethyl-6,7,8,9-tetrahydropyrimido[1,2-a]pyrimidin-4-one (S)-9-Imidazo[1,2-a]pyridin-2-ylmethyl-2-((R)-3-methylmorpholin-4-yl)-8-trifluoromethyl-6,7,8,9-tetrahydropyrimido[1,2-a]pyrimidin-4-one (S)-9-(4-Chloropyridin-2-ylmethyl)-2-((R)-3-methylmorpholin-4-yl)-8-trifluoromethyl-6,7,8,9-tetrahydropyrimido[1,2-a]pyrimidin-4-one (S)-9-(3-Chloropyridin-4-ylmethyl)-2-((R)-3-methylmorpholin-4-yl)-8-trifluoromethyl-6,7,8,9-tetrahydropyrimido[1,2-a]pyrimidin-4-one (S)-2-((R)-3-Methylmorpholin-4-yl)-9-(2-oxo-3-pyridin-2-ylpropyl)-8-trifluoromethyl-6,7,8,9-tetrahydropyrimido[1,2-a]pyrimidin-4-one (S)-3-Fluoro-2-((R)-3-methylmorpholin-4-yl)-9-(2-oxo-2-thiazol-2-ylethyl)-8-trifluoromethyl-6,7,8,9-tetrahydropyrimido[1,2-a]pyrimidin-4-one (S)-3-Fluoro-2-((R)-3-methylmorpholin-4-yl)-9-thiazol-4-ylmethyl-8-trifluoromethyl-6,7,8,9-tetrahydropyrimido[1,2-a]pyrimidin-4-one (S)-9-[2-(5-Fluoropyridin-2-yl)-2-oxoethyl]-2-((R)-3-methylmorpholin-4-yl)-8-trifluoromethyl-6,7,8,9-tetrahydropyrimido[1,2-a]pyrimidin-4-one 3-Fluoro-8,8-dimethyl-2-((R)-3-methylmorpholin-4-yl)-9-(2-oxo-2-pyridin-2-ylethyl)-6,7,8,9-tetrahydropyrimido[1,2-a]pyrimidin-4-one 9-(2-Difluoromethyl-2H-pyrazol-3-ylmethyl)-8,8-dimethyl-2-((R)-3-methylmorpholin-4-yl)-6,7,8,9-tetrahydropyrimido[1,2-a]pyrimidin-4-one 3-Fluoro-9-isoxazol-3-ylmethyl-8,8-dimethyl-2-((R)-3-methylmorpholin-4-yl)-6,7,8,9-tetrahydropyrimido[1,2-a]pyrimidin-4-one 9-(2-Difluoromethyl-2H-pyrazol-3-ylmethyl)-3-fluoro-8,8-dimethyl-2-((R)-3-methylmorpholin-4-yl)-6,7,8,9-tetrahydropyrimido[1,2-a]pyrimidin-4-one (S)-9-(3-Fluorophenyl)-2-((R)-3-methylmorpholin-4-yl)-8-trifluoromethyl-6,7,8,9-tetrahydropyrimido[1,2-a]pyrimidin-4-one (S)-9-(2-Chloropyridin-4-ylmethyl)-2-((R)-3-methylmorpholin-4-yl)-8-trifluoromethyl-6,7,8,9-tetrahydropyrimido[1,2-a]pyrimidin-4-one (S)-2-((R)-3-Methylmorpholin-4-yl)-9-oxazol-2-ylmethyl-8-trifluoromethyl-6,7,8,9-tetrahydropyrimido[1,2-a]pyrimidin-4-one (S)-2-((R)-3-Methylmorpholin-4-yl)-9-thiazol-4-ylmethyl-8-trifluoromethyl-6,7,8,9-tetrahydropyrimido[1,2-a]pyrimidin-4-one (S)-9-(2-Chloropyridin-4-yl)-2-((R)-3-methylmorpholin-4-yl)-8-trifluoromethyl-6,7,8,9-tetrahydropyrimido[1,2-a]pyrimidin-4-one (S)-9-(2-Methoxypyridin-4-yl)-2-((R)-3-methylmorpholin-4-yl)-8-trifluoromethyl-6,7,8,9-tetrahydropyrimido[1,2-a]pyrimidin-4-one (S)-2-((R)-3-Methylmorpholin-4-yl)-8-trifluoromethyl-9-(6-trifluoromethylpyridin-3-yl)-6,7,8,9-tetrahydropyrimido[1,2-a]pyrimidin-4-one (S)-2-((R)-3-Methylmorpholin-4-yl)-9-[2-(2,2,2-trifluoroethoxy)ethyl]-8-trifluoromethyl-6,7,8,9-tetrahydropyrimido[1,2-a]pyrimidin-4-one (S)-2-((R)-3-Methylmorpholin-4-yl)-9-(6-methylpyridin-3-yl)-8-trifluoromethyl-6,7,8,9-tetrahydropyrimido[1,2-a]pyrimidin-4-one (S)-9-(2-Hydroxy-2-methylpropyl)-2-((R)-3-methylmorpholin-4-yl)-8-trifluoromethyl-6,7,8,9-tetrahydropyrimido[1,2-a]pyrimidin-4-one (S)-9-(6-Isopropoxypyridin-3-yl)-2-((R)-3-methylmorpholin-4-yl)-8-trifluoromethyl-6,7,8,9-tetrahydropyrimido[1,2-a]pyrimidin-4-one (S)-9-(5-Chloropyridin-2-ylmethyl)-2-((R)-3-methylmorpholin-4-yl)-8-trifluoromethyl-6,7,8,9-tetrahydropyrimido[1,2-a]pyrimidin-4-one (S)-2-((R)-3-Methylmorpholin-4-yl)-9-thiazol-5-ylmethyl-8-trifluoromethyl-6,7,8,9-tetrahydropyrimido[1,2-a]pyrimidin-4-one (S)-9-(6-Cyclobutylpyridin-3-yl)-2-((R)-3-methylmorpholin-4-yl)-8-trifluoromethyl-6,7,8,9-tetrahydropyrimido[1,2-a]pyrimidin-4-one (S)-9-(2-Cyclopropylpyridin-4-yl)-2-((R)-3-methylmorpholin-4-yl)-8-trifluoromethyl-6,7,8,9-tetrahydropyrimido[1,2-a]pyrimidin-4-one (S)-9-(2-Methoxyethyl)-2-((R)-3-methylmorpholin-4-yl)-8-trifluoromethyl-6,7,8,9-tetrahydropyrimido[1,2-a]pyrimidin-4-one (S)-2-((R)-3-Methylmorpholin-4-yl)-9-oxazol-5-ylmethyl-8-trifluoromethyl-6,7,8,9-tetrahydropyrimido[1,2-a]pyrimidin-4-one (S)-9-(5-Fluoropyridin-2-ylmethyl)-2-((R)-3-methylmorpholin-4-yl)-8-trifluoromethyl-6,7,8,9-tetrahydropyrimido[1,2-a]pyrimidin-4-one (S)-9-(2,5-Dimethyloxazol-4-ylmethyl)-2-((R)-3-methylmorpholin-4-yl)-8-trifluoromethyl-6,7,8,9-tetrahydropyrimido[1,2-a]pyrimidin-4-one (S)-9-(5-Fluoropyridin-3-ylmethyl)-2-((R)-3-methylmorpholin-4-yl)-8-trifluoromethyl-6,7,8,9-tetrahydropyrimido[1,2-a]pyrimidin-4-one (S)-9-(5-Chloropyridin-3-ylmethyl)-2-((R)-3-methylmorpholin-4-yl)-8-trifluoromethyl-6,7,8,9-tetrahydropyrimido[1,2-a]pyrimidin-4-one (S)-2-((R)-3-Methylmorpholin-4-yl)-9-(5-methyl-[1,3,4]oxadiazol-2-ylmethyl)-8-trifluoromethyl-6,7,8,9-tetrahydropyrimido[1,2-a]pyrimidin-4-one (S)-9-(3,3-Dimethyl-2-oxobutyl)-3-fluoro-2-((R)-3-methylmorpholin-4-yl)-8-trifluoromethyl-6,7,8,9-tetrahydropyrimido[1,2-a]pyrimidin-4-one (S)-9-(5-Chlorothiophen-2-ylmethyl)-2-((R)-3-methylmorpholin-4-yl)-8-trifluoromethyl-6,7,8,9-tetrahydropyrimido[1,2-a]pyrimidin-4-one (S)-2-((R)-3-Methylmorpholin-4-yl)-9-(2-oxo-2-phenylethyl)-8-trifluoromethyl-6,7,8,9-tetrahydropyrimido[1,2-a]pyrimidin-4-one (S)-9-((S)-2-Methoxy-2-phenylethyl)-2-((R)-3-methylmorpholin-4-yl)-8-trifluoromethyl-6,7,8,9-tetrahydropyrimido[1,2-a]pyrimidin-4-one (S)-9-(3-Methylisoxazol-5-ylmethyl)-2-((R)-3-methylmorpholin-4-yl)-8-trifluoromethyl-6,7,8,9-tetrahydropyrimido[1,2-a]pyrimidin-4-one (R)-2-((R)-3-Methylmorpholin-4-yl)-9-(2-oxo-2-pyridin-2-ylethyl)-6-trifluoromethyl-6,7,8,9-tetrahydropyrimido[1,2-a]pyrimidin-4-one (S)-2-((R)-3-Methylmorpholin-4-yl)-9-oxazol-4-ylmethyl-8-trifluoromethyl-6,7,8,9-tetrahydropyrimido[1,2-a]pyrimidin-4-one (S)-2-((R)-3-Methylmorpholin-4-yl)-9-(toluene-4-sulfonyl)-8-trifluoromethyl-6,7,8,9-tetrahydropyrimido[1,2-a]pyrimidin-4-one (R)-9-Isoxazol-5-ylmethyl-2-((R)-3-methylmorpholin-4-yl)-6-trifluoromethyl-6,7,8,9-tetrahydropyrimido[1,2-a]pyrimidin-4-one (R)-9-Isoxazol-3-ylmethyl-2-((R)-3-methylmorpholin-4-yl)-6-trifluoromethyl-6,7,8,9-tetrahydropyrimido[1,2-a]pyrimidin-4-one (R)-9-(6-Cyclopropylpyridin-3-yl)-2-((R)-3-methylmorpholin-4-yl)-6-trifluoromethyl-6,7,8,9-tetrahydropyrimido[1,2-a]pyrimidin-4-one (R)-9-(2-Chloropyridin-4-yl)-2-((R)-3-methylmorpholin-4-yl)-6-trifluoromethyl-6,7,8,9-tetrahydropyrimido[1,2-a]pyrimidin-4-one (R)-9-(2-Methoxypyridin-4-yl)-2-((R)-3-methylmorpholin-4-yl)-6-trifluoromethyl-6,7,8,9-tetrahydropyrimido[1,2-a]pyrimidin-4-one (R)-2-((R)-3-Methylmorpholin-4-yl)-9-oxazol-4-ylmethyl-6-trifluoromethyl-6,7,8,9-tetrahydropyrimido[1,2-a]pyrimidin-4-one (S)-3-Fluoro-2-((R)-3-methylmorpholin-4-yl)-9-oxazol-5-ylmethyl-8-trifluoromethyl-6,7,8,9-tetrahydropyrimido[1,2-a]pyrimidin-4-one (R)-9-(2-Chloropyridin-4-ylmethyl)-2-((R)-3-methylmorpholin-4-yl)-6-trifluoromethyl-6,7,8,9-tetrahydropyrimido[1,2-a]pyrimidin-4-one (R)-9-(2-Hydroxy-2-methylpropyl)-2-((R)-3-methylmorpholin-4-yl)-6-trifluoromethyl-6,7,8,9-tetrahydropyrimido[1,2-a]pyrimidin-4-one (R)-9-(2-Isopropoxypyridin-4-yl)-2-((R)-3-methylmorpholin-4-yl)-6-trifluoromethyl-6,7,8,9-tetrahydropyrimido[1,2-a]pyrimidin-4-one (R)-9-(6-Chloropyridin-3-ylmethyl)-2-((R)-3-methylmorpholin-4-yl)-6-trifluoromethyl-6,7,8,9-tetrahydropyrimido[1,2-a]pyrimidin-4-one (R)-9-(6-Isopropoxypyridin-3-yl)-2-((R)-3-methylmorpholin-4-yl)-6-trifluoromethyl-6,7,8,9-tetrahydropyrimido[1,2-a]pyrimidin-4-one (R)-2-((R)-3-Methylmorpholin-4-yl)-9-oxazol-5-ylmethyl-6-trifluoromethyl-6,7,8,9-tetrahydropyrimido[1,2-a]pyrimidin-4-one (R)-9-(2-Cyclopropyl-2-oxoethyl)-2-((R)-3-methylmorpholin-4-yl)-6-trifluoromethyl-6,7,8,9-tetrahydropyrimido[1,2-a]pyrimidin-4-one (R)-3-Fluoro-9-(2-methoxypyridin-4-yl)-2-((R)-3-methylmorpholin-4-yl)-6-trifluoromethyl-6,7,8,9-tetrahydropyrimido[1,2-a]pyrimidin-4-one (R)-9-(2-Cyclopropyl-2-oxoethyl)-3-fluoro-2-((R)-3-methylmorpholin-4-yl)-6-trifluoromethyl-6,7,8,9-tetrahydropyrimido[1,2-a]pyrimidin-4-one (R)-9-(6-Difluoromethylpyridin-3-yl)-3-fluoro-2-((R)-3-methylmorpholin-4-yl)-6-trifluoromethyl-6,7,8,9-tetrahydropyrimido[1,2-a]pyrimidin-4-one (R)-9-(2-Chloropyridin-4-yl)-3-fluoro-2-((R)-3-methylmorpholin-4-yl)-6-trifluoromethyl-6,7,8,9-tetrahydropyrimido[1,2-a]pyrimidin-4-one (S)-2-((R)-3-Methylmorpholin-4-yl)-9-(5-methyl-[1,3,4]thiadiazol-2-ylmethyl)-8-trifluoromethyl-6,7,8,9-tetrahydropyrimido[1,2-a]pyrimidin-4-one (S)-9-(6-Difluoromethoxypyridin-3-yl)-2-((R)-3-methylmorpholin-4-yl)-8-trifluoromethyl-6,7,8,9-tetrahydropyrimido[1,2-a]pyrimidin-4-one (S)-2-((R)-3-Methylmorpholin-4-yl)-9-(4-methyl-[1,2,3]thiadiazol-5-ylmethyl)-8-trifluoromethyl-6,7,8,9-tetrahydropyrimido[1,2-a]pyrimidin-4-one (R)-3-Fluoro-2-((R)-3-methylmorpholin-4-yl)-9-(2-oxo-2-pyridin-3-ylethyl)-6-trifluoromethyl-6,7,8,9-tetrahydropyrimido[1,2-a]pyrimidin-4-one (R)-9-(6-Difluoromethoxypyridin-3-yl)-3-fluoro-2-((R)-3-methylmorpholin-4-yl)-6-trifluoromethyl-6,7,8,9-tetrahydropyrimido[1,2-a]pyrimidin-4-one (R)-3-Fluoro-2-((R)-3-methylmorpholin-4-yl)-9-(3-methyl-2-oxobutyl)-6-trifluoromethyl-6,7,8,9-tetrahydropyrimido[1,2-a]pyrimidin-4-one (R)-3-Fluoro-2-((R)-3-methylmorpholin-4-yl)-9-oxazol-2-ylmethyl-6-trifluoromethyl-6,7,8,9-tetrahydropyrimido[1,2-a]pyrimidin-4-one (R)-2-((R)-3-Methylmorpholin-4-yl)-9-(3-methyl-2-oxobutyl)-6-trifluoromethyl-6,7,8,9-tetrahydropyrimido[1,2-a]pyrimidin-4-one (R)-2-((R)-3-Methylmorpholin-4-yl)-9-[2-oxo-2-(tetrahydropyran-4-yl)ethyl]-6-trifluoromethyl-6,7,8,9-tetrahydropyrimido[1,2-a]pyrimidin-4-one (R)-3-Fluoro-2-((R)-3-methylmorpholin-4-yl)-9-[2-oxo-2-(tetrahydropyran-4-yl)ethyl]-6-trifluoromethyl-6,7,8,9-tetrahydropyrimido[1,2-a]pyrimidin-4-one (S)-2-((R)-3-Methylmorpholin-4-yl)-9-oxetan-3-ylmethyl-8-trifluoromethyl-6,7,8,9-tetrahydropyrimido[1,2-a]pyrimidin-4-one 9-(6-Difluoromethylpyridin-3-yl)-2-((R)-3-methylmorpholin-4-yl)-8-trifluoromethyl-6,7,8,9-tetrahydropyrimido[1,2-a]pyrimidin-4-one (R)-3-Fluoro-2-((R)-3-methylmorpholin-4-yl)-9-(2-oxo-2-pyridin-2-ylethyl)-6-trifluoromethyl-6,7,8,9-tetrahydropyrimido[1,2-a]pyrimidin-4-one (S)-2-((R)-3-Methylmorpholin-4-yl)-9-[1-(tetrahydrofuran-2-yl)methyl]-8-trifluoromethyl-6,7,8,9-tetrahydropyrimido[1,2-a]pyrimidin-4-one, single stereoisomer (S)-2-((R)-3-Methylmorpholin-4-yl)-9-[1-(tetrahydrofuran-2-yl)methyl]-8-trifluoromethyl-6,7,8,9-tetrahydropyrimido[1,2-a]pyrimidin-4-one, single stereoisomer (S)-2-((R)-3-Methylmorpholin-4-yl)-9-[1-(tetrahydropyran-2-yl)methyl]-8-trifluoromethyl-6,7,8,9-tetrahydropyrimido[1,2-a]pyrimidin-4-one, single stereoisomer (S)-2-((R)-3-Methylmorpholin-4-yl)-9-[1-(tetrahydropyran-2-yl)methyl]-8-trifluoromethyl-6,7,8,9-tetrahydropyrimido[1,2-a]pyrimidin-4-one, single stereoisomer (S)-2-((R)-3-Methylmorpholin-4-yl)-8-trifluoromethyl-9-(5-trifluoromethyl-[1,3,4]oxadiazol-2-ylmethyl)-6,7,8,9-tetrahydropyrimido[1,2-a]pyrimidin-4-one (R)-2-((R)-3-Methylmorpholin-4-yl)-9-(2-oxo-2-pyridin-3-ylethyl)-6-trifluoromethyl-6,7,8,9-tetrahydropyrimido[1,2-a]pyrimidin-4-one (S)-9-(5-Cyclopropyl-[1,3,4]oxadiazol-2-ylmethyl)-2-((R)-3-methylmorpholin-4-yl)-8-trifluoromethyl-6,7,8,9-tetrahydropyrimido[1,2-a]pyrimidin-4-one (R)-9-(3-Methylisoxazol-4-ylmethyl)-2-((R)-3-methylmorpholin-4-yl)-6-trifluoromethyl-6,7,8,9-tetrahydropyrimido[1,2-a]pyrimidin-4-one (R)-2-((R)-3-Methyl morpholin-4-yl)-6-trifluoromethyl-9-(3-trifluoromethyl-[1,2,4]oxadiazol-5-ylmethyl)-6,7,8,9-tetrahydropyrimido[1,2-a]pyrimidin-4-one (R)-2-((R)-3-Methylmorpholin-4-yl)-9-(2-oxopropyl)-6-trifluoromethyl-6,7,8,9-tetrahydropyrimido[1,2-a]pyrimidin-4-one (R)-3-Fluoro-9-(3-methyl isoxazol-4-ylmethyl)-2-((R)-3-methylmorpholin-4-yl)-6-trifluoromethyl-6,7,8,9-tetrahydropyrimido[1,2-a]pyrimidin-4-one (R)-9-(3-Cyclopropyl-[1,2,4]oxadiazol-5-ylmethyl)-3-fluoro-2-((R)-3-methylmorpholin-4-yl)-6-trifluoromethyl-6,7,8,9-tetrahydropyrimido[1,2-a]pyrimidin-4-one (R)-3-Fluoro-2-((R)-3-methylmorpholin-4-yl)-9-(2-oxopropyl)-6-trifluoromethyl-6,7,8,9-tetrahydropyrimido[1,2-a]pyrimidin-4-one (R)-3-Fluoro-2-((R)-3-methylmorpholin-4-yl)-9-(3-methyl-[1,2,4]oxadiazol-5-ylmethyl)-6-trifluoromethyl-6,7,8,9-tetrahydropyrimido[1,2-a]pyrimidin-4-one (S)-2-(3,3-Dimethylmorpholin-4-yl)-9-(2-oxo-2-phenylethyl)-8-trifluoromethyl-6,7,8,9-tetrahydropyrimido[1,2-a]pyrimidin-4-one (S)-9-(5-Chlorothiophen-2-ylmethyl)-2-((3S,5R)-3,5-dimethylmorpholin-4-yl)-8-trifluoromethyl-6,7,8,9-tetrahydropyrimido[1,2-a]pyrimidin-4-one
single stereoisomer.

(S)-9-(5-Chlorothiophen-2-ylmethyl)-2-((3S,5S)-3,5-dimethylmorpholin-4-yl)-8-trifluoromethyl-6,7,8,9-tetrahydropyrimido[1,2-a]pyrimidin-4-one (S)-2-((3S,5S)-3,5-Dimethylmorpholin-4-yl)-9-(2-oxo-2-phenylethyl)-8-trifluoromethyl-6,7,8,9-tetrahydropyrimido[1,2-a]pyrimidin-4-one (S)-9-(2-Difluoromethyl-2H-pyrazol-3-ylmethyl)-2-((3R,5R)-3,5-dimethylmorpholin-4-yl)-8-trifluoromethyl-6,7,8,9-tetrahydropyrimido[1,2-a]pyrimidin-4-one (S)-2-((3R,5R)-3,5-Dimethylmorpholin-4-yl)-9-(3-methylisoxazol-5-ylmethyl)-8-trifluoromethyl-6,7,8,9-tetrahydropyrimido[1,2-a]pyrimidin-4-one (S)-9-(6-Chloropyridin-3-ylmethyl)-2-((3R,5R)-3,5-dimethylmorpholin-4-yl)-8-trifluoromethyl-6,7,8,9-tetrahydropyrimido[1,2-a]pyrimidin-4-one (S)-9-(2-Chloropyridin-4-ylmethyl)-2-((3R,5R)-3,5-dimethylmorpholin-4-yl)-8-trifluoromethyl-6,7,8,9-tetrahydropyrimido[1,2-a]pyrimidin-4-one (S)-2-((3R,5R)-3,5-Dimethylmorpholin-4-yl)-9-oxazol-2-ylmethyl-8-trifluoromethyl-6,7,8,9-tetrahydropyrimido[1,2-a]pyrimidin-4-one (S)-9-(2-Chloropyridin-4-yl)-2-((3R,5R)-3,5-dimethylmorpholin-4-yl)-8-trifluoromethyl-6,7,8,9-tetrahydropyrimido[1,2-a]pyrimidin-4-one (S)-2-((3R,5R)-3,5-Dimethylmorpholin-4-yl)-9-pyridin-3-yl-8-trifluoromethyl-6,7,8,9-tetrahydropyrimido[1,2-a]pyrimidin-4-one (S)-9-(3,5-Difluorophenyl)-2-(8-oxa-3-aza-bicyclo[3.2.1]oct-3-yl)-8-trifluoromethyl-6,7,8,9-tetrahydropyrimido[1,2-a]pyrimidin-4-one (S)-9-(5-Chlorothiophen-2-ylmethyl)-2-(8-oxa-3-aza-bicyclo[3.2.1]oct-3-yl)-8-trifluoromethyl-6,7,8,9-tetrahydropyrimido[1,2-a]pyrimidin-4-one (S)-2-(8-Oxa-3-aza-bicyclo[3.2.1]oct-3-yl)-9-(2-oxo-2-phenylethyl)-8-trifluoromethyl-6,7,8,9-tetrahydropyrimido[1,2-a]pyrimidin-4-one (S)-9-Isoxazol-5-ylmethyl-2-(8-oxa-3-aza-bicyclo[3.2.1]oct-3-yl)-8-trifluoromethyl-6,7,8,9-tetrahydropyrimido[1,2-a]pyrimidin-4-one (S)-9-(2-Chlorothiazol-5-ylmethyl)-2-(8-oxa-3-aza-bicyclo[3.2.1]oct-3-yl)-8-trifluoromethyl-6,7,8,9-tetrahydropyrimido[1,2-a]pyrimidin-4-one (S)-9-(2-Difluoromethyl-2H-pyrazol-3-ylmethyl)-2-(8-oxa-3-aza-bicyclo[3.2.1]oct-3-yl)-8-trifluoromethyl-6,7,8,9-tetrahydropyrimido[1,2-a]pyrimidin-4-one (S)-9-(1-Difluoromethyl-1H-pyrazol-3-ylmethyl)-2-(8-oxa-3-aza-bicyclo[3.2.1]oct-3-yl)-8-trifluoromethyl-6,7,8,9-tetrahydropyrimido[1,2-a]pyrimidin-4-one (S)-9-(6-Chloropyridin-3-ylmethyl)-2-(8-oxa-3-aza-bicyclo[3.2.1]oct-3-yl)-8-trifluoromethyl-6,7,8,9-tetrahydropyrimido[1,2-a]pyrimidin-4-one (S)-9-Isoxazol-3-ylmethyl-2-(8-oxa-3-aza-bicyclo[3.2.1]oct-3-yl)-8-trifluoromethyl-6,7,8,9-tetrahydropyrimido[1,2-a]pyrimidin-4-one (S)-2-(8-Oxa-3-aza-bicyclo[3.2.1]oct-3-yl)-9-(2-oxo-2-pyridin-3-ylethyl)-8-trifluoromethyl-6,7,8,9-tetrahydropyrimido[1,2-a]pyrimidin-4-one (S)-2-(8-Oxa-3-aza-bicyclo[3.2.1]oct-3-yl)-9-(2-oxo-2-pyridin-2-ylethyl)-8-trifluoromethyl-6,7,8,9-tetrahydropyrimido[1,2-a]pyrimidin-4-one (S)-2-(2-Ethylmorpholin-4-yl)-9-(2-oxo-2-pyridin-2-ylethyl)-8-trifluoromethyl-6,7,8,9-tetrahydropyrimido[1,2-a]pyrimidin-4-one,
single stereoisomer (S)-2-(2-Ethylmorpholin-4-yl)-9-(2-oxo-2-pyridin-2-ylethyl)-8-trifluoromethyl-6,7,8,9-tetrahydropyrimido[1,2-a]pyrimidin-4-one, single stereoisomer (S)-2-(2-Methylmorpholin-4-yl)-9-(2-oxo-2-pyridin-2-ylethyl)-8-trifluoromethyl-6,7,8,9-tetrahydropyrimido[1,2-a]pyrimidin-4-one, single stereoisomer (S)-2-(2-Methylmorpholin-4-yl)-9-(2-oxo-2-pyridin-2-ylethyl)-8-trifluoromethyl-6,7,8,9-tetrahydropyrimido[1,2-a]pyrimidin-4-one, single stereoisomer (S)-9-(3,5-Difluorophenyl)-2-(3-hydroxymethylmorpholin-4-yl)-8-trifluoromethyl-6,7,8,9-tetrahydropyrimido[1,2-a]pyrimidin-4-one, single stereoisomer (S)-9-(5-Chlorothiophen-2-ylmethyl)-2-(3-hydroxymethylmorpholin-4-yl)-8-trifluoromethyl-6,7,8,9-tetrahydropyrimido[1,2-a]pyrimidin-4-one, single stereoisomer (S)-9-(5-Chlorothiophen-2-ylmethyl)-2-((S)-3-methylmorpholin-4-yl)-8-trifluoromethyl-6,7,8,9-tetrahydropyrimido[1,2-a]pyrimidin-4-one (S)-2-Methyl-7-((R)-3-Methylmorpholin-4-yl)-1-(2-oxo-2-pyridin-2-ylethyl)-2-trifluoromethyl-2,3-dihydro-1H-imidazo[1,2-a]pyrimidin-5-one (S)-2-Methyl-7-((R)-3-methylmorpholin-4-yl)-1-(2-oxo-2-pyridin-3-ylethyl)-2-trifluoromethyl-2,3-dihydro-1H-imidazo[1,2-a]pyrimidin-5-one (S)-1-(2-Chloropyridin-4-ylmethyl)-2-methyl-7-((R)-3-methylmorpholin-4-yl)-2-trifluoromethyl-2,3-dihydro-1H-imidazo[1,2-a]pyrimidin-5-one (S)-2-Methyl-7-((R)-3-methylmorpholin-4-yl)-1-oxazol-5-ylmethyl-2-trifluoromethyl-2,3-dihydro-1H-imidazo[1,2-a]pyrimidin-5-one (S)-2-Methyl-7-((R)-3-methylmorpholin-4-yl)-1-oxazol-4-ylmethyl-2-trifluoromethyl-2,3-dihydro-1H-imidazo[1,2-a]pyrimidin-5-one (S)-1-(2-Chloropyridin-4-ylmethyl)-6-fluoro-2-methyl-7-((R)-3-methyl morpholin-4-yl)-2-trifluoromethyl-2,3-dihydro-1H-imidazo[1,2-a]pyrimidin-5-one (S)-6-Fluoro-2-methyl-7-((R)-3-methylmorpholin-4-yl)-1-(3-methyl-2-oxobutyl)-2-trifluoromethyl-2,3-dihydro-1H-imidazo[1,2-a]pyrimidin-5-one (S)-6-Fluoro-2-methyl-7-((R)-3-methylmorpholin-4-yl)-1-[2-oxo-2-(tetrahydropyran-4-yl)ethyl]-2-trifluoromethyl-2,3-dihydro-1H-imidazo[1,2-a]pyrimidin-5-one (S)-1-(2-Cyclopropyl-2-oxoethyl)-6-fluoro-2-methyl-7-((R)-3-methylmorpholin-4-yl)-2-trifluoromethyl-2,3-dihydro-1H-imidazo[1,2-a]pyrimidin-5-one (S)-2-Methyl-7-((R)-3-methylmorpholin-4-yl)-1-(3-methyl-2-oxobutyl)-2-trifluoromethyl-2,3-dihydro-1H-imidazo[1,2-a]pyrimidin-5-one (S)-6-Fluoro-2-methyl-7-((R)-3-methylmorpholin-4-yl)-1-(2-oxo-2-pyridin-3-ylethyl)-2-trifluoromethyl-2,3-dihydro-1H-imidazo[1,2-a]pyrimidin-5-one (S)-2-Methyl-7-((R)-3-methylmorpholin-4-yl)-1-[2-oxo-2-(tetrahydropyran-4-yl)ethyl]-2-trifluoromethyl-2,3-dihydro-1H-imidazo[1,2-a]pyrimidin-5-one (S)-9-Benzyl-2-(2-methylmorpholin-4-yl)-8-trifluoromethyl-6,7,8,9-tetrahydropyrimido[1,2-a]pyrimidin-4-one, single stereoisomer (S)-9-Benzyl-2-(2-methylmorpholin-4-yl)-8-trifluoromethyl-6,7,8,9-tetrahydropyrimido[1,2-a]pyrimidin-4-one, single stereoisomer (S)-9-Benzyl-2-(2-fluoromethylmorpholin-4-yl)-8-trifluoromethyl-6,7,8,9-tetrahydropyrimido[1,2-a]pyrimidin-4-one (S)-9-Benzyl-2-(2-fluoromethylmorpholin-4-yl)-8-trifluoromethyl-6,7,8,9-tetrahydropyrimido[1,2-a]pyrimidin-4-one, single stereoisomer (S)-9-Benzyl-2-(2-fluoromethylmorpholin-4-yl)-8-trifluoromethyl-6,7,8,9-tetrahydropyrimido[1,2-a]pyrimidin-4-one, single stereoisomer N-Methoxy-N-methyl-2-[(S)-8-((R)-3-methylmorpholin-4-yl)-6-oxo-2-trifluoromethyl-3,4-dihydro-2H,6H-pyrimido[1,2-a]pyrimidin-1-yl]acetamide N-Methoxy-2-[(S)-8-((R)-3-methylmorpholin-4-yl)-6-oxo-2-trifluoromethyl-3,4-dihydro-2H,6H-pyrimido[1,2-a]pyrimidin-1-yl]acetamide (S)-2-((R)-3-methylmorpholin-4-yl)-9-pyridin-4-yl-8-trifluoromethyl-6,7,8,9-tetrahydropyrimido[1,2-a]pyrimidin-4-one (S)-6-Fluoro-2-methyl-7-((R)-3-methylmorpholin-4-yl)-1-(2-oxo-2-pyridin-2-ylethyl)-2-trifluoromethyl-2,3-dihydro-1H-imidazo[1,2-a]pyrimidin-5-one (S)-9-(2-Hydroxy-2-methylpropyl)-8-methyl-2-((R)-3-methylmorpholin-4-yl)-8-trifluoromethyl-6,7,8,9-tetrahydropyrimido[1,2-a]pyrimidin-4-one (S)-9-(5-Isopropyl-[1,2,4]oxadiazol-3-ylmethyl)-2-((R)-3-methylmorpholin-4-yl)-8-trifluoromethyl-6,7,8,9-tetrahydropyrimido[1,2-a]pyrimidin-4-one (S)-9-(5-Cyclopropyl-[1,2,4]oxadiazol-3-ylmethyl)-2-((R)-3-methyl morpholin-4-yl)-8-trifluoromethyl-6,7,8,9-tetrahydropyrimido[1,2-a]pyrimidin-4-one (S)-9-(5-tert-Butyl-[1,2,4]oxadiazol-3-ylmethyl)-2-((R)-3-methylmorpholin-4-yl)-8-trifluoromethyl-6,7,8,9-tetrahydropyrimido[1,2-a]pyrimidin-4-one (S)-3-Fluoro-9-(2-hydroxyethyl)-2-((R)-3-methylmorpholin-4-yl)-8-trifluoromethyl-6,7,8,9-tetrahydropyrimido[1,2-a]pyrimidin-4-one (S)-9-((S)-2-Hydroxypropyl)-2-((R)-3-methylmorpholin-4-yl)-8-trifluoromethyl-6,7,8,9-tetrahydropyrimido[1,2-a]pyrimidin-4-one (S)-9-((S)-2-Methoxy-2-phenylethyl)-2-(1R,5S)-8-oxa-3-aza-bicyclo[3.2.1]oct-3-yl-8-trifluoromethyl-6,7,8,9-tetrahydropyrimido[1,2-a]pyrimidin-4-one (S)-6-Fluoro-2-methyl-7-((R)-3-methylmorpholin-4-yl)-1-(3-methyl-[1,2,4]oxadiazol-5-ylmethyl)-2-trifluoromethyl-2,3-dihydro-1H-imidazo[1,2-a]pyrimidin-5-one (S)-2-Methyl-7-((R)-3-methylmorpholin-4-yl)-1-(3-methyl-[1,2,4]oxadiazol-5-ylmethyl)-2-trifluoromethyl-2,3-dihydro-1H-imidazo[1,2-a]pyrimidin-5-one (S)-9-(2-Hydroxy-2-pyridin-3-ylethyl)-2-((R)-3-methylmorpholin-4-yl)-8-trifluoromethyl-6,7,8,9-tetrahydropyrimido[1,2-a]pyrimidin-4-one, single stereoisomer (S)-9-(2-Hydroxy-2-pyridin-3-ylethyl)-2-((R)-3-methylmorpholin-4-yl)-8-trifluoromethyl-6,7,8,9-tetrahydropyrimido[1,2-a]pyrimidin-4-one, single stereoisomer (S)-8-Methyl-2-((R)-3-methylmorpholin-4-yl)-9-(5-methyl-[1,2,4]oxadiazol-3-ylmethyl)-8-trifluoromethyl-6,7,8,9-tetrahydropyrimido[1,2-a]pyrimidin-4-one (S)-9-(2-Hydroxy-2-pyridin-2-ylethyl)-2-((R)-3-methylmorpholin-4-yl)-8-trifluoromethyl-6,7,8,9-tetrahydropyrimido[1,2-a]pyrimidin-4-one, single stereoisomer (S)-9-(2-Hydroxy-2-pyridin-2-ylethyl)-2-((R)-3-methylmorpholin-4-yl)-8-trifluoromethyl-6,7,8,9-tetrahydropyrimido[1,2-a]pyrimidin-4-one (S)-9-(2-Difluoromethyl-2H-pyrazol-3-ylmethyl)-8-methyl-2-((R)-3-methylmorpholin-4-yl)-8-trifluoromethyl-6,7,8,9-tetrahydropyrimido[1,2-a]pyrimidin-4-one (S)-9-Isoxazol-3-ylmethyl-8-methyl-2-((R)-3-methylmorpholin-4-yl)-8-trifluoromethyl-6,7,8,9-tetrahydropyrimido[1,2-a]pyrimidin-4-one (S)-2-((R)-3-Methylmorpholin-4-yl)-9-pyridin-4-ylmethyl-8-trifluoromethyl-6,7,8,9-tetrahydropyrimido[1,2-a]pyrimidin-4-one (S)-2-((R)-3-Methylmorpholin-4-yl)-9-pyridin-3-ylmethyl-8-trifluoromethyl-6,7,8,9-tetrahydropyrimido[1,2-a]pyrimidin-4-one (S)-2-((R)-3-Methylmorpholin-4-yl)-9-pyridin-2-ylmethyl-8-trifluoromethyl-6,7,8,9-tetrahydropyrimido[1,2-a]pyrimidin-4-one (S)-9-[2-(4-Fluorophenyl)ethyl]-2-((R)-3-methylmorpholin-4-yl)-8-trifluoromethyl-6,7,8,9-tetrahydropyrimido[1,2-a]pyrimidin-4-one (S)-2-((R)-3-Methylmorpholin-4-yl)-9-(2-pyridin-2-ylethyl)-8-trifluoromethyl-6,7,8,9-tetrahydropyrimido[1,2-a]pyrimidin-4-one (S)-9-(2-Fluoropyridin-3-ylmethyl)-2-((R)-3-methylmorpholin-4-yl)-8-trifluoromethyl-6,7,8,9-tetrahydropyrimido[1,2-a]pyrimidin-4-one N,N-Dimethyl-2-[(S)-8-((R)-3-methylmorpholin-4-yl)-6-oxo-2-trifluoromethyl-3,4-dihydro-2H,6H-pyrimido[1,2-a]pyrimidin-1-yl]acetamide N-Methyl-2-[(S)-8-((R)-3-methylmorpholin-4-yl)-6-oxo-2-trifluoromethyl-3,4-dihydro-2H,6H-pyrimido[1,2-a]pyrimidin-1-yl]acetamide (S)-9-(6-Fluoropyridin-2-ylmethyl)-2-((R)-3-methylmorpholin-4-yl)-8-trifluoromethyl-6,7,8,9-tetrahydropyrimido[1,2-a]pyrimidin-4-one (S)-9-(2-Isopropoxypyridin-4-ylmethyl)-2-((R)-3-methylmorpholin-4-yl)-8-trifluoromethyl-6,7,8,9-tetrahydropyrimido[1,2-a]pyrimidin-4-one (S)-9-(3-Isopropyl-[1,2,4]oxadiazol-5-ylmethyl)-2-((R)-3-methylmorpholin-4-yl)-8-trifluoromethyl-6,7,8,9-tetrahydropyrimido[1,2-a]pyrimidin-4-one (S)-9-(3-Cyclopropyl-[1,2,4]oxadiazol-5-ylmethyl)-2-((R)-3-methylmorpholin-4-yl)-8-trifluoromethyl-6,7,8,9-tetrahydropyrimido[1,2-a]pyrimidin-4-one (S)-9-(3-tert-Butyl-[1,2,4]oxadiazol-5-ylmethyl)-2-((R)-3-methylmorpholin-4-yl)-8-trifluoromethyl-6,7,8,9-tetrahydropyrimido[1,2-a]pyrimidin-4-one (S)-9-(6-Isopropoxypyridin-3-ylmethyl)-2-((R)-3-methylmorpholin-4-yl)-8-trifluoromethyl-6,7,8,9-tetrahydropyrimido[1,2-a]pyrimidin-4-one (S)-9-(2-Isopropoxypyridin-3-ylmethyl)-2-((R)-3-methylmorpholin-4-yl)-8-trifluoromethyl-6,7,8,9-tetrahydropyrimido[1,2-a]pyrimidin-4-one (S)-2-((R)-3-Methylmorpholin-4-yl)-9-thiazol-2-ylmethyl-8-trifluoromethyl-6,7,8,9-tetrahydropyrimido[1,2-a]pyrimidin-4-one (S)-3-Fluoro-2-((R)-3-methylmorpholin-4-yl)-9-thiazol-2-ylmethyl-8-trifluoromethyl-6,7,8,9-tetrahydropyrimido[1,2-a]pyrimidin-4-one (S)-2-((R)-3-Methylmorpholin-4-yl)-9-(2-oxo-2-piperidin-1-ylethyl)-8-trifluoromethyl-6,7,8,9-tetrahydropyrimido[1,2-a]pyrimidin-4-one (S)-2-((R)-3-methylmorpholin-4-yl)-9-(2-morpholin-4-yl-2-oxoethyl)-8-trifluoromethyl-6,7,8,9-tetrahydropyrimido[1,2-a]pyrimidin-4-one (S)-3-Fluoro-2-((R)-3-methylmorpholin-4-yl)-9-(2-morpholin-4-yl-2-oxoethyl)-8-trifluoromethyl-6,7,8,9-tetrahydropyrimido[1,2-a]pyrimidin-4-one 2-[(S)-8-((R)-3-Methylmorpholin-4-yl)-6-oxo-2-trifluoromethyl-3,4-dihydro-2H,6H-pyrimido[1,2-a]pyrimidin-1-yl]-N-phenylacetamide (S)-3-Fluoro-2-((R)-3-methylmorpholin-4-yl)-9-(2-oxo-2-piperidin-1-ylethyl)-8-trifluoromethyl-6,7,8,9-tetrahydropyrimido[1,2-a]pyrimidin-4-one (S)-9-Acetyl-2-((R)-3-methylmorpholin-4-yl)-8-trifluoromethyl-6,7,8,9-tetrahydropyrimido[1,2-a]pyrimidin-4-one (S)-8-Methyl-2-((R)-3-methylmorpholin-4-yl)-9-oxazol-2-ylmethyl-8-trifluoromethyl-6,7,8,9-tetrahydropyrimido[1,2-a]pyrimidin-4-one (S)-2-Methyl-7-((R)-3-methylmorpholin-4-yl)-1-(5-methyl-[1,2,4]oxadiazol-3-ylmethyl)-2-trifluoromethyl-2,3-dihydro-1H-imidazo[1,2-a]pyrimidin-5-one (S)-9-(2-Cyclopropyl-2-oxoethyl)-2-((R)-3-methylmorpholin-4-yl)-8-trifluoromethyl-6,7,8,9-tetrahydropyrimido[1,2-a]pyrimidin-4-one (S)-2-((R)-3-Methylmorpholin-4-yl)-9-(2-oxo-2-thiazol-2-ylethyl)-8-trifluoromethyl-6,7,8,9-tetrahydropyrimido[1,2-a]pyrimidin-4-one

[(S)-8-((R)-3-Methylmorpholin-4-yl)-6-oxo-2-trifluoromethyl-3,4-dihydro-2H,6H-pyrimido[1,2-a]pyrimidin-1-yl] acetic acid cyclopentyl ester (S)-9-(2-Cyclopentyl-2-oxoethyl)-2-((R)-3-methylmorpholin-4-yl)-8-trifluoromethyl-6,7,8,9-tetrahydropyrimido[1,2-a]pyrimidin-4-one (S)-2-((R)-3-Methylmorpholin-4-yl)-9-[2-oxo-2-(tetrahydropyran-4-yl)ethyl]-8-trifluoromethyl-6,7,8,9-tetrahydropyrimido[1,2-a]pyrimidin-4-one (S)-3-Fluoro-9-(5-isopropyl-[1,2,4]oxadiazol-3-ylmethyl)-2-((R)-3-methylmorpholin-4-yl)-8-trifluoromethyl-6,7,8,9-tetrahydropyrimido[1,2-a]pyrimidin-4-one (S)-9-(5-Cyclopropyl-[1,2,4]oxadiazol-3-ylmethyl)-3-fluoro-2-((R)-3-methylmorpholin-4-yl)-8-trifluoromethyl-6,7,8,9-tetrahydropyrimido[1,2-a]pyrimidin-4-one (S)-3-Fluoro-9-(3-isopropyl-[1,2,4]oxadiazol-5-ylmethyl)-2-((R)-3-methylmorpholin-4-yl)-8-trifluoromethyl-6,7,8,9-tetrahydropyrimido[1,2-a]pyrimidin-4-one (S)-9-(3-Cyclopropyl-[1,2,4]oxadiazol-5-ylmethyl)-3-fluoro-2-((R)-3-methylmorpholin-4-yl)-8-trifluoromethyl-6,7,8,9-tetrahydropyrimido[1,2-a]pyrimidin-4-one (S)-9-(3-tert-Butyl-[1,2,4]oxadiazol-5-ylmethyl)-3-fluoro-2-((R)-3-methylmorpholin-4-yl)-8-trifluoromethyl-6,7,8,9-tetrahydropyrimido[1,2-a]pyrimidin-4-one (S)-3-Fluoro-2-((R)-3-methylmorpholin-4-yl)-8-trifluoromethyl-9-(3-trifluoromethyl-[1,2,4]oxadiazol-5-ylmethyl)-6,7,8,9-tetrahydropyrimido[1,2-a]pyrimidin-4-one (S)-8-Methyl-2-((R)-3-methylmorpholin-4-yl)-9-(3-methyl-2-oxobutyl)-8-trifluoromethyl-6,7,8,9-tetrahydropyrimido[1,2-a]pyrimidin-4-one (S)-9-[2-(1-Methylcyclopentyl)-2-oxoethyl]-2-((R)-3-methylmorpholin-4-yl)-8-trifluoromethyl-6,7,8,9-tetrahydropyrimido[1,2-a]pyrimidin-4-one

[(S)-8-((R)-3-Methylmorpholin-4-yl)-6-oxo-2-trifluoromethyl-3,4-dihydro-2H,6H-pyrimido[1,2-a]pyrimidin-1-yl] acetic acid isopropyl ester (S)-9-(3,3-Dimethyl-2-oxobutyl)-2-((R)-3-methylmorpholin-4-yl)-8-trifluoromethyl-6,7,8,9-tetrahydropyrimido[1,2-a]pyrimidin-4-one (S)-2-((R)-3-Methylmorpholin-4-yl)-9-(2-oxopropyl)-8-trifluoromethyl-6,7,8,9-tetrahydropyrimido[1,2-a]pyrimidin-4-one (S)-9-(2-Fluoropyridin-4-ylmethyl)-2-((R)-3-methylmorpholin-4-yl)-8-trifluoromethyl-6,7,8,9-tetrahydropyrimido[1,2-a]pyrimidin-4-one (S)-9-(2-Cyclohexyl-2-oxoethyl)-2-((R)-3-methylmorpholin-4-yl)-8-trifluoromethyl-6,7,8,9-tetrahydropyrimido[1,2-a]pyrimidin-4-one (S)-2-((R)-3-Methylmorpholin-4-yl)-9-pyridazin-4-ylmethyl-8-trifluoromethyl-6,7,8,9-tetrahydropyrimido[1,2-a]pyrimidin-4-one

[(S)-8-((R)-3-Methylmorpholin-4-yl)-6-oxo-2-trifluoromethyl-3,4-dihydro-2H,6H-pyrimido[1,2-a]pyrimidin-1-yl] acetic acid tert-butyl ester 2-{2-[(S)-8-((R)-3-Methylmorpholin-4-yl)-6-oxo-2-trifluoromethyl-3,4-dihydro-2H,6H-pyrimido[1,2-a]pyrimidin-1-yl]acetyl}pyrrolidine-1-carboxylic acid tert-butyl ester

[(S)-8-((R)-3-Methylmorpholin-4-yl)-6-oxo-2-trifluoromethyl-3,4-dihydro-2H,6H-pyrimido[1,2-a]pyrimidin-1-yl] acetic acid methyl ester 2-[(S)-8-((R)-3-Methylmorpholin-4-yl)-6-oxo-2-trifluoromethyl-3,4-dihydro-2H,6H-pyrimido[1,2-a]pyrimidin-1-yl] acetamide (S)-2-((R)-3-Methylmorpholin-4-yl)-9-(4H-[1,2,4]triazol-3-ylmethyl)-8-trifluoromethyl-6,7,8,9-tetrahydropyrimido[1,2-a]pyrimidin-4-one (S)-2-((R)-3-Methylmorpholin-4-yl)-9-(2-oxo-2-piperidin-4-ylethyl)-8-trifluoromethyl-6,7,8,9-tetrahydropyrimido[1,2-a]pyrimidin-4-one (S)-9-(3-Methylbut-2-enyl)-2-((R)-3-methylmorpholin-4-yl)-8-trifluoromethyl-6,7,8,9-tetrahydropyrimido[1,2-a]pyrimidin-4-one (S)-9-(3-Fluoro-3-methylbutyl)-2-((R)-3-methylmorpholin-4-yl)-8-trifluoromethyl-6,7,8,9-tetrahydropyrimido[1,2-a]pyrimidin-4-one (S)-9-[2-(3-Methylisoxazol-4-yl)-2-oxoethyl]-2-((R)-3-methylmorpholin-4-yl)-8-trifluoromethyl-6,7,8,9-tetrahydropyrimido[1,2-a]pyrimidin-4-one (S)-2-((R)-3-Methylmorpholin-4-yl)-9-[2-oxo-2-(tetrahydrofuran-3-yl)ethyl]-8-trifluoromethyl-6,7,8,9-tetrahydropyrimido[1,2-a]pyrimidin-4-one (S)-9-(5-Methyl-[1,2,4]oxadiazol-3-ylmethyl)-2-(8-oxa-3-aza-bicyclo[3.2.1]oct-3-yl)-8-trifluoromethyl-6,7,8,9-tetrahydropyrimido[1,2-a]pyrimidin-4-one (S)-9-(2-Cyclopropyl-2-oxoethyl)-2-(8-oxa-3-aza-bicyclo[3.2.1]oct-3-yl)-8-trifluoromethyl-6,7,8,9-tetrahydropyrimido[1,2-a]pyrimidin-4-one (S)-9-(3-Methyl-2-oxobutyl)-2-(8-oxa-3-aza-bicyclo[3.2.1]oct-3-yl)-8-trifluoromethyl-6,7,8,9-tetrahydropyrimido[1,2-a]pyrimidin-4-one (S)-9-(2-Cyclopropyl-2-oxoethyl)-3-fluoro-2-(8-oxa-3-aza-bicyclo[3.2.1]oct-3-yl)-8-trifluoromethyl-6,7,8,9-tetrahydropyrimido[1,2-a]pyrimidin-4-one (S)-3-Fluoro-9-(3-methyl-2-oxobutyl)-2-(8-oxa-3-aza-bicyclo[3.2.1]oct-3-yl)-8-trifluoromethyl-6,7,8,9-tetrahydropyrimido[1,2-a]pyrimidin-4-one (S)-3-Fluoro-9-(5-methyl-[1,2,4]oxadiazol-3-ylmethyl)-2-(8-oxa-3-aza-bicyclo[3.2.1]oct-3-yl)-8-trifluoromethyl-6,7,8,9-tetrahydropyrimido[1,2-a]pyrimidin-4-one (S)-2-((R)-3-Methylmorpholin-4-yl)-9-(4-methyl-2-oxopentyl)-8-trifluoromethyl-6,7,8,9-tetrahydropyrimido[1,2-a]pyrimidin-4-one (S)-2-((S)-3-Methylmorpholin-4-yl)-9-(3-methyl-2-oxobutyl)-8-trifluoromethyl-6,7,8,9-tetrahydropyrimido[1,2-a]pyrimidin-4-one (S)-3-Fluoro-2-((S)-3-methylmorpholin-4-yl)-9-(3-methyl-2-oxobutyl)-8-trifluoromethyl-6,7,8,9-tetrahydropyrimido[1,2-a]pyrimidin-4-one (S)-3-Fluoro-2-((R)-3-methylmorpholin-4-yl)-9-(5-methyl-2-oxohexyl)-8-trifluoromethyl-6,7,8,9-tetrahydropyrimido[1,2-a]pyrimidin-4-one (S)-3-Fluoro-2-((R)-3-methylmorpholin-4-yl)-9-(4-methyl-2-oxopentyl)-8-trifluoromethyl-6,7,8,9-tetrahydropyrimido[1,2-a]pyrimidin-4-one (S)-9-(3-Ethyl-2-oxopentyl)-2-((R)-3-methylmorpholin-4-yl)-8-trifluoromethyl-6,7,8,9-tetrahydropyrimido[1,2-a]pyrimidin-4-one (S)-9-(3-Ethyl-2-oxopentyl)-3-fluoro-2-((R)-3-methylmorpholin-4-yl)-8-trifluoromethyl-6,7,8,9-tetrahydropyrimido[1,2-a]pyrimidin-4-one

[(S)-7-Fluoro-8-((R)-3-methylmorpholin-4-yl)-6-oxo-2-trifluoromethyl-3,4-dihydro-2H,6H-pyrimido[1,2-a]pyrimidin-1-yl]acetic acid methyl ester (S)-9-sec-Butyl-2-((R)-3-methylmorpholin-4-yl)-8-trifluoromethyl-6,7,8,9-tetrahydropyrimido[1,2-a]pyrimidin-4-one, single stereoisomer (S)-9-sec-Butyl-2-((R)-3-methylmorpholin-4-yl)-8-trifluoromethyl-6,7,8,9-tetrahydropyrimido[1,2-a]pyrimidin-4-one, single stereoisomer (S)-9-(2-Hydroxy-3-methylbutyl)-2-((R)-3-methylmorpholin-4-yl)-8-trifluoromethyl-6,7,8,9-tetrahydropyrimido[1,2-a]pyrimidin-4-one (S)-9-(2-Hydroxy-3-methylbutyl)-2-((R)-3-methylmorpholin-4-yl)-8-trifluoromethyl-6,7,8,9-tetrahydropyrimido[1,2-a]pyrimidin-4-one (S)-9-(2-Methoxy-3-methylbutyl)-2-((R)-3-methylmorpholin-4-yl)-8-trifluoromethyl-6,7,8,9-tetrahydropyrimido[1,2-a]pyrimidin-4-one, single stereoisomer (S)-9-(2-Methoxy-3-methylbutyl)-2-((R)-3-methylmorpholin-4-yl)-8-trifluoromethyl-6,7,8,9-tetrahydropyrimido[1,2-a]pyrimidin-4-one single stereoisomer (S)-2-((R)-3-Methylmorpholin-4-yl)-9-(5-methyl-2-oxohexyl)-8-trifluoromethyl-6,7,8,9-tetrahydropyrimido[1,2-a]pyrimidin-4-one (S)-2-((R)-3-Methylmorpholin-4-yl)-9-(3-methyl-2-oxopentyl)-8-trifluoromethyl-6,7,8,9-tetrahydropyrimido[1,2-a]pyrimidin-4-one (S)-2-((R)-3-Methylmorpholin-4-yl)-8-trifluoromethyl-9-(3-trifluoromethyl-[1,2,4]oxadiazol-5-ylmethyl)-6,7,8,9-tetrahydropyrimido[1,2-a]pyrimidin-4-one (S)-3-Fluoro-2-((R)-3-methylmorpholin-4-yl)-9-[2-(2-oxa-6-azaspiro[3.3]hept-6-yl)-2-oxoethyl]-8-trifluoromethyl-6,7,8,9-tetrahydropyrimido[1,2-a]pyrimidin-4-one (S)-3-Fluoro-9-[2-(5-methylisoxazol-3-yl)-2-oxoethyl]-2-((R)-3-methylmorpholin-4-yl)-8-trifluoromethyl-6,7,8,9-tetrahydropyrimido[1,2-a]pyrimidin-4-one (S)-9-(2-Fluoro-2-phenylethyl)-2-((R)-3-methylmorpholin-4-yl)-8-trifluoromethyl-6,7,8,9-tetrahydropyrimido[1,2-a]pyrimidin-4-one (S)-3-Fluoro-9-isoxazol-3-ylmethyl-2-((R)-3-methylmorpholin-4-yl)-8-trifluoromethyl-6,7,8,9-tetrahydropyrimido[1,2-a]pyrimidin-4-one (S)-9-(2-Difluoromethyl-2H-pyrazol-3-ylmethyl)-3-fluoro-2-((R)-3-methylmorpholin-4-yl)-8-trifluoromethyl-6,7,8,9-tetrahydropyrimido[1,2-a]pyrimidin-4-one 9-Isoxazol-3-ylmethyl-8,8-dimethyl-2-((R)-3-methylmorpholin-4-yl)-6,7,8,9-tetrahydropyrimido[1,2-a]pyrimidin-4-one (S)-3-Fluoro-9-(3-methylisoxazol-5-ylmethyl)-2-((R)-3-methylmorpholin-4-yl)-8-trifluoromethyl-6,7,8,9-tetrahydropyrimido[1,2-a]pyrimidin-4-one (S)-9-(2-Isopropoxyethyl)-2-((R)-3-methylmorpholin-4-yl)-8-trifluoromethyl-6,7,8,9-tetrahydropyrimido[1,2-a]pyrimidin-4-one (S)-2-((R)-3-Methylmorpholin-4-yl)-9-pyridin-3-yl-8-trifluoromethyl-6,7,8,9-tetrahydropyrimido[1,2-a]pyrimidin-4-one (S)-9-(6-Cyclopropylpyridin-3-yl)-2-((R)-3-methylmorpholin-4-yl)-8-trifluoromethyl-6,7,8,9-tetrahydropyrimido[1,2-a]pyrimidin-4-one (S)-2-((R)-3-Methylmorpholin-4-yl)-9-{2-[2-((R)-3-methylmorpholin-4-yl)-pyridin-4-yl]-2-oxoethyl}-8-trifluoromethyl-6,7,8,9-tetrahydropyrimido[1,2-a]pyrimidin-4-one (S)-9-{2-Cyclopropyl-2-[(Z)-hydroxyimino]ethyl}-2-((R)-3-methylmorpholin-4-yl)-8-trifluoromethyl-6,7,8,9-tetrahydropyrimido[1,2-a]pyrimidin-4-one, isomer 1 of undetermined configuration Z or E (S)-9-{2-Cyclopropyl-2-[(E)-hydroxyimino]ethyl}-2-((R)-3-methylmorpholin-4-yl)-8-trifluoromethyl-6,7,8,9-tetrahydropyrimido[1,2-a]pyrimidin-4-one, isomer 2 of undetermined configuration Z or E (S)-9-{2-Cyclopropyl-2-[(E)-methoxyimino]ethyl}-2-((R)-3-methylmorpholin-4-yl)-8-trifluoromethyl-6,7,8,9-tetrahydropyrimido[1,2-a]pyrimidin-4-one, isomer 1 of undetermined configuration Z or E (S)-9-{2-Cyclopropyl-2-[(Z)-methoxyimino]ethyl}-2-((R)-3-methylmorpholin-4-yl)-8-trifluoromethyl-6,7,8,9-tetrahydropyrimido[1,2-a]pyrimidin-4-one, isomer 2 of undetermined configuration Z or E (S)-9-(2-Cyclopropyloxetan-2-ylmethyl)-2-((R)-3-methylmorpholin-4-yl)-8-trifluoromethyl-6,7,8,9-tetrahydropyrimido[1,2-a]pyrimidin-4-one, diastereoisomer 1 of undetermined absolute configuration on the asymmetric carbon of the side chain (S)-9-(2-Cyclopropyloxetan-2-ylmethyl)-2-((R)-3-methylmorpholin-4-yl)-8-trifluoromethyl-6,7,8,9-tetrahydropyrimido[1,2-a]pyrimidin-4-one, diastereoisomer 2 of undetermined absolute configuration on the asymmetric carbon of the side chain (S)-2-((R)-3-Methylmorpholin-4-yl)-9-[2-(4-methyltetrahydropyran-4-yl)-2-oxoethyl]-8-trifluoromethyl-6,7,8,9-tetrahydropyrimido[1,2-a]pyrimidin-4-one (S)-9-[2-(5-Methylisoxazol-3-yl)-2-oxoethyl]-2-((R)-3-methylmorpholin-4-yl)-8-trifluoromethyl-6,7,8,9-tetrahydropyrimido[1,2-a]pyrimidin-4-one (S)-9-(2-Chlorothiazol-5-ylmethyl)-2-((3R,5R)-3,5-dimethylmorpholin-4-yl)-8-trifluoromethyl-6,7,8,9-tetrahydropyrimido[1,2-a]pyrimidin-4-one (S)-2-((3R,5R)-3,5-Dimethylmorpholin-4-yl)-9-isoxazol-3-ylmethyl-8-trifluoromethyl-6,7,8,9-tetrahydropyrimido[1,2-a]pyrimidin-4-one (S)-3-Fluoro-9-(2-isoxazolidin-2-yl-2-oxoethyl)-2-((R)-3-methylmorpholin-4-yl)-8-trifluoromethyl-6,7,8,9-tetrahydropyrimido[1,2-a]pyrimidin-4-one (S)-9-(2-Hydroxyethyl)-2-((R)-3-methylmorpholin-4-yl)-8-trifluoromethyl-6,7,8,9-tetrahydropyrimido[1,2-a]pyrimidin-4-one (S)-3-Fluoro-2-((R)-3-methylmorpholin-4-yl)-9-[2-(6-oxa-1-azaspiro[3.3]hept-1-yl)-2-oxoethyl]-8-trifluoromethyl-6,7,8,9-tetrahydropyrimido[1,2-a]pyrimidin-4-one (S)-3-Fluoro-2-((R)-3-methylmorpholin-4-yl)-9-(2-[1,2]oxazinan-2-yl-2-oxoethyl)-8-trifluoromethyl-6,7,8,9-tetrahydropyrimido[1,2-a]pyrimidin-4-one (S)-2-((R)-3-Methylmorpholin-4-yl)-9-(2-[1,2]oxazinan-2-yl-2-oxoethyl)-8-trifluoromethyl-6,7,8,9-tetrahydropyrimido[1,2-a]pyrimidin-4-one (S)-9-(2-Isoxazolidin-2-yl-2-oxoethyl)-2-((R)-3-methylmorpholin-4-yl)-8-trifluoromethyl-6,7,8,9-tetrahydropyrimido[1,2-a]pyrimidin-4-one (S)-2-(2-Methylmorpholin-4-yl)-9-(3-methyl-2-oxobutyl)-8-trifluoromethyl-6,7,8,9-tetrahydropyrimido[1,2-a]pyrimidin-4-one, diastereoisomer 1 of undetermined absolute configuration on the asymmetric carbon of the morpholine (S)-9-(2-Cyclopropyl-2-oxoethyl)-3-fluoro-2-((S)-3-methylmorpholin-4-yl)-8-trifluoromethyl-6,7,8,9-tetrahydropyrimido[1,2-a]pyrimidin-4-one (S)-9-(2-Cyclopropyl-2-oxoethyl)-3-fluoro-2-(2-methylmorpholin-4-yl)-8-trifluoromethyl-6,7,8,9-tetrahydropyrimido[1,2-a]pyrimidin-4-one, diastereoisomer 1 of undetermined absolute configuration on the asymmetric carbon of the morpholine (S)-9-(2-Fluoro-3-methylbutyl)-2-((R)-3-methylmorpholin-4-yl)-8-trifluoromethyl-6,7,8,9-tetrahydropyrimido[1,2-a]pyrimidin-4-one, diastereoisomer 1 of undetermined absolute configuration on the asymmetric carbon of the 2-fluoro-3-methylbutyl chain (S)-9-(2-Fluoro-3-methylbutyl)-2-((R)-3-methylmorpholin-4-yl)-8-trifluoromethyl-6,7,8,9-tetrahydropyrimido[1,2-a]pyrimidin-4-one, diastereoisomer 2 of undetermined absolute configuration on the asymmetric carbon of the 2-fluoro-3-methylbutyl chain (S)-9-(2-Cyclopropyl-2-fluoroethyl)-2-((R)-3-methylmorpholin-4-yl)-8-trifluoromethyl-6,7,8,9-tetrahydropyrimido[1,2-a]pyrimidin-4-one, diastereoisomer 1 of undetermined absolute configuration on the asymmetric carbon of the 2-cyclopropyl-2-fluoroethyl chain (S)-9-(2-Cyclopropyl-2-fluoroethyl)-2-((R)-3-methylmorpholin-4-yl)-8-trifluoromethyl-6,7,8,9-tetrahydropyrimido[1,2-a]pyrimidin-4-one, diastereoisomer 2 of undetermined absolute configuration on the asymmetric carbon of the 2-cyclopropyl-2-fluoroethyl chain (S)-8-Methyl-2-((R)-3-methylmorpholin-4-yl)-9-(2-oxopropyl)-8-trifluoromethyl-6,7,8,9-tetrahydropyrimido[1,2-a]pyrimidin-4-one (S)-3-Fluoro-9-(2-fluoro-3-methylbutyl)-2-((R)-3-methylmorpholin-4-yl)-8-trifluoromethyl-6,7,8,9-tetrahydropyrimido[1,2-a]pyrimidin-4-one, diastereoisomer 1 of undetermined absolute configuration on the asymmetric carbon of the 2-fluoro-3-methylbutyl chain (S)-3-Fluoro-9-(2-fluoro-3-methylbutyl)-2-((R)-3-methylmorpholin-4-yl)-8-trifluoromethyl-6,7,8,9-tetrahydropyrimido[1,2-a]pyrimidin-4-one, diastereoisomer 2 of undetermined absolute configuration on the asymmetric carbon of the 2-fluoro-3-methylbutyl chain (S)-2-((R)-3-Methylmorpholin-4-yl)-9-[2-(1-oxa-6-azaspiro[3.3]hept-6-yl)-2-oxoethyl]-8-trifluoromethyl-6,7,8,9-tetrahydropyrimido[1,2-a]pyrimidin-4-one (S)-9-(2-Cyclopropyl-2-fluoroethyl)-3-fluoro-2-((R)-3-methylmorpholin-4-yl)-8-trifluoromethyl-6,7,8,9-tetrahydropyrimido[1,2-a]pyrimidin-4-one, diastereoisomer 1 of undetermined absolute configuration on the asymmetric carbon of the 2-cyclopropyl-2-fluoroethyl chain (S)-9-(2-Cyclopropyl-2-fluoroethyl)-3-fluoro-2-((R)-3-methylmorpholin-4-yl)-8-trifluoromethyl-6,7,8,9-tetrahydropyrimido[1,2-a]pyrimidin-4-one, diastereoisomer 2 of undetermined absolute configuration on the asymmetric carbon of the 2-cyclopropyl-2-fluoroethyl chain (S)-3-Fluoro-2-((R)-3-methylmorpholin-4-yl)-9-[2-(1-oxa-6-azaspiro[3.3]hept-6-yl)-2-oxoethyl]-8-trifluoromethyl-6,7,8,9-tetrahydropyrimido[1,2-a]pyrimidin-4-one and also the addition salts with inorganic and organic acids or with inorganic and organic bases of said products of formula (I).

A subject of the present invention is also any process for preparing the products of formula (I) as defined above.

The products according to the invention can be prepared using conventional organic chemistry methods.

A subject of the present invention is thus in particular a process for synthesis of the products of formula (I) as defined above, described in scheme 1 or scheme 2.

Preparation of compounds of formula (I)

The products of formula (I) according to the present invention, as defined above, can be prepared according to the usual methods known to those skilled in the art, and in particular according to the process described in scheme 1 below.

Scheme 1 below illustrates the methods used for preparing the products of formula (I). In this respect, they could not constitute a limitation of the scope of the invention, with regard to the methods for preparing the compounds claimed.

A subject of the present invention is thus also the process for preparing products of formula (I) according to scheme 1 as defined hereinafter.

A subject of the present invention is thus also the process for preparing products of formula (I) according to scheme 2 as defined hereinafter.

The products of formula (I) as defined above according to the present invention can thus in particular be prepared according to the process described in scheme 3 as defined hereinafter.

Scheme 1:

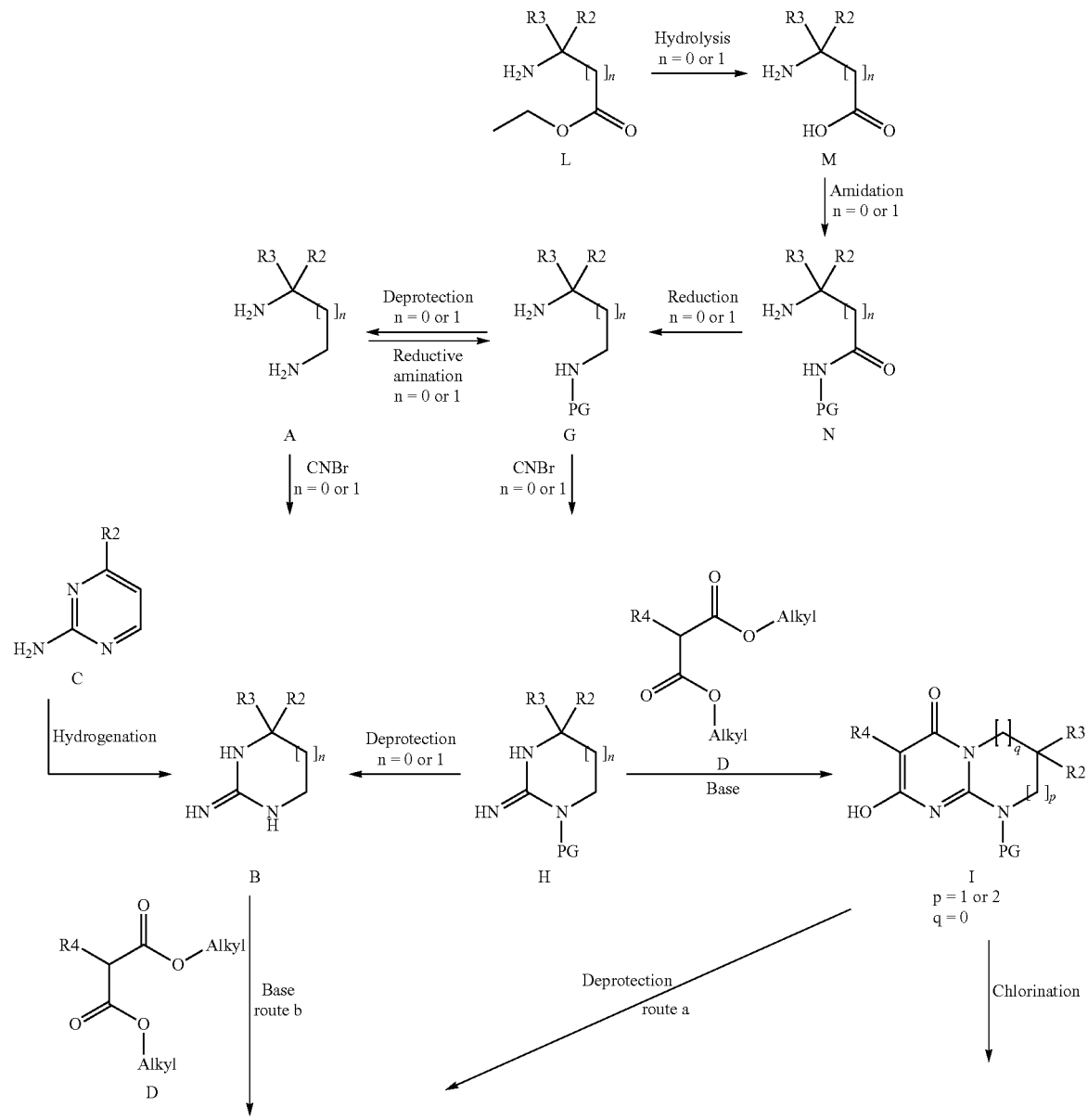

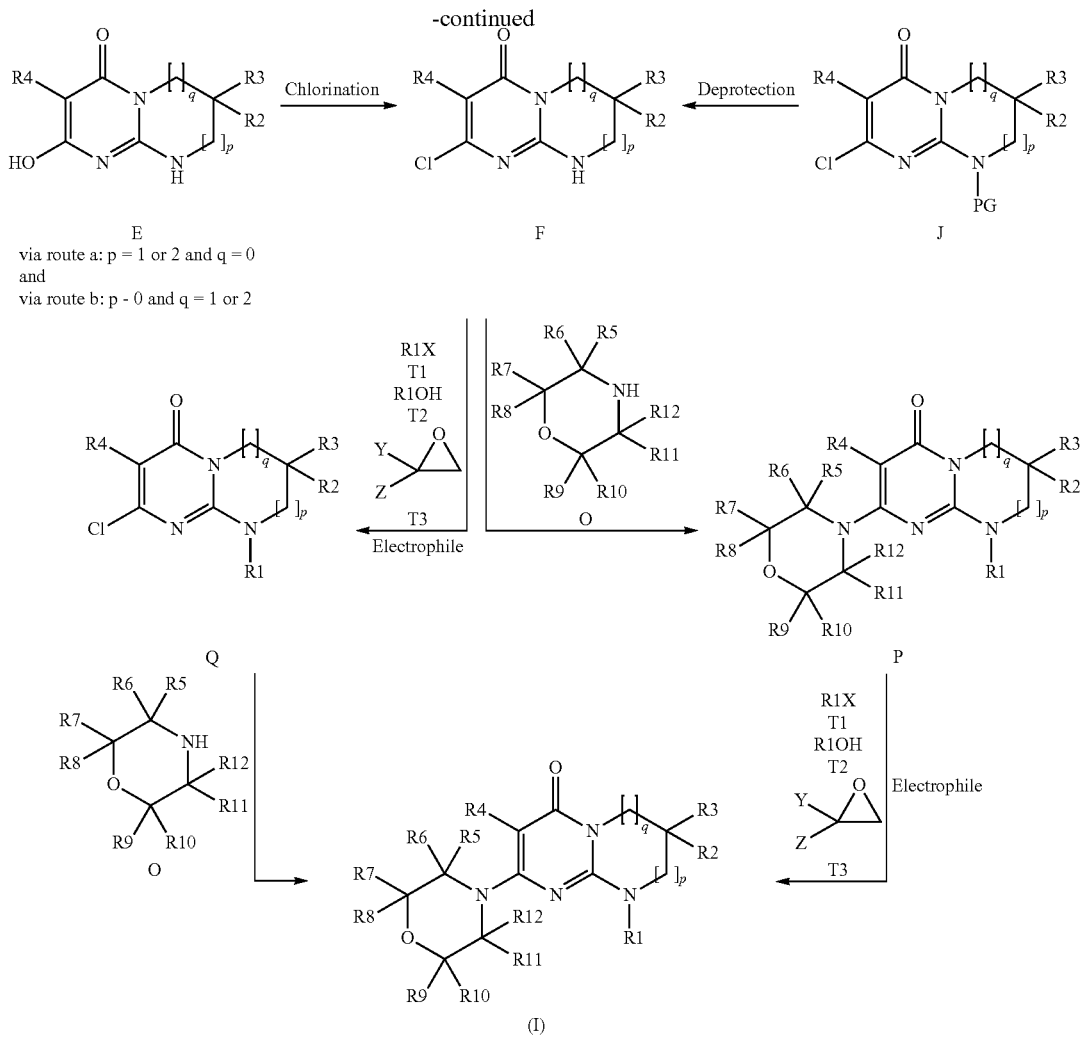
in which the substituents n, p, q, PG, R1, R2, R3, R4, R5, R6, R7, R8, R9, R10, R11, R12 and alkyl have the meanings indicated above for the products of formula (I).
In particular, when n=1, the intermediate L can be prepared according to the following scheme under the conditions indicated hereinafter:
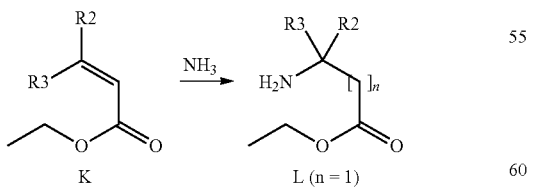
in which the substituents R2 and R3 have the meanings indicated above for the products of formula (I).

Scheme 2:
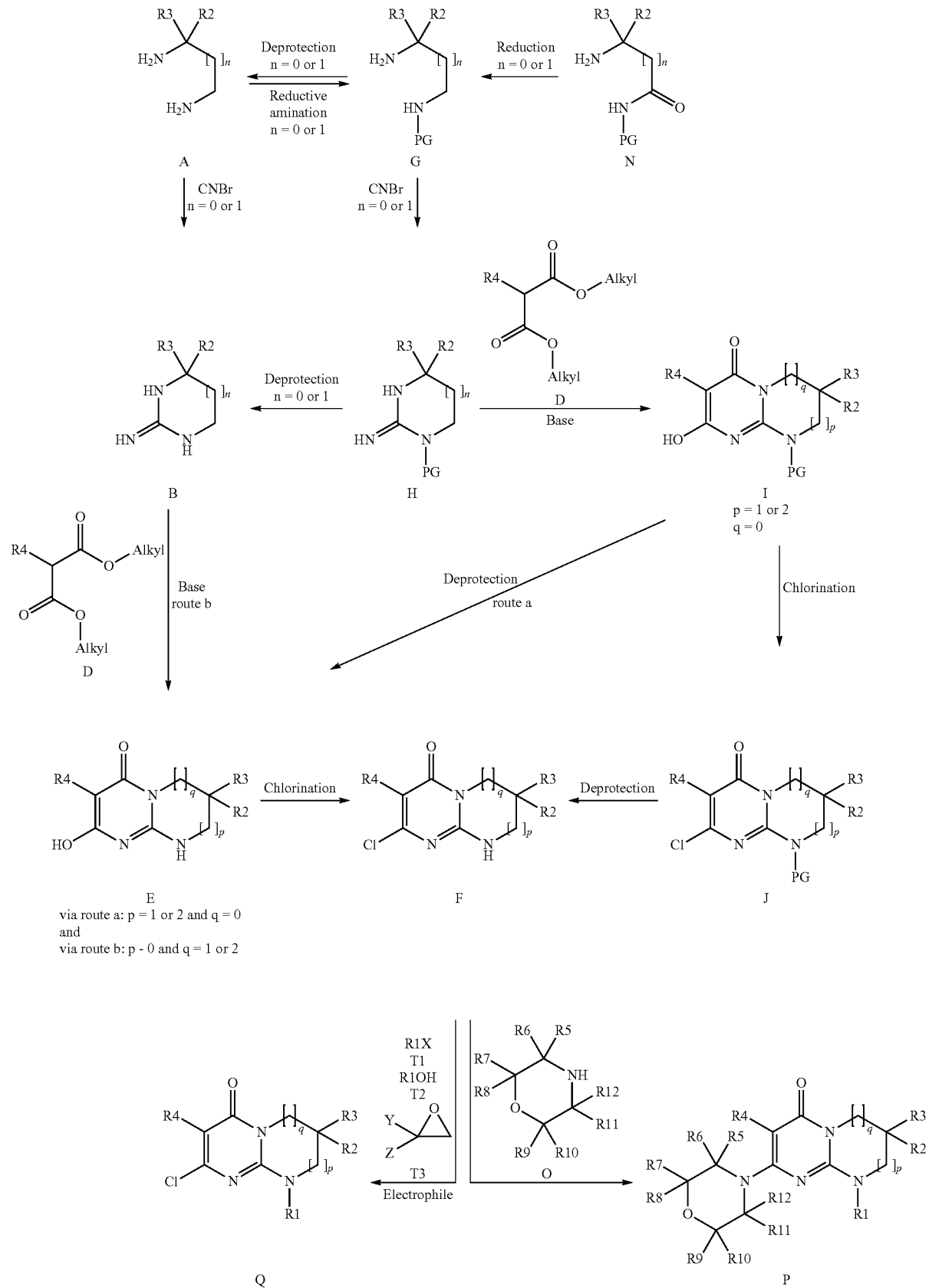

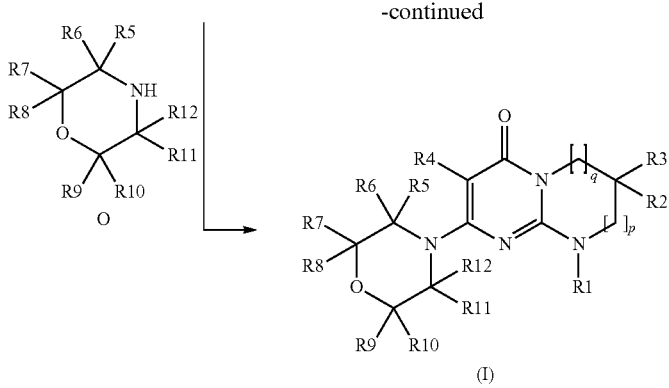
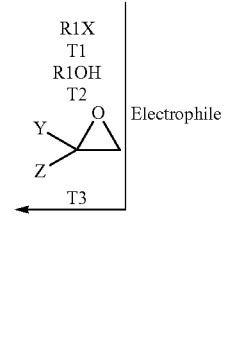

(I)

in which the substituents n, p, q, PG, R1, R2, R3, R4, R5, R6, R7, R8, R9, R10, R11, R12 and alkyl have the meanings indicated above for the products of formula (I).

Scheme 3:

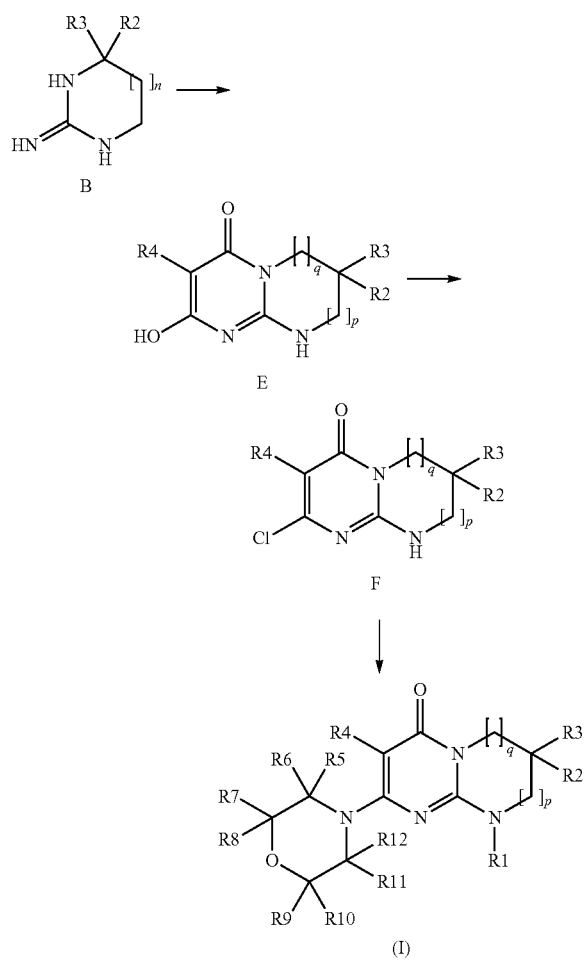

in which the substituents n, p, q, R1, R2, R3, R4, R5, R6, R7, R8, R9, R10, R11 and R12 have the meanings indicated above for the products of formula (I).

In schemes 1, 2 and 3 as defined above, the procedure can be carried out according to the usual methods known to those skilled in the art and in particular according to the conditions described hereinafter.

The diamines A are either commercially available, or prepared, in the achiral, chiral or racemic version, according to the methods known to those skilled in the art, such as, in particular, by analogy and homologation with the process described by Brigaud, T. et al. in J. Org. Chem. 2006, 71(18), 7075-7078, for the values of n, R2 and R3 as defined above.

Alternatively, the diamines A can be obtained according to the methods known to those skilled in the art, such as in particular from the amino esters L (alpha-amino esters n=0, or beta-amino esters n=1), which are either commercially available or prepared respectively as described, for example, by Robert M. Williams in Synthesis of Optically Active α-Amino Acids from Pergamon Press or, for example (n=1), by 1,4 Michael addition of an amine such as aqueous ammonia, for example, on the corresponding acrylates K as described, for example, by P. Perlmutter in Tetrahedron Organic Chemistry Series Volume 9 Conjugate Addition Reactions in Organic Synthesis from Pergamon Press, by stringing together the conventional sequences of hydrolysis of the ester function L to give the acid M, followed by an N amidation in the presence of an amine such as, for example, benzylamine, para-methoxybenzylamine, dimethoxybenzylamine or 4-methoxyphenylethylamine, followed by reduction of the amide function N to give the amine G in the presence, for example, of lithium aluminum tetrahydride, then by deprotection of the amine G, if necessary, given that all of the sequences can be carried out by conventional methods as described, for example, by Larock, Richard, C. et al. in Comprehensive Organic Transformations A Guide to Functional Group Preparations from VCH and by Theodora W. Greene and Peter G. M. Wuts in Protective Groups in Organic Synthesis Third Edition from Wiley-Interscience, for the values of R2, R3, PG and n as defined above.

Alternatively, the diamines G can be obtained in particular by means of a reductive amination reaction of the commercially available diamines A via a conventional method as described, for example, by Larock, Richard, C. et al. in Comprehensive Organic Transformations A Guide to Functional Group Preparations from VCH and by Theodora W. Greene and Peter G. M. Wuts in Protective Groups in Organic Synthesis Third Edition from Wiley-Interscience, for the values of R2, R3, PG and n as defined above.

The guanidines B (n=1) are either commercially available or prepared from C according to the methods known to those skilled in the art, such as, in particular, according to the processes described in Lochead, A. W. et al. (EP1460076 2002), Lochead, A. W. et al. (EP1340761 2003), Lochead, A.

W. et al. (EP1454909 2004), Lochead, A. W. et al. (WO2005/058908 2005), and Bacque, Eric et al. (WO2011001112A1 and WO2011001113A2) or by analogy with this same reference in the other cases, for the values of n, R2 and R3 as defined above.

The guanidines B can be obtained in particular by reacting a diamine A and cyanogen bromide in a solvent such as water or acetonitrile, at a temperature between 0° C. and the boiling point of the solvent, according to the conditions described, for example, by Gallet, T. et al. (EP1340761 2003) and Bacque, Eric et al. (WO2011001112A1 and WO2011001113A2), for the values of n, R2 and R3 as defined above.

Alternatively, the guanidines B can be obtained by deprotection of the guanidines H according to the conventional methods known to those skilled in the art as described, for example, by Theodora W. Greene and Peter G. M. Wuts in Protective Groups in Organic Synthesis Third Edition from Wiley-Interscience, for the values of n, R2, R3 and PG as defined above.

The guanidines H can be obtained in particular by reacting a diamine G and cyanogen bromide in a solvent such as water or acetonitrile, at a temperature between 0° C. and the boiling point of the solvent, according to the conditions described, for example, by Gallet, T. et al. (EP1340761 2003) and Bacque, Eric et al. (WO2011001112A1 and WO2011001113A2), for the values of n, R2, R3 and PG as defined above.

The compounds E can be obtained in particular by condensation of the guanidines B with a dialkyl malonate (preferably dimethyl or diethyl malonate) D, in the presence of a base such as sodium methoxide, at a temperature between 0° C. and 150° C., as described, for example, by Badawey E.-S. A. M. et al. (Eur J Med Chem, 1998, 33(5), 349-361) and Bacque, Eric et al. (WO2011001112A1 and WO2011001113A2), for the values of n, p, q, R2, R3 and R4 as defined above.

Alternatively, the compound E can be obtained by deprotection of the compound I according to the conventional methods known to those skilled in the art as described, for example, by Theodora W. Greene and Peter G. M. Wuts in Protective Groups in Organic Synthesis Third Edition from Wiley-Interscience, for the values of p, q, R2, R3, R4 and PG as defined above.

The compounds I can be obtained in particular by condensation of the guanidines H with a dialkyl malonate (preferably dimethyl or diethyl malonate) D, in the presence of a base such as sodium methoxide, at a temperature between 0° C. and 150° C., as described, for example, by Badawey E.-S. A. M. et al. (Eur J Med Chem, 1998, 33(5), 349-361) and Bacque, Eric et al. (WO2011001112A1 and WO2011001113A2), for the values of n, p, q, R2, R3, R4 and PG as defined above.

The compounds F can be obtained in particular from the compounds E by treatment with a chlorinating agent such as phosphorus oxychloride, in the absence of solvent, at a temperature between 20° C. and 150° C., or in the presence of a solvent such as dichloroethane, at a temperature between 20° C. and the boiling point of the solvent, for instance under the conditions described by Yamashita, A. et al. (Syn. Commun. (2004), 34(5), 795-803) and Bacque, Eric et al. (WO2011001112A1 and WO2011001113A2), for the values of p, q, R2, R3 and R4 as defined above.

Alternatively, the compound F can be obtained by deprotection of the compound J according to the conventional methods known to those skilled in the art as described, for example, by Theodora W. Greene and Peter G. M. Wuts in Protective Groups in Organic Synthesis Third Edition from Wiley-Interscience, for the values of R2, R3, R4, p and q as defined above.

The compounds J can be obtained in particular from the compounds I by treatment with a chlorinating agent such as phosphorus oxychloride, in the absence of solvent, at a temperature between 20° C. and 150° C., or in the presence of a solvent such as dichloroethane, at a temperature between 20° C. and the boiling point of the solvent, for instance under the conditions described by Yamashita, A. et al. (Syn. Commun. (2004), 34(5), 795-803) and Bacque, Eric et al. (WO2011001112A1 and WO2011001113A2), for the values of p, q, R2, R3, R4 and PG as defined above.

The compounds P can be obtained from the compounds F by reacting with a substituted morpholine, in the absence or in the presence of a solvent such as acetonitrile, at a temperature between 20° C. and 200° C., in the presence or absence of a base such as triethylamine or sodium carbonate for example, by analogy as described, for example, by Aliabiev S. B. (Lett. Org. Chem. (2007), 4(4), 273-280) and Bacque, Eric et al. (WO2011001112A1 and WO2011001113A2), for the values of p, q, R2, R3, R4, R5, R6, R7, R8, R9, R10, R11 and R12 as defined above.

The products of formulae (I) can be obtained from the compounds Q by reacting with a substituted morpholine, in the absence or in the presence of a solvent such as acetonitrile, at a temperature between 20° C. and 200° C., in the presence or absence of a base such as triethylamine or sodium carbonate for example, by analogy as described, for example, by Aliabiev S. B. (Lett. Org. Chem. (2007), 4(4), 273-280) and Bacque, Eric et al. (WO2011001112A1 and WO2011001113A2), for the values of p, q, R1, R2, R3, R4, R5, R6, R7, R8, R9, R10, R11 and R12 as defined above.

The compounds Q or alternatively the products of formulae (I), as indicated on the schemes above, can be obtained respectively from the compounds F and P, for example by reacting with an electrophile by addition of a compound T1, T2 or T3 as defined above and as follows:

T1 is R1'-X in which R1' represents values of R1 as defined above for the products of formula (I): when R1' represents the values of R1 with the exception of the aryl and heteroaryl values, then the addition reaction of R1'X in which X is in particular Cl, Br, I, OMs, OTs or OTf, respectively with the compounds F and P, can be carried out, for example, in the presence of a base such as caesium carbonate, potassium phosphate or sodium hydride in excess, in a solvent such as acetonitrile, tetrahydrofuran, N,N-dimethylformamide or dimethyl sulfoxide, at a temperature between ambient temperature and 200° C., as described, for example, by Larock, Richard, C. et al. in Comprehensive Organic Transformations A Guide to Functional Group Preparations from VCH in the case of the alkylation reaction. When R1' represents the aryl and heteroaryl values of R1, then the addition reaction of R1'X, in which X is in particular I or Br, respectively with the compounds P, can be carried out, for example, by a reaction or a coupling of Ullmann type in the presence of a base such as potassium phosphate in excess with cuprous iodide, in a solvent such as N,N-dimethylformamide, at a temperature between 100 and 200° C., as described, for example, by Ulmann, F. in Chem. Ber. 1903, 36, 2389 and Bacque, Eric et al. (WO2011001112A1 and WO2011001113A2) in the case of the Ullmann-type reaction.

T2 is R1"—OH in which R1" represents values of R1 with the exception of the aryl and heteroaryl values as defined above for the products of formula (I): the addition reaction of T2, respectively with the compounds F and P, can be carried out, for example, in the presence of supported or nonsupported triphenylphosphine and of diethyl azodicarboxylate and of a base such as diisopropylethylamine, in a solvent such as tetrahydrofuran, at a temperature between ambient temperature and 100° C., as described, for example, by Mitsunobu, O. in "The Use of Diethyl Azodicarboxylate and Triphenylphosphine in Synthesis and Transformation of Natural Products" Synthesis 1981 (1) 1-28 in the case of the Mitsunobu reaction.

T3 is an epoxyethylene radical disubstituted in position 1 with substituents Y,Z, which may be identical or different, chosen from a hydrogen atom and alkyl (such as, for example, methyl or ethyl), aryl or heteroaryl radicals, all optionally substituted as indicated for R1 in the products of formula (I) as defined above: the addition reaction of T3, respectively with the compounds F and P, can be carried out, for example, in the presence of a base such as sodium hydride, sodium hydroxide, potassium phosphate or caesium carbonate in excess, in the absence of solvent or in a solvent such as tetrahydrofuran, dimethyl sulfoxide, N,N-dimethylformamide, N,N-dimethylacetamide, acetonitrile, or an acetone and water mixture with a phase-transfer agent such as, for example, benzyltriethylammonium chloride, at a temperature between 20° C. and 200° C., as described, for example, by Hepperle, Michael E. et al., PCT Int. Appl., 2007097981, 30 Aug. 2007 and Bacque, Eric et al. (WO2011001112A1 and WO2011001113A2).

In general schemes 2 and 3 above:

The compound B can be obtained according to the 3 routes indicated in scheme 1 from the compounds A, C and H as defined above and according to the steps also defined above.

The compound E can be obtained according to the 2 routes indicated in scheme 1 from the compounds I and B as defined above and according to the steps also defined above.

The compound F can be obtained according to the 2 routes indicated in scheme 1 from the compounds E and J as defined above and according to the steps also defined above.

The products of formula (I) can be obtained according to the 2 routes indicated in scheme 1 from the compounds P and Q as defined above and according to the steps also defined above.

When R2 is different from R3 and if the synthesis is not stereoselective, the enantiomers or the possible diastereoisomers of the synthesis intermediates or of the compounds (I) can be separated by chromatography on a chiral support.

The following examples of products of formula (I) illustrate the invention without, however, limiting it.

Among the starting products of formulae A, B, C, D, G, H, K, L, M, N, O and T, some are known and can be obtained either commercially, or according to the usual methods known to those skilled in the art as described, for example, by Larock, Richard, C. et al., in Comprehensive Organic Transformations A Guide to Functional Group Preparations from VCH, for example starting from commercial products.

It is understood by those skilled in the art that, in order to implement the processes according to the invention previously described, it may be necessary to introduce function-protective groups, such as, for example, the PG protective group, as described in particular by Theodora W. Greene and Peter G. M. Wuts in Protective Groups in Organic Synthesis Third Edition from Wiley-Interscience. Thus, the amine group protected by PG may be, for example, a benzylamine, para-methoxybenzylamine, 2,4-dimethoxybenzylamine or 4-methoxyphenylethylamine.

It may be noted that, if desired and if necessary, it is possible to subject intermediate products or products of formula (I) thus obtained by means of the processes indicated above, in order to obtain other intermediates or other products of formula (I), to one or more conversion reactions known to those skilled in the art, as described, for example, by Larock, Richard, C. et al. in Comprehensive Organic Transformations A Guide to Functional Group Preparations from VCH.

The products of formula (I) as defined above and also the addition salts thereof with acids exhibit advantageous pharmacological properties, in particular owing to their kinase-inhibiting properties as is indicated above.

The products of the present invention are in particular of use for antitumour therapies.

The products of the invention can thus also increase the therapeutic effects of commonly used antitumour agents.

The products of the invention can thus also increase the therapeutic effects of commonly used radiotherapies.

These properties justify the therapeutic application thereof, and the subject of the invention is in particular, as medicaments, the products of formula (I) as defined above, said products of formula (I) being in any of the possible racemic, enantiomeric and diastereoisomeric isomer forms, and also the pharmaceutically acceptable addition salts with inorganic and organic acids or with inorganic and organic bases of said products of formula (I).

A subject of the invention is quite particularly, as medicaments, the products corresponding to the following formulae:

(S)-2-((R)-3-Methylmorpholin-4-yl)-9-(5-methyl-[1,2,4]oxadiazol-3-ylmethyl)-8-trifluoromethyl-6,7,8,9-tetrahydropyrimido[1,2-a]pyrimidin-4-one (S)-2-((R)-3-Methylmorpholin-4-yl)-9-(3-methyl-2-oxobutyl)-8-trifluoromethyl-6,7,8,9-tetrahydropyrimido[1,2-a]pyrimidin-4-one (S)-3-Fluoro-2-((R)-3-methylmorpholin-4-yl)-9-(3-methyl-2-oxobutyl)-8-trifluoromethyl-6,7,8,9-tetrahydropyrimido[1,2-a]pyrimidin-4-one (S)-3-Fluoro-9-(2-fluoropyridin-4-ylmethyl)-2-((R)-3-methylmorpholin-4-yl)-8-trifluoromethyl-6,7,8,9-tetrahydropyrimido[1,2-a]pyrimidin-4-one (S)-9-(2-Cyclopropyl-2-oxoethyl)-3-fluoro-2-((R)-3-methylmorpholin-4-yl)-8-trifluoromethyl-6,7,8,9-tetrahydropyrimido[1,2-a]pyrimidin-4-one (S)-3-Fluoro-2-((R)-3-methylmorpholin-4-yl)-9-(2-oxopropyl)-8-trifluoromethyl-6,7,8,9-tetrahydropyrimido[1,2-a]pyrimidin-4-one (S)-3-Fluoro-9-((S)-2-hydroxypropyl)-2-((R)-3-methylmorpholin-4-yl)-8-trifluoromethyl-6,7,8,9-tetrahydropyrimido[1,2-a]pyrimidin-4-one (S)-2-((3R,5R)-3,5-Dimethylmorpholin-4-yl)-9-isoxazol-5-ylmethyl-8-trifluoromethyl-6,7,8,9-tetrahydropyrimido[1,2-a]pyrimidin-4-one (S)-9-[2-(2-Chloropyridin-4-yl)-2-oxoethyl]-2-((R)-3-methylmorpholin-4-yl)-8-trifluoromethyl-6,7,8,9-tetrahydropyrimido[1,2-a]pyrimidin-4-one (S)-2-((R)-3-Methylmorpholin-4-yl)-9-(2-oxo-2-pyridin-3-ylethyl)-8-trifluoromethyl-6,7,8,9-tetrahydropyrimido[1,2-a]pyrimidin-4-one

- (S)-9-(3-Methylisoxazol-4-ylmethyl)-2-((R)-3-methylmorpholin-4-yl)-8-trifluoromethyl-6,7,8,9-tetrahydropyrimido[1,2-a]pyrimidin-4-one
- (R)-2-((R)-3-Methylmorpholin-4-yl)-9-oxazol-2-ylmethyl-6-trifluoromethyl-6,7,8,9-tetrahydropyrimido[1,2-a]pyrimidin-4-one
- [(S)-8-((R)-3-Methylmorpholin-4-yl)-6-oxo-2-trifluoromethyl-3,4-dihydro-2H,6H-pyrimido[1,2-a]pyrimidin-1-yl]acetic acid ethyl ester
- (S)-3-Fluoro-2-((R)-3-methylmorpholin-4-yl)-9-(5-methyl-[1,2,4]oxadiazol-3-ylmethyl)-8-trifluoromethyl-6,7,8,9-tetrahydropyrimido[1,2-a]pyrimidin-4-one
- (S)-2-((R)-3-Methylmorpholin-4-yl)-9-(2-oxobutyl)-8-trifluoromethyl-6,7,8,9-tetrahydropyrimido[1,2-a]pyrimidin-4-one
- (S)-2-((R)-3-Methylmorpholin-4-yl)-9-(3-methyl-[1,2,4]oxadiazol-5-ylmethyl)-8-trifluoromethyl-6,7,8,9-tetrahydropyrimido[1,2-a]pyrimidin-4-one
- (S)-3-Fluoro-2-((R)-3-methylmorpholin-4-yl)-9-[2-oxo-2-(tetrahydropyran-4-yl)ethyl]-8-trifluoromethyl-6,7,8,9-tetrahydropyrimido[1,2-a]pyrimidin-4-one
- (S)-3-Fluoro-2-((R)-3-methylmorpholin-4-yl)-9-(3-methyl-[1,2,4]oxadiazol-5-ylmethyl)-8-trifluoromethyl-6,7,8,9-tetrahydropyrimido[1,2-a]pyrimidin-4-one
- (S)-3-Fluoro-9-(2-methoxyethyl)-2-((R)-3-methylmorpholin-4-yl)-8-trifluoromethyl-6,7,8,9-tetrahydropyrimido[1,2-a]pyrimidin-4-one
- (R)-3-Fluoro-2-((R)-3-methylmorpholin-4-yl)-9-(5-methyl-[1,2,4]oxadiazol-3-ylmethyl)-6-trifluoromethyl-6,7,8,9-tetrahydropyrimido[1,2-a]pyrimidin-4-one
- (S)-3-Fluoro-2-((R)-3-methylmorpholin-4-yl)-9-(2-oxobutyl)-8-trifluoromethyl-6,7,8,9-tetrahydropyrimido[1,2-a]pyrimidin-4-one
- 2-[(S)-7-Fluoro-8-((R)-3-methylmorpholin-4-yl)-6-oxo-2-trifluoromethyl-3,4-dihydro-2H,6H-pyrimido[1,2-a]pyrimidin-1-yl]-N-methoxy-N-methylacetamide
- (S)-9-(6-Fluoropyridin-3-ylmethyl)-2-((R)-3-methylmorpholin-4-yl)-8-trifluoromethyl-6,7,8,9-tetrahydropyrimido[1,2-a]pyrimidin-4-one
- (S)-9-[2-(2-Fluoropyridin-4-yl)-2-oxoethyl]-2-((R)-3-methylmorpholin-4-yl)-8-trifluoromethyl-6,7,8,9-tetrahydropyrimido[1,2-a]pyrimidin-4-one
- (R)-2-((R)-3-Methylmorpholin-4-yl)-9-(2-oxobutyl)-6-trifluoromethyl-6,7,8,9-tetrahydropyrimido[1,2-a]pyrimidin-4-one
- (R)-2-((R)-3-Methylmorpholin-4-yl)-9-(5-methyl-[1,2,4]oxadiazol-3-ylmethyl)-6-trifluoromethyl-6,7,8,9-tetrahydropyrimido[1,2-a]pyrimidin-4-one
- (R)-3-Fluoro-2-((R)-3-methylmorpholin-4-yl)-6-trifluoromethyl-9-(3-trifluoromethyl-[1,2,4]oxadiazol-5-ylmethyl)-6,7,8,9-tetrahydropyrimido[1,2-a]pyrimidin-4-one
- (R)-3-Fluoro-2-((R)-3-methylmorpholin-4-yl)-9-(2-oxobutyl)-6-trifluoromethyl-6,7,8,9-tetrahydropyrimido[1,2-a]pyrimidin-4-one
- (S)-6-Fluoro-2-methyl-7-((R)-3-methylmorpholin-4-yl)-1-(5-methyl-[1,2,4]oxadiazol-3-ylmethyl)-2-trifluoromethyl-2,3-dihydro-1H-imidazo[1,2-a]pyrimidin-5-one
- (S)-1-(2-Cyclopropyl-2-oxoethyl)-2-methyl-7-((R)-3-methylmorpholin-4-yl)-2-trifluoromethyl-2,3-dihydro-1H-imidazo[1,2-a]pyrimidin-5-one
- (S)-9-(1-Difluoromethyl-1H-pyrazol-3-ylmethyl)-2-((R)-3-methylmorpholin-4-yl)-8-trifluoromethyl-6,7,8,9-tetrahydropyrimido[1,2-a]pyrimidin-4-one
- (S)-9-Isoxazol-3-ylmethyl-2-((R)-3-methylmorpholin-4-yl)-8-trifluoromethyl-6,7,8,9-tetrahydropyrimido[1,2-a]pyrimidin-4-one
- (S)-9-(2-Chlorothiazol-5-ylmethyl)-2-((R)-3-methylmorpholin-4-yl)-8-trifluoromethyl-6,7,8,9-tetrahydropyrimido[1,2-a]pyrimidin-4-one
- (S)-9-(6-Chloropyridin-3-ylmethyl)-2-((R)-3-methylmorpholin-4-yl)-8-trifluoromethyl-6,7,8,9-tetrahydropyrimido[1,2-a]pyrimidin-4-one
- (S)-9-Isoxazol-5-ylmethyl-2-((R)-3-methylmorpholin-4-yl)-8-trifluoromethyl-6,7,8,9-tetrahydropyrimido[1,2-a]pyrimidin-4-one
- (S)-9-(2-Difluoromethyl-2H-pyrazol-3-ylmethyl)-2-((R)-3-methylmorpholin-4-yl)-8-trifluoromethyl-6,7,8,9-tetrahydropyrimido[1,2-a]pyrimidin-4-one
- (S)-3-Fluoro-2-((R)-3-methylmorpholin-4-yl)-9-(2-oxo-2-pyridin-2-ylethyl)-8-trifluoromethyl-6,7,8,9-tetrahydropyrimido[1,2-a]pyrimidin-4-one
- (S)-9-(2-Fluoro-2-phenylethyl)-2-((R)-3-methylmorpholin-4-yl)-8-trifluoromethyl-6,7,8,9-tetrahydropyrimido[1,2-a]pyrimidin-4-one, single stereoisomer
- (S)-3-Fluoro-9-(2-methoxypyridin-4-yl)-2-((R)-3-methylmorpholin-4-yl)-8-trifluoromethyl-6,7,8,9-tetrahydropyrimido[1,2-a]pyrimidin-4-one
- (S)-9-(2-Chloropyridin-4-ylmethyl)-3-fluoro-2-((R)-3-methylmorpholin-4-yl)-8-trifluoromethyl-6,7,8,9-tetrahydropyrimido[1,2-a]pyrimidin-4-one
- (S)-3-Fluoro-2-((R)-3-methylmorpholin-4-yl)-9-oxazol-2-ylmethyl-8-trifluoromethyl-6,7,8,9-tetrahydropyrimido[1,2-a]pyrimidin-4-one
- (S)-9-(6-Cyclopropylpyridin-3-yl)-3-fluoro-2-((R)-3-methylmorpholin-4-yl)-8-trifluoromethyl-6,7,8,9-tetrahydropyrimido[1,2-a]pyrimidin-4-one
- (S)-3-Fluoro-2-((R)-3-methylmorpholin-4-yl)-9-oxazol-4-ylmethyl-8-trifluoromethyl-6,7,8,9-tetrahydropyrimido[1,2-a]pyrimidin-4-one
- (S)-9-(2-Chloropyridin-4-yl)-3-fluoro-2-((R)-3-methylmorpholin-4-yl)-8-trifluoromethyl-6,7,8,9-tetrahydropyrimido[1,2-a]pyrimidin-4-one
- (S)-3-Fluoro-9-isoxazol-5-ylmethyl-2-((R)-3-methylmorpholin-4-yl)-8-trifluoromethyl-6,7,8,9-tetrahydropyrimido[1,2-a]pyrimidin-4-one
- (S)-3-Fluoro-2-((R)-3-methylmorpholin-4-yl)-9-pyridin-3-yl-8-trifluoromethyl-6,7,8,9-tetrahydropyrimido[1,2-a]pyrimidin-4-one
- (S)-3-Fluoro-2-((R)-3-methylmorpholin-4-yl)-9-[2-(2,2,2-trifluoroethoxy)-ethyl]-8-trifluoromethyl-6,7,8,9-tetrahydropyrimido[1,2-a]pyrimidin-4-one
- (S)-3-Fluoro-9-(2-hydroxy-2-methylpropyl)-2-((R)-3-methylmorpholin-4-yl)-8-trifluoromethyl-6,7,8,9-tetrahydropyrimido[1,2-a]pyrimidin-4-one
- (S)-3-Fluoro-2-((R)-3-methylmorpholin-4-yl)-9-(2-oxo-2-pyridin-3-ylethyl)-8-trifluoromethyl-6,7,8,9-tetrahydropyrimido[1,2-a]pyrimidin-4-one
- (S)-3-Fluoro-9-(6-fluoropyridin-3-ylmethyl)-2-((R)-3-methylmorpholin-4-yl)-8-trifluoromethyl-6,7,8,9-tetrahydropyrimido[1,2-a]pyrimidin-4-one
- (S)-9-(6-Chloropyridin-3-ylmethyl)-3-fluoro-2-((R)-3-methylmorpholin-4-yl)-8-trifluoromethyl-6,7,8,9-tetrahydropyrimido[1,2-a]pyrimidin-4-one
- (S)-9-(6-Difluoromethylpyridin-3-yl)-3-fluoro-2-((R)-3-methylmorpholin-4-yl)-8-trifluoromethyl-6,7,8,9-tetrahydropyrimido[1,2-a]pyrimidin-4-one
- (S)-9-(5-tert-Butyl-[1,2,4]oxadiazol-3-ylmethyl)-3-fluoro-2-((R)-3-methylmorpholin-4-yl)-8-trifluoromethyl-6,7,8,9-tetrahydropyrimido[1,2-a]pyrimidin-4-one
- (S)-3-Fluoro-2-((R)-3-methylmorpholin-4-yl)-9-pyridin-4-yl-8-trifluoromethyl-6,7,8,9-tetrahydropyrimido[1,2-a]pyrimidin-4-one (S)-3-Fluoro-9-(5-fluoropyridin-2-ylmethyl)-2-((R)-3-methylmorpholin-4-yl)-8-trifluoromethyl-6,7,8,9-tetrahydropyrimido[1,2-a]pyrimidin-4-one (S)-3-Fluoro-9-(5-fluoropyridin-3-ylmethyl)-2-((R)-3-methylmorpholin-4-yl)-8-trifluoromethyl-6,7,8,9-tetrahydropyrimido[1,2-a]pyrimidin-4-one (S)-3-Fluoro-9-(2-fluoropyridin-3-ylmethyl)-2-((R)-3-methylmorpholin-4-yl)-8-trifluoromethyl-6,7,8,9-tetrahydropyrimido[1,2-a]pyrimidin-4-one (S)-3-Fluoro-9-[2-(3-fluoropyridin-2-yl)-2-oxoethyl]-2-((R)-3-methylmorpholin-4-yl)-8-trifluoromethyl-6,7,8,9-tetrahydropyrimido[1,2-a]pyrimidin-4-one (S)-9-[2-(3-Fluoropyridin-2-yl)-2-oxoethyl]-2-((R)-3-methylmorpholin-4-yl)-8-trifluoromethyl-6,7,8,9-tetrahydropyrimido[1,2-a]pyrimidin-4-one (S)-9-[2-(2-Methoxypyridin-4-yl)-2-oxoethyl]-2-((R)-3-methylmorpholin-4-yl)-8-trifluoromethyl-6,7,8,9-tetrahydropyrimido[1,2-a]pyrimidin-4-one (S)-3-Fluoro-9-(3-methylisoxazol-4-ylmethyl)-2-((R)-3-methylmorpholin-4-yl)-8-trifluoromethyl-6,7,8,9-tetrahydropyrimido[1,2-a]pyrimidin-4-one (S)-9-[2-(6-Fluoropyridin-2-yl)-2-oxoethyl]-2-((R)-3-methylmorpholin-4-yl)-8-trifluoromethyl-6,7,8,9-tetrahydropyrimido[1,2-a]pyrimidin-4-one (S)-9-Imidazo[1,2-a]pyridin-2-ylmethyl-2-((R)-3-methylmorpholin-4-yl)-8-trifluoromethyl-6,7,8,9-tetrahydropyrimido[1,2-a]pyrimidin-4-one (S)-9-(4-Chloropyridin-2-ylmethyl)-2-((R)-3-methylmorpholin-4-yl)-8-trifluoromethyl-6,7,8,9-tetrahydropyrimido[1,2-a]pyrimidin-4-one (S)-9-(3-Chloropyridin-4-ylmethyl)-2-((R)-3-methylmorpholin-4-yl)-8-trifluoromethyl-6,7,8,9-tetrahydropyrimido[1,2-a]pyrimidin-4-one (S)-2-((R)-3-Methylmorpholin-4-yl)-9-(2-oxo-3-pyridin-2-ylpropyl)-8-trifluoromethyl-6,7,8,9-tetrahydropyrimido[1,2-a]pyrimidin-4-one (S)-3-Fluoro-2-((R)-3-methylmorpholin-4-yl)-9-(2-oxo-2-thiazol-2-ylethyl)-8-trifluoromethyl-6,7,8,9-tetrahydropyrimido[1,2-a]pyrimidin-4-one (S)-3-Fluoro-2-((R)-3-methylmorpholin-4-yl)-9-thiazol-4-ylmethyl-8-trifluoromethyl-6,7,8,9-tetrahydropyrimido[1,2-a]pyrimidin-4-one (S)-9-[2-(5-Fluoropyridin-2-yl)-2-oxoethyl]-2-((R)-3-methylmorpholin-4-yl)-8-trifluoromethyl-6,7,8,9-tetrahydropyrimido[1,2-a]pyrimidin-4-one 3-Fluoro-8,8-dimethyl-2-((R)-3-methylmorpholin-4-yl)-9-(2-oxo-2-pyridin-2-ylethyl)-6,7,8,9-tetrahydropyrimido[1,2-a]pyrimidin-4-one 9-(2-Difluoromethyl-2H-pyrazol-3-ylmethyl)-8,8-dimethyl-2-((R)-3-methylmorpholin-4-yl)-6,7,8,9-tetrahydropyrimido[1,2-a]pyrimidin-4-one 3-Fluoro-9-isoxazol-3-ylmethyl-8,8-dimethyl-2-((R)-3-methylmorpholin-4-yl)-6,7,8,9-tetrahydropyrimido[1,2-a]pyrimidin-4-one 9-(2-Difluoromethyl-2H-pyrazol-3-ylmethyl)-3-fluoro-8,8-dimethyl-2-((R)-3-methylmorpholin-4-yl)-6,7,8,9-tetrahydropyrimido[1,2-a]pyrimidin-4-one (S)-9-(3-Fluorophenyl)-2-((R)-3-methylmorpholin-4-yl)-8-trifluoromethyl-6,7,8,9-tetrahydropyrimido[1,2-a]pyrimidin-4-one (S)-9-(2-Chloropyridin-4-ylmethyl)-2-((R)-3-methylmorpholin-4-yl)-8-trifluoromethyl-6,7,8,9-tetrahydropyrimido[1,2-a]pyrimidin-4-one (S)-2-((R)-3-Methylmorpholin-4-yl)-9-oxazol-2-ylmethyl-8-trifluoromethyl-6,7,8,9-tetrahydropyrimido[1,2-a]pyrimidin-4-one (S)-2-((R)-3-Methylmorpholin-4-yl)-9-thiazol-4-ylmethyl-8-trifluoromethyl-6,7,8,9-tetrahydropyrimido[1,2-a]pyrimidin-4-one (S)-9-(2-Chloropyridin-4-yl)-2-((R)-3-methylmorpholin-4-yl)-8-trifluoromethyl-6,7,8,9-tetrahydropyrimido[1,2-a]pyrimidin-4-one (S)-9-(2-Methoxypyridin-4-yl)-2-((R)-3-methylmorpholin-4-yl)-8-trifluoromethyl-6,7,8,9-tetrahydropyrimido[1,2-a]pyrimidin-4-one (S)-2-((R)-3-Methylmorpholin-4-yl)-8-trifluoromethyl-9-(6-trifluoromethylpyridin-3-yl)-6,7,8,9-tetrahydropyrimido[1,2-a]pyrimidin-4-one (S)-2-((R)-3-Methylmorpholin-4-yl)-9-[2-(2,2,2-trifluoroethoxy)ethyl]-8-trifluoromethyl-6,7,8,9-tetrahydropyrimido[1,2-a]pyrimidin-4-one (S)-2-((R)-3-Methyl morpholin-4-yl)-9-(6-methylpyridin-3-yl)-8-trifluoromethyl-6,7,8,9-tetrahydropyrimido[1,2-a]pyrimidin-4-one (S)-9-(2-Hydroxy-2-methylpropyl)-2-((R)-3-methylmorpholin-4-yl)-8-trifluoromethyl-6,7,8,9-tetrahydropyrimido[1,2-a]pyrimidin-4-one (S)-9-(6-Isopropoxypyridin-3-yl)-2-((R)-3-methylmorpholin-4-yl)-8-trifluoromethyl-6,7,8,9-tetrahydropyrimido[1,2-a]pyrimidin-4-one (S)-9-(5-Chloropyridin-2-ylmethyl)-2-((R)-3-methylmorpholin-4-yl)-8-trifluoromethyl-6,7,8,9-tetrahydropyrimido[1,2-a]pyrimidin-4-one (S)-2-((R)-3-Methylmorpholin-4-yl)-9-thiazol-5-ylmethyl-8-trifluoromethyl-6,7,8,9-tetrahydropyrimido[1,2-a]pyrimidin-4-one (S)-9-(6-Cyclobutylpyridin-3-yl)-2-((R)-3-methylmorpholin-4-yl)-8-trifluoromethyl-6,7,8,9-tetrahydropyrimido[1,2-a]pyrimidin-4-one (S)-9-(2-Cyclopropylpyridin-4-yl)-2-((R)-3-methylmorpholin-4-yl)-8-trifluoromethyl-6,7,8,9-tetrahydropyrimido[1,2-a]pyrimidin-4-one (S)-9-(2-Methoxyethyl)-2-((R)-3-methylmorpholin-4-yl)-8-trifluoromethyl-6,7,8,9-tetrahydropyrimido[1,2-a]pyrimidin-4-one (S)-2-((R)-3-Methylmorpholin-4-yl)-9-oxazol-5-ylmethyl-8-trifluoromethyl-6,7,8,9-tetrahydropyrimido[1,2-a]pyrimidin-4-one (S)-9-(5-Fluoropyridin-2-ylmethyl)-2-((R)-3-methylmorpholin-4-yl)-8-trifluoromethyl-6,7,8,9-tetrahydropyrimido[1,2-a]pyrimidin-4-one (S)-9-(2,5-Dimethyloxazol-4-ylmethyl)-2-((R)-3-methylmorpholin-4-yl)-8-trifluoromethyl-6,7,8,9-tetrahydropyrimido[1,2-a]pyrimidin-4-one (S)-9-(5-Fluoropyridin-3-ylmethyl)-2-((R)-3-methylmorpholin-4-yl)-8-trifluoromethyl-6,7,8,9-tetrahydropyrimido[1,2-a]pyrimidin-4-one (S)-9-(5-Chloropyridin-3-ylmethyl)-2-((R)-3-methylmorpholin-4-yl)-8-trifluoromethyl-6,7,8,9-tetrahydropyrimido[1,2-a]pyrimidin-4-one (S)-2-((R)-3-Methylmorpholin-4-yl)-9-(5-methyl-[1,3,4]oxadiazol-2-ylmethyl)-8-trifluoromethyl-6,7,8,9-tetrahydropyrimido[1,2-a]pyrimidin-4-one (S)-9-(3,3-Dimethyl-2-oxobutyl)-3-fluoro-2-((R)-3-methylmorpholin-4-yl)-8-trifluoromethyl-6,7,8,9-tetrahydropyrimido[1,2-a]pyrimidin-4-one (S)-9-(5-Chlorothiophen-2-ylmethyl)-2-((R)-3-methylmorpholin-4-yl)-8-trifluoromethyl-6,7,8,9-tetrahydropyrimido[1,2-a]pyrimidin-4-one (S)-2-((R)-3-Methylmorpholin-4-yl)-9-(2-oxo-2-phenylethyl)-8-trifluoromethyl-6,7,8,9-tetrahydropyrimido[1,2-a]pyrimidin-4-one (S)-9-((S)-2-Methoxy-2-phenylethyl)-2-((R)-3-methylmorpholin-4-yl)-8-trifluoromethyl-6,7,8,9-tetrahydropyrimido[1,2-a]pyrimidin-4-one (S)-9-(3-Methylisoxazol-5-ylmethyl)-2-((R)-3-methylmorpholin-4-yl)-8-trifluoromethyl-6,7,8,9-tetrahydropyrimido[1,2-a]pyrimidin-4-one (R)-2-((R)-3-Methylmorpholin-4-yl)-9-(2-oxo-2-pyridin-2-ylethyl)-6-trifluoromethyl-6,7,8,9-tetrahydropyrimido[1,2-a]pyrimidin-4-one (S)-2-((R)-3-Methylmorpholin-4-yl)-9-oxazol-4-ylmethyl-8-trifluoromethyl-6,7,8,9-tetrahydropyrimido[1,2-a]pyrimidin-4-one (S)-2-((R)-3-Methylmorpholin-4-yl)-9-(toluene-4-sulfonyl)-8-trifluoromethyl-6,7,8,9-tetrahydropyrimido[1,2-a]pyrimidin-4-one (R)-9-Isoxazol-5-ylmethyl-2-((R)-3-methylmorpholin-4-yl)-6-trifluoromethyl-6,7,8,9-tetrahydropyrimido[1,2-a]pyrimidin-4-one (R)-9-Isoxazol-3-ylmethyl-2-((R)-3-methylmorpholin-4-yl)-6-trifluoromethyl-6,7,8,9-tetrahydropyrimido[1,2-a]pyrimidin-4-one (R)-9-(6-Cyclopropylpyridin-3-yl)-2-((R)-3-methylmorpholin-4-yl)-6-trifluoromethyl-6,7,8,9-tetrahydropyrimido[1,2-a]pyrimidin-4-one (R)-9-(2-Chloropyridin-4-yl)-2-((R)-3-methylmorpholin-4-yl)-6-trifluoromethyl-6,7,8,9-tetrahydropyrimido[1,2-a]pyrimidin-4-one (R)-9-(2-Methoxypyridin-4-yl)-2-((R)-3-methylmorpholin-4-yl)-6-trifluoromethyl-6,7,8,9-tetrahydropyrimido[1,2-a]pyrimidin-4-one (R)-2-((R)-3-Methylmorpholin-4-yl)-9-oxazol-4-ylmethyl-6-trifluoromethyl-6,7,8,9-tetrahydropyrimido[1,2-a]pyrimidin-4-one (S)-3-Fluoro-2-((R)-3-methylmorpholin-4-yl)-9-oxazol-5-ylmethyl-8-trifluoromethyl-6,7,8,9-tetrahydropyrimido[1,2-a]pyrimidin-4-one (R)-9-(2-Chloropyridin-4-ylmethyl)-2-((R)-3-methylmorpholin-4-yl)-6-trifluoromethyl-6,7,8,9-tetrahydropyrimido[1,2-a]pyrimidin-4-one (R)-9-(2-Hydroxy-2-methylpropyl)-2-((R)-3-methylmorpholin-4-yl)-6-trifluoromethyl-6,7,8,9-tetrahydropyrimido[1,2-a]pyrimidin-4-one (R)-9-(2-Isopropoxypyridin-4-yl)-2-((R)-3-methylmorpholin-4-yl)-6-trifluoromethyl-6,7,8,9-tetrahydropyrimido[1,2-a]pyrimidin-4-one (R)-9-(6-Chloropyridin-3-ylmethyl)-2-((R)-3-methylmorpholin-4-yl)-6-trifluoromethyl-6,7,8,9-tetrahydropyrimido[1,2-a]pyrimidin-4-one (R)-9-(6-Isopropoxypyridin-3-yl)-2-((R)-3-methylmorpholin-4-yl)-6-trifluoromethyl-6,7,8,9-tetrahydropyrimido[1,2-a]pyrimidin-4-one (R)-2-((R)-3-Methylmorpholin-4-yl)-9-oxazol-5-ylmethyl-6-trifluoromethyl-6,7,8,9-tetrahydropyrimido[1,2-a]pyrimidin-4-one (R)-9-(2-Cyclopropyl-2-oxoethyl)-2-((R)-3-methylmorpholin-4-yl)-6-trifluoromethyl-6,7,8,9-tetrahydropyrimido[1,2-a]pyrimidin-4-one (R)-3-Fluoro-9-(2-methoxypyridin-4-yl)-2-((R)-3-methylmorpholin-4-yl)-6-trifluoromethyl-6,7,8,9-tetrahydropyrimido[1,2-a]pyrimidin-4-one (R)-9-(2-Cyclopropyl-2-oxoethyl)-3-fluoro-2-((R)-3-methylmorpholin-4-yl)-6-trifluoromethyl-6,7,8,9-tetrahydropyrimido[1,2-a]pyrimidin-4-one (R)-9-(6-Difluoromethylpyridin-3-yl)-3-fluoro-2-((R)-3-methylmorpholin-4-yl)-6-trifluoromethyl-6,7,8,9-tetrahydropyrimido[1,2-a]pyrimidin-4-one (R)-9-(2-Chloropyridin-4-yl)-3-fluoro-2-((R)-3-methylmorpholin-4-yl)-6-trifluoromethyl-6,7,8,9-tetrahydropyrimido[1,2-a]pyrimidin-4-one (S)-2-((R)-3-Methylmorpholin-4-yl)-9-(5-methyl-[1,3,4]thiadiazol-2-ylmethyl)-8-trifluoromethyl-6,7,8,9-tetrahydropyrimido[1,2-a]pyrimidin-4-one (S)-9-(6-Difluoromethoxypyridin-3-yl)-2-((R)-3-methylmorpholin-4-yl)-8-trifluoromethyl-6,7,8,9-tetrahydropyrimido[1,2-a]pyrimidin-4-one (S)-2-((R)-3-Methylmorpholin-4-yl)-9-(4-methyl-[1,2,3]thiadiazol-5-ylmethyl)-8-trifluoromethyl-6,7,8,9-tetrahydropyrimido[1,2-a]pyrimidin-4-one (R)-3-Fluoro-2-((R)-3-methylmorpholin-4-yl)-9-(2-oxo-2-pyridin-3-ylethyl)-6-trifluoromethyl-6,7,8,9-tetrahydropyrimido[1,2-a]pyrimidin-4-one (R)-9-(6-Difluoromethoxypyridin-3-yl)-3-fluoro-2-((R)-3-methylmorpholin-4-yl)-6-trifluoromethyl-6,7,8,9-tetrahydropyrimido[1,2-a]pyrimidin-4-one (R)-3-Fluoro-2-((R)-3-methylmorpholin-4-yl)-9-(3-methyl-2-oxobutyl)-6-trifluoromethyl-6,7,8,9-tetrahydropyrimido[1,2-a]pyrimidin-4-one (R)-3-Fluoro-2-((R)-3-methylmorpholin-4-yl)-9-oxazol-2-ylmethyl-6-trifluoromethyl-6,7,8,9-tetrahydropyrimido[1,2-a]pyrimidin-4-one (R)-2-((R)-3-Methylmorpholin-4-yl)-9-(3-methyl-2-oxobutyl)-6-trifluoromethyl-6,7,8,9-tetrahydropyrimido[1,2-a]pyrimidin-4-one (R)-2-((R)-3-Methylmorpholin-4-yl)-9-[2-oxo-2-(tetrahydropyran-4-yl)ethyl]-6-trifluoromethyl-6,7,8,9-tetrahydropyrimido[1,2-a]pyrimidin-4-one (R)-3-Fluoro-2-((R)-3-methylmorpholin-4-yl)-9-[2-oxo-2-(tetrahydropyran-4-yl)ethyl]-6-trifluoromethyl-6,7,8,9-tetrahydropyrimido[1,2-a]pyrimidin-4-one (S)-2-((R)-3-Methylmorpholin-4-yl)-9-oxetan-3-ylmethyl-8-trifluoromethyl-6,7,8,9-tetrahydropyrimido[1,2-a]pyrimidin-4-one 9-(6-Difluoromethylpyridin-3-yl)-2-((R)-3-methylmorpholin-4-yl)-8-trifluoromethyl-6,7,8,9-tetrahydropyrimido[1,2-a]pyrimidin-4-one (R)-3-Fluoro-2-((R)-3-methylmorpholin-4-yl)-9-(2-oxo-2-pyridin-2-ylethyl)-6-trifluoromethyl-6,7,8,9-tetrahydropyrimido[1,2-a]pyrimidin-4-one (S)-2-((R)-3-Methylmorpholin-4-yl)-9-[1-(tetrahydrofuran-2-yl)methyl]-8-trifluoromethyl-6,7,8,9-tetrahydropyrimido[1,2-a]pyrimidin-4-one, single stereoisomer (S)-2-((R)-3-Methylmorpholin-4-yl)-9-[1-(tetrahydrofuran-2-yl)methyl]-8-trifluoromethyl-6,7,8,9-tetrahydropyrimido[1,2-a]pyrimidin-4-one, single stereoisomer (S)-2-((R)-3-Methylmorpholin-4-yl)-9-[1-(tetrahydropyran-2-yl)methyl]-8-trifluoromethyl-6,7,8,9-tetrahydropyrimido[1,2-a]pyrimidin-4-one, single stereoisomer (S)-2-((R)-3-Methylmorpholin-4-yl)-9-[1-(tetrahydropyran-2-yl)methyl]-8-trifluoromethyl-6,7,8,9-tetrahydropyrimido[1,2-a]pyrimidin-4-one, single stereoisomer (S)-2-((R)-3-Methylmorpholin-4-yl)-8-trifluoromethyl-9-(5-trifluoromethyl-[1,3,4]oxadiazol-2-ylmethyl)-6,7,8,9-tetrahydropyrimido[1,2-a]pyrimidin-4-one (R)-2-((R)-3-Methylmorpholin-4-yl)-9-(2-oxo-2-pyridin-3-ylethyl)-6-trifluoromethyl-6,7,8,9-tetrahydropyrimido[1,2-a]pyrimidin-4-one (S)-9-(5-Cyclopropyl-[1,3,4]oxadiazol-2-ylmethyl)-2-((R)-3-methylmorpholin-4-yl)-8-trifluoromethyl-6,7,8,9-tetrahydropyrimido[1,2-a]pyrimidin-4-one (R)-9-(3-Methylisoxazol-4-ylmethyl)-2-((R)-3-methylmorpholin-4-yl)-6-trifluoromethyl-6,7,8,9-tetrahydropyrimido[1,2-a]pyrimidin-4-one (R)-2-((R)-3-Methyl morpholin-4-yl)-6-trifluoromethyl-9-(3-trifluoromethyl-[1,2,4]oxadiazol-5-ylmethyl)-6,7,8,9-tetrahydropyrimido[1,2-a]pyrimidin-4-one (R)-2-((R)-3-Methylmorpholin-4-yl)-9-(2-oxopropyl)-6-trifluoromethyl-6,7,8,9-tetrahydropyrimido[1,2-a]pyrimidin-4-one (R)-3-Fluoro-9-(3-methyl isoxazol-4-ylmethyl)-2-((R)-3-methylmorpholin-4-yl)-6-trifluoromethyl-6,7,8,9-tetrahydropyrimido[1,2-a]pyrimidin-4-one (R)-9-(3-Cyclopropyl-[1,2,4]oxadiazol-5-ylmethyl)-3-fluoro-2-((R)-3-methylmorpholin-4-yl)-6-trifluoromethyl-6,7,8,9-tetrahydropyrimido[1,2-a]pyrimidin-4-one (R)-3-Fluoro-2-((R)-3-Methylmorpholin-4-yl)-9-(2-oxopropyl)-6-trifluoromethyl-6,7,8,9-tetrahydropyrimido[1,2-a]pyrimidin-4-one (R)-3-Fluoro-2-((R)-3-Methylmorpholin-4-yl)-9-(3-methyl-[1,2,4]oxadiazol-5-ylmethyl)-6-trifluoromethyl-6,7,8,9-tetrahydropyrimido[1,2-a]pyrimidin-4-one (S)-2-(3,3-Dimethylmorpholin-4-yl)-9-(2-oxo-2-phenylethyl)-8-trifluoromethyl-6,7,8,9-tetrahydropyrimido[1,2-a]pyrimidin-4-one (S)-9-(5-Chlorothiophen-2-ylmethyl)-2-((3S,5R)-3,5-dimethylmorpholin-4-yl)-8-trifluoromethyl-6,7,8,9-tetrahydropyrimido[1,2-a]pyrimidin-4-one
single stereoisomer.

(S)-9-(5-Chlorothiophen-2-ylmethyl)-2-((3S,5S)-3,5-dimethylmorpholin-4-yl)-8-trifluoromethyl-6,7,8,9-tetrahydropyrimido[1,2-a]pyrimidin-4-one (S)-2-((3S,5S)-3,5-Dimethylmorpholin-4-yl)-9-(2-oxo-2-phenylethyl)-8-trifluoromethyl-6,7,8,9-tetrahydropyrimido[1,2-a]pyrimidin-4-one (S)-9-(2-Difluoromethyl-2H-pyrazol-3-ylmethyl)-2-((3R,5R)-3,5-dimethylmorpholin-4-yl)-8-trifluoromethyl-6,7,8,9-tetrahydropyrimido[1,2-a]pyrimidin-4-one (S)-2-((3R,5R)-3,5-Dimethylmorpholin-4-yl)-9-(3-methylisoxazol-5-ylmethyl)-8-trifluoromethyl-6,7,8,9-tetrahydropyrimido[1,2-a]pyrimidin-4-one (S)-9-(6-Chloropyridin-3-ylmethyl)-2-((3R,5R)-3,5-dimethylmorpholin-4-yl)-8-trifluoromethyl-6,7,8,9-tetrahydropyrimido[1,2-a]pyrimidin-4-one (S)-9-(2-Chloropyridin-4-ylmethyl)-2-((3R,5R)-3,5-dimethylmorpholin-4-yl)-8-trifluoromethyl-6,7,8,9-tetrahydropyrimido[1,2-a]pyrimidin-4-one (S)-2-((3R,5R)-3,5-Dimethylmorpholin-4-yl)-9-oxazol-2-ylmethyl-8-trifluoromethyl-6,7,8,9-tetrahydropyrimido[1,2-a]pyrimidin-4-one (S)-9-(2-Chloropyridin-4-yl)-2-((3R,5R)-3,5-dimethylmorpholin-4-yl)-8-trifluoromethyl-6,7,8,9-tetrahydropyrimido[1,2-a]pyrimidin-4-one (S)-2-((3R,5R)-3,5-Dimethylmorpholin-4-yl)-9-pyridin-3-yl-8-trifluoromethyl-6,7,8,9-tetrahydropyrimido[1,2-a]pyrimidin-4-one (S)-9-(3,5-Difluorophenyl)-2-(8-oxa-3-aza-bicyclo[3.2.1]oct-3-yl)-8-trifluoromethyl-6,7,8,9-tetrahydropyrimido[1,2-a]pyrimidin-4-one (S)-9-(5-Chlorothiophen-2-ylmethyl)-2-(8-oxa-3-aza-bicyclo[3.2.1]oct-3-yl)-8-trifluoromethyl-6,7,8,9-tetrahydropyrimido[1,2-a]pyrimidin-4-one (S)-2-(8-Oxa-3-aza-bicyclo[3.2.1]oct-3-yl)-9-(2-oxo-2-phenylethyl)-8-trifluoromethyl-6,7,8,9-tetrahydropyrimido[1,2-a]pyrimidin-4-one (S)-9-Isoxazol-5-ylmethyl-2-(8-oxa-3-aza-bicyclo[3.2.1]oct-3-yl)-8-trifluoromethyl-6,7,8,9-tetrahydropyrimido[1,2-a]pyrimidin-4-one (S)-9-(2-Chlorothiazol-5-ylmethyl)-2-(8-oxa-3-aza-bicyclo[3.2.1]oct-3-yl)-8-trifluoromethyl-6,7,8,9-tetrahydropyrimido[1,2-a]pyrimidin-4-one (S)-9-(2-Difluoromethyl-2H-pyrazol-3-ylmethyl)-2-(8-oxa-3-aza-bicyclo[3.2.1]oct-3-yl)-8-trifluoromethyl-6,7,8,9-tetrahydropyrimido[1,2-a]pyrimidin-4-one (S)-9-(1-Difluoromethyl-1H-pyrazol-3-ylmethyl)-2-(8-oxa-3-aza-bicyclo[3.2.1]oct-3-yl)-8-trifluoromethyl-6,7,8,9-tetrahydropyrimido[1,2-a]pyrimidin-4-one (S)-9-(6-Chloropyridin-3-ylmethyl)-2-(8-oxa-3-aza-bicyclo[3.2.1]oct-3-yl)-8-trifluoromethyl-6,7,8,9-tetrahydropyrimido[1,2-a]pyrimidin-4-one (S)-9-Isoxazol-3-ylmethyl-2-(8-oxa-3-aza-bicyclo[3.2.1]oct-3-yl)-8-trifluoromethyl-6,7,8,9-tetrahydropyrimido[1,2-a]pyrimidin-4-one (S)-2-(8-Oxa-3-aza-bicyclo[3.2.1]oct-3-yl)-9-(2-oxo-2-pyridin-3-ylethyl)-8-trifluoromethyl-6,7,8,9-tetrahydropyrimido[1,2-a]pyrimidin-4-one (S)-2-(8-Oxa-3-aza-bicyclo[3.2.1]oct-3-yl)-9-(2-oxo-2-pyridin-2-ylethyl)-8-trifluoromethyl-6,7,8,9-tetrahydropyrimido[1,2-a]pyrimidin-4-one (S)-2-(2-Ethylmorpholin-4-yl)-9-(2-oxo-2-pyridin-2-ylethyl)-8-trifluoromethyl-6,7,8,9-tetrahydropyrimido[1,2-a]pyrimidin-4-one,
single stereoisomer (S)-2-(2-Ethylmorpholin-4-yl)-9-(2-oxo-2-pyridin-2-ylethyl)-8-trifluoromethyl-6,7,8,9-tetrahydropyrimido[1,2-a]pyrimidin-4-one, single stereoisomer (S)-2-(2-Methylmorpholin-4-yl)-9-(2-oxo-2-pyridin-2-ylethyl)-8-trifluoromethyl-6,7,8,9-tetrahydropyrimido[1,2-a]pyrimidin-4-one, single stereoisomer (S)-2-(2-Methylmorpholin-4-yl)-9-(2-oxo-2-pyridin-2-ylethyl)-8-trifluoromethyl-6,7,8,9-tetrahydropyrimido[1,2-a]pyrimidin-4-one, single stereoisomer (S)-9-(3,5-Difluorophenyl)-2-(3-hydroxymethylmorpholin-4-yl)-8-trifluoromethyl-6,7,8,9-tetrahydropyrimido[1,2-a]pyrimidin-4-one, single stereoisomer (S)-9-(5-Chlorothiophen-2-ylmethyl)-2-(3-hydroxymethylmorpholin-4-yl)-8-trifluoromethyl-6,7,8,9-tetrahydropyrimido[1,2-a]pyrimidin-4-one, single stereoisomer (S)-9-(5-Chlorothiophen-2-ylmethyl)-2-((S)-3-methylmorpholin-4-yl)-8-trifluoromethyl-6,7,8,9-tetrahydropyrimido[1,2-a]pyrimidin-4-one (S)-2-Methyl-7-((R)-3-ethylmorpholin-4-yl)-1-(2-oxo-2-pyridin-2-ylethyl)-2-trifluoromethyl-2,3-dihydro-1H-imidazo[1,2-a]pyrimidin-5-one (S)-2-Methyl-7-((R)-3-methylmorpholin-4-yl)-1-(2-oxo-2-pyridin-3-ylethyl)-2-trifluoromethyl-2,3-dihydro-1H-imidazo[1,2-a]pyrimidin-5-one (S)-1-(2-Chloropyridin-4-ylmethyl)-2-methyl-7-((R)-3-methylmorpholin-4-yl)-2-trifluoromethyl-2,3-dihydro-1H-imidazo[1,2-a]pyrimidin-5-one (S)-2-Methyl-7-((R)-3-methylmorpholin-4-yl)-1-oxazol-5-ylmethyl-2-trifluoromethyl-2,3-dihydro-1H-imidazo[1,2-a]pyrimidin-5-one (S)-2-Methyl-7-((R)-3-methylmorpholin-4-yl)-1-oxazol-4-ylmethyl-2-trifluoromethyl-2,3-dihydro-1H-imidazo[1,2-a]pyrimidin-5-one (S)-1-(2-Chloropyridin-4-ylmethyl)-6-fluoro-2-methyl-7-((R)-3-methyl morpholin-4-yl)-2-trifluoromethyl-2,3-dihydro-1H-imidazo[1,2-a]pyrimidin-5-one (S)-6-Fluoro-2-methyl-7-((R)-3-methylmorpholin-4-yl)-1-(3-methyl-2-oxobutyl)-2-trifluoromethyl-2,3-dihydro-1H-imidazo[1,2-a]pyrimidin-5-one (S)-6-Fluoro-2-methyl-7-((R)-3-methylmorpholin-4-yl)-1-[2-oxo-2-(tetrahydropyran-4-yl)ethyl]-2-trifluoromethyl-2,3-dihydro-1H-imidazo[1,2-a]pyrimidin-5-one (S)-1-(2-Cyclopropyl-2-oxoethyl)-6-fluoro-2-methyl-7-((R)-3-methylmorpholin-4-yl)-2-trifluoromethyl-2,3-dihydro-1H-imidazo[1,2-a]pyrimidin-5-one (S)-2-Methyl-7-((R)-3-Methylmorpholin-4-yl)-1-(3-methyl-2-oxobutyl)-2-trifluoromethyl-2,3-dihydro-1H-imidazo[1,2-a]pyrimidin-5-one (S)-6-Fluoro-2-methyl-7-((R)-3-methylmorpholin-4-yl)-1-(2-oxo-2-pyridin-3-ylethyl)-2-trifluoromethyl-2,3-dihydro-1H-imidazo[1,2-a]pyrimidin-5-one (S)-2-Methyl-7-((R)-3-methylmorpholin-4-yl)-1-[2-oxo-2-(tetrahydropyran-4-yl)ethyl]-2-trifluoromethyl-2,3-dihydro-1H-imidazo[1,2-a]pyrimidin-5-one (S)-9-Benzyl-2-(2-methylmorpholin-4-yl)-8-trifluoromethyl-6,7,8,9-tetrahydropyrimido[1,2-a]pyrimidin-4-one, single stereoisomer (S)-9-Benzyl-2-(2-methylmorpholin-4-yl)-8-trifluoromethyl-6,7,8,9-tetrahydropyrimido[1,2-a]pyrimidin-4-one, single stereoisomer (S)-9-Benzyl-2-(2-fluoromethylmorpholin-4-yl)-8-trifluoromethyl-6,7,8,9-tetrahydropyrimido[1,2-a]pyrimidin-4-one (S)-9-Benzyl-2-(2-fluoromethylmorpholin-4-yl)-8-trifluoromethyl-6,7,8,9-tetrahydropyrimido[1,2-a]pyrimidin-4-one, single stereoisomer (S)-9-Benzyl-2-(2-fluoromethylmorpholin-4-yl)-8-trifluoromethyl-6,7,8,9-terahydropyrimido[1,2-a]pyrimidin-4-one, single stereoisomer N-Methoxy-N-methyl-2-[(S)-8-((R)-3-methylmorpholin-4-yl)-6-oxo-2-trifluoromethyl-3,4-dihydro-2H,6H-pyrimido[1,2-a]pyrimidin-1-yl]acetamide N-Methoxy-2-[(S)-8-((R)-3-methylmorpholin-4-yl)-6-oxo-2-trifluoromethyl-3,4-dihydro-2H,6H-pyrimido[1,2-a]pyrimidin-1-yl]acetamide (S)-2-((R)-3-methylmorpholin-4-yl)-9-pyridin-4-yl-8-trifluoromethyl-6,7,8,9-tetrahydropyrimido[1,2-a]pyrimidin-4-one (S)-6-Fluoro-2-methyl-7-((R)-3-methylmorpholin-4-yl)-1-(2-oxo-2-pyridin-2-ylethyl)-2-trifluoromethyl-2,3-dihydro-1H-imidazo[1,2-a]pyrimidin-5-one (S)-9-(2-Hydroxy-2-methylpropyl)-8-methyl-2-((R)-3-methylmorpholin-4-yl)-8-trifluoromethyl-6,7,8,9-tetrahydropyrimido[1,2-a]pyrimidin-4-one (S)-9-(5-Isopropyl-[1,2,4]oxadiazol-3-ylmethyl)-2-((R)-3-methylmorpholin-4-yl)-8-trifluoromethyl-6,7,8,9-tetrahydropyrimido[1,2-a]pyrimidin-4-one (S)-9-(5-Cyclopropyl-[1,2,4]oxadiazol-3-ylmethyl)-2-((R)-3-methyl morpholin-4-yl)-8-trifluoromethyl-6,7,8,9-tetrahydropyrimido[1,2-a]pyrimidin-4-one (S)-9-(5-tert-Butyl-[1,2,4]oxadiazol-3-ylmethyl)-2-((R)-3-methylmorpholin-4-yl)-8-trifluoromethyl-6,7,8,9-tetrahydropyrimido[1,2-a]pyrimidin-4-one (S)-3-Fluoro-9-(2-hydroxyethyl)-2-((R)-3-methylmorpholin-4-yl)-8-trifluoromethyl-6,7,8,9-tetrahydropyrimido[1,2-a]pyrimidin-4-one (S)-9-((S)-2-Hydroxypropyl)-2-((R)-3-methylmorpholin-4-yl)-8-trifluoromethyl-6,7,8,9-tetrahydropyrimido[1,2-a]pyrimidin-4-one (S)-9-((S)-2-Methoxy-2-phenylethyl)-2-(1R,5S)-8-oxa-3-aza-bicyclo[3.2.1]oct-3-yl-8-trifluoromethyl-6,7,8,9-tetrahydropyrimido[1,2-a]pyrimidin-4-one (S)-6-Fluoro-2-methyl-7-((R)-3-methylmorpholin-4-yl)-1-(3-methyl-[1,2,4]oxadiazol-5-ylmethyl)-2-trifluoromethyl-2,3-dihydro-1H-imidazo[1,2-a]pyrimidin-5-one (S)-2-Methyl-7-((R)-3-methylmorpholin-4-yl)-1-(3-methyl-[1,2,4]oxadiazol-5-ylmethyl)-2-trifluoromethyl-2,3-dihydro-1H-imidazo[1,2-a]pyrimidin-5-one (S)-9-(2-Hydroxy-2-pyridin-3-ylethyl)-2-((R)-3-methylmorpholin-4-yl)-8-trifluoromethyl-6,7,8,9-tetrahydropyrimido[1,2-a]pyrimidin-4-one, single stereoisomer (S)-9-(2-Hydroxy-2-pyridin-3-ylethyl)-2-((R)-3-methylmorpholin-4-yl)-8-trifluoromethyl-6,7,8,9-tetrahydropyrimido[1,2-a]pyrimidin-4-one, single stereoisomer (S)-8-Methyl-2-((R)-3-methylmorpholin-4-yl)-9-(5-methyl-[1,2,4]oxadiazol-3-ylmethyl)-8-trifluoromethyl-6,7,8,9-tetrahydropyrimido[1,2-a]pyrimidin-4-one (S)-9-(2-Hydroxy-2-pyridin-2-ylethyl)-2-((R)-3-methylmorpholin-4-yl)-8-trifluoromethyl-6,7,8,9-tetrahydropyrimido[1,2-a]pyrimidin-4-one, single stereoisomer (S)-9-(2-Hydroxy-2-pyridin-2-ylethyl)-2-((R)-3-methylmorpholin-4-yl)-8-trifluoromethyl-6,7,8,9-tetrahydropyrimido[1,2-a]pyrimidin-4-one (S)-9-(2-Difluoromethyl-2H-pyrazol-3-ylmethyl)-8-methyl-2-((R)-3-methylmorpholin-4-yl)-8-trifluoromethyl-6,7,8,9-tetrahydropyrimido[1,2-a]pyrimidin-4-one (S)-9-Isoxazol-3-ylmethyl-8-methyl-2-((R)-3-methylmorpholin-4-yl)-8-trifluoromethyl-6,7,8,9-tetrahydropyrimido[1,2-a]pyrimidin-4-one (S)-2-((R)-3-Methylmorpholin-4-yl)-9-pyridin-4-ylmethyl-8-trifluoromethyl-6,7,8,9-tetrahydropyrimido[1,2-a]pyrimidin-4-one (S)-2-((R)-3-Methylmorpholin-4-yl)-9-pyridin-3-ylmethyl-8-trifluoromethyl-6,7,8,9-tetrahydropyrimido[1,2-a]pyrimidin-4-one (S)-2-((R)-3-Methylmorpholin-4-yl)-9-pyridin-2-ylmethyl-8-trifluoromethyl-6,7,8,9-tetrahydropyrimido[1,2-a]pyrimidin-4-one (S)-9-[2-(4-Fluorophenyl)ethyl]-2-((R)-3-methylmorpholin-4-yl)-8-trifluoromethyl-6,7,8,9-tetrahydropyrimido[1,2-a]pyrimidin-4-one (S)-2-((R)-3-Methylmorpholin-4-yl)-9-(2-pyridin-2-ylethyl)-8-trifluoromethyl-6,7,8,9-tetrahydropyrimido[1,2-a]pyrimidin-4-one (S)-9-(2-Fluoropyridin-3-ylmethyl)-2-((R)-3-methylmorpholin-4-yl)-8-trifluoromethyl-6,7,8,9-tetrahydropyrimido[1,2-a]pyrimidin-4-one N,N-Dimethyl-2-[(S)-8-((R)-3-methylmorpholin-4-yl)-6-oxo-2-trifluoromethyl-3,4-dihydro-2H,6H-pyrimido[1,2-a]pyrimidin-1-yl]acetamide N-Methyl-2-[(S)-8-((R)-3-methylmorpholin-4-yl)-6-oxo-2-trifluoromethyl-3,4-dihydro-2H,6H-pyrimido[1,2-a]pyrimidin-1-yl]acetamide (S)-9-(6-Fluoropyridin-2-ylmethyl)-2-((R)-3-methylmorpholin-4-yl)-8-trifluoromethyl-6,7,8,9-tetrahydropyrimido[1,2-a]pyrimidin-4-one (S)-9-(2-Isopropoxypyridin-4-ylmethyl)-2-((R)-3-methylmorpholin-4-yl)-8-trifluoromethyl-6,7,8,9-tetrahydropyrimido[1,2-a]pyrimidin-4-one (S)-9-(3-Isopropyl-[1,2,4]oxadiazol-5-ylmethyl)-2-((R)-3-methylmorpholin-4-yl)-8-trifluoromethyl-6,7,8,9-tetrahydropyrimido[1,2-a]pyrimidin-4-one (S)-9-(3-Cyclopropyl-[1,2,4]oxadiazol-5-ylmethyl)-2-((R)-3-methylmorpholin-4-yl)-8-trifluoromethyl-6,7,8,9-tetrahydropyrimido[1,2-a]pyrimidin-4-one (S)-9-(3-tert-Butyl-[1,2,4]oxadiazol-5-ylmethyl)-2-((R)-3-methylmorpholin-4-yl)-8-trifluoromethyl-6,7,8,9-tetrahydropyrimido[1,2-a]pyrimidin-4-one (S)-9-(6-Isopropoxypyridin-3-ylmethyl)-2-((R)-3-methylmorpholin-4-yl)-8-trifluoromethyl-6,7,8,9-tetrahydropyrimido[1,2-a]pyrimidin-4-one (S)-9-(2-Isopropoxypyridin-3-ylmethyl)-2-((R)-3-methylmorpholin-4-yl)-8-trifluoromethyl-6,7,8,9-tetrahydropyrimido[1,2-a]pyrimidin-4-one (S)-2-((R)-3-Methylmorpholin-4-yl)-9-thiazol-2-ylmethyl-8-trifluoromethyl-6,7,8,9-tetrahydropyrimido[1,2-a]pyrimidin-4-one (S)-3-Fluoro-2-((R)-3-methylmorpholin-4-yl)-9-thiazol-2-ylmethyl-8-trifluoromethyl-6,7,8,9-tetrahydropyrimido[1,2-a]pyrimidin-4-one (S)-2-((R)-3-Methylmorpholin-4-yl)-9-(2-oxo-2-piperidin-1-ylethyl)-8-trifluoromethyl-6,7,8,9-tetrahydropyrimido[1,2-a]pyrimidin-4-one (S)-2-((R)-3-methylmorpholin-4-yl)-9-(2-morpholin-4-yl-2-oxoethyl)-8-trifluoromethyl-6,7,8,9-tetrahydropyrimido[1,2-a]pyrimidin-4-one (S)-3-Fluoro-2-((R)-3-Methylmorpholin-4-yl)-9-(2-morpholin-4-yl-2-oxoethyl)-8-trifluoromethyl-6,7,8,9-tetrahydropyrimido[1,2-a]pyrimidin-4-one 2-[(S)-8-((R)-3-Methylmorpholin-4-yl)-6-oxo-2-trifluoromethyl-3,4-dihydro-2H,6H-pyrimido[1,2-a]pyrimidin-1-yl]-N-phenylacetamide (S)-3-Fluoro-2-((R)-3-methylmorpholin-4-yl)-9-(2-oxo-2-piperidin-1-ylethyl)-8-trifluoromethyl-6,7,8,9-tetrahydropyrimido[1,2-a]pyrimidin-4-one (S)-9-Acetyl-2-((R)-3-methylmorpholin-4-yl)-8-trifluoromethyl-6,7,8,9-tetrahydropyrimido[1,2-a]pyrimidin-4-one (S)-8-Methyl-2-((R)-3-methylmorpholin-4-yl)-9-oxazol-2-ylmethyl-8-trifluoromethyl-6,7,8,9-tetrahydropyrimido[1,2-a]pyrimidin-4-one (S)-2-Methyl-7-((R)-3-methylmorpholin-4-yl)-1-(5-methyl-[1,2,4]oxadiazol-3-ylmethyl)-2-trifluoromethyl-2,3-dihydro-1H-imidazo[1,2-a]pyrimidin-5-one (S)-9-(2-Cyclopropyl-2-oxoethyl)-2-((R)-3-methylmorpholin-4-yl)-8-trifluoromethyl-6,7,8,9-tetrahydropyrimido[1,2-a]pyrimidin-4-one (S)-2-((R)-3-Methylmorpholin-4-yl)-9-(2-oxo-2-thiazol-2-ylethyl)-8-trifluoromethyl-6,7,8,9-tetrahydropyrimido[1,2-a]pyrimidin-4-one

[(S)-8-((R)-3-Methylmorpholin-4-yl)-6-oxo-2-trifluoromethyl-3,4-dihydro-2H,6H-pyrimido[1,2-a]pyrimidin-1-yl] acetic acid cyclopentyl ester (S)-9-(2-Cyclopentyl-2-oxoethyl)-2-((R)-3-Methylmorpholin-4-yl)-8-trifluoromethyl-6,7,8,9-tetrahydropyrimido[1,2-a]pyrimidin-4-one (S)-2-((R)-3-Methylmorpholin-4-yl)-9-[2-oxo-2-(tetrahydropyran-4-yl)ethyl]-8-trifluoromethyl-6,7,8,9-tetrahydropyrimido[1,2-a]pyrimidin-4-one (S)-3-Fluoro-9-(5-isopropyl-[1,2,4]oxadiazol-3-ylmethyl)-2-((R)-3-methylmorpholin-4-yl)-8-trifluoromethyl-6,7,8,9-tetrahydropyrimido[1,2-a]pyrimidin-4-one (S)-9-(5-Cyclopropyl-[1,2,4]oxadiazol-3-ylmethyl)-3-fluoro-2-((R)-3-methylmorpholin-4-yl)-8-trifluoromethyl-6,7,8,9-tetrahydropyrimido[1,2-a]pyrimidin-4-one (S)-3-Fluoro-9-(3-isopropyl-[1,2,4]oxadiazol-5-ylmethyl)-2-((R)-3-methylmorpholin-4-yl)-8-trifluoromethyl-6,7,8,9-tetrahydropyrimido[1,2-a]pyrimidin-4-one (S)-9-(3-Cyclopropyl-[1,2,4]oxadiazol-5-ylmethyl)-3-fluoro-2-((R)-3-methylmorpholin-4-yl)-8-trifluoromethyl-6,7,8,9-tetrahydropyrimido[1,2-a]pyrimidin-4-one (S)-9-(3-tert-Butyl-[1,2,4]oxadiazol-5-ylmethyl)-3-fluoro-2-((R)-3-methylmorpholin-4-yl)-8-trifluoromethyl-6,7,8,9-tetrahydropyrimido[1,2-a]pyrimidin-4-one (S)-3-Fluoro-2-((R)-3-methylmorpholin-4-yl)-8-trifluoromethyl-9-(3-trifluoromethyl-[1,2,4]oxadiazol-5-ylmethyl)-6,7,8,9-tetrahydropyrimido[1,2-a]pyrimidin-4-one (S)-8-Methyl-2-((R)-3-methylmorpholin-4-yl)-9-(3-methyl-2-oxobutyl)-8-trifluoromethyl-6,7,8,9-tetrahydropyrimido[1,2-a]pyrimidin-4-one (S)-9-[2-(1-Methylcyclopentyl)-2-oxoethyl]-2-((R)-3-methylmorpholin-4-yl)-8-trifluoromethyl-6,7,8,9-tetrahydropyrimido[1,2-a]pyrimidin-4-one

[(S)-8-((R)-3-Methylmorpholin-4-yl)-6-oxo-2-trifluoromethyl-3,4-dihydro-2H,6H-pyrimido[1,2-a]pyrimidin-1-yl] acetic acid isopropyl ester (S)-9-(3,3-Dimethyl-2-oxobutyl)-2-((R)-3-methylmorpholin-4-yl)-8-trifluoromethyl-6,7,8,9-tetrahydropyrimido[1,2-a]pyrimidin-4-one (S)-2-((R)-3-Methylmorpholin-4-yl)-9-(2-oxopropyl)-8-trifluoromethyl-6,7,8,9-tetrahydropyrimido[1,2-a]pyrimidin-4-one (S)-9-(2-Fluoropyridin-4-ylmethyl)-2-((R)-3-methylmorpholin-4-yl)-8-trifluoromethyl-6,7,8,9-tetrahydropyrimido[1,2-a]pyrimidin-4-one (S)-9-(2-Cyclohexyl-2-oxoethyl)-2-((R)-3-methylmorpholin-4-yl)-8-trifluoromethyl-6,7,8,9-tetrahydropyrimido[1,2-a]pyrimidin-4-one (S)-2-((R)-3-Methylmorpholin-4-yl)-9-pyridazin-4-ylmethyl-8-trifluoromethyl-6,7,8,9-tetrahydropyrimido[1,2-a]pyrimidin-4-one

[(S)-8-((R)-3-Methylmorpholin-4-yl)-6-oxo-2-trifluoromethyl-3,4-dihydro-2H,6H-pyrimido[1,2-a]pyrimidin-1-yl] acetic acid tert-butyl ester 2-{2-[(S)-8-((R)-3-Methylmorpholin-4-yl)-6-oxo-2-trifluoromethyl-3,4-dihydro-2H,6H-pyrimido[1,2-a]pyrimidin-1-yl]acetyl}pyrrolidine-1-carboxylic acid tert-butyl ester

[(S)-8-((R)-3-Methylmorpholin-4-yl)-6-oxo-2-trifluoromethyl-3,4-dihydro-2H,6H-pyrimido[1,2-a]pyrimidin-1-yl] acetic acid methyl ester 2-[(S)-8-((R)-3-Methylmorpholin-4-yl)-6-oxo-2-trifluoromethyl-3,4-dihydro-2H,6H-pyrimido[1,2-a]pyrimidin-1-yl] acetamide (S)-2-((R)-3-Methylmorpholin-4-yl)-9-(4H-[1,2,4]triazol-3-ylmethyl)-8-trifluoromethyl-6,7,8,9-tetrahydropyrimido[1,2-a]pyrimidin-4-one (S)-2-((R)-3-Methylmorpholin-4-yl)-9-(2-oxo-2-piperidin-4-ylethyl)-8-trifluoromethyl-6,7,8,9-tetrahydropyrimido[1,2-a]pyrimidin-4-one (S)-9-(3-Methylbut-2-enyl)-2-((R)-3-methylmorpholin-4-yl)-8-trifluoromethyl-6,7,8,9-tetrahydropyrimido[1,2-a]pyrimidin-4-one (S)-9-(3-Fluoro-3-methylbutyl)-2-((R)-3-methylmorpholin-4-yl)-8-trifluoromethyl-6,7,8,9-tetrahydropyrimido[1,2-a]pyrimidin-4-one (S)-9-[2-(3-Methylisoxazol-4-yl)-2-oxoethyl]-2-((R)-3-methylmorpholin-4-yl)-8-trifluoromethyl-6,7,8,9-tetrahydropyrimido[1,2-a]pyrimidin-4-one (S)-2-((R)-3-Methylmorpholin-4-yl)-9-[2-oxo-2-(tetrahydrofuran-3-yl)ethyl]-8-trifluoromethyl-6,7,8,9-tetrahydropyrimido[1,2-a]pyrimidin-4-one (S)-9-(5-Methyl-[1,2,4]oxadiazol-3-ylmethyl)-2-(8-oxa-3-aza-bicyclo[3.2.1]oct-3-yl)-8-trifluoromethyl-6,7,8,9-tetrahydropyrimido[1,2-a]pyrimidin-4-one (S)-9-(2-Cyclopropyl-2-oxoethyl)-2-(8-oxa-3-aza-bicyclo[3.2.1]oct-3-yl)-8-trifluoromethyl-6,7,8,9-tetrahydropyrimido[1,2-a]pyrimidin-4-one (S)-9-(3-Methyl-2-oxobutyl)-2-(8-oxa-3-aza-bicyclo[3.2.1]oct-3-yl)-8-trifluoromethyl-6,7,8,9-tetrahydropyrimido[1,2-a]pyrimidin-4-one (S)-9-(2-Cyclopropyl-2-oxoethyl)-3-fluoro-2-(8-oxa-3-aza-bicyclo[3.2.1]oct-3-yl)-8-trifluoromethyl-6,7,8,9-tetrahydropyrimido[1,2-a]pyrimidin-4-one (S)-3-Fluoro-9-(3-methyl-2-oxobutyl)-2-(8-oxa-3-aza-bicyclo[3.2.1]oct-3-yl)-8-trifluoromethyl-6,7,8,9-tetrahydropyrimido[1,2-a]pyrimidin-4-one (S)-3-Fluoro-9-(5-methyl-[1,2,4]oxadiazol-3-ylmethyl)-2-(8-oxa-3-aza-bicyclo[3.2.1]oct-3-yl)-8-trifluoromethyl-6,7,8,9-tetrahydropyrimido[1,2-a]pyrimidin-4-one (S)-2-((R)-3-Methylmorpholin-4-yl)-9-(4-methyl-2-oxopentyl)-8-trifluoromethyl-6,7,8,9-tetrahydropyrimido[1,2-a]pyrimidin-4-one (S)-2-((S)-3-Methylmorpholin-4-yl)-9-(3-methyl-2-oxobutyl)-8-trifluoromethyl-6,7,8,9-tetrahydropyrimido[1,2-a]pyrimidin-4-one (S)-3-Fluoro-2-((S)-3-methylmorpholin-4-yl)-9-(3-methyl-2-oxobutyl)-8-trifluoromethyl-6,7,8,9-tetrahydropyrimido[1,2-a]pyrimidin-4-one (S)-3-Fluoro-2-((R)-3-methylmorpholin-4-yl)-9-(5-methyl-2-oxohexyl)-8-trifluoromethyl-6,7,8,9-tetrahydropyrimido[1,2-a]pyrimidin-4-one (S)-3-Fluoro-2-((R)-3-methylmorpholin-4-yl)-9-(4-methyl-2-oxopentyl)-8-trifluoromethyl-6,7,8,9-tetrahydropyrimido[1,2-a]pyrimidin-4-one (S)-9-(3-ethyl-2-oxopentyl)-2-((R)-3-methylmorpholin-4-yl)-8-trifluoromethyl-6,7,8,9-tetrahydropyrimido[1,2-a]pyrimidin-4-one (S)-9-(3-ethyl-2-oxopentyl)-3-fluoro-2-((R)-3-methylmorpholin-4-yl)-8-trifluoromethyl-6,7,8,9-tetrahydropyrimido[1,2-a]pyrimidin-4-one

[(S)-7-Fluoro-8-((R)-3-methylmorpholin-4-yl)-6-oxo-2-trifluoromethyl-3,4-dihydro-2H,6H-pyrimido[1,2-a]pyrimidin-1-yl]acetic acid methyl ester (S)-9-sec-Butyl-2-((R)-3-methylmorpholin-4-yl)-8-trifluoromethyl-6,7,8,9-tetrahydropyrimido[1,2-a]pyrimidin-4-one, single stereoisomer (S)-9-sec-Butyl-2-((R)-3-methylmorpholin-4-yl)-8-trifluoromethyl-6,7,8,9-tetrahydropyrimido[1,2-a]pyrimidin-4-one, single stereoisomer (S)-9-(2-Hydroxy-3-methylbutyl)-2-((R)-3-methylmorpholin-4-yl)-8-trifluoromethyl-6,7,8,9-tetrahydropyrimido[1,2-a]pyrimidin-4-one (S)-9-(2-Hydroxy-3-methylbutyl)-2-((R)-3-methylmorpholin-4-yl)-8-trifluoromethyl-6,7,8,9-tetrahydropyrimido[1,2-a]pyrimidin-4-one (S)-9-(2-Methoxy-3-methylbutyl)-2-((R)-3-methylmorpholin-4-yl)-8-trifluoromethyl-6,7,8,9-tetrahydropyrimido[1,2-a]pyrimidin-4-one, single stereoisomer (S)-9-(2-Methoxy-3-methylbutyl)-2-((R)-3-methylmorpholin-4-yl)-8-trifluoromethyl-6,7,8,9-tetrahydropyrimido[1,2-a]pyrimidin-4-one single stereoisomer (S)-2-((R)-3-Methylmorpholin-4-yl)-9-(5-methyl-2-oxohexyl)-8-trifluoromethyl-6,7,8,9-tetrahydropyrimido[1,2-a]pyrimidin-4-one (S)-2-((R)-3-Methylmorpholin-4-yl)-9-(3-methyl-2-oxopentyl)-8-trifluoromethyl-6,7,8,9-tetrahydropyrimido[1,2-a]pyrimidin-4-one (S)-2-((R)-3-Methylmorpholin-4-yl)-8-trifluoromethyl-9-(3-trifluoromethyl-[1,2,4]oxadiazol-5-ylmethyl)-6,7,8,9-tetrahydropyrimido[1,2-a]pyrimidin-4-one (S)-3-Fluoro-2-((R)-3-methylmorpholin-4-yl)-9-[2-(2-oxa-6-azaspiro[3.3]hept-6-yl)-2-oxoethyl]-8-trifluoromethyl-6,7,8,9-tetrahydropyrimido[1,2-a]pyrimidin-4-one (S)-3-Fluoro-9-[2-(5-methylisoxazol-3-yl)-2-oxoethyl]-2-((R)-3-methylmorpholin-4-yl)-8-trifluoromethyl-6,7,8,9-tetrahydropyrimido[1,2-a]pyrimidin-4-one (S)-9-(2-Fluoro-2-phenylethyl)-2-((R)-3-methylmorpholin-4-yl)-8-trifluoromethyl-6,7,8,9-tetrahydropyrimido[1,2-a]pyrimidin-4-one (S)-3-Fluoro-9-isoxazol-3-ylmethyl-2-((R)-3-methylmorpholin-4-yl)-8-trifluoromethyl-6,7,8,9-tetrahydropyrimido[1,2-a]pyrimidin-4-one (S)-9-(2-Difluoromethyl-2H-pyrazol-3-ylmethyl)-3-fluoro-2-((R)-3-methylmorpholin-4-yl)-8-trifluoromethyl-6,7,8,9-tetrahydropyrimido[1,2-a]pyrimidin-4-one 9-Isoxazol-3-ylmethyl-8,8-dimethyl-2-((R)-3-methylmorpholin-4-yl)-6,7,8,9-tetrahydropyrimido[1,2-a]pyrimidin-4-one (S)-3-Fluoro-9-(3-methylisoxazol-5-ylmethyl)-2-((R)-3-methylmorpholin-4-yl)-8-trifluoromethyl-6,7,8,9-tetrahydropyrimido[1,2-a]pyrimidin-4-one (S)-9-(2-Isopropoxyethyl)-2-((R)-3-methylmorpholin-4-yl)-8-trifluoromethyl-6,7,8,9-tetrahydropyrimido[1,2-a]pyrimidin-4-one (S)-2-((R)-3-Methylmorpholin-4-yl)-9-pyridin-3-yl-8-trifluoromethyl-6,7,8,9-tetrahydropyrimido[1,2-a]pyrimidin-4-one (S)-9-(6-Cyclopropylpyridin-3-yl)-2-((R)-3-methylmorpholin-4-yl)-8-trifluoromethyl-6,7,8,9-tetrahydropyrimido[1,2-a]pyrimidin-4-one (S)-2-((R)-3-Methylmorpholin-4-yl)-9-{2-[2-((R)-3-methylmorpholin-4-yl)-pyridin-4-yl]-2-oxoethyl}-8-trifluoromethyl-6,7,8,9-tetrahydropyrimido[1,2-a]pyrimidin-4-one (S)-9-{2-Cyclopropyl-2-[(Z)-hydroxyimino]ethyl}-2-((R)-3-methylmorpholin-4-yl)-8-trifluoromethyl-6,7,8,9-tetrahydropyrimido[1,2-a]pyrimidin-4-one, isomer 1 of undetermined configuration Z or E (S)-9-{2-Cyclopropyl-2-[(E)-hydroxyimino]ethyl}-2-((R)-3-methylmorpholin-4-yl)-8-trifluoromethyl-6,7,8,9-tetrahydropyrimido[1,2-a]pyrimidin-4-one, isomer 2 of undetermined configuration Z or E (S)-9-{2-Cyclopropyl-2-[(E)-methoxyimino]ethyl}-2-((R)-3-methylmorpholin-4-yl)-8-trifluoromethyl-6,7,8,9-tetrahydropyrimido[1,2-a]pyrimidin-4-one, isomer 1 of undetermined configuration Z or E (S)-9-{2-Cyclopropyl-2-[(Z)-methoxyimino]ethyl}-2-((R)-3-methylmorpholin-4-yl)-8-trifluoromethyl-6,7,8,9-tetrahydropyrimido[1,2-a]pyrimidin-4-one, isomer 2 of undetermined configuration Z or E (S)-9-(2-Cyclopropyloxetan-2-ylmethyl)-2-((R)-3-methylmorpholin-4-yl)-8-trifluoromethyl-6,7,8,9-tetrahydropyrimido[1,2-a]pyrimidin-4-one, diastereoisomer 1 of undetermined absolute configuration on the asymmetric carbon of the side chain (S)-9-(2-Cyclopropyloxetan-2-ylmethyl)-2-((R)-3-methylmorpholin-4-yl)-8-trifluoromethyl-6,7,8,9-tetrahydropyrimido[1,2-a]pyrimidin-4-one, diastereoisomer 2 of undetermined absolute configuration on the asymmetric carbon of the side chain (S)-2-((R)-3-Methylmorpholin-4-yl)-9-[2-(4-methyltetrahydropyran-4-yl)-2-oxoethyl]-8-trifluoromethyl-6,7,8,9-tetrahydropyrimido[1,2-a]pyrimidin-4-one (S)-9-[2-(5-Methylisoxazol-3-yl)-2-oxoethyl]-2-((R)-3-methylmorpholin-4-yl)-8-trifluoromethyl-6,7,8,9-tetrahydropyrimido[1,2-a]pyrimidin-4-one (S)-9-(2-Chlorothiazol-5-ylmethyl)-2-((3R,5R)-3,5-dimethylmorpholin-4-yl)-8-trifluoromethyl-6,7,8,9-tetrahydropyrimido[1,2-a]pyrimidin-4-one (S)-2-((3R,5R)-3,5-Dimethylmorpholin-4-yl)-9-isoxazol-3-ylmethyl-8-trifluoromethyl-6,7,8,9-tetrahydropyrimido[1,2-a]pyrimidin-4-one (S)-3-Fluoro-9-(2-isoxazolidin-2-yl-2-oxoethyl)-2-((R)-3-methylmorpholin-4-yl)-8-trifluoromethyl-6,7,8,9-tetrahydropyrimido[1,2-a]pyrimidin-4-one (S)-9-(2-Hydroxyethyl)-2-((R)-3-methylmorpholin-4-yl)-8-trifluoromethyl-6,7,8,9-tetrahydropyrimido[1,2-a]pyrimidin-4-one (S)-3-Fluoro-2-((R)-3-methylmorpholin-4-yl)-9-[2-(6-oxa-1-azaspiro[3.3]hept-1-yl)-2-oxoethyl]-8-trifluoromethyl-6,7,8,9-tetrahydropyrimido[1,2-a]pyrimidin-4-one (S)-3-Fluoro-2-((R)-3-methylmorpholin-4-yl)-9-(2-[1,2]ox-azinan-2-yl-2-oxoethyl)-8-trifluoromethyl-6,7,8,9-tetra-hydropyrimido[1,2-a]pyrimidin-4-one (S)-2-((R)-3-Methylmorpholin-4-yl)-9-(2-[1,2]oxazinan-2-yl-2-oxoethyl)-8-trifluoromethyl-6,7,8,9-tetrahydropy-rimido[1,2-a]pyrimidin-4-one (S)-9-(2-Isoxazolidin-2-yl-2-oxoethyl)-2-((R)-3-methyl-morpholin-4-yl)-8-trifluoromethyl-6,7,8,9-tetrahydropy-rimido[1,2-a]pyrimidin-4-one (S)-2-(2-Methylmorpholin-4-yl)-9-(3-methyl-2-oxobutyl)-8-trifluoromethyl-6,7,8,9-tetrahydropyrimido[1,2-a]py-rimidin-4-one, diastereoisomer 1 of undetermined absolute configuration on the asymmetric carbon of the morpholine (S)-9-(2-Cyclopropyl-2-oxoethyl)-3-fluoro-2-((S)-3-meth-ylmorpholin-4-yl)-8-trifluoromethyl-6,7,8,9-tetrahydro-pyrimido[1,2-a]pyrimidin-4-one (S)-9-(2-Cyclopropyl-2-oxoethyl)-3-fluoro-2-(2-methyl-morpholin-4-yl)-8-trifluoromethyl-6,7,8,9-tetrahydropy-rimido[1,2-a]pyrimidin-4-one, diastereoisomer 1 of undetermined absolute configuration on the asymmetric carbon of the morpholine (S)-9-(2-Fluoro-3-methylbutyl)-2-((R)-3-methylmorpholin-4-yl)-8-trifluoromethyl-6,7,8,9-tetrahydropyrimido[1,2-a]pyrimidin-4-one, diastereoisomer 1 of undetermined absolute configuration on the asymmetric carbon of the 2-fluoro-3-methylbutyl chain (S)-9-(2-Fluoro-3-methylbutyl)-2-((R)-3-methylmorpholin-4-yl)-8-trifluoromethyl-6,7,8,9-tetrahydropyrimido[1,2-a]pyrimidin-4-one, diastereoisomer 2 of undetermined absolute configuration on the asymmetric carbon of the 2-fluoro-3-methylbutyl chain (S)-9-(2-Cyclopropyl-2-fluoroethyl)-2-((R)-3-methylmor-pholin-4-yl)-8-trifluoromethyl-6,7,8,9-tetrahydropy-rimido[1,2-a]pyrimidin-4-one, diastereoisomer 1 of undetermined absolute configuration on the asymmetric carbon of the 2-cyclopropyl-2-fluoroethyl chain (S)-9-(2-Cyclopropyl-2-fluoroethyl)-2-((R)-3-methylmor-pholin-4-yl)-8-trifluoromethyl-6,7,8,9-tetrahydropy-rimido[1,2-a]pyrimidin-4-one, diastereoisomer 2 of undetermined absolute configuration on the asymmetric carbon of the 2-cyclopropyl-2-fluoroethyl chain (S)-8-Methyl-2-((R)-3-methylmorpholin-4-yl)-9-(2-oxopro-pyl)-8-trifluoromethyl-6,7,8,9-tetrahydropyrimido[1,2-a]pyrimidin-4-one (S)-3-Fluoro-9-(2-fluoro-3-methylbutyl)-2-((R)-3-methyl-morpholin-4-yl)-8-trifluoromethyl-6,7,8,9-tetrahydropy-rimido[1,2-a]pyrimidin-4-one, diastereoisomer 1 of undetermined absolute configuration on the asymmetric carbon of the 2-fluoro-3-methylbutyl chain (S)-3-Fluoro-9-(2-fluoro-3-methylbutyl)-2-((R)-3-methyl-morpholin-4-yl)-8-trifluoromethyl-6,7,8,9-tetrahydropy-rimido[1,2-a]pyrimidin-4-one, diastereoisomer 2 of undetermined absolute configuration on the asymmetric carbon of the 2-fluoro-3-methylbutyl chain (S)-2-((R)-3-Methylmorpholin-4-yl)-9-[2-(1-oxa-6-azaspiro[3.3]hept-6-yl)-2-oxoethyl]-8-trifluoromethyl-6,7,8,9-tet-rahydropyrimido[1,2-a]pyrimidin-4-one (S)-9-(2-Cyclopropyl-2-fluoroethyl)-3-fluoro-2-((R)-3-methylmorpholin-4-yl)-8-trifluoromethyl-6,7,8,9-tetra-hydropyrimido[1,2-a]pyrimidin-4-one, diastereoisomer 1 of undetermined absolute configuration on the asymmet-ric carbon of the 2-cyclopropyl-2-fluoroethyl chain (S)-9-(2-Cyclopropyl-2-fluoroethyl)-3-fluoro-2-((R)-3-methylmorpholin-4-yl)-8-trifluoromethyl-6,7,8,9-tetra-hydropyrimido[1,2-a]pyrimidin-4-one, diastereoisomer 2 of undetermined absolute configuration on the asymmet-ric carbon of the 2-cyclopropyl-2-fluoroethyl chain (S)-3-Fluoro-2-((R)-3-methylmorpholin-4-yl)-9-[2-(1-oxa-6-azaspiro[3.3]hept-6-yl)-2-oxoethyl]-8-trifluoromethyl-6,7,8,9-tetrahydropyrimido[1,2-a]pyrimidin-4-one and also the pharmaceutically acceptable addition salts with inorganic and organic acids or with inorganic and organic bases of said products of formula (I).

The invention also relates to pharmaceutical compositions containing, as active ingredient, at least one of the products of formula (I) as defined above or a pharmaceutically acceptable salt of this product or a prodrug of this product and, where appropriate, a pharmaceutically acceptable carrier.

The invention also extends to the pharmaceutical compositions containing, as active ingredient, at least one of the medicaments as defined above.

Such pharmaceutical compositions of the present invention can also, where appropriate, contain active ingredients of other anti-mitotic medicaments, such as, in particular, those based on taxol, cisplatin, DNA-intercalating agents, and the like.

These pharmaceutical compositions can be administered orally, parenterally or locally by topical application to the skin and the mucous membranes or by intravenous or intramuscular injection.

These compositions may be solid or liquid and be in any of the pharmaceutical forms commonly used in human medicine, for instance simple or sugar-coated tablets, pills, lozenges, gel capsules, drops, granules, injectable preparations, ointments, creams or gels; they are prepared according to the usual methods. The active ingredient may be incorporated therein with excipients normally used in these pharmaceutical compositions, such as talc, gum arabic, lactose, starch, magnesium stearate, cocoa butter, aqueous or nonaqueous vehicles, fatty substances of animal or vegetable origin, paraffin derivatives, glycols, various wetting agents, dispersants or emulsifiers, or preservatives.

The usual dosage, which is variable according to the product used, the individual treated and the condition in question, can be, for example, from 0.05 to 5 g per day in adults, or preferably from 0.1 to 2 g per day.

A subject of the present invention is also the use of products of formula (I) as defined above, for preparing a medicament intended for the treatment or prevention of a disease characterized by the dysregulation of the activity of a protein or lipid kinase.

Such a medicament can in particular be intended for the treatment or prevention of a disease in a mammal.

A subject of the present invention is in particular the use of a product of formula (I) as defined above, for preparing a medicament intended for the prevention or treatment of diseases associated with an uncontrolled proliferation.

A subject of the present invention is thus quite particularly the use of a product of formula (I) as defined above, for preparing a medicament intended for the treatment or prevention of diseases in oncology, and in particular intended for the treatment of cancers. A subject of the present invention is the products of formula (I) as defined above, for use thereof in the treatment of solid or liquid tumours.

The cited products of the present invention can in particular be used for the treatment of primary tumours and/or of metastases, in particular in gastric, hepatic, renal, ovarian, colon, prostate, endometrial and lung (NSCLC and SCLC) cancers, glioblastomas, thyroid, bladder and breast cancers, in melanoma, in lymphoid or myeloid haematopoietic tumours, in sarcomas, in brain, larynx and lymphatic system cancers, bone and pancreatic cancers, and in hamartomas.

A subject of the present invention is also the use of the products of formula (I) as defined above, for preparing medicaments intended for cancer chemotherapy. A subject of the present invention is therefore the products of formula (I) as defined above, for use thereof in cancer chemotherapy, alone or in combination. The products of the present application can in particular be administered alone or in combination with chemotherapy or radiotherapy or else in combination, for example, with other therapeutic agents. Such therapeutic agents may be commonly used antitumour agents.

A therapeutic benefit can in particular be expected when administering the products of the present application in combinations with varied targeted therapies. These targeted therapies are in particular the following: i) targeted therapies which inhibit kinases or pseudo-kinases such as EGFR, HER2, HER3, PI3K, AKT, mTOR, Bcr-Abl, Kit, PDGFR or Src (QW. Fan et al., Since signaling 2010, A. Gupta et al. PNAS 2010, X Li et al. Cancer Res 2010, A Vazquez-Martin et al. PLos One 2009, Z. Wu et al. Genes Cancer 2010) ii) targeted therapies which inhibit the oestrogen receptor, the proteasome, the HDAC protein (J S Samaddar et al. Mol Cancer Ther 2008, B; Hoang et al. Mol Cancer Ther 2009, J S Carew et al. Blood 2007). A therapeutic effect can also be expected when combining the products of the present application with chemotherapy agents such as camptothecin, taxotere or 5-FU, for example; or else when combining them with radiotherapy (J Li et al. Eur J of Cancer 2010, A. Appel et al. Cancer Res 2008).

A subject of the present invention is in particular the use of a product of formula (I) as defined above, for preparing a medicament intended for the prevention or treatment of lysosomal diseases such as glycogenosis type II (or Pompe's disease) or Danon disease, for example (N. Raben et al., Autophagy 2010, B Levine et al. Cell 2008, N. Mizushima et al. Nature 2008). Such medicaments intended for the treatment of lysosomal diseases can be used alone or in combination, for example, with other therapeutic agents.

A subject of the present invention is also the use of a product of formula (I) as defined above, for preparing a medicament intended for the prevention or treatment of X-linked myotubular myopathies, Charcot-Marie-Tooth disease; where mutations of the proteins of the myotubularin family have been described (I. Vergne et al., FEBS Lett, 2010). A subject of the present invention is thus the use as defined above, in which said products of formula (I) are alone or in combination.

Among the cancers, the treatment of solid or liquid tumours, and the treatment of cancers resistant to cytotoxic agents are of interest.

The products of the present application can in particular be administered alone or in combination with chemotherapy or radiotherapy or else in combination, for example, with other therapeutic agents.

Such therapeutic agents may be commonly used antitumour agents.

As kinase inhibitors, mention may be made of butyrolactone, flavopiridol, 2(2-hydroxyethylamino)-6-benzylamino-9-methylpurine known as olomucine, sorafenib, imatinib, erlotinib, gefitinib and lapatinib. Thus, the present application relates in particular to the products of formula (I) as defined above, for use thereof as a VPS34 inhibitor.

Thus, the present application relates in particular to the products of formula (I) as defined above, for use thereof in the treatment of cancers.

Thus, the present application relates in particular to the products of formula (I) as defined above, for use thereof in the treatment of solid or liquid tumours.

Thus, the present application relates in particular to the products of formula (I) as defined above, for use thereof in the treatment of cancers resistant to cytotoxic agents.

Thus, the present application relates in particular to the products of formula (I) as defined above, for use thereof in the treatment of primary tumours and/or of metastases, in particular in gastric, hepatic, renal, ovarian, colon, prostate and lung (NSCLC and SCLC) cancers, glioblastomas, thyroid, bladder and breast cancers, in melanoma, in lymphoid or myeloid haematopoietic tumours, in sarcomas, in brain, larynx and lymphatic system cancers, bone and pancreatic cancers, and in hamartomas.

Thus, the present application relates in particular to the products of formula (I) as defined above, for use thereof in cancer chemotherapy.

Thus, the present application relates in particular to the products of formula (I) as defined above, for use thereof in cancer chemotherapy, alone or in combination.

Thus, the present application relates in particular to the products of formula (I) as defined above, for use thereof in the treatment of lysosomal diseases such as glycogenosis type II (or Pompe's disease) or Danon disease.

Thus, the present application relates in particular to the products of formula (I) as defined above, for use thereof in the treatment of X-linked myotubular myopathies and Charcot-Marie-Tooth disease.

A subject of the present invention is also, as novel industrial products, certain starting products or synthesis intermediates of formulae A, B, C, D, E, F, G, H, I, J, K, L, M, N, O, P, Q, T1, T2 and T3 as defined above.

A subject of the present invention is thus in particular, as novel industrial products, the starting products or synthesis intermediates as defined above and hereinafter:

of formulae A, B, G and N:

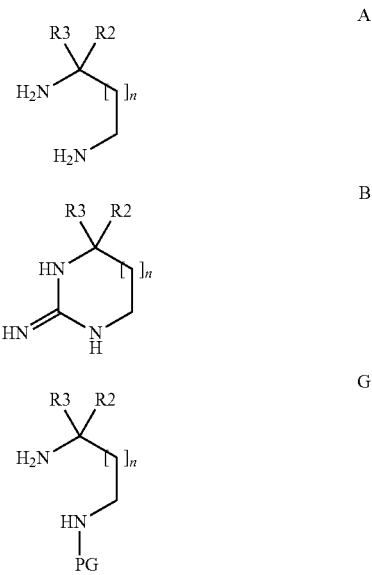

-continued

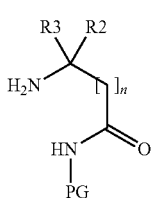
N in which n=1, one of R2 and R3 is alkyl and the other is alkyl substituted with one or more fluorine atoms, and PG is a protective group for amine;

of formulae E, F, I and J:

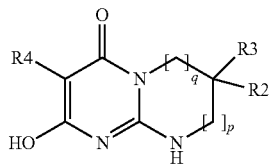
E

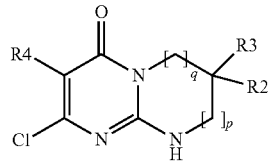
F

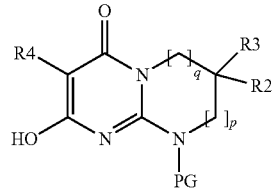
I

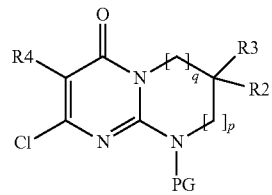
J in which q=0, one of R2 and R3 is alkyl and the other is alkyl substituted with one or more fluorine atoms, and the substituents p, PG, R1 and R4 have the definitions indicated above and hereinafter;

of formulae P and H:

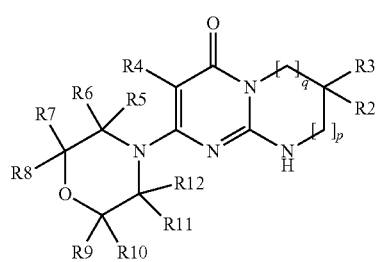
P

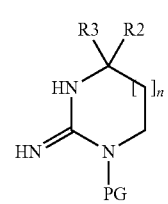
H in which the substituents n, p, q, PG, R2, R3, R4, R5, R6, R7, R8, R9, R10, R11 and R12 have the definitions indicated above and hereinafter;

of formula Q:

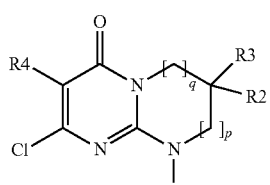
Q in which either q=0, one of R2 and R3 is alkyl and the other is alkyl substituted with one or more fluorine atoms, and the substituents p, PG, R1 and R4 have the definitions indicated above and hereinafter, or R1 is —(CH$_2$)$_m$—Ra with Ra being —CO-cycloalkyl, —CO-heterocycloalkyl, —CO—Rb, —C(Rb)=N—ORc, —CO$_2$Rd or —CONRxRy, and the substituents p, q, R2, R3 and R4 have the definitions indicated above and hereinafter.

The following examples which are products of formula (I) illustrate the invention without, however, limiting it.

The following examples which are products of formula (I) according to the present invention can be prepared according to the usual methods known to those skilled in the art, and in particular as indicated above or below, and in the schemes and Tables 1 to 10.

EXPERIMENTAL SECTION

The nomenclature of the compounds of this present invention was performed with the ACDLABS version 10.0 software.

The microwave oven used is a Biotage, Initiator™ Eight, 400 W max, 2450 MHz apparatus.

The $^1$H NMR spectra at 400 MHz and $^1$H NMR spectra at 500 MHz were carried out on a Bruker Avance 250 or Bruker Avance DRX-400 or Bruker Avance DPX-500 spectrometer with the chemical shifts (δ in ppm) in the solvent dimethyl sulfoxide-d$_6$ (DMSO-d$_6$) referenced at 2.5 ppm at the temperature of 303K.

The mass spectra (MS) were obtained either by method A or by method B.

Method A:

Waters UPLC-SQD apparatus; Ionization: positive and/or negative mode electrospray (ES+/−); Chromatographic conditions: Column: Acquity BEH C18 1.7 μm-2.1×50 mm; Solvents: A: H$_2$O (0.1% formic acid) B: CH$_3$CN (0.1% formic acid); Column temperature: 50° C.; Flow rate: 1 ml/min; Gradient (2 min): from 5% to 50% of B in 0.8 min; 1.2 min: 100% of B; 1.85 min: 100% of B; 1.95 min: 5% of B; Retention time=Tr (min).

Method B:

Waters ZQ apparatus; Ionization: positive and/or negative mode electrospray (ES+/−); Chromatographic conditions: Column: XBridge C18 2.5 μm-3×50 mm; Solvents: A: H$_2$O (0.1% formic acid) B: CH$_3$CN (0.1% formic acid); Column temperature: 70° C.; Flow rate: 0.9 ml/min; Gradient (7 min): from 5% to 100% of B in 5.3 min; 5.5 min: 100% of B; 6.3 min: 5% of B; Retention time=Tr (min).

The optical rotations (ORs) were measured on a model 341 polarimeter from Perkin Elmer. Wavelength: sodium α line (589 nm).

The intermediates of type F as defined in the schemes above, i.e. F1 to F9 defined in Table 1 below, resulting in Examples 1 to 295, can be prepared in the following way:

Intermediate F1

(S)-2-Chloro-8-(trifluoromethyl)-6,7,8,9-tetrahydro-4H-pyrimido[1,2-a]pyrimidin-4-one can be prepared in the following way.

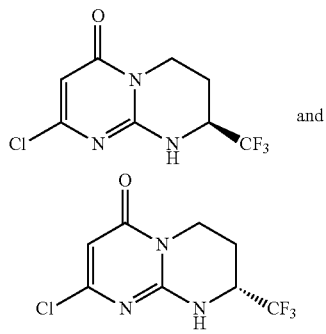

The separation of the two enantiomers of (8R,8S)-2-chloro-8-(trifluoromethyl)-6,7,8,9-tetrahydro-4H-pyrimido[1,2-a]pyrimidin-4-one (17 g) is carried out by chiral chromatography: stationary phase: Chiralpak AD; mobile phase: EtOH (20%) Heptane (80%). The laevorotatory enantiomer is concentrated so as to give 8.52 g of (R)-2-chloro-8-(trifluoromethyl)-6,7,8,9-tetrahydro-4H-pyrimido[1,2-a]pyrimidin-4-one, in the form of a white powder. The dextrorotatory enantiomer is concentrated so as to obtain 8.21 g of (S)-2-chloro-8-(trifluoromethyl)-6,7,8,9-tetrahydro-4H-pyrimido[1,2-a]pyrimidin-4-one, in the form of a white powder, the characteristics of which are the following:

Mass spectrum (method A), ES+/−: [M+H]+: m/z 254; [M−H]−: m/z 252; Tr (min)=0.51

$[\alpha]_D^{25}$ at 589 nm=+21.3+/−0.5 (MeOH)

(8R,8S)-2-Chloro-8-(trifluoromethyl)-6,7,8,9-tetrahydro-4H-pyrimido[1,2-a]pyrimidin-4-one can be prepared in the following way.

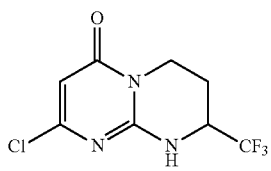 [SMILES: O=c1cc(Cl)nc2n1CCC(C(F)(F)F)N2]

60 ml of phosphorus oxychloride are added, at ambient temperature and under an argon atmosphere, to a suspension of 34 g of (8R,8S)-2-hydroxy-8-(trifluoromethyl)-6,7,8,9-tetrahydro-4H-pyrimido[1,2-a]pyrimidin-4-one in 500 ml of 1,2-dichloroethane. The mixture obtained is then heated to 65° C. After three hours of stirring at 65° C., the reaction is complete according to the verification by LC/MS. After cooling, the reaction mixture is evaporated to dryness under reduced pressure. The residue obtained is taken up in 100 ml of cold water and 400 ml of ethyl acetate. 32% sodium hydroxide is added to the mixture obtained, to pH=6. The resulting organic phase is separated and then dried over magnesium sulfate, filtered, and concentrated under reduced pressure, so as to give an orange residue. This residue is purified by chromatography on silica (eluent: CH$_2$Cl$_2$/MeOH: 97/03) so as to give 20 g of (8R,8S)-2-chloro-8-(trifluoromethyl)-6,7,8,9-tetrahydro-4H-pyrimido[1,2-a]pyrimidin-4-one, in the form of a white solid, the characteristics of which are the following:

Mass spectrum (method A), ES+/−: [M+H]+: m/z 254; [M−H]−: m/z 252; Tr (min)=0.51

(8R,8S)-2-Hydroxy-8-(trifluoromethyl)-6,7,8,9-tetrahydro-4H-pyrimido[1,2-a]pyrimidin-4-one can be prepared in the following way.

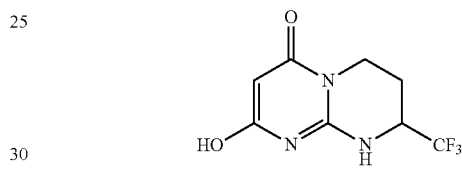

10 g of (4R,4S)-4-(trifluoromethyl)-1,4,5,6-tetrahydropyrimidin-2-ylamine hydrochloride and 10 g of sodium methoxide are added to 50 ml of diethyl malonate. The mixture obtained is brought to 100° C. for 75 minutes. The heterogeneous mixture thickens and becomes yellow, with a slight release of gas. After cooling, the reaction mixture is evaporated to dryness under reduced pressure. The residue obtained is triturated with ethyl ether. The solid formed is filtered off through a sintered glass funnel and then taken up with 20 ml of cold water. 12N hydrochloric acid is added to the thick suspension obtained, to pH=5-6. The suspension obtained is filtered through a sintered glass funnel and the insoluble matter is rinsed with ethyl ether so as to give 11.5 g of (8R,8S)-2-hydroxy-8-(trifluoromethyl)-6,7,8,9-tetrahydro-4H-pyrimido[1,2-a]pyrimidin-4-one, in the form of a white solid, the characteristics of which are the following:

Mass spectrum (method A), ES+/−: [M+H]+: m/z 236; [M−H]−: m/z 234; Tr (min)=0.26

(4R,4S)-4-(Trifluoromethyl)-1,4,5,6-tetrahydropyrimidin-2-ylamine hydrochloride can be prepared in the following way.

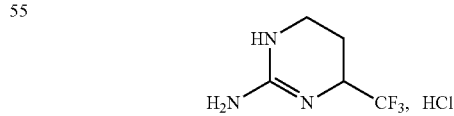

A mixture of 1.1 g of 10% Pd/C, 22 g of 2-amino-4-(trifluoromethyl)pyrimidine dissolved in 200 ml of water, 50 ml of methanol and 50 ml of 12N HCl is hydrogenated at 3 bar, at 22° C., for 24 hours in an autoclave. The resulting mixture is then filtered and the filtrate is concentrated under reduced pressure. The residue obtained is oven-dried, in the presence of P$_2$O$_5$, so as to give 27 g of (4R,4S)-4-(trifluoromethyl)-1,4,5,6-tetrahydropyrimidin-2-ylamine hydrochloride, in the form of a grey solid, the characteristics of which are the following:

Mass spectrum (method A), ES+/−: [M+H]+: m/z 168; Tr (min)=0.17

Intermediate F2

(8S)-2-chloro-3-fluoro-8-(trifluoromethyl)-6,7,8,9-tetrahydro-4H-pyrimido[1,2-a]pyrimidin-4-one can be prepared in the following way.

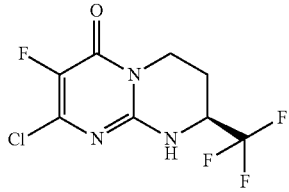 [SMILES: O=c1c(F)c(Cl)nc2n1CC[C@@H](C(F)(F)F)N2]

The separation of the enantiomers of (8R,8S)-2-chloro-3-fluoro-8-(trifluoromethyl)-6,7,8,9-tetrahydro-4H-pyrimido[1,2-a]pyrimidin-4-one is carried out by chiral chromatography (Chiralpak AD 20 μm 80×350 mm 250 ml/min 254 nm; 5% EtOH 5% MeOH 90% Heptane +0.1% TEA), using 6.8 g of a racemic mixture. The dextrorotatory enantiomer is concentrated so as to obtain 3.13 g of (8S)-2-chloro-3-fluoro-8-(trifluoromethyl)-6,7,8,9-tetrahydro-4H-pyrimido[1,2-a]pyrimidin-4-one, in the form of a white solid, the characteristics of which are the following:

$[\alpha]_D^{25}$ at 589 nm=+19.6+/−0.6 (c=2.488 mg/0.5 ml MeOH)

Mass spectrum (method A) (ES+/−) [M+H]+: m/z 272; [M−H]−: m/z 270; Tr (min)=0.62

(8R,8S)-2-Chloro-3-fluoro-8-(trifluoromethyl)-6,7,8,9-tetrahydro-4H-pyrimido[1,2-a]pyrimidin-4-one can be prepared in the following way.

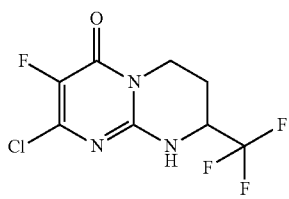 [SMILES: O=c1c(F)c(Cl)nc2n1CCC(C(F)(F)F)N2]

8 ml of phosphorus oxychloride are added to a solution of 6.5 g of (8R,8S)-3-fluoro-2-hydroxy-8-(trifluoromethyl)-6,7,8,9-tetrahydro-4H-pyrimido[1,2-a]pyrimidin-4-one in 80 ml of 1,2-dichloroethane. After stirring for 4 hours at a temperature of 65° C. and returning to a temperature of about 20° C., the reaction mixture is concentrated to dryness under reduced pressure. The residue is diluted in 150 ml of ethyl acetate and 10 ml of ice-cold water. At a temperature between 0° C. and 10° C., a concentrated sodium hydroxide solution is added until a pH between 6 and 7 is obtained. The solid form is filtered off so as to give 3.5 g of a beige solid S1. The filtrate is separated by settling out, and the organic phase is dried over anhydrous magnesium sulfate, filtered, and concentrated to dryness under reduced pressure. After purification of the residue on a silica column (eluent: 97/03 CH$_2$Cl$_2$/MeOH), 3.3 g of a pale yellow solid S2 are obtained. The two solids S1 and S2 are combined so as to give 6.8 g of (8R,8S)-2-chloro-3-fluoro-8-(trifluoromethyl)-6,7,8,9-tetrahydro-4H-pyrimido[1,2-a]pyrimidin-4-one, in the form of a pale yellow powder, the characteristics of which are the following:

Mass spectrum (method B) (ES+/−) [M+H]+: m/z 272; [M−H]−: m/z 270; Tr (min)=2.9

(8R,8S)-3-Fluoro-2-hydroxy-8-(trifluoromethyl)-6,7,8,9-tetrahydro-4H-pyrimido[1,2-a]pyrimidin-4-one can be prepared in the following way.

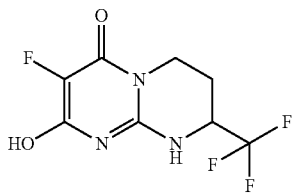 [SMILES: O=c1c(F)c(O)nc2n1CCC(C(F)(F)F)N2]

5.6 g of sodium methoxide are added to a suspension of 7 g of (4R,4S)-4-(trifluoromethyl)-1,4,5,6-tetrahydropyrimidin-2-ylamine hydrochloride in 35 ml of dimethyl fluoropropanedioate. After stirring the suspension for 3 hours at a temperature of 100° C., the medium obtained is concentrated to dryness under reduced pressure. The residue is taken up in diethyl ether and then dried with suction under vacuum. The solid obtained is taken up in 14 ml of water, and the resulting mixture is cooled in ice, before acidification to pH 5-6 by addition of concentrated hydrochloric acid (25%). After 2 hours of stirring at a temperature of 0° C. and then overnight at a temperature of about 20° C., the suspension is filtered and then the solid is dried with suction and dried under vacuum over P$_2$O$_5$. 6.5 g of (8R,8S)-3-fluoro-2-hydroxy-8-(trifluoromethyl)-6,7,8,9-tetrahydro-4H-pyrimido[1,2-a]pyrimidin-4-one are obtained in the form of a yellow powder, the characteristics of which are the following:

Mass spectrum (method A) (ES+/−) [M+H]+: m/z 254; [M−H]−: m/z 252; Tr (min)=0.28

Intermediate F3

(R)-8-chloro-4-(trifluoromethyl)-3,4-dihydro-1H-pyrimido[1,2-a]pyrimidin-6(2H)-one can be prepared in the following way.

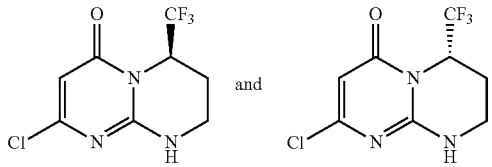 [SMILES: O=c1cc(Cl)nc2n1[C@@H](C(F)(F)F)CCN2 ; O=c1cc(Cl)nc2n1[C@H](C(F)(F)F)CCN2]

The separation of the two enantiomers of (4R,4S)-chloro-4-(trifluoromethyl)-3,4-dihydro-1H-pyrimido[1,2-a]pyrimidin-6(2H)-one (4.5 g) is carried out by chiral chromatography: stationary phase: AS 20 μm; mobile phase: 5% MeOH; 10% EtOH; 85% Heptane; 0.1% TEA. The laevorotatory enantiomer is concentrated so as to give 2.07 g of (R)-8-chloro-4-(trifluoromethyl)-3,4-dihydro-1H-pyrimido[1,2-a]pyrimidin-6(2H)-one, in the form of a white powder, $[\alpha]_D^{25}$ at 589 nm=−32.7+/−0.7 (DMSO). The dextrorotatory enantiomer is concentrated so as to obtain 2.19 g of (S)-8-chloro-4-(trifluoromethyl)-3,4-dihydro-1H-pyrimido[1,2-a]

pyrimidin-6(2H)-one, in the form of a cream powder, $[\alpha]_D^{25}$ at 589 nm=+29.2+/−0.8 (DMSO).

8-Chloro-4-(trifluoromethyl)-3,4-dihydro-1H-pyrimido[1,2-a]pyrimidin-6(2H)-one can be prepared in the following way.

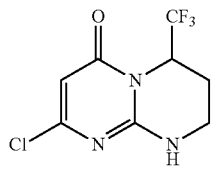 [SMILES: O=c1cc(Cl)nc2n1C(C(F)(F)F)CCN2]

16 ml of trifluoromethanesulfonic acid are added, at ambient temperature and under an argon atmosphere, to a solution of 8.1 g of 2-chloro-9-(2,4-dimethoxybenzyl)-6-trifluoromethyl-6,7,8,9-tetrahydropyrimido[1,2-a]pyrimidin-4-one in 200 ml of 1,2-dichloromethane. The mixture obtained is then stirred at ambient temperature for one hour. The reaction is complete according to the verification by LC/MS. The reaction medium is cooled in an ice bath. 32% sodium hydroxide is added dropwise to pH=10. The white solid formed is filtered off so as to give 7 g of the solid S1. After separation of the filtrate by settling out, the organic phase is dried over magnesium sulfate, filtered, and concentrated under reduced pressure, so as to give 0.9 g of the solid S2. The solid S1 is taken up with water and ethyl acetate. After separation by settling out, the organic phase is dried over magnesium sulfate, filtered, and concentrated under reduced pressure, so as to give 3.5 g of the solid S3. The two solids S2 and S3 are combined for purification by chromatography on silica (eluent: CH₂Cl₂/EtOAc: 90/10) so as to give 4.08 g of 8-chloro-4-(trifluoromethyl)-3,4-dihydro-1H-pyrimido[1,2-a]pyrimidin-6(2H)-one, in the form of a white solid, the characteristics of which are the following:

Mass spectrum (method A): ES+/−: [M+H]+: m/z 254; [M−H]−: m/z 252; Tr (min)=0.56

2-Chloro-9-(2,4-dimethoxybenzyl)-6-trifluoromethyl-6,7,8,9-tetrahydropyrimido[1,2-a]pyrimidin-4-one can be prepared in the following way.

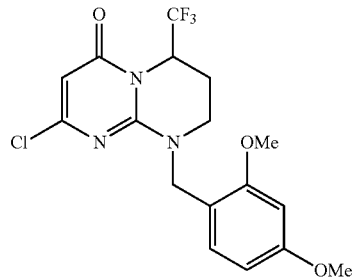 [SMILES: COc1ccc(CN2CCC(C(F)(F)F)n3c2nc(Cl)cc3=O)c(OC)c1]

14 ml of phosphorus oxychloride are added, at ambient temperature and under an argon atmosphere, to a suspension of 11.5 g of 9-(2,4-dimethoxybenzyl)-2-hydroxy-6-trifluoromethyl-6,7,8,9-tetrahydropyrimido[1,2-a]pyrimidin-4-one in 140 ml of 1,2-dichloroethane. The mixture obtained is then heated to 65° C. After one hour of stirring at 60° C., the reaction is complete according to the verification by LC/MS. After cooling, the reaction mixture is evaporated to dryness under reduced pressure. The residue obtained is taken up in 30 ml of cold water and 200 ml of ethyl acetate. 32% sodium hydroxide is added to the mixture obtained, to pH=8. The resulting organic phase is separated and then dried over magnesium sulfate, filtered, and concentrated under reduced pressure. The residue obtained is purified by chromatography on silica, eluents:

dichloromethane/EtOAc: 97/03, so as to give 8.2 g of 2-chloro-9-(2,4-dimethoxybenzyl)-6-trifluoromethyl-6,7,8,9-tetrahydropyrimido[1,2-a]pyrimidin-4-one, the characteristics of which are the following:

Mass spectrum (method B): ES+/−: [M+H]+: m/z 404; Tr (min)=4.54 then CH₂Cl₂/EtOAc: 85/15, so as to give 0.64 g of 8-chloro-4-(trifluoromethyl)-3,4-dihydro-1H-pyrimido[1,2-a]pyrimidin-6(2H)-one, in the form of a white solid, the characteristics of which are the following:

Mass spectrum (method A): ES+/−: [M+H]+: m/z 254; [M−H]−: m/z 252; Tr (min)=0.56

9-(2,4-Dimethoxybenzyl)-2-hydroxy-6-trifluoromethyl-6,7,8,9-tetrahydropyrimido[1,2-a]pyrimidin-4-one can be prepared in the following way.

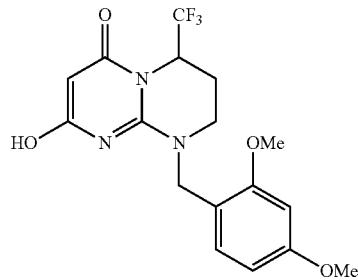 [SMILES: COc1ccc(CN2CCC(C(F)(F)F)n3c2nc(O)cc3=O)c(OC)c1]

35 ml of methyl malonate and 13 g of anhydrous sodium methoxide are added, at ambient temperature and under an argon atmosphere, to a suspension of 19.1 g of 1-(2,4-dimethoxybenzyl)-4-trifluoromethyl-1,4,5,6-tetrahydropyrimidin-2-ylamine in 175 ml of methanol. The mixture obtained is then heated at reflux. After six hours of stirring at reflux, the reaction is complete according to the verification by LC/MS. After cooling, the reaction mixture is evaporated to dryness under reduced pressure. The residue obtained is taken up in 20 ml of cold water and 400 ml of ethyl acetate. 36% HCl is added dropwise to pH=5-6. The resulting organic phase is separated and then dried over magnesium sulfate, filtered, and concentrated under reduced pressure. The residue obtained is purified by chromatography on silica, eluents: dichloromethane/MeOH: 98/02, so as to give 11.6 g of 9-(2,4-dimethoxybenzyl)-2-hydroxy-6-trifluoromethyl-6,7,8,9-tetrahydropyrimido[1,2-a]pyrimidin-4-one, the characteristics of which are the following:

Mass spectrum (method A): ES+/−: [M+H]+: m/z 386; [M−H]−: m/z 384; Tr (min)=0.78

1-(2,4-Dimethoxybenzyl)-4-trifluoromethyl-1,4,5,6-tetrahydropyrimidin-2-ylamine can be prepared in the following way.

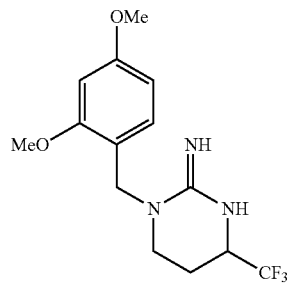 [SMILES: COc1ccc(CN2CCC(C(F)(F)F)NC2=N)c(OC)c1]

5.7 g of cyanogen bromide are added, in small amounts, at ambient temperature and under an argon atmosphere, to a solution of 14.2 g of N1-(2,4-dimethoxybenzyl)-4,4,4-trifluorobutane-1,3-diamine in 150 ml of acetonitrile. At the end of the addition, the mixture obtained is then heated at reflux for three hours in an oil bath preheated to 100° C. After cooling, the reaction mixture is evaporated to dryness under reduced pressure, so as to give 19.11 g of 1-(2,4-dimethoxybenzyl)-4-trifluoromethyl-1,4,5,6-tetrahydropyrimidin-2-ylamine in the form of a pale yellow foam, which will be used as it is in the next step and the characteristics of which are the following:

Mass spectrum (method B): ES+/−: [M+H]+: m/z 318; Tr (min)=2.67

N1-(2,4-Dimethoxybenzyl)-4,4,4-trifluorobutane-1,3-diamine can be prepared in the following way.

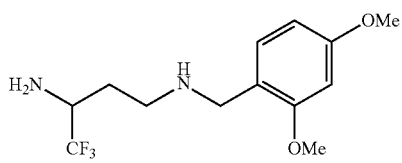 [SMILES: COc1ccc(CNCCC(N)C(F)(F)F)c(OC)c1]

8 g of LiAlH$_4$ are added, in small portions, at ambient temperature and under an argon atmosphere, to a solution of 10.6 g of 3-amino-N-(2,4-dimethoxybenzyl)-4,4,4-trifluorobutyramide in 500 ml of anhydrous ethyl ether. At the end of the addition, the reaction medium, a suspension, is stirred at ambient temperature for 48 hours. The reaction medium is cooled to 4° C. in an ice bath, and then 11 ml of water, followed by 11 ml of 4N NaOH and then 22 ml of water are added dropwise. The white precipitate formed is filtered off. The filtrate is dried over magnesium sulfate and then concentrated under reduced pressure, so as to give 9.5 g of N1-(2,4-dimethoxybenzyl)-4,4,4-trifluorobutane-1,3-diamine, in the form of a colourless oil, which is used as it is in the next step.

Mass spectrum (method A): ES+/−: [M+H]+: m/z 293; ES+ base peak: m/z 151; Tr (min)=0.33

3-Amino-N-(2,4-dimethoxybenzyl)-4,4,4-trifluorobutyramide can be prepared in the following way.

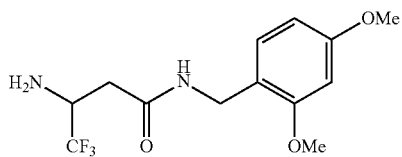 [SMILES: COc1ccc(CNC(=O)CC(N)C(F)(F)F)c(OC)c1]

23.4 g of 2,4-dimethoxybenzylamine are added in one step to a suspension of 20 g of 3-amino-4-trifluorobutyric acid in 120 ml of DMF, followed, dropwise, by 41 g of phenylsilane, said additions being carried out while maintaining the temperature of the reaction medium between 20 and 28° C. At the end of the addition, the reaction medium, a suspension, is stirred at ambient temperature for 48 hours. The reaction medium is cooled to 4° C. in an ice bath, and then 200 ml of water, followed by 300 ml of ethyl acetate, are added dropwise. The resulting organic phase is separated and then dried over magnesium sulfate, filtered, and concentrated under reduced pressure. The residue obtained is taken up with 500 ml of methanol. The white solid formed is filtered off. The filtrate is concentrated under reduced pressure. The residue obtained is purified by chromatography on silica, eluents: dichloromethane/MeOH: 95/05, so as to give 25 g of 3-amino-N-(2,4-dimethoxybenzyl)-4,4,4-trifluorobutyramide, in the form of a pasty white solid, the characteristics of which are the following:

Mass spectrum (method A): ES+/−: [M+H]+: m/z 307; ES+ base peak: m/z 151; Tr (min)=2.38

Alternative Intermediate F3

Alternatively, (R)-8-chloro-4-(trifluoromethyl)-3,4-dihydro-1H-pyrimido[1,2-a]pyrimidin-6(2H)-one can be prepared in the following way.

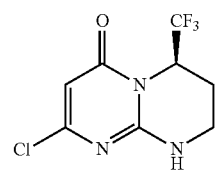 [SMILES: O=c1cc(Cl)nc2n1[C@@H](C(F)(F)F)CCN2]

3.7 ml of phosphorus oxychloride are added, at ambient temperature and under an argon atmosphere, to a suspension of 3.2 g of (R)-8-hydroxy-4-(trifluoromethyl)-3,4-dihydro-1H-pyrimido[1,2-a]pyrimidin-6(2H)-one in 37 ml of 1,2-dichloroethane. The mixture obtained is then heated to 65° C. After 4 hours of stirring at 60° C., the reaction is complete according to the verification by LC/MS. After cooling, the reaction mixture is evaporated to dryness under reduced pressure. The residue obtained is taken up in 50 ml of cold water and 200 ml of ethyl acetate. 32% sodium hydroxide is added to the mixture obtained, to pH=10. The resulting organic phase is separated and then dried over magnesium sulfate, filtered, and concentrated under reduced pressure. The residue obtained is purified by chromatography on silica, eluents: CH$_2$Cl$_2$/MeOH: 96/04), so as to give 2.53 g of (R)-8-chloro-4-(trifluoromethyl)-3,4-dihydro-1H-pyrimido[1,2-a]pyrimidin-6(2H)-one, in the form of a white solid, the characteristics of which are the following:

Mass spectrum (method A): ES+/−: [M+H]+: m/z 254; [M−H]−: m/z 252; Tr (min)=0.56

(R)-8-Hydroxy-4-(trifluoromethyl)-3,4-dihydro-1H-pyrimido[1,2-a]pyrimidin-6(2H)-one can be prepared in the following way.

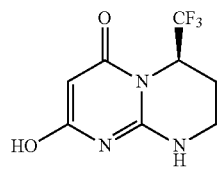 [SMILES: O=c1cc(O)nc2n1[C@@H](C(F)(F)F)CCN2]

50 ml of trifluoroacetic acid are added, at ambient temperature and under an argon atmosphere, to a suspension of 7.5 g of (R)-8-hydroxy-1-((S)-1-(4-methoxyphenyl)ethyl)-4-(trifluoromethyl)-3,4-dihydro-1H-pyrimido[1,2-a]pyrimidin-6(2H)-one in 50 ml of 1,2-dichloromethane. The reaction medium is stirred at ambient temperature for 18 hours. After a verification by LC/MS, 51% of the starting product remains. 25 ml of trifluoroacetic acid are added. After 40 hours of stirring, the reaction is complete according to the verification by LC/MS. The reaction medium is concentrated to dryness under reduced pressure. The residue obtained is taken up with 10 ml of ice-cold water. 32% sodium hydroxide is added dropwise to pH=6. The mixture is concentrated to dryness under reduced pressure. The residue obtained is taken up with an 80/20 dichloromethane/MeOH mixture and filtered, and then the filtrate is concentrated to dryness under reduced pressure. The residue obtained is purified by chromatography on silica (eluent: CH$_2$Cl$_2$/MeOH: 75/25), so as to give 2.4 g of (R)-8-hydroxy-7-fluoro-4-(trifluoromethyl)-3,4-dihydro-1H-pyrimido[1,2-a]pyrimidin-6(2H)-one, in the form of a white solid, the characteristics of which are the following:

OR=−22.5+/−0.6. C=2.702 mg/0.5 ml DMSO. On 589 nm.

(R)-8-hydroxy-1-((S)-1-(4-methoxyphenyl)ethyl)-4-(trifluoromethyl)-3,4-dihydro-1H-pyrimido[1,2-a]pyrimidin-6(2H)-one can be prepared in the following way.

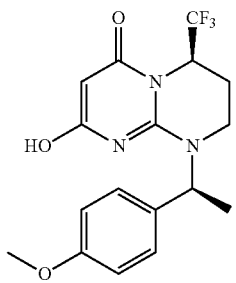 [SMILES: COc1ccc([C@H](C)N2CC[C@H](C(F)(F)F)n3c2nc(O)cc3=O)cc1]

29 g of methyl malonate and 10 g of anhydrous sodium methoxide are added, at ambient temperature and under an argon atmosphere, to a suspension of 11 g of (S)-1-[(S)-1-(4-methoxyphenyl)ethyl]-4-trifluoromethyl-1,4,5,6-tetrahydropyrimidin-2-ylamine in 150 ml of methanol. The mixture obtained is then heated at reflux. After 4 hours of stirring at reflux, the reaction is complete according to the verification by LC/MS. After cooling, the reaction mixture is evaporated to dryness under reduced pressure. The residue obtained is purified by chromatography on silica, eluents: dichloromethane/MeOH: 95/05, so as to give 11.6 g of (R)-8-hydroxy-1-((S)-1-(4-methoxyphenyl)ethyl)-4-(trifluoromethyl)-3,4-dihydro-1H-pyrimido[1,2-a]pyrimidin-6(2H)-one, in the form of a white solid, the characteristics of which are the following:

Mass spectrum (method A): ES+/−: [M+H]+: m/z 370; [M−H]−: m/z 368; Tr (min)=1.06

OR=−96.3 +/−1.7 at 589 nm weighed 1.623 mg ds 0.5 ml DMSO (S)-1-[(S)-1-(4-Methoxyphenyl)ethyl]-4-trifluoromethyl-1,4,5,6-tetrahydropyrimidin-2-ylamine can be prepared in the following way.

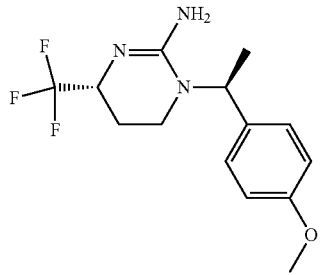 [SMILES: COc1ccc([C@H](C)N2CC[C@H](C(F)(F)F)N=C2N)cc1]

4.6 g of cyanogen bromide are added, in small amounts, at ambient temperature and under an argon atmosphere, to a solution of 11 g of (S)-4,4,4-trifluoro-N1-[(S)-1-(4-methoxyphenyl)ethyl]butane-1,3-diamine in 100 ml of acetonitrile. At the end of the addition, the mixture obtained is then heated at reflux for two hours in an oil bath preheated to 100° C. After cooling, the reaction mixture is evaporated to dryness under reduced pressure, so as to give 11 g of a brown foam. 50 ml of water and 200 ml of EtOAc are added to this foam, followed by 32% sodium hydroxide to pH=14. After separation by settling out, the organic phase is dried over magnesium sulfate, filtered, and then concentrated under reduced pressure, so as to give a residue of 11 g of a thick oil.

This residue is purified on a silica column, eluent: dichloromethane/MeOH28% NH$_4$OH: 90/10/0.5 then dichloromethane/MeOH/28% NH$_4$OH: 60/40/5, so as to give 8 g of (S)-1-[(S)-1-(4-methoxyphenyl)ethyl]-4-trifluoromethyl-1,4,5,6-tetrahydropyrimidin-2-ylamine, in the form of a pale yellow foam, which will be used as it is in the next step and the characteristics of which are the following:

Mass spectrum (method A): ES+/−: [M+H]+: m/z 302; Tr (min)=0.57

(S)-4,4,4-Trifluoro-N1-[(S)-1-(4-methoxyphenyl)ethyl]butane-1,3-diamine can be prepared in the following way.

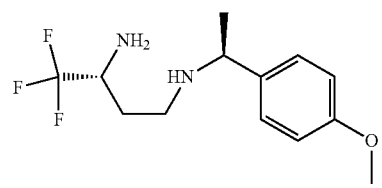 [SMILES: COc1ccc([C@H](C)NCC[C@@H](N)C(F)(F)F)cc1]

11.7 g of LiAlH$_4$ are added, in small portions, at ambient temperature and under an argon atmosphere, to a solution of 15 g of (S)-3-amino-4,4,4-trifluoro-N—[(S)-1-(4-methoxyphenyl)ethyl]butyramide in 600 ml of anhydrous ethyl ether. At the end of the addition, the reaction medium, a suspension, is stirred at ambient temperature for 72 hours. The reaction medium is cooled to 4° C. in an ice bath, and then 9.7 ml of water, followed by 9.7 ml of 4N NaOH and then 19.4 ml of water, are added dropwise. The white precipitate formed is filtered off. The filtrate is dried over MgSO$_4$ and then concentrated under reduced pressure, so as to give 11.2 g of (S)-4,4,4-trifluoro-N1-[(S)-1-(4-methoxyphenyl)ethyl]butane-1,3-diamine, in the form of a colourless oil, which is used as it is in the next step and the characteristics of which are the following:

Mass spectrum (method A): ES+/−: [M+H]+: m/z 277; Tr (min)=0.32

(S)-3-Amino-4,4,4-trifluoro-N—[(S)-1-(4-methoxyphenyl)ethyl]butyramide and (R)-3-amino-4,4,4-trifluoro-N—[(S)-1-(4-methoxyphenyl)ethyl]butyramide can be prepared in the following way.

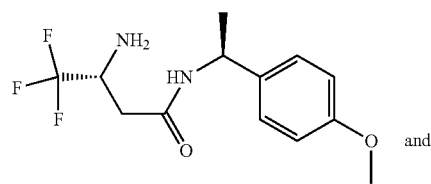

and

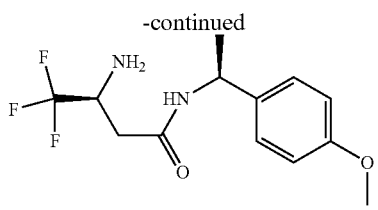

32.8 g of (S)-(−)-1-(4-methoxyphenyl)ethylamine are added in one step to a suspension of 31 g of 3-amino-4-trifluorobutyric acid in 300 ml of DMF, followed, dropwise, by 64 g of phenylsilane, said additions being carried out while maintaining the temperature of the reaction medium between 25 and 35° C. At the end of the addition, the reaction medium, a suspension, is stirred at ambient temperature for 48 hours. The reaction medium is cooled to 4° C. in an ice bath, and then 200 ml of water, followed by 400 ml of ethyl acetate, are added dropwise. The resulting organic phase is separated and then dried over magnesium sulfate, filtered, and concentrated under reduced pressure. The residue obtained is taken up with 500 ml of methanol. The white solid formed is filtered off. The filtrate is concentrated under reduced pressure. The residue obtained is purified by chromatography on silica, eluents: 90/10 dichloromethane/EtOAc, so as to give 15 g of (S)-3-amino-4,4,4-trifluoro-N—[(S)-1-(4-methoxyphenyl)ethyl]butyramide, in the form of a white solid, the characteristics of which are the following:

Mass spectrum (method A): ES+/−: [M+H]+: m/z 291; [M−H]−: m/z 289; ES+ base peak: m/z 135; Tr (min)=0.46
$[\alpha]_D^{25}$ at 589 nm=−31.8 +/−0.9 (DMSO)
Then eluent with 50/50 dichloromethane/EtOAc, so as to give 12 g of (R)-3-amino-4,4,4-trifluoro-N—[(S)-1-(4-methoxyphenyl)ethyl]butyramide, in the form of a white solid, the characteristics of which are the following:
Mass spectrum (method A): ES+/−: [M+H]+: m/z 291; ES+ base peak: m/z 135; Tr (min)=0.47
$[\alpha]_D^{25}$ at 589 nm=−78+/−1.5 (DMSO)

Intermediate F4

(R)-8-Chloro-7-fluoro-4-(trifluoromethyl)-3,4-dihydro-1H-pyrimido[1,2-a]pyrimidin-6(2H)-one can be prepared in the following way.

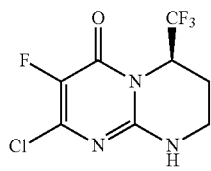 [SMILES: O=c1c(F)c(Cl)nc2n1[C@@H](C(F)(F)F)CCN2]

30 ml of trifluoroacetic acid are added, at ambient temperature and under an argon atmosphere, to a solution of 4 g of (R)-8-chloro-7-fluoro-1-((S)-1-(4-methoxyphenyl)ethyl)-4-(trifluoromethyl)-3,4-dihydro-1H-pyrimido[1,2-a]pyrimidin-6(2H)-one in 30 ml of 1,2-dichloromethane. The reaction medium is stirred at ambient temperature for 18 hours. The reaction medium turns a dark violet colour. The reaction is complete according to the verification by LC/MS. The reaction medium is concentrated to dryness under reduced pressure. The residue obtained is taken up with 100 ml of dichloromethane and 50 ml of ice-cold water. 32% sodium hydroxide is added dropwise to pH=10. After separation by settling out, the organic phase is dried over magnesium sulfate, filtered, and concentrated under reduced pressure. The residue obtained is taken up with ethyl ether and the white solid formed is filtered off, so as to give 2.1 g of the solid S1. The filtrate is concentrated to dryness under reduced pressure and the residue obtained is purified by chromatography on silica (eluent: $CH_2Cl_2$/EtOAc: 97/03), so as to give 0.35 g of the solid S2. The two solids S1 and S2 are combined so as to give 2.45 g of (R)-8-chloro-7-fluoro-4-(trifluoromethyl)-3,4-dihydro-1H-pyrimido[1,2-a]pyrimidin-6(2H)-one, in the form of a white solid, used as it is in the next step.

(R)-8-Chloro-7-fluoro-1-((S)-1-(4-methoxyphenyl)ethyl)-4-(trifluoromethyl)-3,4-dihydro-1H-pyrimido[1,2-a]pyrimidin-6(2H)-one can be prepared in the following way.

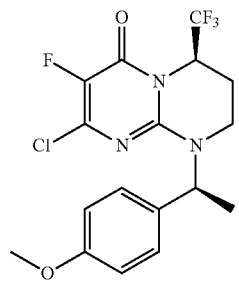 [SMILES: COc1ccc([C@H](C)N2CC[C@H](C(F)(F)F)n3c2nc(Cl)c(F)c3=O)cc1]

10.8 ml of phosphorus oxychloride are added, at ambient temperature and under an argon atmosphere, to a suspension of 15 g of (R)-7-fluoro-8-hydroxy-1-((S)-1-(4-methoxyphenyl)ethyl)-4-(trifluoromethyl)-3,4-dihydro-1H-pyrimido[1,2-a]pyrimidin-6(2H)-one in 100 ml of 1,2-dichloroethane. The mixture obtained is then heated to 65° C. After 3 hours of stirring at 60° C., the reaction is complete according to the verification by LC/MS. After cooling, the reaction mixture is evaporated to dryness under reduced pressure. The residue obtained is taken up in 100 ml of cold water and 300 ml of ethyl acetate. 32% sodium hydroxide is added to the mixture obtained, to pH=10. The resulting organic phase is separated and then dried over magnesium sulfate, filtered, and concentrated under reduced pressure. The residue obtained is purified by chromatography on silica, eluents:
dichloromethane/EtOAc: 98/02, so as to give 4 g of (R)-8-chloro-7-fluoro-1-((S)-1-(4-methoxyphenyl)ethyl)-4-(trifluoromethyl)-3,4-dihydro-1H-pyrimido[1,2-a]pyrimidin-6(2H)-one, used in the next step.
$CH_2Cl_2$/EtOAc: 95/05, so as to give 2.5 g of (R)-8-chloro-7-fluoro-4-(trifluoromethyl)-3,4-dihydro-1H-pyrimido[1,2-a]pyrimidin-6(2H)-one, in the form of a white solid.
(R)-7-Fluoro-8-hydroxy-1-((S)-1-(4-methoxyphenyl)ethyl)-4-(trifluoromethyl)-3,4-dihydro-1H-pyrimido[1,2-a]pyrimidin-6(2H)-one can be prepared in the following way.

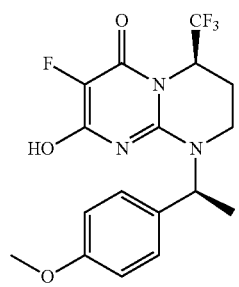 [SMILES: COc1ccc([C@H](C)N2CC[C@H](C(F)(F)F)n3c2nc(O)c(F)c3=O)cc1]

30 g of methyl fluoromalonate and 10.8 g of anhydrous sodium methoxide are added, at ambient temperature and under an argon atmosphere, to a suspension of 12 g of (S)-1-[(S)-1-(4-methoxyphenyl)ethyl]-4-trifluoromethyl-1,4,5,6-tetrahydropyrimidin-2-ylamine in 150 ml of methanol. The mixture obtained is then heated at reflux. After one hour of stirring at reflux, the reaction is complete according to the verification by LC/MS. After cooling, the reaction mixture is evaporated to dryness under reduced pressure. The residue obtained is taken up with 100 ml of cold water. 36% HCl is added dropwise to pH=6. The solid formed is filtered off and then washed three times with ethyl ether. The solid is oven-dried under vacuum in the presence of $P_2O_5$, so as to give 15 g of (R)-7-fluoro-8-hydroxy-1-((S)-1-(4-methoxyphenyl)ethyl)-4-(trifluoromethyl)-3,4-dihydro-1H-pyrimido[1,2-a]pyrimidin-6(2H)-one, which is used as it is in the next step.

Intermediate F5

(8S)-2-Chloro-8-methyl-8-(trifluoromethyl)-6,7,8,9-tetrahydro-4H-pyrimido[1,2-a]pyrimidin-4-one and (8R)-2-chloro-8-methyl-8-(trifluoromethyl)-6,7,8,9-tetrahydro-4H-pyrimido[1,2-a]pyrimidin-4-one can be prepared in the following way.

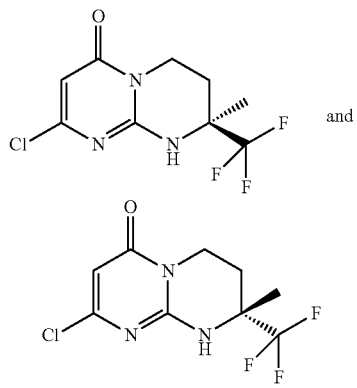

and

A suspension of 410 mg (1.645 mmol) of 2-hydroxy-8-methyl-8-(trifluoromethyl)-6,7,8,9-tetrahydro-4H-pyrimido[1,2-a]pyrimidin-4-one in 22 ml of 1,2-dichloroethane is treated at ambient temperature with 0.767 ml of phosphorus trichloride. The reaction medium is heated at 65° C. for 7 h 15 min. It is then evaporated to dryness under reduced pressure (2.7 kPa). The residue obtained is taken up with 3 ml of water and 30 ml of ethyl acetate, cooled in an ice bath and basified to pH 9 with 32% aqueous NaOH, and then the organic phase is separated. The aqueous phase is extracted with 20 ml of ethyl acetate. The organic phases are combined, dried over magnesium sulfate and then filtered through a sintered glass funnel, and the filtrate is evaporated to dryness under reduced pressure (2.7 kPa). The crude obtained is purified by flash chromatography on silica [eluent: dichloromethane/1-propanol/acetonitrile (100/0/0 then 96/2/2 by volume)]. After evaporation of the fractions under reduced pressure, 217 mg of 2-chloro-8-methyl-8-(trifluoromethyl)-6,7,8,9-tetrahydro-4H-pyrimido[1,2-a]pyrimidin-4-one are obtained, in the form of a white solid (mixture of enantiomers).

Mass spectrum (method A): ES+/−: [M+H]+: m/z 268; [M−H]−: m/z 266; Tr (min)=0.58

The mixture of enantiomers is purified by preparative chromatography on a chiral column under the following conditions:
Technique: Prochrom
Chiral stationary phase: AD 20 μm, lot CFB03
Mobile phase: 85% Heptane—15% EtOH
Flow rate: 260 ml/min
Detection: UV 254 nm
After evaporation of the fractions under reduced pressure, 93 mg of (8R)-2-chloro-8-methyl-8-(trifluoromethyl)-6,7,8,9-tetrahydro-4H-pyrimido[1,2-a]pyrimidin-4-one are obtained, in the form of a white solid.

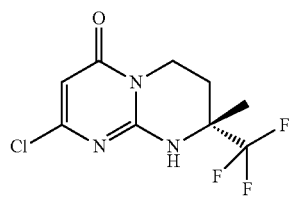 [SMILES: C[C@]1(C(F)(F)F)CCn2c(nc(Cl)cc2=O)N1]

The characteristics of this product are the following:
Mass spectrum (method A): ES+/−: [M+H]+: m/z 268; [M−H]−: m/z 266; Tr (min)=0.59
Retention time by chiral phase HPLC: 6.6 minutes
Conditions used for the chiral phase HPLC:
Technique: Gilson
Chiral stationary phase: AD-H 5 μm 250×4.6 mm
Mobile phase: 85% Heptane—15% EtOH
Flow rate: 1 ml/min
Detection: UV 254 nm
After evaporation of the fractions, 104 mg of (8S)-2-chloro-8-methyl-8-(trifluoromethyl)-6,7,8,9-tetrahydro-4H-pyrimido[1,2-a]pyrimidin-4-one are also obtained, in the form of a white solid.

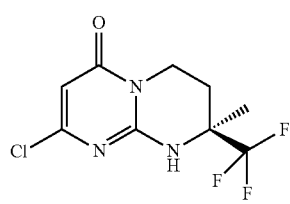 [SMILES: C[C@@]1(C(F)(F)F)CCn2c(nc(Cl)cc2=O)N1]

The characteristics of this product are the following:
Mass spectrum (method A): ES+/−: [M+H]+: m/z 268; [M−H]−: m/z 266; Tr (min)=0.59
$^1$H NMR spectrum (300 MHz, δ in ppm, DMSO-d6): 1.45 (q, J=0.5 Hz, 3 H); 2.00 (m, 1 H); 2.35 (td, J=4, 4 and 14.7 Hz, 1 H); 3.45 (m, 1 H); 4.11 (m, 1 H); 5.81 (s, 1 H); 9.16 (broad s, 1H).
Retention time by chiral phase HPLC: 15.6 minutes
Conditions used for the chiral phase HPLC:
Technique: Gilson
Chiral stationary phase: AD-H 5 μm 250×4.6 mm
Mobile phase: 85% Heptane—15% EtOH
Flow rate: 1 ml/min
Detection: UV 254 nm
2-Hydroxy-8-methyl-8-(trifluoromethyl)-6,7,8,9-tetrahydro-4H-pyrimido[1,2-a]pyrimidin-4-one can be prepared in the following way.

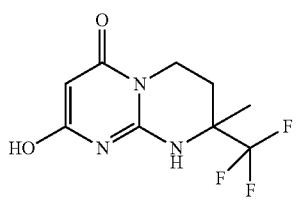 [SMILES: CC1(C(F)(F)F)CCn2c(nc(O)cc2=O)N1]

44 mg (1.927 mmol) of sodium are dissolved in 4 ml of methanol under argon and then 101 mg (0.385 mmol) of 4-methyl-4-(trifluoromethyl)tetrahydropyrimidin-2(1H)-imine hydrobromide in 2 ml of methanol are added, followed by 305 mg (2.312 mmol) of methyl malonate at ambient temperature. The reaction medium is heated at reflux for 5 h 45 min. After cooling, the reaction medium is evaporated to dryness under reduced pressure. The residue obtained is taken up in 0.5 ml of water and then, after cooling in a water-ice bath, 0.1 ml of an aqueous 8N hydrochloric acid solution is added to approximately pH=5. The reaction medium is stirred in the cold bath for approximately 15 minutes and then, after having added approximately 3 ml of ethyl ether to the reaction medium, the latter is filtered through a sintered glass funnel. After drying under vacuum, 92 mg of 2-hydroxy-8-methyl-8-(trifluoromethyl)-6,7,8,9-tetrahydro-4H-pyrimido[1,2-a]pyrimidin-4-one are obtained, in the form of a beige solid.

Mass spectrum (method A): ES+/−: [M+H]+: m/z 250; [M−H]−: m/z 248; Tr (min)=0.32

$^1$H NMR spectrum (300 MHz, δ in ppm, DMSO-d6): 1.40 (s, 3 H); 1.92 (m, 1 H); 2.22 (m, 1 H); 3.45 (m, 1 H); 3.95 (m, 1 H); 4.61 (broad s, 1 H); 10, 30 (broad m, 2 H).

4-Methyl-4-(trifluoromethyl)tetrahydropyrimidin-2(1H)-imine hydrobromide can be prepared in the following way.

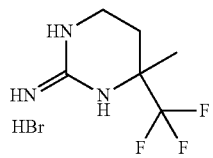

A solution of 458 mg (2.933 mmol) of 2-methyl-2-(trifluoromethyl)butane-1,4-diamine in 4 ml of acetonitrile is treated at ambient temperature with 311 mg (2.933 mmol) of cyanogen bromide. 12 ml of acetonitrile are then added and the solution is heated at reflux for 2 h 30 min. After evaporation to dryness under reduced pressure, 695 mg of 4-methyl-4-(trifluoromethyl)tetrahydropyrimidin-2(1H)-imine hydrobromide are obtained in the form of a yellow solid.

Mass spectrum (method A): ES+/−: [M+H]+: m/z 182; Tr (min) (ELSD) =0.24

$^1$H NMR spectrum (300 MHz, δ in ppm, DMSO-d6): 1.45 (s, 3 H); 1.94 (m, 1 H); 2.17 (m, 1 H); 3.11 to 3.44 (partially masked m, 2 H); 6.97 (broad s, 2 H); 8.17 (broad s, 1 H); 8.60 (broad s, 1 H).

2-Methyl-2-(trifluoromethyl)butane-1,4-diamine can be prepared in the following way.

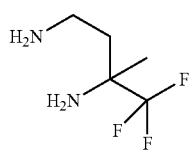

A suspension of 1.17 g (4.751 mmol) of N[1]-benzyl-4,4,4-trifluoro-3-methylbutane-1,3-diamine and 758 mg (0.713 mmol) of palladium-on-carbon (10%) in 55 ml of ethanol and 2.090 ml (10.45 mmol) of an aqueous 5N hydrochloric acid solution is hydrogenated at 50° C. under 10 bar of hydrogen for 68 h. The reaction medium is then filtered through celite and the filtrate is then evaporated to dryness. Toluene is added to the residue obtained and then the resulting product is evaporated to dryness, so as to give 1.231 g of a yellow solid. This yellow solid is dissolved in 5 ml of water and then the solution is basified with approximately 2 ml of an aqueous 32% sodium hydroxide solution to pH=12. The aqueous phase is extracted with ethyl ether, then the organic phases are combined, dried over magnesium sulfate and then filtered through a sintered glass funnel, and the filtrate is evaporated in a rotary evaporator under reduced pressure (the bath temperature is maintained below 25° C. and the pump vacuum is maintained above 100 mbar). 469 mg of 2-methyl-2-(trifluoromethyl)butane-1,4-diamine are obtained, in the form of a yellow liquid.

Mass spectrum (method A): ES+/−: [M+H]+: m/z 157; Tr (min)=0.11

$^1$H NMR spectrum (300 MHz, δ in ppm, DMSO-d6): 1.11 (s, 3 H); 1.55 (m, 2 H); 1.87 (broad m, 4 H); 2.68 (m, 2 H).

N[1]-benzyl-4,4,4-trifluoro-3-methylbutane-1,3-diamine can be prepared in the following way.

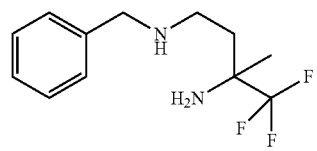 [SMILES: CC(N)(CCNCc1ccccc1)C(F)(F)F]

A solution of 2.494 g (9.583 mmol) of 3-amino-N-benzyl-4,4,4-trifluoro-3-methylbutanamide in 80 ml of ethyl ether is treated at ambient temperature, under a light argon stream, with 2.182 g (57.500 mmol) of powdered lithium aluminium hydride. The reaction medium is stirred at ambient temperature for 72 h and is then diluted with 80 ml of ethyl ether and 15 ml of THF and cooled to approximately 0° C., and 2.18 ml of water, 2.18 ml of an aqueous 15% sodium hydroxide solution and 6.54 ml of water are successively added slowly, and the mixture is filtered through a sintered glass funnel. The filtrate is dried over magnesium sulfate and then, after filtration through a sintered glass funnel, the filtrate obtained is evaporated to dryness under reduced pressure (2.7 kPa). The crude is purified by flash chromatography on silica [eluent: dichloromethane/methanol/acetonitrile (90/5/5 to 80/10/10 by volume)]. After evaporation of the fractions under reduced pressure, 1.176 g of N[1]-benzyl-4,4,4-trifluoro-3-methylbutane-1,3-diamine are obtained, in the form of a yellow oil.

Mass spectrum (method B): ES+/−: [M+H]+: m/z 247; Tr (min)=7.74 (ELSD).

$^1$H NMR spectrum (300 MHz, δ in ppm, DMSO-d6): 1.10 (q, J=0.6 Hz, 3 H); 1.52 to 1.74 (m, 2 H); 2.02 (broad m, 3 H); 2.53 to 2.76 (m, 2 H); 3.68 (s, 2 H); 7.15 to 7.39 (m, 5 H).

3-Amino-N-benzyl-4,4,4-trifluoro-3-methylbutanamide can be prepared in the following way.

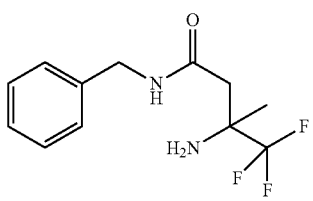 [SMILES: CC(N)(CC(=O)NCc1ccccc1)C(F)(F)F]

A suspension of 3.100 g (14.93 mmol) of 3-amino-4,4,4-trifluoro-3-methylbutanoic acid hydrochloride, 2.862 g (14.93 mmol) of N-[3-(dimethylamino)propyl]-N'-ethylcarbodiimide hydrochloride and 2.017 g (14.93 mmol) of 1-hydroxybenzotriazole in 100 ml of methylene chloride is treated at ambient temperature with 4.363 ml (31.350 mmol) of triethylamine and then with 1.631 ml (14.93 mmol) of benzylamine. The reaction medium is stirred at ambient temperature for 62 h and then 3.26 ml (29.86 mmol) of benylamine are added. The reaction medium is stirred at ambient temperature for 27 h and then evaporated to dryness under reduced pressure (2.7 kPa). The crude obtained is purified by flash chromatography on silica [eluent: dichloromethane/1-propanol/acetonitrile (96/2/2 then 90/5/5 by volume)]. After evaporation of the fractions under reduced pressure, 2.504 g of 3-amino-N-benzyl-4,4,4-trifluoro-3-methylbutanamide are obtained, in the form of a brown oil.

Mass spectrum (method A): ES+/−: [M+H]+: m/z 261; [M−H]−: m/z 259; Tr (min)=0.38

$^1$H NMR spectrum (300 MHz, δ in ppm, DMSO-d6): 1.23 (broad s, 3H); 2.27 (s, 2 H); 2.31 (d, J=13.8 Hz, 1 H); 2.43 (d, J=13.8 Hz, 1 H); 4.30 (d, J=5.7 Hz, 2 H); 7.18 to 7.38 (m, 5 H); 8.53 (broad t, J=5.7 Hz, 1 H).

3-Amino-4,4,4-trifluoro-3-methylbutanoic acid hydrochloride can be prepared in the following way.

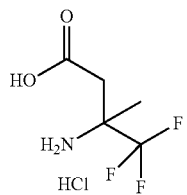

A mixture of 4.460 g (22.393 mmol) of ethyl 3-amino-4,4,4-trifluoro-3-methylbutanoate and 1.776 g (9.592 mmol) of methyl 3-amino-4,4,4-trifluoro-3-methylbutanoate is treated at ambient temperature with an aqueous 5N hydrochloric acid solution. The reaction medium is heated at 90° C. for 4 h. A mixture of acetonitrile and toluene is added and then the mixture is evaporated to dryness under reduced pressure. 4.61 g of 3-amino-4,4,4-trifluoro-3-methylbutanoic acid hydrochloride are obtained, in the form of a beige solid.

Mass spectrum (method A): ES+/−: [M+H]+: m/z 172; [M−H]−: m/z 170; Tr (min)=0.13

$^1$H NMR spectrum (400 MHz, δ in ppm, DMSO-d6): 1.60 (s, 3 H); 2.93 (m, 2 H); 10.11 (broad m, 3 H).

Ethyl 3-amino-4,4,4-trifluoro-3-methylbutanoate and methyl 3-amino-4,4,4-trifluoro-3-methylbutanoate can be prepared in the following way.

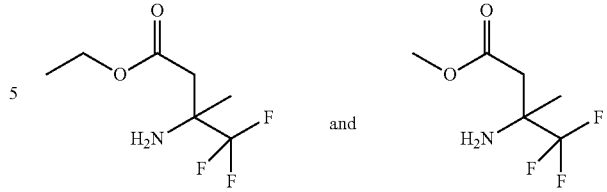

A solution of 1.5 g (8.235 mmol) of ethyl 3-(trifluoromethyl)crotonate in 6 ml of acetonitrile and 11.76 ml (82.350 mmol) of 7N aqueous ammonia in methanol is microwave-heated at 130° C. for 1 h 20 min. The reaction medium is diluted with 20 ml of methylene chloride and then evaporated to dryness under reduced pressure (the bath temperature is maintained below 25° C. and the pump vacuum is maintained above 100 mbar). A mixture of 969 mg (4.865 mmol) of ethyl 3-amino-4,4,4-trifluoro-3-methylbutanoate and 386 mg (2.085 mmol) of methyl 3-amino-4,4,4-trifluoro-3-methylbutanoate (70% ethyl ester-30% methyl ester ratio) is obtained, in the form of a yellow liquid, the characteristics of which are the following:

Mass spectrum (method A): ES+/−: [M+H]+: m/z 200; Tr (min)=0.32 (ethyl ester).

Mass spectrum (method A): ES+/−: [M+H]+: m/z 186; Tr (min)=0.21 (methyl ester).

$^1$H NMR spectrum (400 MHz, δ in ppm, DMSO-d6): 1.19 (t, J=7.1 Hz, 3 H); 1.28 (s, 3 H); 2.19 (broad m, 2 H); 3.17 (m, 2 H); 4.08 (q, J=7.1 Hz, 2 H) (ethyl ester).

$^1$H NMR spectrum (400 MHz, δ in ppm, DMSO-d6): 1.28 (s, 3 H); 2.19 (broad m, 2 H); 3.17 (m, 2 H); 3.61 (s, 3 H) (methyl ester).

Intermediate F6

2-Chloro-8,8-dimethyl-6,7,8,9-tetrahydro-4H-pyrimido[1,2-a]pyrimidin-4-one can be prepared in the following way.

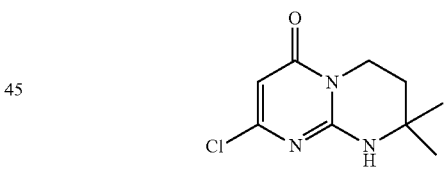

1.7 g of 2-hydroxy-8,8-dimethyl-6,7,8,9-tetrahydro-4H-pyrimido[1,2-a]pyrimidin-4-one are placed in suspension in 24 ml of 1,2-dichloroethane. 2.4 ml of POCl$_3$ are added and then the medium is heated at 65° C. for 2 h. The medium is concentrated to dryness. The residue is taken up in 50 ml of ethyl acetate and 10 ml of water and then cooled in an ice bath. 32% NaOH is added to pH=7. The aqueous phase is extracted with ethyl acetate and then the organic phase is dried over magnesium sulfate. After the solvent has been evaporated off, 0.9 g (yield=55%) of 2-chloro-8,8-dimethyl-6,7,8,9-tetrahydro-4H-pyrimido[1,2-a]pyrimidin-4-one are obtained, in the form of a brown solid, the characteristics of which are the following:

Mass spectrum (method A) ES+/−: Tr: 2.14 min, m/z=214.

2-Hydroxy-8,8-dimethyl-6,7,8,9-tetrahydro-4H-pyrimido[1,2-a]pyrimidin-4-one can be prepared in the following way.

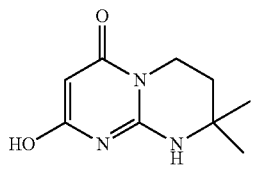

A mixture of 2 g of 4,4-dimethyl-1,4,5,6-tetrahydropyrimidin-2-amine hydrobromide, 10 ml of ethyl malonate and 2.6 g of sodium methoxide is heated to 100° C. After 4 h of heating, the reaction medium is concentrated to dryness. The oil obtained is taken up in ethyl ether. The precipitate is filtered off and then the residue is taken up in 7 ml of water and acidified with 25% HCl to pH 6. The precipitate formed is filtered off, washed with ethyl ether and oven-dried under vacuum. 1.7 g (yield=90%) of 2-hydroxy-8,8-dimethyl-6,7,8,9-tetrahydro-4H-pyrimido[1,2-a]pyrimidin-4-one are obtained, in the form of a beige solid, the characteristics of which are the following:

Mass spectrum (method A) (ES+/−) [M+H]+: m/z 196; [M−H]−: m/z 194; Tr (min)=0.22

4,4-Dimethyl-1,4,5,6-tetrahydropyrimidin-2-amine hydrobromide can be prepared in the following way.

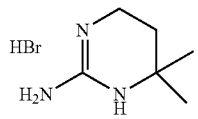

1.95 g of 3-methylbutane-1,3-diamine dihydrobromide are placed in suspension in 20 ml of MeOH and 1.2 g of sodium methanolate are added. The mixture is stirred at ambient temperature for 2 h. The mixture is filtered and then evaporated to dryness. The reaction crude is solubilised in 20 ml of water, cooled with an ice bath. 0.78 g of CNBr is added and the mixture is stirred at ambient temperature for 12 h. The mixture is evaporated to dryness, and 3 g (yield=quantitative) of 4,4-dimethyl-1,4,5,6-tetrahydropyrimidin-2-amine hydrobromide are obtained, in the form of a translucent oil, which will subsequently be used as it is.

Mass spectrum (method A) (ES+/−) [M+H]+: m/z 128; Tr (min)=0.12

3-Methylbutane-1,3-diamine dihydrobromide can be prepared in the following way.

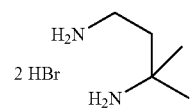

2.8 g of ethyl (3-amino-1,1-dimethylpropyl)carbamate are cooled using an ice bath. 9.9 ml of HBr at 33% in acetic acid are added dropwise and then the mixture is heated at reflux for 2 h. After a return to ambient temperature, the product is precipitated with ethyl ether and filtration is carried out. The powder obtained is oven-dried at 70° C. 2.34 g (yield=55%) of 3-methylbutane-1,3-diamine dihydrobromide are obtained, in the form of a white powder, the characteristics of which are the following:

Mass spectrum (method A) (ES+/−) [M+H]+: m/z 103; Tr (min)=0.12

Ethyl (3-amino-1,1-dimethylpropyl)carbamate can be prepared in the following way.

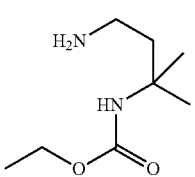

5.12 g of ethyl[3-(1,3-dioxo-1,3-dihydroisoindol-2-yl)-1,1-dimethylpropyl]carbamate are placed in solution in 47 ml of ethanol. 4 ml of hydrazine hydrate are added and then the mixture is heated at reflux for 30 minutes. After a return to ambient temperature, the reaction medium is filtered and then the solvent is evaporated off. 2.8 g (yield=88%) of ethyl (3-amino-1,1-dimethylpropyl)carbamate are obtained in the form of a brown gum, the characteristics of which are the following:

Mass spectrum (method A) (ES+/−) [M+H]+: m/z 175; Tr (min)=0.22

Ethyl[3-(1,3-dioxo-1,3-dihydroisoindol-2-yl)-1,1-dimethylpropyl]carbamate can be prepared in the following way.

34.2 g of ethyl carbamate are placed in solution in toluene, 22 ml of BF₃.Et₂O are added and the mixture is heated for 1 h 30 min at 70° C. 11 g of 2-(3-methylbut-2-en-1-yl)-1H-isoindole-1,3-dione are added and the mixture is heated at reflux for 12 h. After a return to ambient temperature, the mixture is evaporated to dryness and then taken up in an H₂O/EtOAc mixture. The organic phase is separated by settling out, washed with a saturated NaCl solution and then dried over magnesium sulfate. The crude is purified by flash chromatography on silica gel (CH₂Cl₂/MeOH, 99/1). 5.12 g (yield=31%) of ethyl[3-(1,3-dioxo-1,3-dihydroisoindol-2-yl)-1,1-dimethylpropyl]carbamate are obtained, in the form of a brown powder, the characteristics of which are the following:

Mass spectrum (method A) (ES+/−) [M+H]+: m/z 305; Tr (min)=0.86

2-(3-Methylbut-2-en-1-yl)-1H-isoindole-1,3-dione can be prepared in the following way.

20 g of 1-bromo-3-methylbut-2-ene and 26.1 g of phthalimide are placed in suspension in anhydrous DMF and then the mixture is heated at reflux for 12 h. After a return to ambient temperature, the reaction medium is filtered and then taken up with a saturated aqueous NH₄Cl solution. The aqueous phase is extracted with ethyl acetate, washed with an NaCl solution, then dried over magnesium sulfate and evaporated to dryness. The solid obtained is placed in suspension in 100 ml of water and stirred. The precipitated product is filtered off, rinsed with ether and then oven-dried under vacuum at 65° C. 18.3 g (yield=63%) of 2-(3-methylbut-2-en-1-yl)-1H-isoindole-1,3-dione are obtained, in the form of a white powder, the characteristics of which are the following:

Mass spectrum (method A) (ES+/−) [M+H]+: m/z 216; Tr (min)=0.99

Intermediate F7

2-Chloro-3-fluoro-8,8-dimethyl-6,7,8,9-tetrahydro-4H-pyrimido[1,2-a]pyrimidin-4-one can be prepared in the following way.

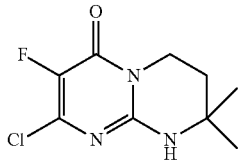

3.15 g of 2-hydroxy-3-fluoro-8,8-dimethyl-6,7,8,9-tetrahydro-4H-pyrimido[1,2-a]pyrimidin-4-one are placed in suspension in 42 ml of 1,2-dichloroethane. 4.15 ml of POCl₃ are added and then the medium is heated at 65° C. for 3 h. The medium is concentrated to dryness. The residue is taken up in 150 ml of ethyl acetate and 10 ml of water and then cooled in an ice bath. Concentrated NaOH is added to pH 10. After separation by settling out, the organic phase is dried over magnesium sulfate, filtered, and then concentrated to dryness under reduced pressure. The residue obtained is triturated from ethyl ether and the solid is filtered and then dried, so as to give 2.23 g of 2-chloro-3-fluoro-8,8-dimethyl-6,7,8,9-tetrahydro-4H-pyrimido[1,2-a]pyrimidin-4-one in the form of a brown solid, the characteristics of which are the following:

Mass spectrum (method A) (ES+/−) [M+H]+: m/z 214; [M−H]−: m/z 212; Tr (min)=0.42

2-Hydroxy-3-fluoro-8,8-dimethyl-6,7,8,9-tetrahydro-4H-pyrimido[1,2-a]pyrimidin-4-one can be prepared in the following way.

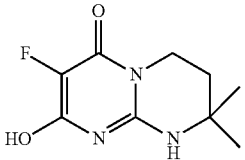

A suspension of 5 g of 4,4-dimethyl-1,4,5,6-tetrahydropyrimidin-2-amine, 29 g of dimethyl fluoromalonate and 3.9 g of sodium methoxide is heated at 100° C. for 3 hours. The reaction medium is concentrated to dryness under reduced pressure. The residue obtained is taken up with ethyl ether. The solid formed is filtered off and then dried. 10 ml of water are added to the solid obtained, and the resulting mixture is cooled on ice, before acidification to pH 5-6 by adding concentrated hydrochloric acid (25%). The suspension is filtered and then the solid is washed with 5 ml of water and then dried under vacuum over P₂O₅, so as to give 3.15 g of 2-Hydroxy-3-fluoro-8,8-dimethyl-6,7,8,9-tetrahydro-4H-pyrimido[1,2-a]pyrimidin-4-one, in the form of a yellow powder, the characteristics of which are the following:

Mass spectrum (method A) (ES+/−) [M+H]+: m/z 232; [M−H]−: m/z 230; Tr (min)=0.86

Intermediate F8

(S)-7-chloro-2-methyl-2-(trifluoromethyl)-2,3-dihydroimidazo[1,2-a]pyrimidin-5(1H)-one can be prepared in the following way.

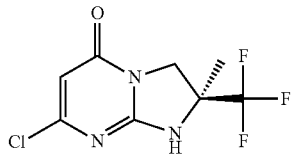 [SMILES: C[C@@]1(C(F)(F)F)Cn2c(nc(Cl)cc2=O)N1]

11 ml of phosphorus oxychloride are added, at ambient temperature and under an argon atmosphere, to a suspension of 5.6 g of (S)-7-hydroxy-2-methyl-2-(trifluoromethyl)-2,3-dihydroimidazo[1,2-a]pyrimidin-5(1H)-one in 100 ml of 1,2-dichloroethane. The resulting mixture is then heated to 70° C. After two hours of stirring and after verification by LC/MS, the reaction is complete. After cooling, the reaction mixture is evaporated to dryness under reduced pressure. The residue obtained is taken up in 5 ml of cold water and 200 ml of ethyl acetate. 32% sodium hydroxide is added to the mixture obtained, to pH=6. The organic phase is then separated and then dried over magnesium sulfate, filtered and concentrated under reduced pressure, so as to give 6 g of (S)-7-chloro-2-methyl-2-(trifluoromethyl)-2,3-dihydroimidazo[1,2-a]pyrimidin-5(1H)-one, the characteristics of which are the following:

Mass spectrum (method A), ES+/−: [M+H]+: m/z 254; [M−H]−: m/z 252; Tr (min)=0.51

[α]$_D^{25}$ at 589 nm=−64.8+/−1.1 (c=2.2 mg/0.5 ml DMSO)

(S)-7-hydroxy-2-methyl-2-(trifluoromethyl)-2,3-dihydroimidazo[1,2-a]pyrimidin-5(1H)-one can be prepared in the following way.

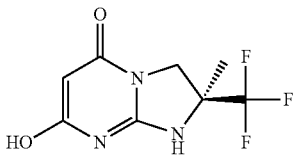 [SMILES: C[C@@]1(C(F)(F)F)Cn2c(nc(O)cc2=O)N1]

8.4 g of (S)-4-methyl-4-(trifluoromethyl)imidazolidin-2-ylideneamine hydrobromide and 2.16 g of sodium methoxide are added to a mixture of 5.4 g of diethyl malonate in 50 ml of methanol. The resulting mixture is refluxed for 18 hours. After cooling, the mixture obtained is concentrated to dryness under reduced pressure. 20 ml of cold water are added to the residue obtained, so as to obtain a thick suspension, to which is added 25% hydrochloric acid to pH=5. The resulting suspension is stirred in an ice bath for two hours and then filtered through a sintered glass funnel. The insoluble matter obtained is rinsed with water (twice 4 ml) and then dried so as to give 5.6 g of (S)-7-hydroxy-2- methyl-2-(trifluoromethyl)-2,3-dihydroimidazo[1,2-a]pyrimidin-5(1H)-one in the form of a white solid, the characteristics of which are the following:

Mass spectrum (method A), ES+/−: [M+H]+: m/z 236; [M−H]−: m/z 234; Tr (min)=0.32

$[\alpha]_D^{25}$ at 589 nm=−5.6+/−0.6 (c=1.789 mg/0.5 ml DMSO)

(S)-4-methyl-4-(trifluoromethyl)imidazolidin-2-ylideneamine hydrobromide can be prepared in the following way.

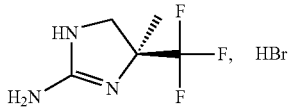

1.7 g of cyanogen bromide are added, in small amounts, to a solution, cooled to 5° C., of 2.3 g of (S)-3,3,3-trifluoro-2-methylpropane-1,2-diamine in 10 ml of water, while maintaining the temperature between 5 and 10° C. At the end of the addition, the reaction mixture is stirred at 5° C. for 30 minutes. The ice bath is then withdrawn and the mixture obtained is stirred at ambient temperature for 3 hours. The resulting mixture is then concentrated under reduced pressure. The residue obtained is taken up twice with 100 ml of ethanol and then twice with 100 ml of toluene, and evaporated to dryness each time. The solid obtained is triturated with ethyl ether and then filtered off, so as to give 4.5 g of (S)-4-methyl-4-(trifluoromethyl)imidazolidin-2-ylideneamine hydrobromide, in the form of a white solid, the characteristics of which are the following:

Mass spectrum (method A), ES+/−: [M+H]+: m/z 168; Tr (min)=0.14

$[\alpha]_D^{25}$ at 589 nm:−5.2+/−0.3 (c=4.909 mg/0.5 ml DMSO)

(S)-3,3,3-Trifluoro-2-methylpropane-1,2-diamine can be prepared in the following way.

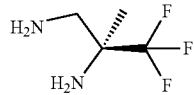

4.8 g of (S)-3,3,3-trifluoro-2-methylpropane-1,2-diamine hydrochloride, 2.5 ml of water and 100 ml of ethyl ether are placed in a round-bottomed flask. 4.5 ml of 32% sodium hydroxide are added, dropwise, to the resulting mixture, to pH=12. The aqueous phase is subsequently separated by settling out and then extracted with 4 times 200 ml of ethyl ether. The organic phases are combined, dried over magnesium sulfate, filtered, and then concentrated under reduced pressure (300 mbar/bath temperature=25° C.), so as to give 2.3 g of (S)-3,3,3-trifluoro-2-methylpropane-1,2-diamine, in the form of a pale yellow oil, the characteristics of which are the following:

Mass spectrum (method B), ES+/−: [M+H]+: m/z 143; base peak: m/z 126; Tr (min)=0.34

$[\alpha]_D^{25}$ at 589 nm=−4.3+/−0.6 (c=1.778 mg/0.5 ml DMSO)

(S)-3,3,3-Trifluoro-2-methylpropane-1,2-diamine dihydrochloride can be prepared in the following way.

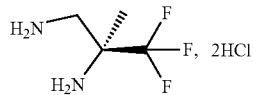

A mixture of 7 g of (2R)-2-((S)-1-aminomethyl-2,2,2-trifluoro-1-methylethylamino)-2-phenylethanol in 40.5 ml of methanol, 23.5 ml of 3N hydrochloric acid and 0.94 g of Pd(OH)$_2$/C (20%) is hydrogenated at 22° C. in an autoclave, under a hydrogen pressure of 5 bar, for 18 hours. The mixture obtained is then filtered and the filtrate is evaporated to dryness. The oil obtained is taken up with a 3N hydrochloric acid solution (50 ml). The mixture obtained is extracted with diethyl ether (3×50 ml). The aqueous phase is then evaporated to dryness, taken up with methanol, and then again evaporated to dryness. The yellowish solid obtained is dried under vacuum, so as to give 5.54 g (yield 79%) of (S)-3,3,3-trifluoro-2-methylpropane-1,2-diamine dihydrochloride, in the form of an off-white solid, the characteristics of which are the following:

$^1$H NMR spectrum (400 MHz, D$_2$O): 1.55 (s, 3 H), 3.40 (d, J=14.6 Hz, 1 H), 3.51 (d, J=14.6 Hz, 1 H).

$^{19}$F NMR spectrum (400 MHz, D$_2$O): −81.08 (not calibrated with C$_6$F$_6$)

$[\alpha]_D^{25}$ at 589 nm=+4.65+/−0.6 (c=2.2; MeOH)

(2R)-2-((S)-1-Aminomethyl-2,2,2-trifluoro-1-methylethylamino)-2-phenylethanol can be prepared in the following way.

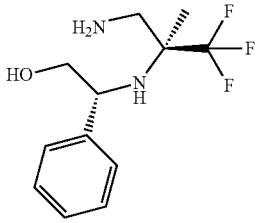 [SMILES: C[C@@](CN)(N[C@@H](CO)c1ccccc1)C(F)(F)F]

1.6 g of lithium aluminium hydride are added, in small portions, to a solution, cooled to 4° C., of 2.5 g of (2S)-3,3,3-trifluoro-2-((R)-2-hydroxy-1-phenylethylamino)-2-methylpropionitrile in 250 ml of anhydrous ethyl ether, in a three-necked flask under argon. Substantial evolution of gas and a temperature rise to 8° C. are observed. At the end of the addition, the temperature is left to come back up to ambient temperature, and then the reaction mixture is left stirring for 18 h. The mixture obtained is cooled to 4° C., followed by very slow dropwise addition of 2 ml of water. Substantial evolution of gas and a temperature rise to 12° C. are observed. 2 ml of 15% potassium hydroxide are added, dropwise and very slowly, to the resulting mixture, maintained at 4° C., followed, still dropwise and very slowly, by 4 ml of water. The white precipitate formed is filtered off and the filtrate obtained is dried over magnesium sulfate and then concentrated under reduced pressure, so as to give 2.2 g of (2R)-2-((S)-1-aminomethyl-2,2,2-trifluoro-1-methylethylamino)-2-phenylethanol, the characteristics of which are the following:

Mass spectrum (method A), ES+/−: [M+H]+: m/z 263; Tr (min)=0.43

$[\alpha]_D^{25}$ at 589 nm=−51.2+/−1.3 (c=1.576 mg/0.5 ml DMSO)

(2S)-3,3,3-Trifluoro-2-((R)-2-hydroxy-1-phenylethyl-amino)-2-methylpropionitrile can be prepared in the following way.

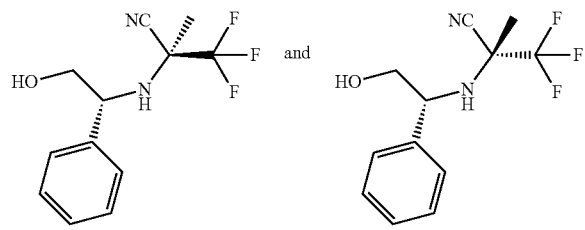 [SMILES: C[C@@](C#N)(N[C@@H](CO)c1ccccc1)C(F)(F)F ; C[C@](C#N)(N[C@@H](CO)c1ccccc1)C(F)(F)F]

3.4 g of trimethylsilyl cyanide are added, dropwise, to a solution, cooled to 0° C., of 5.3 g of (2R,2S)-2-methyl-4-(R)-phenyl-2-(trifluoromethyl)oxazolidine in 100 ml of dichloromethane in a three-necked flask under argon, followed by dropwise addition of 4.9 g of boron trifluoride etherate. The cold bath is then withdrawn to allow the mixture to warm up to ambient temperature. The resulting mixture is stirred at ambient temperature for 18 hours, followed by addition of a saturated sodium bicarbonate solution to pH=8. The organic phase is separated and then dried over magnesium sulfate, filtered, and concentrated under reduced pressure. The residue obtained is purified by chromatography on silica (eluent: cyclohexane/EtOAc: 80/20), so as to give 3 g of (2R)-3,3,3-trifluoro-2-((R)-2-hydroxy-1-phenylethylamino)-2-methylpropionitrile, in the form of a colourless oil, and 2.5 g of (2S)-3,3,3-trifluoro-2-((R)-2-hydroxy-1-phenylethylamino)-2-methylpropionitrile, in the form of a white solid, the characteristics of which are:

Mass spectrum (method A), ES+/−: [M+H]+: m/z 259; [M−H+HCO$_2$H]—: m/z 303; Tr (min)=0.86

$[\alpha]_D^{25}$ at 589 nm=−89.0+/−1.4 (c=2.444 mg/0.5 ml CHCl$_3$)

$[\alpha]_D^{25}$ at 589 nm=−77.6+/−1.4 (c=1.818 mg/0.5 ml DMSO)

(2R,2S)-2-Methyl-4-(R)-phenyl-2-(trifluoromethyl)oxazolidine can be prepared in the following way.

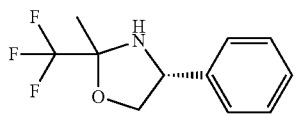 [SMILES: CC1(C(F)(F)F)N[C@H](c2ccccc2)CO1]

4.8 g of (R)-phenylglycinol and then, in one step, 0.8 g of pyridinium para-toluenesulfonate are added to a solution of 5 g of trifluoroacetone in 180 ml of toluene in a three-necked flask on which is mounted a Dean-Stark apparatus. The mixture obtained is then heated at reflux for 18 hours, during which time 0.3 ml of water is collected. After cooling, the reaction mixture is concentrated under reduced pressure. The residue obtained is purified by filtration on silica (eluent: dichloromethane), so as to give 5.3 g of (2R,2S)-2-methyl-4-(R)-phenyl-2-(trifluoromethyl)oxazolidine, in the form of a colourless liquid, the characteristics of which are the following:

Mass spectrum (method A), ES+/−: [M+H]+: m/z 232; Tr (min)=0.96

$[\alpha]_D^{25}$ at 589 nm=−23.4+/−0.8 (c=1.794 mg/0.5 ml MeOH)

Intermediate F9:

(S)-6-Fluoro-7-chloro-2-methyl-2-(trifluoromethyl)-2,3-dihydroimidazo[1,2-a]pyrimidin-5(1H)-one can be obtained in the following way.

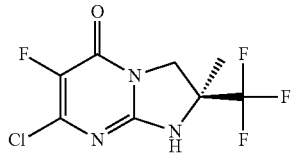 [SMILES: C[C@@]1(C(F)(F)F)Cn2c(nc(Cl)c(F)c2=O)N1]

9 ml of phosphorus oxychloride are added, at ambient temperature and under an argon atmosphere, to a suspension of 8.20 g of (S)-6-fluoro-7-hydroxy-2-methyl-2-(trifluoromethyl)-2,3-dihydroimidazo[1,2-a]pyrimidin-5(1H)-one in 90 ml of 1,2-dichloroethane. The resulting mixture is then heated to 70° C. After 3 hours of stirring and after verification by LC/MS, the reaction is complete. After cooling, the reaction mixture is evaporated to dryness under reduced pressure. The residue obtained is taken up in 50 ml of cold water and 200 ml of ethyl acetate. 32% sodium hydroxide is added to the mixture obtained, to pH=10. The organic phase is then separated and then dried over magnesium sulfate, filtered, and concentrated under reduced pressure. The residue obtained is purified by silica column chromatography (eluent: 98.5/1.5 dichloromethane/methanol), so as to give 4 g of (S)-6-fluoro-7-chloro-2-methyl-2-(trifluoromethyl)-2,3-dihydroimidazo[1,2-a]pyrimidin-5(1H)-one, the characteristics of which are the following:

Mass Spectrometry: Method B:

Retention time Tr (min)=2.92, [M+H]+: m/z 272; [M−H]−: m/z 270

(S)-6-Fluoro-7-hydroxy-2-methyl-2-(trifluoromethyl)-2,3-dihydroimidazo[1,2-a]pyrimidin-5(1H)-one can be obtained in the following way.

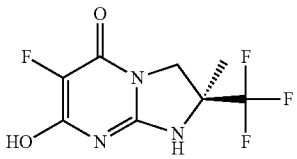 [SMILES: C[C@@]1(C(F)(F)F)Cn2c(nc(O)c(F)c2=O)N1]

11 g of (S)-4-methyl-4-(trifluoromethyl)imidazolidin-2-ylideneamine hydrobromide and 4.79 g of sodium methoxide are added to a mixture of 6.7 g of diethyl fluoromalonate in 110 ml of methanol. The resulting mixture is refluxed for 3 hours. After cooling, the mixture obtained is concentrated to dryness under reduced pressure. 15 ml of cold water are added to the residue obtained, so as to obtain a thick suspension, to which is added 25% hydrochloric acid to pH=5-6. The reaction mixture is evaporated to dryness under reduced pressure. The residue obtained is taken up with an 80/20 dichloromethane/MeOH mixture and then filtered. The filtrate is concentrated under reduced pressure and the residue obtained is purified by chromatography on silica (eluent: 70/30 dichloromethane/MeOH), so as to give 8.14 g of (2S)-7-hydroxy-2-methyl-2-(trifluoromethyl)-2,3-dihydroimidazo[1,2-a]pyrimidin-5(1H)-one, in the form of a pale orange foam, which is used as it is in the next step.

TABLE 1

Starting intermediates of type F

| Intermediate of type F | Structure | Substituents |
|---|---|---|
| F1 | (structure) | R4 = H; p = 0; q = 2; R2 = H; R3 = CF3 (S) |
| F2 | (structure) | R4 = F; p = 0; q = 2; R2 = H; R3 = CF3 (S) |
| F3 | (structure) | R4 = H; p = 2; q = 0; R2 = H; R3 = CF3 (R) |
| F4 | (structure) | R4 = F; p = 2; q = 0; R2 = H; R3 = CF3 (R) |
| F5 | (structure) | R4 = H; p = 0; q = 2; R2 = Me; R3 = CF3 (S) |
| F6 | (structure) | R4 = H; p = 0; q = 2; R2 = Me; R3 = Me |
| F7 | (structure) | R4 = F; p = 0; q = 2; R2 = Me; R3 = Me |
| F8 | (structure) | R4 = H; p = 0; q = 1; R2 = Me; R3 = CF3 (S) |
| F9 | (structure) | R4 = F; p = 0; q = 1; R2 = Me; R3 = CF3 (S) |

Experimental section: Table 2: Examples from 1 to 295, starting intermediates of type F and amount of each example isolated

| EXAMPLE | Example name | Intermediate of type F | Example structure | Amount isolated (mg) |
|---|---|---|---|---|
| EXAMPLE-1 | (S)-2-((R)-3-Methyl-morpholin-4-yl)-9-(2-oxo-2-pyridin-2-yl-ethyl)-8-trifluoromethyl-6,7,8,9-tetrahydro-pyrimido[1,2-a]-pyrimidin-4-one | R4 = H; p = 0; q = 2; R2 = H; R3 = CF3 (S) | Chiral (structure) | 1300 |

Experimental section: Table 2: Examples from 1 to 295, starting intermediates of type F and amount of each example isolated

| EXAMPLE | Example name | Intermediate of type F | Example structure | Amount isolated (mg) |
|---|---|---|---|---|
| EXAMPLE-2 | (S)-2-((R)-3-Methyl-morpholin-4-yl)-9-(5-methyl-[1,2,4]oxadiazol-3-yl-methyl)-8-trifluoromethyl-6,7,8,9-tetrahydro-pyrimido[1,2-a]-pyrimidin-4-one | R4 = H; p = 0; q = 2; R2 = H; R3 = CF3 (S) | Chiral 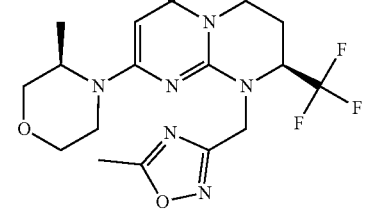 | 109 |
| EXAMPLE-3 | (S)-2-((R)-3-Methyl-morpholin-4-yl)-9-(3-methyl-2-oxobutyl)-8-trifluoromethyl-6,7,8,9-tetrahydro-pyrimido[1,2-a]-pyrimidin-4-one | R4 = H; p = 0; q = 2; R2 = H; R3 = CF3 (S) | Chiral 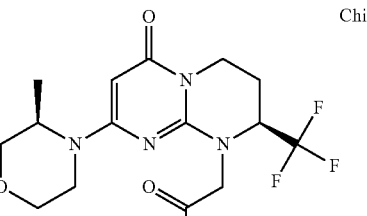 | 151 |
| EXAMPLE-4 | (S)-3-Fluoro-2-((R)-3-methylmorpholin-4-yl)-9-(3-methyl-2-oxo-butyl)-8-trifluoromethyl-6,7,8,9-tetrahydro-pyrimido[1,2-a]-pyrimidin-4-one | R4 = F; p = 0; q = 2; R2 = H; R3 = CF3 (S) | Chiral 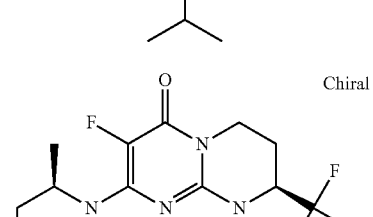 | 65 |
| EXAMPLE-5 | (S)-3-Fluoro-9-(2-fluoropyridin-4-yl-methyl)-2-((R)-3-methylmorpholin-4-yl)-8-trifluoromethyl-6,7,8,9-tetrahydro-pyrimido[1,2-a]-pyrimidin-4-one | R4 = F; p = 0; q = 2; R2 = H; R3 = CF3 (S) | Chiral 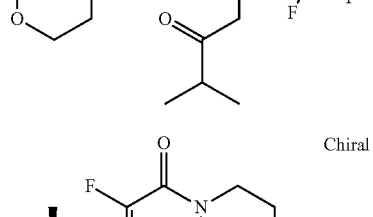 | 1200 |
| EXAMPLE-6 | (S)-9-(2-Cyclopropyl-2-oxoethyl)-3-fluoro-2-((R)-3-methyl-morpholin-4-yl)-8-trifluoromethyl-6,7,8,9-tetrahydro-pyrimido[1,2-a]-pyrimidin-4-one | R4 = F; p = 0; q = 2; R2 = H; R3 = CF3 (S) | Chiral 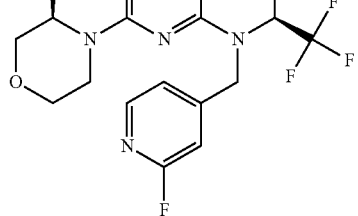 | 1450 |

Experimental section: Table 2: Examples from 1 to 295, starting intermediates of type F and amount of each example isolated

| EXAMPLE | Example name | Intermediate of type F | Example structure | Amount isolated (mg) |
|---|---|---|---|---|
| EXAMPLE-7 | (S)-3-Fluoro-2-((R)-3-methylmorpholin-4-yl)-9-(2-oxopropyl)-8-trifluoromethyl-6,7,8,9-tetrahydro-pyrimido[1,2-a]-pyrimidin-4-one | R4 = F; p = 0; q = 2; R2 = H; R3 = CF3 (S) | | 45 |
| EXAMPLE-8 | (S)-3-Fluoro-9-((S)-2-hydroxypropyl)-2-((R)-3-methylmorpholin-4-yl)-8-trifluoromethyl-6,7,8,9-tetrahydro-pyrimido[1,2-a]-pyrimidin-4-one | R4 = F; p = 0; q = 2; R2 = H; R3 = CF3 (S) | | 181 |
| EXAMPLE-9 | (S)-2-((3R,5R)-3,5-Dimethylmorpholin-4-yl)-9-isoxazol-5-yl-methyl-8-trifluoromethyl-6,7,8,9-tetrahydro-pyrimido[1,2-a]-pyrimidin-4-one | R4 = H; p = 0; q = 2; R2 = H; R3 = CF3 (S) | | 95 |
| EXAMPLE-10 | (S)-9-[2-(2-Chloro-pyridin-4-yl)-2-oxo-ethyl]-2-((R)-3-methyl-morpholin-4-yl)-8-trifluoromethyl-6,7,8,9-tetrahydro-pyrimido[1,2-a]-pyrimidin-4-one | R4 = H; p = 0; q = 2; R2 = H; R3 = CF3 (S) | | 35 |

Experimental section: Table 2: Examples from 1 to 295, starting intermediates of type F and amount of each example isolated

| EXAMPLE | Example name | Intermediate of type F | Example structure | Amount isolated (mg) |
|---|---|---|---|---|
| EXAMPLE-11 | (S)-2-((R)-3-Methyl-morpholin-4-yl)-9-(2-oxo-2-pyridin-3-yl-ethyl)-8-trifluoromethyl-6,7,8,9-tetrahydro-pyrimido[1,2-a]-pyrimidin-4-one | R4 = H; p = 0; q = 2; R2 = H; R3 = CF3 (S) | Chiral | 35 |
| EXAMPLE-12 | (S)-9-(3-Methyl-isoxazol-4-ylmethyl)-2-((R)-3-methyl-morpholin-4-yl)-8-trifluoromethyl-6,7,8,9-tetrahydro-pyrimido[1,2-a]-pyrimidin-4-one | R4 = H; p = 0; q = 2; R2 = H; R3 = CF3 (S) | Chiral | 186 |
| EXAMPLE-13 | (R)-2-((R)-3-Methyl-morpholin-4-yl)-9-oxazol-2-ylmethyl-6-trifluoromethyl-6,7,8,9-tetrahydro-pyrimido[1,2-a]-pyrimidin-4-one | R4 = H; p = 2; q = 0; R2 = H; R3 = CF3 (R) | Chiral | 120 |
| EXAMPLE-14 | [(S)-8-((R)-3-Methyl-morpholin-4-yl)-6-oxo-2-trifluoromethyl-3,4-dihydro-2H,6H-pyrimido[1,2-a]-pyrimidin-1-yl]acetic acid ethyl ester | R4 = H; p = 0; q = 2; R2 = H; R3 = CF3 (S) | Chiral | 134 |

Experimental section: Table 2: Examples from 1 to 295, starting intermediates of type F and amount of each example isolated

| EXAMPLE | Example name | Intermediate of type F | Example structure | Amount isolated (mg) |
|---|---|---|---|---|
| EXAMPLE-15 | (S)-3-Fluoro-2-((R)-3-methylmorpholin-4-yl)-9-(5-methyl-[1,2,4]oxadiazol-3-yl-methyl)-8-trifluoromethyl-6,7,8,9-tetrahydro-pyrimido[1,2-a]-pyrimidin-4-one | R4 = F; p = 0; q = 2; R2 = H; R3 = CF3 (S) | 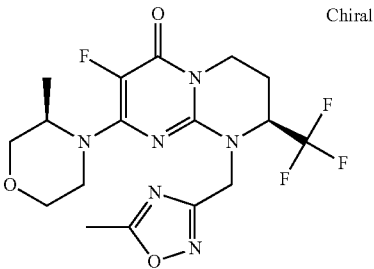 [SMILES: Cc1nc(CN2c3nc(N4CCOC[C@H]4C)c(F)c(=O)n3CC[C@H]2C(F)(F)F)no1] Chiral | 75 |
| EXAMPLE-16 | (S)-2-((R)-3-Methyl-morpholin-4-yl)-9-(2-oxobutyl)-8-trifluoromethyl-6,7,8,9-tetrahydro-pyrimido[1,2-a]-pyrimidin-4-one | R4 = H; p = 0; q = 2; R2 = H; R3 = CF3 (S) | 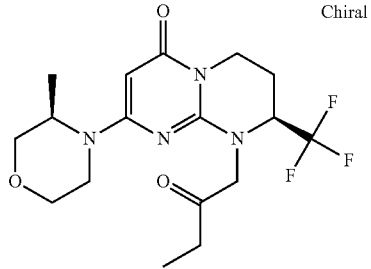 [SMILES: CCC(=O)CN1c2nc(N3CCOC[C@H]3C)cc(=O)n2CC[C@H]1C(F)(F)F] Chiral | 25 |
| EXAMPLE-17 | (S)-2-((R)-3-Methyl-morpholin-4-yl)-9-(3-methyl-[1,2,4]oxadiazol-5-yl-methyl)-8-trifluoromethyl-6,7,8,9-tetrahydro-pyrimido[1,2-a]-pyrimidin-4-one | R4 = H; p = 0; q = 2; R2 = H; R3 = CF3 (S) | 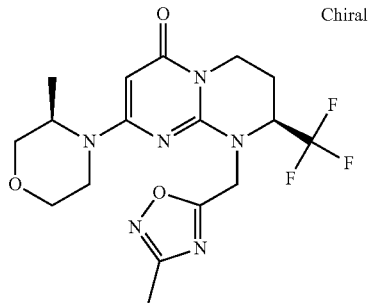 [SMILES: Cc1noc(CN2c3nc(N4CCOC[C@H]4C)cc(=O)n3CC[C@H]2C(F)(F)F)n1] Chiral | 50 |
| EXAMPLE-18 | (S)-3-Fluoro-2-((R)-3-methylmorpholin-4-yl)-9-[2-oxo-2-(tetrahydro-pyran-4-yl)ethyl]-8-trifluoromethyl-6,7,8,9-tetrahydro-pyrimido[1,2-a]-pyrimidin-4-one | R4 = F; p = 0; q = 2; R2 = H; R3 = CF3 (S) | 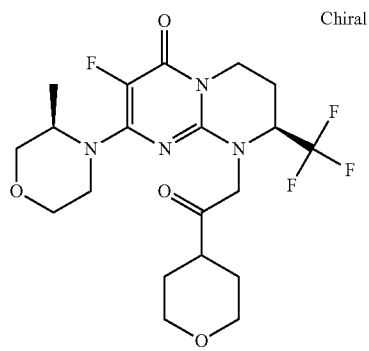 [SMILES: C[C@@H]1COCCN1c1nc2n(c(=O)c1F)CC[C@@H](C(F)(F)F)N2CC(=O)C1CCOCC1] Chiral | 140 |

Experimental section: Table 2: Examples from 1 to 295, starting intermediates of type F and amount of each example isolated

| EXAMPLE | Example name | Intermediate of type F | Example structure | Amount isolated (mg) |
|---|---|---|---|---|
| EXAMPLE-19 | (S)-3-Fluoro-2-((R)-3-methylmorpholin-4-yl)-9-(3-methyl-[1,2,4]oxadiazol-5-yl-methyl)-8-trifluoromethyl-6,7,8,9-tetrahydro-pyrimido[1,2-a]-pyrimidin-4-one | R4 = F; p = 0; q = 2; R2 = H; R3 = CF3 (S) | Chiral | 95 |
| EXAMPLE-20 | (S)-3-Fluoro-9-(2-methoxy-ethyl)-2-((R)-3-methylmorpholin-4-yl)-8-trifluoromethyl-6,7,8,9-tetrahydro-pyrimido[1,2-a]-pyrimidin-4-one | R4 = F; p = 0; q = 2; R2 = H; R3 = CF3 (S) | Chiral | 38 |
| EXAMPLE-21 | (R)-3-Fluoro-2-((R)-3-methylmorpholin-4-yl)-9-(5-methyl-[1,2,4]oxadiazol-3-yl-methyl)-6-trifluoromethyl-6,7,8,9-tetrahydro-pyrimido[1,2-a]-pyrimidin-4-one | R4 = F; p = 2; q = 0; R2 = H; R3 = CF3 (R) | | 86 |
| EXAMPLE-22 | (S)-3-Fluoro-2-((R)-3-methylmorpholin-4-yl)-9-(2-oxobutyl)-8-trifluoromethyl-6,7,8,9-tetrahydro-pyrimido[1,2-a]-pyrimidin-4-one | R4 = F; p = 0; q = 2; R2 = H; R3 = CF3 (S) | Chiral | 62 |

Experimental section: Table 2: Examples from 1 to 295, starting intermediates of type F and amount of each example isolated

| EXAMPLE | Example name | Intermediate of type F | Example structure | Amount isolated (mg) |
|---|---|---|---|---|
| EXAMPLE-23 | 2-[(S)-7-Fluoro-8-((R)-3-methylmorpholin-4-yl)-6-oxo-2-trifluoromethyl-3,4-dihydro-2H,6H-pyrimido[1,2-a]pyrimidin-1-yl]-N-methoxy-N-methyl-acetamide | R4 = F; p = 0; q = 2; R2 = H; R3 = CF3 (S) | Chiral | 550 |
| EXAMPLE-24 | (S)-9-(6-Fluoropyridin-3-ylmethyl)-2-((R)-3-methylmorpholin-4-yl)-8-trifluoromethyl-6,7,8,9-tetrahydro-pyrimido[1,2-a]pyrimidin-4-one | R4 = H; p = 0; q = 2; R2 = H; R3 = CF3 (S) | Chiral | 84 |
| EXAMPLE-25 | (S)-9-[2-(2-Fluoro-pyridin-4-yl)-2-oxo-ethyl]-2-((R)-3-methyl-morpholin-4-yl)-8-trifluoromethyl-6,7,8,9-tetrahydro-pyrimido[1,2-a]-pyrimidin-4-one | R4 = H; p = 0; q = 2; R2 = H; R3 = CF3 (S) | Chiral | 46 |
| EXAMPLE-26 | (R)-2-((R)-3-Methyl-morpholin-4-yl)-9-(2-oxobutyl)-6-trifluoromethyl-6,7,8,9-tetrahydro-pyrimido[1,2-a]-pyrimidin-4-one | R4 = H; p = 2; q = 0; R2 = H; R3 = CF3 (R) | Chiral | 98 |

Experimental section: Table 2: Examples from 1 to 295, starting intermediates of type F and amount of each example isolated

| EXAMPLE | Example name | Intermediate of type F | Example structure | Amount isolated (mg) |
|---|---|---|---|---|
| EXAMPLE-27 | (R)-2-((R)-3-Methyl-morpholin-4-yl)-9-(5-methyl-[1,2,4]oxadiazol-3-yl-methyl)-6-trifluoromethyl-6,7,8,9-tetrahydro-pyrimido[1,2-a]-pyrimidin-4-one | R4 = H; p = 2; q = 0; R2 = H; R3 = CF3 (R) | Chiral | 77 |
| EXAMPLE-28 | (R)-3-Fluoro-2-((R)-3-methylmorpholin-4-yl)-6-trifluoromethyl-9-(3-trifluoromethyl-[1,2,4]oxadiazol-5-yl-methyl)-6,7,8,9-tetrahydro-pyrimido[1,2-a]-pyrimidin-4-one | R4 = F; p = 2; q = 0; R2 = H; R3 = CF3 (R) | Chiral | 139 |
| EXAMPLE-29 | (R)-3-Fluoro-2-((R)-3-methylmorpholin-4-yl)-9-(2-oxobutyl)-6-trifluoromethyl-6,7,8,9-tetrahydro-pyrimido[1,2-a]-pyrimidin-4-one | R4 = F; p = 2; q = 0; R2 = H; R3 = CF3 (R) | Chiral | 44 |
| EXAMPLE-30 | (S)-6-Fluoro-2-methyl-7-((R)-3-methyl-morpholin-4-yl)-1-(5-methyl-[1,2,4]oxadiazol-3-yl-methyl)-2-trifluoromethyl-2,3-dihydro-1H-imidazo[1,2-a]-pyrimidin-5-one | R4 = F; p = 0; q = 1; R2 = Me; R3 = CF3 (S) | Chiral | 87 |

Experimental section: Table 2: Examples from 1 to 295, starting intermediates of type F and amount of each example isolated

| EXAMPLE | Example name | Intermediate of type F | Example structure | Amount isolated (mg) |
|---|---|---|---|---|
| EXAMPLE-31 | (S)-1-(2-Cyclopropyl-2-oxoethyl)-2-methyl-7-((R)-3-methyl-morpholin-4-yl)-2-trifluoromethyl-2,3-dihydro-1H-imidazo[1,2-a]-pyrimidin-5-one | R4 = H; p = 0; q = 1; R2 = Me; R3 = CF3 (S) | Chiral | 45 |
| EXAMPLE-32 | (S)-9-(1-Difluoromethyl-1H-pyrazol-3-ylmethyl)-2-((R)-3-methyl-morpholin-4-yl)-8-trifluoromethyl-6,7,8,9-tetrahydro-pyrimido[1,2-a]-pyrimidin-4-one | R4 = H; p = 0; q = 2; R2 = H; R3 = CF3 (S) | Chiral | 100 |
| EXAMPLE-33 | (S)-9-Isoxazol-3-yl-methyl-2-((R)-3-methylmorpholin-4-yl)-8-trifluoromethyl-6,7,8,9-tetrahydro-pyrimido[1,2-a]-pyrimidin-4-one | R4 = H; p = 0; q = 2; R2 = H; R3 = CF3 (S) | Chiral | 50 |
| EXAMPLE-34 | (S)-9-(2-Chloro-thiazol-5-ylmethyl)-2-((R)-3-methyl-morpholin-4-yl)-8-trifluoromethyl-6,7,8,9-tetrahydro-pyrimido[1,2-a]-pyrimidin-4-one | R4 = H; p = 0; q = 2; R2 = H; R3 = CF3 (S) | Chiral | 25 |

-continued

Experimental section: Table 2: Examples from 1 to 295, starting intermediates of type F and amount of each example isolated

| EXAMPLE | Example name | Intermediate of type F | Example structure | Amount isolated (mg) |
|---|---|---|---|---|
| EXAMPLE-35 | (S)-9-(6-Chloro-pyridin-3-ylmethyl)-2-((R)-3-methyl-morpholin-4-yl)-8-trifluoromethyl-6,7,8,9-tetrahydro-pyrimido[1,2-a]-pyrimidin-4-one | R4 = H; p = 0; q = 2; R2 = H; R3 = CF3 (S) | Chiral | 45 |
| EXAMPLE-36 | (S)-9-Isoxazol-5-yl-methyl-2-((R)-3-methylmorpholin-4-yl)-8-trifluoromethyl-6,7,8,9-tetrahydro-pyrimido[1,2-a]-pyrimidin-4-one | R4 = H; p = 0; q = 2; R2 = H; R3 = CF3 (S) | Chiral | 45 |
| EXAMPLE-37 | (S)-9-(2-Difluoromethyl-2H-pyrazol-3-ylmethyl)-2-((R)-3-methyl-morpholin-4-yl)-8-trifluoromethyl-6,7,8,9-tetrahydro-pyrimido[1,2-a]-pyrimidin-4-one | R4 = H; p = 0; q = 2; R2 = H; R3 = CF3 (S) | Chiral | 30 |
| EXAMPLE-38 | (S)-3-Fluoro-2-((R)-3-methylmorpholin-4-yl)-9-(2-oxo-2-pyridin-2-ylethyl)-8-trifluoromethyl-6,7,8,9-tetrahydro-pyrimido[1,2-a]-pyrimidin-4-one | R4 = F; p = 0; q = 2; R2 = H; R3 = CF3 (S) | Chiral | 20 |

Experimental section: Table 2: Examples from 1 to 295, starting intermediates of type F and amount of each example isolated

| EXAMPLE | Example name | Intermediate of type F | Example structure | Amount isolated (mg) |
|---|---|---|---|---|
| EXAMPLE-39 | (S)-9-(2-Fluoro-2-phenylethyl)-2-((R)-3-methylmorpholin-4-yl)-8-trifluoromethyl-6,7,8,9-tetrahydro-pyrimido[1,2-a]pyrimidin-4-one, single stereoisomer | R4 = H; p = 0; q = 2; R2 = H; R3 = CF3 (S) | Chiral | 46 |
| EXAMPLE-40 | (S)-3-Fluoro-9-(2-methoxypyridin-4-yl)-2-((R)-3-Methyl-morpholin-4-yl)-8-trifluoromethyl-6,7,8,9-tetrahydro-pyrimido[1,2-a]-pyrimidin-4-one | R4 = F; p = 0; q = 2; R2 = H; R3 = CF3 (S) | Chiral | 98 |
| EXAMPLE-41 | (S)-9-(2-Chloro-pyridin-4-ylmethyl)-3-fluoro-2-((R)-3-methyl-morpholin-4-yl)-8-trifluoromethyl-6,7,8,9-tetrahydro-pyrimido[1,2-a]-pyrimidin-4-one | R4 = F; p = 0; q = 2; R2 = H; R3 = CF3 (S) | Chiral | 48 |
| EXAMPLE-42 | (S)-3-Fluoro-2-((R)-3-methylmorpholin-4-yl)-9-oxazol-2-ylmethyl-8-trifluoromethyl-6,7,8,9-tetrahydro-pyrimido[1,2-a]-pyrimidin-4-one | R4 = F; p = 0; q = 2; R2 = H; R3 = CF3 (S) | Chiral | 85 |

Experimental section: Table 2: Examples from 1 to 295, starting intermediates of type F and amount of each example isolated

| EXAMPLE | Example name | Intermediate of type F | Example structure | Amount isolated (mg) |
|---|---|---|---|---|
| EXAMPLE-43 | (S)-9-(6-Cyclopropyl-pyridin-3-yl)-3-fluoro-2-((R)-3-methyl-morpholin-4-yl)-8-trifluoromethyl-6,7,8,9-tetrahydro-pyrimido[1,2-a]-pyrimidin-4-one | R4 = F; p = 0; q = 2; R2 = H; R3 = CF3 (S) | Chiral | 40 |
| EXAMPLE-44 | (S)-3-Fluoro-2-((R)-3-methylmorpholin-4-yl)-9-oxazol-4-ylmethyl-8-trifluoromethyl-6,7,8,9-tetrahydro-pyrimido[1,2-a]-pyrimidin-4-one | R4 = F; p = 0; q = 2; R2 = H; R3 = CF3 (S) | Chiral | 46 |
| EXAMPLE-45 | (S)-9-(2-Chloro-pyridin-4-yl)-3-fluoro-2-((R)-3-methyl-morpholin-4-yl)-8-trifluoromethyl-6,7,8,9-tetrahydro-pyrimido[1,2-a]-pyrimidin-4-one | R4 = F; p = 0; q = 2; R2 = H; R3 = CF3 (S) | Chiral | 62 |
| EXAMPLE-46 | (S)-3-Fluoro-9-isoxazol-5-ylmethyl-2-((R)-3-methyl-morpholin-4-yl)-8-trifluoromethyl-6,7,8,9-tetrahydro-pyrimido[1,2-a]-pyrimidin-4-one | R4 = F; p = 0; q = 2; R2 = H; R3 = CF3 (S) | Chiral | 68 |

Experimental section: Table 2: Examples from 1 to 295, starting intermediates of type F and amount of each example isolated

| EXAMPLE | Example name | Intermediate of type F | Example structure | Amount isolated (mg) |
|---|---|---|---|---|
| EXAMPLE-47 | (S)-3-Fluoro-2-((R)-3-methylmorpholin-4-yl)-9-pyridin-3-yl-8-trifluoromethyl-6,7,8,9-tetrahydro-pyrimido[1,2-a]-pyrimidin-4-one | R4 = F; p = 0; q = 2; R2 = H; R3 = CF3 (S) | Chiral 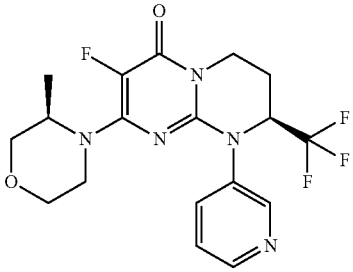 | 21 |
| EXAMPLE-48 | (S)-3-Fluoro-2-((R)-3-methylmorpholin-4-yl)-9-[2-(2,2,2-trifluoro-ethoxy)ethyl]-8-trifluoromethyl-6,7,8,9-tetrahydro-pyrimido[1,2-a]-pyrimidin-4-one | R4 = F; p = 0; q = 2; R2 = H; R3 = CF3 (S) | Chiral 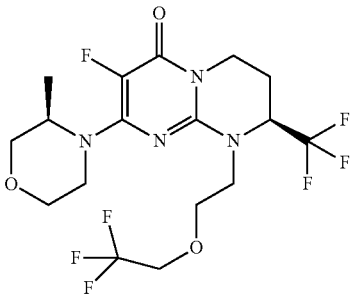 | 17 |
| EXAMPLE-49 | (S)-3-Fluoro-9-(2-hydroxy-2-methyl-propyl)-2-((R)-3-methylmorpholin-4-yl)-8-trifluoromethyl-6,7,8,9-tetrahydro-pyrimido[1,2-a]-pyrimidin-4-one | R4 = F; p = 0; q = 2; R2 = H; R3 = CF3 (S) | Chiral 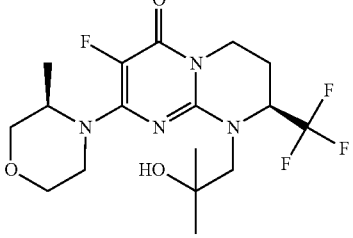 | 30 |
| EXAMPLE-50 | (S)-3-Fluoro-2-((R)-3-methylmorpholin-4-yl)-9-(2-oxo-2-pyridin-3-ylethyl)-8-trifluoromethyl-6,7,8,9-tetrahydro-pyrimido[1,2-a]-pyrimidin-4-one | R4 = F; p = 0; q = 2; R2 = H; R3 = CF3 (S) | Chiral 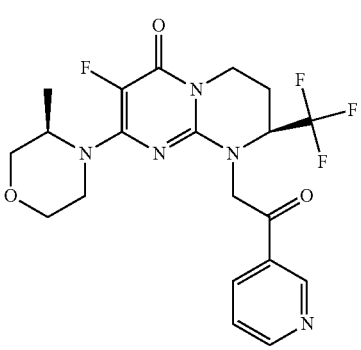 | 16 |

Experimental section: Table 2: Examples from 1 to 295, starting intermediates of type F and amount of each example isolated

| EXAMPLE | Example name | Intermediate of type F | Example structure | Amount isolated (mg) |
|---|---|---|---|---|
| EXAMPLE-51 | (S)-3-Fluoro-9-(6-fluoropyridin-3-yl-methyl)-2-((R)-3-methylmorpholin-4-yl)-8-trifluoromethyl-6,7,8,9-tetrahydro-pyrimido[1,2-a]-pyrimidin-4-one | R4 = F; p = 0; q = 2; R2 = H; R3 = CF3 (S) | Chiral | 80 |
| EXAMPLE-52 | (S)-9-(6-Chloro-pyridin-3-ylmethyl)-3-fluoro-2-((R)-3-methyl-morpholin-4-yl)-8-trifluoromethyl-6,7,8,9-tetrahydro-pyrimido[1,2-a]-pyrimidin-4-one | R4 = F; p = 0; q = 2; R2 = H; R3 = CF3 (S) | Chiral | 73 |
| EXAMPLE-53 | (S)-9-(6-Difluoromethylpyridin-3-yl)-3-fluoro-2-((R)-3-methylmorpholin-4-yl)-8-trifluoromethyl-6,7,8,9-tetrahydro-pyrimido[1,2-a]-pyrimidin-4-one | R4 = F; p = 0; q = 2; R2 = H; R3 = CF3 (S) | Chiral | 40 |

-continued

Experimental section: Table 2: Examples from 1 to 295, starting intermediates of type F and amount of each example isolated

| EXAMPLE | Example name | Intermediate of type F | Example structure | Amount isolated (mg) |
|---|---|---|---|---|
| EXAMPLE-54 | (S)-9-(5-tert-Butyl-[1,2,4]oxadiazol-3-yl-methyl)-3-fluoro-2-((R)-3-methyl-morpholin-4-yl)-8-trifluoromethyl-6,7,8,9-tetrahydro-pyrimido[1,2-a]-pyrimidin-4-one | R4 = F; p = 0; q = 2; R2 = H; R3 = CF3 (S) | Chiral | 70 |
| EXAMPLE-55 | (S)-3-Fluoro-2-((R)-3-methylmorpholin-4-yl)-9-pyridin-4-yl-8-trifluoromethyl-6,7,8,9-tetrahydro-pyrimido[1,2-a]-pyrimidin-4-one | R4 = F; p = 0; q = 2; R2 = H; R3 = CF3 (S) | Chiral | 30 |
| EXAMPLE-56 | (S)-3-Fluoro-9-(5-fluoropyridin-2-yl-methyl)-2-((R)-3-methylmorpholin-4-yl)-8-trifluoromethyl-6,7,8,9-tetrahydro-pyrimido[1,2-a]-pyrimidin-4-one | R4 = F; p = 0; q = 2; R2 = H; R3 = CF3 (S) | Chiral | 65 |
| EXAMPLE-57 | (S)-3-Fluoro-9-(5-fluoropyridin-3-yl-methyl)-2-((R)-3-methylmorpholin-4-yl)-8-trifluoromethyl-6,7,8,9-tetrahydro-pyrimido[1,2-a]-pyrimidin-4-one | R4 = F; p = 0; q = 2; R2 = H; R3 = CF3 (S) | Chiral | 62 |

Experimental section: Table 2: Examples from 1 to 295, starting intermediates of type F and amount of each example isolated

| EXAMPLE | Example name | Intermediate of type F | Example structure | Amount isolated (mg) |
|---|---|---|---|---|
| EXAMPLE-58 | (S)-3-Fluoro-9-(2-fluoropyridin-3-yl-methyl)-2-((R)-3-methylmorpholin-4-yl)-8-trifluoromethyl-6,7,8,9-tetrahydro-pyrimido[1,2-a]-pyrimidin-4-one | R4 = F; p = 0; q = 2; R2 = H; R3 = CF3 (S) | Chiral 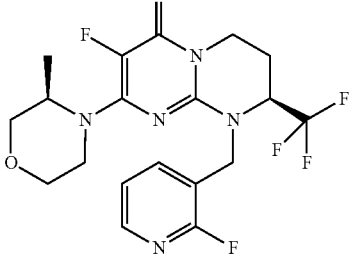 | 65 |
| EXAMPLE-59 | (S)-3-Fluoro-9-[2-(3-fluoropyridin-2-yl)-2-oxoethyl]-2-((R)-3-methylmorpholin-4-yl)-8-trifluoromethyl-6,7,8,9-tetrahydro-pyrimido[1,2-a]-pyrimidin-4-one | R4 = F; p = 0; q = 2; R2 = H; R3 = CF3 (S) | Chiral 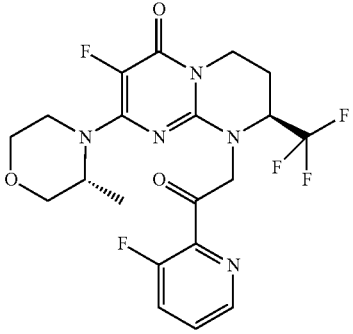 | 80 |
| EXAMPLE-60 | (S)-9-[2-(3-Fluoro-pyridin-2-yl)-2-oxo-ethyl]-2-((R)-3-methyl-morpholin-4-yl)-8-trifluoromethyl-6,7,8,9-tetrahydro-pyrimido[1,2-a]-pyrimidin-4-one | R4 = H; p = 0; q = 2; R2 = H; R3 = CF3 (S) | Chiral 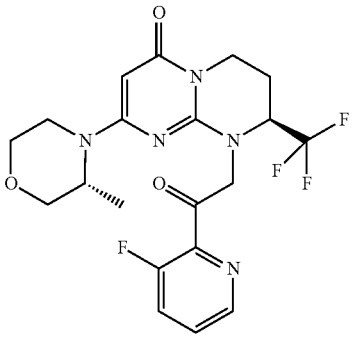 | 130 |

Experimental section: Table 2: Examples from 1 to 295, starting intermediates of type F and amount of each example isolated

| EXAMPLE | Example name | Intermediate of type F | Example structure | Amount isolated (mg) |
|---|---|---|---|---|
| EXAMPLE-61 | (S)-9-[2-(2-Methoxy-pyridin-4-yl)-2-oxo-ethyl]-2-((R)-3-methyl-morpholin-4-yl)-8-trifluoromethyl-6,7,8,9-tetrahydro-pyrimido[1,2-a]-pyrimidin-4-one | R4 = H; p = 0; q = 2; R2 = H; R3 = CF3 (S) | Chiral | 18 |
| EXAMPLE-62 | (S)-3-Fluoro-9-(3-methylisoxazol-4-yl-methyl)-2-((R)-3-methylmorpholin-4-yl)-8-trifluoromethyl-6,7,8,9-tetrahydro-pyrimido[1,2-a]-pyrimidin-4-one | R4 = F; p = 0; q = 2; R2 = H; R3 = CF3 (S) | Chiral | 104 |
| EXAMPLE-63 | (S)-9-[2-(6-Fluoro-pyridin-2-yl)-2-oxo-ethyl]-2-((R)-3-methyl-morpholin-4-yl)-8-trifluoromethyl-6,7,8,9-tetrahydro-pyrimido[1,2-a]-pyrimidin-4-one | R4 = H; p = 0; q = 2; R2 = H; R3 = CF3 (S) | Chiral | 30 |

Experimental section: Table 2: Examples from 1 to 295, starting intermediates of type F and amount of each example isolated

| EXAMPLE | Example name | Intermediate of type F | Example structure | Amount isolated (mg) |
|---|---|---|---|---|
| EXAMPLE-64 | (S)-9-Imidazo[1,2-a]-pyridin-2-ylmethyl-2-((R)-3-methyl-morpholin-4-yl)-8-trifluoromethyl-6,7,8,9-tetrahydro-pyrimido[1,2-a]-pyrimidin-4-one | R4 = H; p = 0; q = 2; R2 = H; R3 = CF3 (S) | Chiral | 62 |
| EXAMPLE-65 | (S)-9-(4-Chloro-pyridin-2-ylmethyl)-2-((R)-3-methyl-morpholin-4-yl)-8-trifluoromethyl-6,7,8,9-tetrahydro-pyrimido[1,2-a]-pyrimidin-4-one | R4 = H; p = 0; q = 2; R2 = H; R3 = CF3 (S) | Chiral | 87 |
| EXAMPLE-66 | (S)-9-(3-Chloro-pyridin-4-ylmethyl)-2-((R)-3-methyl-morpholin-4-yl)-8-trifluoromethyl-6,7,8,9-tetrahydro-pyrimido[1,2-a]-pyrimidin-4-one | R4 = H; p = 0; q = 2; R2 = H; R3 = CF3 (S) | Chiral | 81 |
| EXAMPLE-67 | (S)-2-((R)-3-Methyl-morpholin-4-yl)-9-(2-oxo-3-pyridin-2-yl-propyl)-8-trifluoromethyl-6,7,8,9-tetrahydro-pyrimido[1,2-a]-pyrimidin-4-one | R4 = H; p = 0; q = 2; R2 = H; R3 = CF3 (S) | Chiral | 20 |

Experimental section: Table 2: Examples from 1 to 295, starting intermediates of type F and amount of each example isolated

| EXAMPLE | Example name | Intermediate of type F | Example structure | Amount isolated (mg) |
|---|---|---|---|---|
| EXAMPLE-68 | (S)-3-Fluoro-2-((R)-3-methylmorpholin-4-yl)-9-(2-oxo-2-thiazol-2-yl-ethyl)-8-trifluoromethyl-6,7,8,9-tetrahydro-pyrimido[1,2-a]-pyrimidin-4-one | R4 = F; p = 0; q = 2; R2 = H; R3 = CF3 (S) | Chiral | 40 |
| EXAMPLE-69 | (S)-3-Fluoro-2-((R)-3-methylmorpholin-4-yl)-9-thiazol-4-ylmethyl-8-trifluoromethyl-6,7,8,9-tetrahydro-pyrimido[1,2-a]-pyrimidin-4-one | R4 = F; p = 0; q = 2; R2 = H; R3 = CF3 (S) | Chiral | 48 |
| EXAMPLE-70 | (S)-9-[2-(5-Fluoro-pyridin-2-yl)-2-oxo-ethyl]-2-((R)-3-methyl-morpholin-4-yl)-8-trifluoromethyl-6,7,8,9-tetrahydro-pyrimido[1,2-a]-pyrimidin-4-one | R4 = H; p = 0; q = 2; R2 = H; R3 = CF3 (S) | Chiral | 24 |
| EXAMPLE-71 | 3-Fluoro-8,8-dimethyl-2-((R)-3-methyl-morpholin-4-yl)-9-(2-oxo-2-pyridin-2-yl-ethyl)-6,7,8,9-tetrahydro-pyrimido[1,2-a]-pyrimidin-4-one | R4 = F; p = 0; q = 2; R2 = Me; R3 = Me | Chiral | 60 |

Experimental section: Table 2: Examples from 1 to 295, starting intermediates of type F and amount of each example isolated

| EXAMPLE | Example name | Intermediate of type F | Example structure | Amount isolated (mg) |
|---|---|---|---|---|
| EXAMPLE-72 | 9-(2-Difluoromethyl-2H-pyrazol-3-yl-methyl)-8,8-dimethyl-2-((R)-3-methyl-morpholin-4-yl)-6,7,8,9-tetrahydro-pyrimido[1,2-a]-pyrimidin-4-one | R4 = H; p = 0; q = 2; R2 = Me; R3 = Me | Chiral | 50 |
| EXAMPLE-73 | 3-Fluoro-9-isoxazol-3-ylmethyl-8,8-dimethyl-2-((R)-3-methyl-morpholin-4-yl)-6,7,8,9-tetrahydro-pyrimido[1,2-a]-pyrimidin-4-one | R4 = F; p = 0; q = 2; R2 = Me; R3 = Me | Chiral | 80 |
| EXAMPLE-74 | 9-(2-Difluoromethyl-2H-pyrazol-3-yl-methyl)-3-fluoro-8,8-dimethyl-2-((R)-3-methylmorpholin-4-yl)-6,7,8,9-tetrahydro-pyrimido[1,2-a]-pyrimidin-4-one | R4 = F; p = 0; q = 2; R2 = Me; R3 = Me | Chiral | 60 |
| EXAMPLE-75 | (S)-9-(3-Fluoro-phenyl)-2-((R)-3-methylmorpholin-4-yl)-8-trifluoromethyl-6,7,8,9-tetrahydro-pyrimido[1,2-a]-pyrimidin-4-one | R4 = H; p = 0; q = 2; R2 = H; R3 = CF3 (S) | Chiral | 96 |

Experimental section: Table 2: Examples from 1 to 295, starting intermediates of type F and amount of each example isolated

| EXAMPLE | Example name | Intermediate of type F | Example structure | Amount isolated (mg) |
|---|---|---|---|---|
| EXAMPLE-76 | (S)-9-(2-Chloro-pyridin-4-ylmethyl)-2-((R)-3-methyl-morpholin-4-yl)-8-trifluoromethyl-6,7,8,9-tetrahydro-pyrimido[1,2-a]-pyrimidin-4-one | R4 = H; p = 0; q = 2; R2 = H; R3 = CF3 (S) | Chiral | 29 |
| EXAMPLE-77 | (S)-2-((R)-3-Methyl-morpholin-4-yl)-9-oxazol-2-ylmethyl-8-trifluoromethyl-6,7,8,9-tetrahydro-pyrimido[1,2-a]-pyrimidin-4-one | R4 = H; p = 0; q = 2; R2 = H; R3 = CF3 (S) | Chiral | 80 |
| EXAMPLE-78 | (S)-2-((R)-3-Methyl-morpholin-4-yl)-9-thiazol-4-ylmethyl-8-trifluoromethyl-6,7,8,9-tetrahydro-pyrimido[1,2-a]-pyrimidin-4-one | R4 = H; p = 0; q = 2; R2 = H; R3 = CF3 (S) | Chiral | 94 |
| EXAMPLE-79 | (S)-9-(2-Chloro-pyridin-4-yl)-2-((R)-3-methylmorpholin-4-yl)-8-trifluoromethyl-6,7,8,9-tetrahydro-pyrimido[1,2-a]-pyrimidin-4-one | R4 = H; p = 0; q = 2; R2 = H; R3 = CF3 (S) | Chiral | 66 |

Experimental section: Table 2: Examples from 1 to 295, starting intermediates of type F and amount of each example isolated

| EXAMPLE | Example name | Intermediate of type F | Example structure | Amount isolated (mg) |
|---|---|---|---|---|
| EXAMPLE-80 | (S)-9-(2-Methoxy-pyridin-4-yl)-2-((R)-3-methylmorpholin-4-yl)-8-trifluoromethyl-6,7,8,9-tetrahydro-pyrimido[1,2-a]-pyrimidin-4-one | R4 = H; p = 0; q = 2; R2 = H; R3 = CF3 (S) | Chiral | 25 |
| EXAMPLE-81 | (S)-2-((R)-3-Methyl-morpholin-4-yl)-8-trifluoromethyl-9-(6-trifluoromethylpyridin-3-yl)-6,7,8,9-tetrahydro-pyrimido[1,2-a]-pyrimidin-4-one | R4 = H; p = 0; q = 2; R2 = H; R3 = CF3 (S) | Chiral | 147 |
| EXAMPLE-82 | (S)-2-((R)-3-Methyl-morpholin-4-yl)-9-[2-(2,2,2-trifluoro-ethoxy)ethyl]-8-trifluoromethyl-6,7,8,9-tetrahydro-pyrimido[1,2-a]-pyrimidin-4-one | R4 = H; p = 0; q = 2; R2 = H; R3 = CF3 (S) | Chiral | 74 |
| EXAMPLE-83 | (S)-2-((R)-3-Methyl-morpholin-4-yl)-9-(6-methylpyridin-3-yl)-8-trifluoromethyl-6,7,8,9-tetrahydro-pyrimido[1,2-a]-pyrimidin-4-one | R4 = H; p = 0; q = 2; R2 = H; R3 = CF3 (S) | Chiral | 20 |

Experimental section: Table 2: Examples from 1 to 295, starting intermediates of type F and amount of each example isolated

| EXAMPLE | Example name | Intermediate of type F | Example structure | Amount isolated (mg) |
|---|---|---|---|---|
| EXAMPLE-84 | (S)-9-(2-Hydroxy-2-methylpropyl)-2-((R)-3-methylmorpholin-4-yl)-8-trifluoromethyl-6,7,8,9-tetrahydro-pyrimido[1,2-a]-pyrimidin-4-one | R4 = H; p = 0; q = 2; R2 = H; R3 = CF3 (S) | Chiral | 42 |
| EXAMPLE-85 | (S)-9-(6-Isopropoxy-pyridin-3-yl)-2-((R)-3-methylmorpholin-4-yl)-8-trifluoromethyl-6,7,8,9-tetrahydro-pyrimido[1,2-a]-pyrimidin-4-one | R4 = H; p = 0; q = 2; R2 = H; R3 = CF3 (S) | Chiral | 25 |
| EXAMPLE-86 | (S)-9-(5-Chloro-pyridin-2-ylmethyl)-2-((R)-3-methyl-morpholin-4-yl)-8-trifluoromethyl-6,7,8,9-tetrahydro-pyrimido[1,2-a]-pyrimidin-4-one | R4 = H; p = 0; q = 2; R2 = H; R3 = CF3 (S) | Chiral | 105 |
| EXAMPLE-87 | (S)-2-((R)-3-Methyl-morpholin-4-yl)-9-thiazol-5-ylmethyl-8-trifluoromethyl-6,7,8,9-tetrahydro-pyrimido[1,2-a]-pyrimidin-4-one | R4 = H; p = 0; q = 2; R2 = H; R3 = CF3 (S) | Chiral | 96 |

Experimental section: Table 2: Examples from 1 to 295, starting intermediates of type F and amount of each example isolated

| EXAMPLE | Example name | Intermediate of type F | Example structure | Amount isolated (mg) |
|---|---|---|---|---|
| EXAMPLE-88 | (S)-9-(6-Cyclobutyl-pyridin-3-yl)-2-((R)-3-methylmorpholin-4-yl)-8-trifluoromethyl-6,7,8,9-tetrahydro-pyrimido[1,2-a]-pyrimidin-4-one | R4 = H; p = 0; q = 2; R2 = H; R3 = CF3 (S) | Chiral | 128 |
| EXAMPLE-89 | (S)-9-(2-Cyclopropyl-pyridin-4-yl)-2-((R)-3-methylmorpholin-4-yl)-8-trifluoromethyl-6,7,8,9-tetrahydro-pyrimido[1,2-a]-pyrimidin-4-one | R4 = H; p = 0; q = 2; R2 = H; R3 = CF3 (S) | Chiral | 96 |
| EXAMPLE-90 | (S)-9-(2-Methoxy-ethyl)-2-((R)-3-methyl-morpholin-4-yl)-8-trifluoromethyl-6,7,8,9-tetrahydro-pyrimido[1,2-a]-pyrimidin-4-one | R4 = H; p = 0; q = 2; R2 = H; R3 = CF3 (S) | Chiral | 69 |
| EXAMPLE-91 | (S)-2-((R)-3-Methyl-morpholin-4-yl)-9-oxazol-5-ylmethyl-8-trifluoromethyl-6,7,8,9-tetrahydro-pyrimido[1,2-a]-pyrimidin-4-one | R4 = H; p = 0; q = 2; R2 = H; R3 = CF3 (S) | Chiral | 40 |

Experimental section: Table 2: Examples from 1 to 295, starting intermediates of type F and amount of each example isolated

| EXAMPLE | Example name | Intermediate of type F | Example structure | Amount isolated (mg) |
|---|---|---|---|---|
| EXAMPLE-92 | (S)-9-(5-Fluoropyridin-2-ylmethyl)-2-((R)-3-methylmorpholin-4-yl)-8-trifluoromethyl-6,7,8,9-tetrahydro-pyrimido[1,2-a]-pyrimidin-4-one | R4 = H; p = 0; q = 2; R2 = H; R3 = CF3 (S) | Chiral 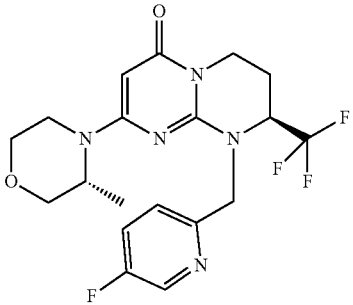 | 110 |
| EXAMPLE-93 | (S)-9-(2,5-Dimethyl-oxazol-4-ylmethyl)-2-((R)-3-methyl-morpholin-4-yl)-8-trifluoromethyl-6,7,8,9-tetrahydro-pyrimido[1,2-a]-pyrimidin-4-one | R4 = H; p = 0; q = 2; R2 = H; R3 = CF3 (S) | Chiral 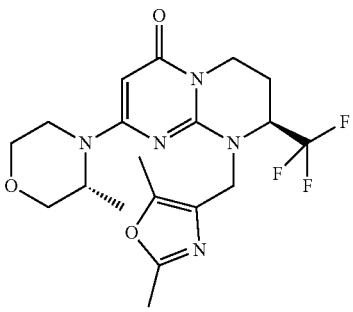 | 66 |
| EXAMPLE-94 | (S)-9-(5-Fluoropyridin-3-ylmethyl)-2-((R)-3-methylmorpholin-4-yl)-8-trifluoromethyl-6,7,8,9-tetrahydro-pyrimido[1,2-a]-pyrimidin-4-one | R4 = H; p = 0; q = 2; R2 = H; R3 = CF3 (S) | Chiral 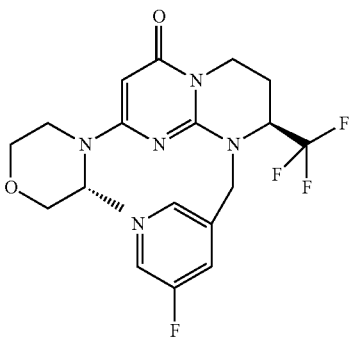 | 95 |
| EXAMPLE-95 | (S)-9-(5-Chloro-pyridin-3-ylmethyl)-2-((R)-3-methyl-morpholin-4-yl)-8-trifluoromethyl-6,7,8,9-tetrahydro-pyrimido[1,2-a]-pyrimidin-4-one | R4 = H; p = 0; q = 2; R2 = H; R3 = CF3 (S) | Chiral 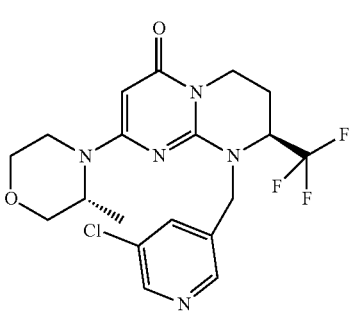 | 6 |

Experimental section: Table 2: Examples from 1 to 295, starting intermediates of type F and amount of each example isolated

| EXAMPLE | Example name | Intermediate of type F | Example structure | Amount isolated (mg) |
|---|---|---|---|---|
| EXAMPLE-96 | (S)-2-((R)-3-Methyl-morpholin-4-yl)-9-(5-methyl-[1,3,4]oxadiazol-2-yl-methyl)-8-trifluoromethyl-6,7,8,9-tetrahydro-pyrimido[1,2-a]-pyrimidin-4-one | R4 = H; p = 0; q = 2; R2 = H; R3 = CF3 (S) | Chiral | 90 |
| EXAMPLE-97 | (S)-9-(3,3-Dimethyl-2-oxobutyl)-3-fluoro-2-((R)-3-methyl-morpholin-4-yl)-8-trifluoromethyl-6,7,8,9-tetrahydro-pyrimido[1,2-a]-pyrimidin-4-one | R4 = F; p = 0; q = 2; R2 = H; R3 = CF3 (S) | Chiral | 104 |
| EXAMPLE-98 | (S)-9-(5-Chloro-thiophen-2-ylmethyl)-2-((R)-3-methyl-morpholin-4-yl)-8-trifluoromethyl-6,7,8,9-tetrahydro-pyrimido[1,2-a]-pyrimidin-4-one | R4 = H; p = 0; q = 2; R2 = H; R3 = CF3 (S) | Chiral | 29 |
| EXAMPLE-99 | (S)-2-((R)-3-Methyl-morpholin-4-yl)-9-(2-oxo-2-phenylethyl)-8-trifluoromethyl-6,7,8,9-tetrahydro-pyrimido[1,2-a]-pyrimidin-4-one | R4 = H; p = 0; q = 2; R2 = H; R3 = CF3 (S) | Chiral | 128 |

-continued

Experimental section: Table 2: Examples from 1 to 295, starting intermediates of type F and amount of each example isolated

| EXAMPLE | Example name | Intermediate of type F | Example structure | Amount isolated (mg) |
|---|---|---|---|---|
| EXAMPLE-100 | (S)-9-((S)-2-Methoxy-2-phenylethyl)-2-((R)-3-methylmorpholin-4-yl)-8-trifluoromethyl-6,7,8,9-tetrahydro-pyrimido[1,2-a]-pyrimidin-4-one | R4 = H; p = 0; q = 2; R2 = H; R3 = CF3 (S) | Chiral | 39 |
| EXAMPLE-101 | (S)-9-(3-Methyl-isoxazol-5-ylmethyl)-2-((R)-3-methyl-morpholin-4-yl)-8-trifluoromethyl-6,7,8,9-tetrahydro-pyrimido[1,2-a]-pyrimidin-4-one | R4 = H; p = 0; q = 2; R2 = H; R3 = CF3 (S) | Chiral | 350 |
| EXAMPLE-102 | (R)-2-((R)-3-Methyl-morpholin-4-yl)-9-(2-oxo-2-pyridin-2-yl-ethyl)-6-trifluoromethyl-6,7,8,9-tetrahydro-pyrimido[1,2-a]-pyrimidin-4-one | R4 = H; p = 2; q = 0; R2 = H; R3 = CF3 (R) | Chiral | 15 |
| EXAMPLE-103 | (S)-2-((R)-3-Methyl-morpholin-4-yl)-9-oxazol-4-ylmethyl-8-trifluoromethyl-6,7,8,9-tetrahydro-pyrimido[1,2-a]-pyrimidin-4-one | R4 = H; p = 0; q = 2; R2 = H; R3 = CF3 (S) | Chiral | 1000 |

Experimental section: Table 2: Examples from 1 to 295, starting intermediates of type F and amount of each example isolated

| EXAMPLE | Example name | Intermediate of type F | Example structure | Amount isolated (mg) |
|---|---|---|---|---|
| EXAMPLE-104 | (S)-2-((R)-3-Methyl-morpholin-4-yl)-9-(toluene-4-sulfonyl)-8-trifluoromethyl-6,7,8,9-tetrahydro-pyrimido[1,2-a]-pyrimidin-4-one | R4 = H; p = 0; q = 2; R2 = H; R3 = CF3 (S) | Chiral | 277 |
| EXAMPLE-105 | (R)-9-Isoxazol-5-yl-methyl-2-((R)-3-methylmorpholin-4-yl)-6-trifluoromethyl-6,7,8,9-tetrahydro-pyrimido[1,2-a]-pyrimidin-4-one | R4 = H; p = 2; q = 0; R2 = H; R3 = CF3 (R) | Chiral | 34 |
| EXAMPLE-106 | (R)-9-Isoxazol-3-yl-methyl-2-((R)-3-methylmorpholin-4-yl)-6-trifluoromethyl-6,7,8,9-tetrahydro-pyrimido[1,2-a]-pyrimidin-4-one | R4 = H; p = 2; q = 0; R2 = H; R3 = CF3 (R) | Chiral | 39 |
| EXAMPLE-107 | (R)-9-(6-Cyclopropyl-pyridin-3-yl)-2-((R)-3-methylmorpholin-4-yl)-6-trifluoromethyl-6,7,8,9-tetrahydro-pyrimido[1,2-a]-pyrimidin-4-one | R4 = H; p = 2; q = 0; R2 = H; R3 = CF3 (R) | Chiral | 60 |

-continued

Experimental section: Table 2: Examples from 1 to 295, starting intermediates of type F and amount of each example isolated

| EXAMPLE | Example name | Intermediate of type F | Example structure | Amount isolated (mg) |
|---|---|---|---|---|
| EXAMPLE-108 | (R)-9-(2-Chloro-pyridin-4-yl)-2-((R)-3-methylmorpholin-4-yl)-6-trifluoromethyl-6,7,8,9-tetrahydro-pyrimido[1,2-a]-pyrimidin-4-one | R4 = H; p = 2; q = 0; R2 = H; R3 = CF3 (R) | Chiral | 106 |
| EXAMPLE-109 | (R)-9-(2-Methoxy-pyridin-4-yl)-2-((R)-3-methylmorpholin-4-yl)-6-trifluoromethyl-6,7,8,9-tetrahydro-pyrimido[1,2-a]-pyrimidin-4-one | R4 = H; p = 2; q = 0; R2 = H; R3 = CF3 (R) | Chiral | 208 |
| EXAMPLE-110 | (R)-2-((R)-3-Methyl-morpholin-4-yl)-9-oxazol-4-ylmethyl-6-trifluoromethyl-6,7,8,9-tetrahydro-pyrimido[1,2-a]-pyrimidin-4-one | R4 = H; p = 2; q = 0; R2 = H; R3 = CF3 (R) | Chiral | 54 |
| EXAMPLE-111 | (S)-3-Fluoro-2-((R)-3-methylmorpholin-4-yl)-9-oxazol-5-ylmethyl-8-trifluoromethyl-6,7,8,9-tetrahydro-pyrimido[1,2-a]-pyrimidin-4-one | R4 = F; p = 0; q = 2; R2 = H; R3 = CF3 (S) | Chiral | 34 |

Experimental section: Table 2: Examples from 1 to 295, starting intermediates of type F and amount of each example isolated

| EXAMPLE | Example name | Intermediate of type F | Example structure | Amount isolated (mg) |
|---|---|---|---|---|
| EXAMPLE-112 | (R)-9-(2-Chloro-pyridin-4-ylmethyl)-2-((R)-3-methyl-morpholin-4-yl)-6-trifluoromethyl-6,7,8,9-tetrahydro-pyrimido[1,2-a]-pyrimidin-4-one | R4 = H; p = 2; q = 0; R2 = H; R3 = CF3 (R) | Chiral | 82 |
| EXAMPLE-113 | (R)-9-(2-Hydroxy-2-methylpropyl)-2-((R)-3-methylmorpholin-4-yl)-6-trifluoromethyl-6,7,8,9-tetrahydro-pyrimido[1,2-a]-pyrimidin-4-one | R4 = H; p = 2; q = 0; R2 = H; R3 = CF3 (R) | Chiral | 51 |
| EXAMPLE-114 | (R)-9-(2-Isopropoxy-pyridin-4-yl)-2-((R)-3-methylmorpholin-4-yl)-6-trifluoromethyl-6,7,8,9-tetrahydro-pyrimido[1,2-a]-pyrimidin-4-one | R4 = H; p = 2; q = 0; R2 = H; R3 = CF3 (R) | Chiral | 95 |

Experimental section: Table 2: Examples from 1 to 295, starting intermediates of type F and amount of each example isolated

| EXAMPLE | Example name | Intermediate of type F | Example structure | Amount isolated (mg) |
|---|---|---|---|---|
| EXAMPLE-115 | (R)-9-(6-Chloro-pyridin-3-ylmethyl)-2-((R)-3-methyl-morpholin-4-yl)-6-trifluoromethyl-6,7,8,9-tetrahydro-pyrimido[1,2-a]-pyrimidin-4-one | R4 = H; p = 2; q = 0; R2 = H; R3 = CF3 (R) | Chiral | 96 |
| EXAMPLE-116 | (R)-9-(6-Isopropoxy-pyridin-3-yl)-2-((R)-3-methylmorpholin-4-yl)-6-trifluoromethyl-6,7,8,9-tetrahydro-pyrimido[1,2-a]-pyrimidin-4-one | R4 = H; p = 2; q = 0; R2 = H; R3 = CF3 (R) | Chiral | 68 |
| EXAMPLE-117 | (R)-2-((R)-3-Methyl-morpholin-4-yl)-9-oxazol-5-ylmethyl-6-trifluoromethyl-6,7,8,9-tetrahydro-pyrimido[1,2-a]-pyrimidin-4-one | R4 = H; p = 2; q = 0; R2 = H; R3 = CF3 (R) | Chiral | 57 |

Experimental section: Table 2: Examples from 1 to 295, starting intermediates of type F and amount of each example isolated

| EXAMPLE | Example name | Intermediate of type F | Example structure | Amount isolated (mg) |
|---|---|---|---|---|
| EXAMPLE-118 | (R)-9-(2-Cyclopropyl-2-oxoethyl)-2-((R)-3-methylmorpholin-4-yl)-6-trifluoromethyl-6,7,8,9-tetrahydro-pyrimido[1,2-a]-pyrimidin-4-one | R4 = H; p = 2; q = 0; R2 = H; R3 = CF3 (R) | Chiral 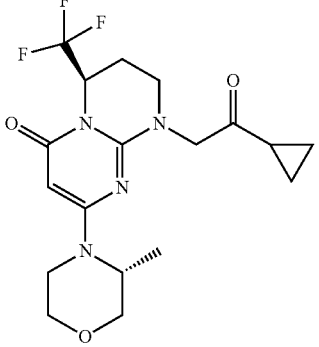 | 90 |
| EXAMPLE-119 | (R)-3-Fluoro-9-(2-methoxypyridin-4-yl)-2-((R)-3-methyl-morpholin-4-yl)-6-trifluoromethyl-6,7,8,9-tetrahydro-pyrimido[1,2-a]-pyrimidin-4-one | R4 = F; p = 2; q = 0; R2 = H; R3 = CF3 (R) | Chiral 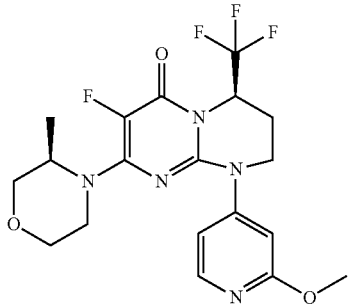 | 55 |
| EXAMPLE-120 | (R)-9-(2-Cyclopropyl-2-oxoethyl)-3-fluoro-2-((R)-3-methyl-morpholin-4-yl)-6-trifluoromethyl-6,7,8,9-tetrahydro-pyrimido[1,2-a]-pyrimidin-4-one | R4 = F; p = 2; q = 0; R2 = H; R3 = CF3 (R) | Chiral 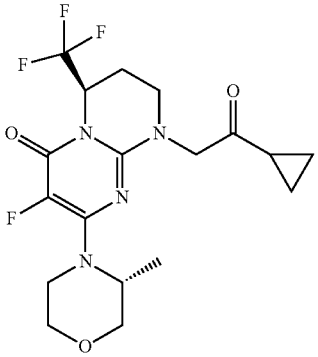 | 70 |

Experimental section: Table 2: Examples from 1 to 295, starting intermediates of type F and amount of each example isolated

| EXAMPLE | Example name | Intermediate of type F | Example structure | Amount isolated (mg) |
|---|---|---|---|---|
| EXAMPLE-121 | (R)-9-(6-Difluoromethylpyridin-3-yl)-3-fluoro-2-((R)-3-methylmorpholin-4-yl)-6-trifluoromethyl-6,7,8,9-tetrahydro-pyrimido[1,2-a]-pyrimidin-4-one | R4 = F; p = 2; q = 0; R2 = H; R3 = CF3 (R) | Chiral | 41 |
| EXAMPLE-122 | (R)-9-(2-Chloro-pyridin-4-yl)-3-fluoro-2-((R)-3-methyl-morpholin-4-yl)-6-trifluoromethyl-6,7,8,9-tetrahydro-pyrimido[1,2-a]-pyrimidin-4-one | R4 = F; p = 2; q = 0; R2 = H; R3 = CF3 (R) | Chiral | 52 |
| EXAMPLE-123 | (S)-2-((R)-3-Methyl-morpholin-4-yl)-9-(5-methyl-[1,3,4]thiadiazol-2-yl-methyl)-8-trifluoromethyl-6,7,8,9-tetrahydro-pyrimido[1,2-a]-pyrimidin-4-one | R4 = H; p = 0; q = 2; R2 = H; R3 = CF3 (S) | Chiral | 198 |
| EXAMPLE-124 | (S)-9-(6-Difluoromethoxy-pyridin-3-yl)-2-((R)-3-methylmorpholin-4-yl)-8-trifluoromethyl-6,7,8,9-tetrahydro-pyrimido[1,2-a]-pyrimidin-4-one | R4 = H; p = 0; q = 2; R2 = H; R3 = CF3 (S) | Chiral | 53 |

Experimental section: Table 2: Examples from 1 to 295, starting intermediates of type F and amount of each example isolated

| EXAMPLE | Example name | Intermediate of type F | Example structure | Amount isolated (mg) |
|---|---|---|---|---|
| EXAMPLE-125 | (S)-2-((R)-3-Methyl-morpholin-4-yl)-9-(4-methyl-[1,2,3]thiadiazol-5-yl-methyl)-8-trifluoromethyl-6,7,8,9-tetrahydro-pyrimido[1,2-a]-pyrimidin-4-one | R4 = H; p = 0; q = 2; R2 = H; R3 = CF3 (S) | Chiral | 42 |
| EXAMPLE-126 | (R)-3-Fluoro-2-((R)-3-methylmorpholin-4-yl)-9-(2-oxo-2-pyridin-3-ylethyl)-6-trifluoromethyl-6,7,8,9-tetrahydro-pyrimido[1,2-a]-pyrimidin-4-one | R4 = F; p = 2; q = 0; R2 = H; R3 = CF3 (R) | Chiral | 131 |
| EXAMPLE-127 | (R)-9-(6-Difluoromethoxy-pyridin-3-yl)-3-fluoro-2-((R)-3-methyl-morpholin-4-yl)-6-trifluoromethyl-6,7,8,9-tetrahydro-pyrimido[1,2-a]-pyrimidin-4-one | R4 = F; p = 2; q = 0; R2 = H; R3 = CF3 (R) | Chiral | 55 |

-continued

Experimental section: Table 2: Examples from 1 to 295, starting intermediates of type F and amount of each example isolated

| EXAMPLE | Example name | Intermediate of type F | Example structure | Amount isolated (mg) |
|---|---|---|---|---|
| EXAMPLE-128 | (R)-3-Fluoro-2-((R)-3-methylmorpholin-4-yl)-9-(3-methyl-2-oxo-butyl)-6-trifluoromethyl-6,7,8,9-tetrahydro-pyrimido[1,2-a]-pyrimidin-4-one | R4 = F; p = 2; q = 0; R2 = H; R3 = CF3 (R) | Chiral | 74 |
| EXAMPLE-129 | (R)-3-Fluoro-2-((R)-3-methylmorpholin-4-yl)-9-oxazol-2-ylmethyl-6-trifluoromethyl-6,7,8,9-tetrahydro-pyrimido[1,2-a]-pyrimidin-4-one | R4 = F; p = 2; q = 0; R2 = H; R3 = CF3 (R) | Chiral | 44 |
| EXAMPLE-130 | (R)-2-((R)-3-Methyl-morpholin-4-yl)-9-(3-methyl-2-oxobutyl)-6-trifluoromethyl-6,7,8,9-tetrahydro-pyrimido[1,2-a]-pyrimidin-4-one | R4 = H; p = 2; q = 0; R2 = H; R3 = CF3 (R) | Chiral | 53 |

Experimental section: Table 2: Examples from 1 to 295, starting intermediates of type F and amount of each example isolated

| EXAMPLE | Example name | Intermediate of type F | Example structure | Amount isolated (mg) |
|---|---|---|---|---|
| EXAMPLE-131 | (R)-2-((R)-3-Methyl-morpholin-4-yl)-9-[2-oxo-2-(tetrahydro-pyran-4-yl)ethyl]-6-trifluoromethyl-6,7,8,9-tetrahydro-pyrimido[1,2-a]-pyrimidin-4-one | R4 = H; p = 2; q = 0; R2 = H; R3 = CF3 (R) | Chiral | 133 |
| EXAMPLE-132 | (R)-3-Fluoro-2-((R)-3-methylmorpholin-4-yl)-9-[2-oxo-2-(tetrahydro-pyran-4-yl)ethyl]-6-trifluoromethyl-6,7,8,9-tetrahydro-pyrimido[1,2-a]-pyrimidin-4-one | R4 = F; p = 2; q = 0; R2 = H; R3 = CF3 (R) | Chiral | 133 |
| EXAMPLE-133 | (S)-2-((R)-3-Methyl-morpholin-4-yl)-9-oxetan-3-ylmethyl-8-trifluoromethyl-6,7,8,9-tetrahydro-pyrimido[1,2-a]-pyrimidin-4-one | R4 = H; p = 0; q = 2; R2 = H; R3 = CF3 (S) | Chiral | 40 |
| EXAMPLE-134 | 9-(6-Difluoromethyl-pyridin-3-yl)-2-((R)-3-methylmorpholin-4-yl)-8-trifluoromethyl-6,7,8,9-tetrahydro-pyrimido[1,2-a]-pyrimidin-4-one | R4 = H; p = 0; q = 2; R2 = H; R3 = CF3 (S) | Chiral | 23 |

Experimental section: Table 2: Examples from 1 to 295, starting intermediates of type F and amount of each example isolated

| EXAMPLE | Example name | Intermediate of type F | Example structure | Amount isolated (mg) |
|---|---|---|---|---|
| EXAMPLE-135 | (R)-3-Fluoro-2-((R)-3-methylmorpholin-4-yl)-9-(2-oxo-2-pyridin-2-ylethyl)-6-trifluoromethyl-6,7,8,9-tetrahydro-pyrimido[1,2-a]-pyrimidin-4-one | R4 = F; p = 2; q = 0; R2 = H; R3 = CF3 (R) | Chiral | 17 |
| EXAMPLE-136 | (S)-2-((R)-3-Methyl-morpholin-4-yl)-9-[1-(tetrahydro-furan-2-yl)methyl]-8-trifluoromethyl-6,7,8,9-tetrahydro-pyrimido[1,2-a]-pyrimidin-4-one, single stereoisomer | R4 = H; p = 0; q = 2; R2 = H; R3 = CF3 (S) | Chiral | 56 |
| EXAMPLE-137 | (S)-2-((R)-3-Methyl-morpholin-4-yl)-9-[1-(tetrahydrofuran-2-yl)methyl]-8-trifluoromethyl-6,7,8,9-tetrahydro-pyrimido[1,2-a]-pyrimidin-4-one, single stereoisomer | R4 = H; p = 0; q = 2; R2 = H; R3 = CF3 (S) | Chiral | 62 |
| EXAMPLE-138 | (S)-2-((R)-3-Methyl-morpholin-4-yl)-9-[1-(tetrahydropyran-2-yl)methyl]-8-trifluoromethyl-6,7,8,9-tetrahydro-pyrimido[1,2-a]-pyrimidin-4-one, single stereoisomer | R4 = H; p = 0; q = 2; R2 = H; R3 = CF3 (S) | Chiral | 74 |

-continued

Experimental section: Table 2: Examples from 1 to 295, starting intermediates of type F and amount of each example isolated

| EXAMPLE | Example name | Intermediate of type F | Example structure | Amount isolated (mg) |
|---|---|---|---|---|
| EXAMPLE-139 | (S)-2-((R)-3-Methyl-morpholin-4-yl)-9-[1-(tetrahydropyran-2-yl)methyl]-8-trifluoromethyl-6,7,8,9-tetrahydro-pyrimido[1,2-a]-pyrimidin-4-one, single stereoisomer | R4 = H; p = 0; q = 2; R2 = H; R3 = CF3 (S) | Chiral 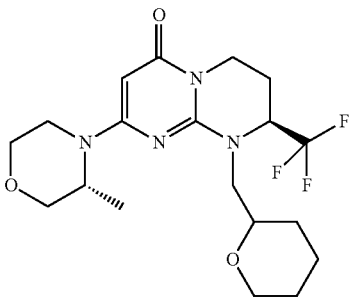 | 94 |
| EXAMPLE-140 | (S)-2-((R)-3-Methyl-morpholin-4-yl)-8-trifluoromethyl-9-(5-trifluoromethyl-[1,3,4]oxadiazol-2-yl-methyl)-6,7,8,9-tetrahydro-pyrimido[1,2-a]-pyrimidin-4-one | R4 = H; p = 0; q = 2; R2 = H; R3 = CF3 (S) | Chiral 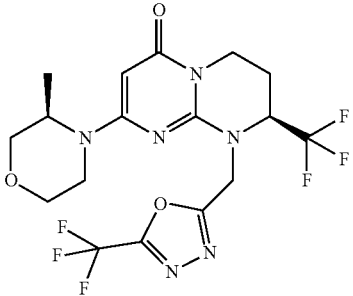 | 33 |
| EXAMPLE-141 | (R)-2-((R)-3-Methyl-morpholin-4-yl)-9-(2-oxo-2-pyridin-3-yl-ethyl)-6-trifluoromethyl-6,7,8,9-tetrahydro-pyrimido[1,2-a]-pyrimidin-4-one | R4 = H; p = 2; q = 0; R2 = H; R3 = CF3 (R) | Chiral 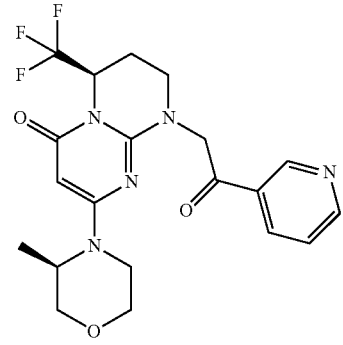 | 86 |
| EXAMPLE-142 | (S)-9-(5-Cyclopropyl-[1,3,4]oxadiazol-2-yl-methyl)-2-((R)-3-methylmorpholin-4-yl)-8-trifluoromethyl-6,7,8,9-tetrahydro-pyrimido[1,2-a]-pyrimidin-4-one | R4 = H; p = 0; q = 2; R2 = H; R3 = CF3 (S) | Chiral 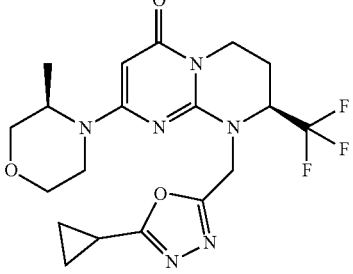 | 211 |

Experimental section: Table 2: Examples from 1 to 295, starting intermediates of type F and amount of each example isolated

| EXAMPLE | Example name | Intermediate of type F | Example structure | Amount isolated (mg) |
|---|---|---|---|---|
| EXAMPLE-143 | (R)-9-(3-Methyl-isoxazol-4-ylmethyl)-2-((R)-3-methyl-morpholin-4-yl)-6-trifluoromethyl-6,7,8,9-tetrahydro-pyrimido[1,2-a]-pyrimidin-4-one | R4 = H; p = 2; q = 0; R2 = H; R3 = CF3 (R) | Chiral | 99 |
| EXAMPLE-144 | (R)-2-((R)-3-Methyl-morpholin-4-yl)-6-trifluoromethyl-9-(3-trifluoromethyl-[1,2,4]oxadiazol-5-yl-methyl)-6,7,8,9-tetrahydro-pyrimido[1,2-a]-pyrimidin-4-one | R4 = H; p = 2; q = 0; R2 = H; R3 = CF3 (R) | Chiral | 183 |
| EXAMPLE-145 | (R)-2-((R)-3-Methyl-morpholin-4-yl)-9-(2-oxopropyl)-6-trifluoromethyl-6,7,8,9-tetrahydro-pyrimido[1,2-a]-pyrimidin-4-one | R4 = H; p = 2; q = 0; R2 = H; R3 = CF3 (R) | Chiral | 93 |
| EXAMPLE-146 | (R)-3-Fluoro-9-(3-methylisoxazol-4-yl-methyl)-2-((R)-3-methylmorpholin-4-yl)-6-trifluoromethyl-6,7,8,9-tetrahydro-pyrimido[1,2-a]-pyrimidin-4-one | R4 = F; p = 2; q = 0; R2 = H; R3 = CF3 (R) | Chiral | 86 |

Experimental section: Table 2: Examples from 1 to 295, starting intermediates of type F and amount of each example isolated

| EXAMPLE | Example name | Intermediate of type F | Example structure | Amount isolated (mg) |
|---|---|---|---|---|
| EXAMPLE-147 | (R)-9-(3-Cyclopropyl-[1,2,4]oxadiazol-5-yl-methyl)-3-fluoro-2-((R)-3-methyl-morpholin-4-yl)-6-trifluoromethyl-6,7,8,9-tetrahydro-pyrimido[1,2-a]-pyrimidin-4-one | R4 = F; p = 2; q = 0; R2 = H; R3 = CF3 (R) | Chiral | 78 |
| EXAMPLE-148 | (R)-3-Fluoro-2-((R)-3-methylmorpholin-4-yl)-9-(2-oxopropyl)-6-trifluoromethyl-6,7,8,9-tetrahydro-pyrimido[1,2-a]-pyrimidin-4-one | R4 = F; p = 2; q = 0; R2 = H; R3 = CF3 (R) | Chiral | 64 |
| EXAMPLE-149 | (R)-3-Fluoro-2-((R)-3-methylmorpholin-4-yl)-9-(3-methyl-[1,2,4]oxadiazol-5-yl-methyl)-6-trifluoromethyl-6,7,8,9-tetrahydro-pyrimido[1,2-a]-pyrimidin-4-one | R4 = F; p = 2; q = 0; R2 = H; R3 = CF3 (R) | Chiral | 36 |
| EXAMPLE-150 | (S)-2-(3,3-Dimethyl-morpholin-4-yl)-9-(2-oxo-2-phenylethyl)-8-trifluoromethyl-6,7,8,9-tetrahydro-pyrimido[1,2-a]-pyrimidin-4-one | R4 = H; p = 0; q = 2; R2 = H; R3 = CF3 (S) | Chiral | 26 |

Experimental section: Table 2: Examples from 1 to 295, starting intermediates of type F and amount of each example isolated

| EXAMPLE | Example name | Intermediate of type F | Example structure | Amount isolated (mg) |
|---|---|---|---|---|
| EXAMPLE-151 | (S)-9-(5-Chloro-thiophen-2-ylmethyl)-2-((3S,5R)-3,5-dimethylmorpholin-4-yl)-8-trifluoromethyl-6,7,8,9-tetrahydro-pyrimido[1,2-a]-pyrimidin-4-one Single stereoisomer. | R4 = H; p = 0; q = 2; R2 = H; R3 = CF3 (S) | Chiral | 57 |
| EXAMPLE-152 | (S)-9-(5-Chloro-thiophen-2-ylmethyl)-2-((3S,5S)-3,5-dimethylmorpholin-4-yl)-8-trifluoromethyl-6,7,8,9-tetrahydro-pyrimido[1,2-a]-pyrimidin-4-one | R4 = H; p = 0; q = 2; R2 = H; R3 = CF3 (S) | Chiral | 73 |
| EXAMPLE-153 | (S)-2-((3S,5S)-3,5-Dimethylmorpholin-4-yl)-9-(2-oxo-2-phenyl-ethyl)-8-trifluoromethyl-6,7,8,9-tetrahydro-pyrimido[1,2-a]-pyrimidin-4-one | R4 = H; p = 0; q = 2; R2 = H; R3 = CF3 (S) | Chiral | 57 |
| EXAMPLE-154 | (S)-9-(2-Difluoromethyl-2H-pyrazol-3-ylmethyl)-2-((3R,5R)-3,5-dimethyl-morpholin-4-yl)-8-trifluoromethyl-6,7,8,9-tetrahydro-pyrimido[1,2-a]-pyrimidin-4-one | R4 = H; p = 0; q = 2; R2 = H; R3 = CF3 (S) | Chiral | 99 |

Experimental section: Table 2: Examples from 1 to 295, starting intermediates of type F and amount of each example isolated

| EXAMPLE | Example name | Intermediate of type F | Example structure | Amount isolated (mg) |
|---|---|---|---|---|
| EXAMPLE-155 | (S)-2-((3R,5R)-3,5-Dimethylmorpholin-4-yl)-9-(3-methyl-isoxazol-5-ylmethyl)-8-trifluoromethyl-6,7,8,9-tetrahydro-pyrimido[1,2-a]-pyrimidin-4-one | R4 = H; p = 0; q = 2; R2 = H; R3 = CF3 (S) | Chiral | 55 |
| EXAMPLE-156 | (S)-9-(6-Chloro-pyridin-3-ylmethyl)-2-((3R,5R)-3,5-dimethyl-morpholin-4-yl)-8-trifluoromethyl-6,7,8,9-tetrahydro-pyrimido[1,2-a]-pyrimidin-4-one | R4 = H; p = 0; q = 2; R2 = H; R3 = CF3 (S) | Chiral | 42 |
| EXAMPLE-157 | (S)-9-(2-Chloro-pyridin-4-ylmethyl)-2-((3R,5R)-3,5-dimethyl-morpholin-4-yl)-8-trifluoromethyl-6,7,8,9-tetrahydro-pyrimido[1,2-a]-pyrimidin-4-one | R4 = H; p = 0; q = 2; R2 = H; R3 = CF3 (S) | Chiral | 53 |

Experimental section: Table 2: Examples from 1 to 295, starting intermediates of type F and amount of each example isolated

| EXAMPLE | Example name | Intermediate of type F | Example structure | Amount isolated (mg) |
|---|---|---|---|---|
| EXAMPLE-158 | (S)-2-((3R,5R)-3,5-Dimethylmorpholin-4-yl)-9-oxazol-2-yl-methyl-8-trifluoromethyl-6,7,8,9-tetrahydro-pyrimido[1,2-a]-pyrimidin-4-one | R4 = H; p = 0; q = 2; R2 = H; R3 = CF3 (S) | Chiral | 121 |
| EXAMPLE-159 | (S)-9-(2-Chloro-pyridin-4-yl)-2-((3R,5R)-3,5-dimethyl-morpholin-4-yl)-8-trifluoromethyl-6,7,8,9-tetrahydro-pyrimido[1,2-a]-pyrimidin-4-one | R4 = H; p = 0; q = 2; R2 = H; R3 = CF3 (S) | Chiral | 116 |
| EXAMPLE-160 | (S)-2-((3R,5R)-3,5-Dimethylmorpholin-4-yl)-9-pyridin-3-yl-8-trifluoromethyl-6,7,8,9-tetrahydro-pyrimido[1,2-a]-pyrimidin-4-one | R4 = H; p = 0; q = 2; R2 = H; R3 = CF3 (S) | Chiral | 93 |
| EXAMPLE-161 | (S)-9-(3,5-Difluoro-phenyl)-2-(8-oxa-3-azabicyclo[3.2.1]oct-3-yl)-8-trifluoromethyl-6,7,8,9-tetrahydro-pyrimido[1,2-a]-pyrimidin-4-one | R4 = H; p = 0; q = 2; R2 = H; R3 = CF3 (S) | Chiral | 20 |

Experimental section: Table 2: Examples from 1 to 295, starting intermediates of type F and amount of each example isolated

| EXAMPLE | Example name | Intermediate of type F | Example structure | Amount isolated (mg) |
|---|---|---|---|---|
| EXAMPLE-162 | (S)-9-(5-Chloro-thiophen-2-ylmethyl)-2-(8-oxa-3-aza-bicyclo[3.2.1]oct-3-yl)-8-trifluoromethyl-6,7,8,9-tetrahydro-pyrimido[1,2-a]-pyrimidin-4-one | R4 = H; p = 0; q = 2; R2 = H; R3 = CF3 (S) | Chiral | 86 |
| EXAMPLE-163 | (S)-2-(8-Oxa-3-aza-bicyclo[3.2.1]oct-3-yl)-9-(2-oxo-2-phenyl-ethyl)-8-trifluoromethyl-6,7,8,9-tetrahydro-pyrimido[1,2-a]-pyrimidin-4-one | R4 = H; p = 0; q = 2; R2 = H; R3 = CF3 (S) | Chiral | 127 |
| EXAMPLE-164 | (S)-9-Isoxazol-5-yl-methyl-2-(8-oxa-3-azabicyclo[3.2.1]oct-3-yl)-8-trifluoromethyl-6,7,8,9-tetrahydro-pyrimido[1,2-a]-pyrimidin-4-one | R4 = H; p = 0; q = 2; R2 = H; R3 = CF3 (S) | Chiral | 56 |
| EXAMPLE-165 | (S)-9-(2-Chloro-thiazol-5-ylmethyl)-2-(8-oxa-3-aza-bicyclo[3.2.1]oct-3-yl)-8-trifluoromethyl-6,7,8,9-tetrahydro-pyrimido[1,2-a]-pyrimidin-4-one | R4 = H; p = 0; q = 2; R2 = H; R3 = CF3 (S) | Chiral | 95 |

Experimental section: Table 2: Examples from 1 to 295, starting intermediates of type F and amount of each example isolated

| EXAMPLE | Example name | Intermediate of type F | | Example structure | Amount isolated (mg) |
|---|---|---|---|---|---|
| EXAMPLE-166 | (S)-9-(2-Difluoromethyl-2H-pyrazol-3-ylmethyl)-2-(8-oxa-3-aza-bicyclo[3.2.1]oct-3-yl)-8-trifluoromethyl-6,7,8,9-tetrahydro-pyrimido[1,2-a]-pyrimidin-4-one | R4 = H; p = 0; q = 2; R2 = H; R3 = CF3 (S) | Chiral | | 103 |
| EXAMPLE-167 | (S)-9-(1-Difluoromethyl-1H-pyrazol-3-ylmethyl)-2-(8-oxa-3-aza-bicyclo[3.2.1]oct-3-yl)-8-trifluoromethyl-6,7,8,9-tetrahydro-pyrimido[1,2-a]-pyrimidin-4-one | R4 = H; p = 0; q = 2; R2 = H; R3 = CF3 (S) | Chiral | | 75 |
| EXAMPLE-168 | (S)-9-(6-Chloro-pyridin-3-ylmethyl)-2-(8-oxa-3-aza-bicyclo[3.2.1]oct-3-yl)-8-trifluoromethyl-6,7,8,9-tetrahydro-pyrimido[1,2-a]-pyrimidin-4-one | R4 = H; p = 0; q = 2; R2 = H; R3 = CF3 (S) | Chiral | | 76 |
| EXAMPLE-169 | (S)-9-Isoxazol-3-yl-methyl-2-(8-oxa-3-azabicyclo[3.2.1]oct-3-yl)-8-trifluoromethyl-6,7,8,9-tetrahydro-pyrimido[1,2-a]-pyrimidin-4-one | R4 = H; p = 0; q = 2; R2 = H; R3 = CF3 (S) | Chiral | | 88 |

Experimental section: Table 2: Examples from 1 to 295, starting intermediates of type F and amount of each example isolated

| EXAMPLE | Example name | Intermediate of type F | Example structure | Amount isolated (mg) |
|---|---|---|---|---|
| EXAMPLE-170 | (S)-2-(8-Oxa-3-aza-bicyclo[3.2.1]oct-3-yl)-9-(2-oxo-2-pyridin-3-ylethyl)-8-trifluoromethyl-6,7,8,9-tetrahydro-pyrimido[1,2-a]-pyrimidin-4-one | R4 = H; p = 0; q = 2; R2 = H; R3 = CF3 (S) | Chiral | 16 |
| EXAMPLE-171 | (S)-2-(8-Oxa-3-aza-bicyclo[3.2.1]oct-3-yl)-9-(2-oxo-2-pyridin-2-ylethyl)-8-trifluoromethyl-6,7,8,9-tetrahydro-pyrimido[1,2-a]-pyrimidin-4-one | R4 = H; p = 0; q = 2; R2 = H; R3 = CF3 (S) | Chiral | 41 |
| EXAMPLE-172 | (S)-2-(-2-Ethyl-morpholin-4-yl)-9-(2-oxo-2-pyridin-2-yl-ethyl)-8-trifluoromethyl-6,7,8,9-tetrahydro-pyrimido[1,2-a]-pyrimidin-4-one, single stereoisomer | R4 = H; p = 0; q = 2; R2 = H; R3 = CF3 (S) | Chiral | 42 |
| EXAMPLE-173 | (S)-2-(-2-Ethyl-morpholin-4-yl)-9-(2-oxo-2-pyridin-2-yl-ethyl)-8-trifluoromethyl-6,7,8,9-tetrahydro-pyrimido[1,2-a]-pyrimidin-4-one, single stereoisomer | R4 = H; p = 0; q = 2; R2 = H; R3 = CF3 (S) | Chiral | 40 |

Experimental section: Table 2: Examples from 1 to 295, starting intermediates of type F and amount of each example isolated

| EXAMPLE | Example name | Intermediate of type F | Example structure | Amount isolated (mg) |
|---|---|---|---|---|
| EXAMPLE-174 | (S)-2-(-2-Methyl-morpholin-4-yl)-9-(2-oxo-2-pyridin-2-yl-ethyl)-8-trifluoromethyl-6,7,8,9-tetrahydro-pyrimido[1,2-a]-pyrimidin-4-one, single stereoisomer | R4 = H; p = 0; q = 2; R2 = H; R3 = CF3 (S) | Chiral 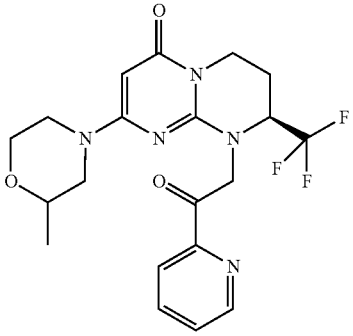 | 41 |
| EXAMPLE-175 | (S)-2-(-2-Methyl-morpholin-4-yl)-9-(2-oxo-2-pyridin-2-yl-ethyl)-8-trifluoromethyl-6,7,8,9-tetrahydro-pyrimido[1,2-a]-pyrimidin-4-one, single stereoisomer | R4 = H; p = 0; q = 2; R2 = H; R3 = CF3 (S) | Chiral 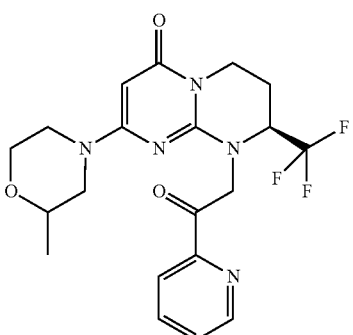 | 38 |
| EXAMPLE-176 | (S)-9-(3,5-Difluoro-phenyl)-2-(3-hydroxymethyl-morpholin-4-yl)-8-trifluoromethyl-6,7,8,9-tetrahydro-pyrimido[1,2-a]-pyrimidin-4-one, single stereoisomer | R4 = H; p = 0; q = 2; R2 = H; R3 = CF3 (S) | Chiral 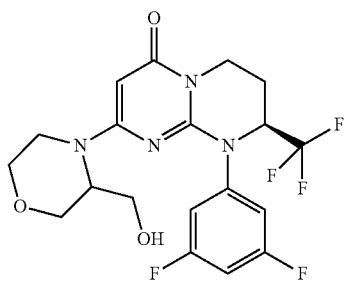 | 32 |
| EXAMPLE-177 | (S)-9-(5-Chloro-thiophen-2-ylmethyl)-2-(-3-hydroxymethyl-morpholin-4-yl)-8-trifluoromethyl-6,7,8,9-tetrahydro-pyrimido[1,2-a]-pyrimidin-4-one, single stereoisomer | R4 = H; p = 0; q = 2; R2 = H; R3 = CF3 (S) | Chiral 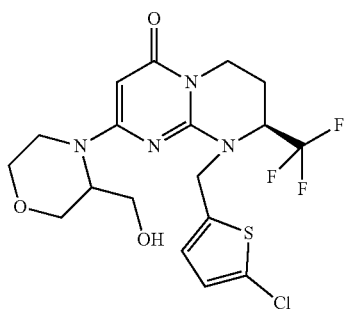 | 40 |

Experimental section: Table 2: Examples from 1 to 295, starting intermediates of type F and amount of each example isolated

| EXAMPLE | Example name | Intermediate of type F | Example structure | Amount isolated (mg) |
|---|---|---|---|---|
| EXAMPLE-178 | (S)-9-(5-Chloro-thiophen-2-ylmethyl)-2-((S)-3-methyl-morpholin-4-yl)-8-trifluoromethyl-6,7,8,9-tetrahydro-pyrimido[1,2-a]-pyrimidin-4-one | R4 = H; p = 0; q = 2; R2 = H; R3 = CF3 (S) | Chiral | 54 |
| EXAMPLE-179 | (S)-2-Methyl-7-((R)-3-methylmorpholin-4-yl)-1-(2-oxo-2-pyridin-2-ylethyl)-2-trifluoromethyl-2,3-dihydro-1H-imidazo[1,2-a]-pyrimidin-5-one | R4 = H; p = 0; q = 1; R2 = Me; R3 = CF3 (S) | Chiral | 29 |
| EXAMPLE-180 | (S)-2-Methyl-7-((R)-3-methylmorpholin-4-yl)-1-(2-oxo-2-pyridin-3-ylethyl)-2-trifluoromethyl-2,3-dihydro-1H-imidazo[1,2-a]-pyrimidin-5-one | R4 = H; p = 0; q = 1; R2 = Me; R3 = CF3 (S) | Chiral | 66 |
| EXAMPLE-181 | (S)-1-(2-Chloro-pyridin-4-ylmethyl)-2-methyl-7-((R)-3-methylmorpholin-4-yl)-2-trifluoromethyl-2,3-dihydro-1H-imidazo[1,2-a]-pyrimidin-5-one | R4 = H; p = 0; q = 1; R2 = Me; R3 = CF3 (S) | Chiral | 77 |

Experimental section: Table 2: Examples from 1 to 295, starting intermediates of type F and amount of each example isolated

| EXAMPLE | Example name | Intermediate of type F | Example structure | Amount isolated (mg) |
|---|---|---|---|---|
| EXAMPLE-182 | (S)-2-Methyl-7-((R)-3-methylmorpholin-4-yl)-1-oxazol-5-ylmethyl-2-trifluoromethyl-2,3-dihydro-1H-imidazo[1,2-a]-pyrimidin-5-one | R4 = H; p = 0; q = 1; R2 = Me; R3 = CF3 (S) | Chiral 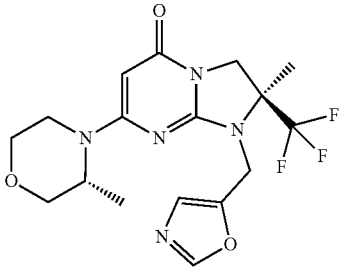 | 25 |
| EXAMPLE-183 | (S)-2-Methyl-7-((R)-3-methylmorpholin-4-yl)-1-oxazol-4-ylmethyl-2-trifluoromethyl-2,3-dihydro-1H-imidazo[1,2-a]-pyrimidin-5-one | R4 = H; p = 0; q = 1; R2 = Me; R3 = CF3 (S) | Chiral 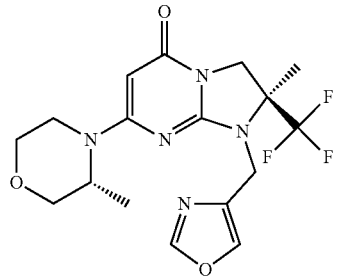 | 56 |
| EXAMPLE-184 | (S)-1-(2-Chloro-pyridin-4-ylmethyl)-6-fluoro-2-methyl-7-((R)-3-methylmorpholin-4-yl)-2-trifluoromethyl-2,3-dihydro-1H-imidazo[1,2-a]-pyrimidin-5-one | R4 = F; p = 0; q = 1; R2 = Me; R3 = CF3 (S) | Chiral 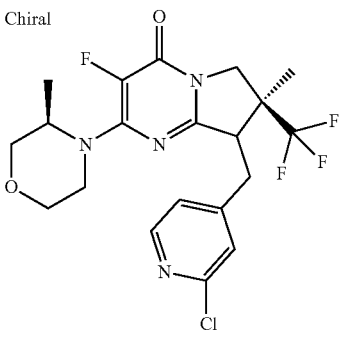 [SMILES: C[C@@H]1COCCN1c1nc2n(c(=O)c1F)C[C@@](C)(C(F)(F)F)C2Cc1ccnc(Cl)c1] | 117 |
| EXAMPLE-185 | (S)-6-Fluoro-2-methyl-7-((R)-3-methyl-morpholin-4-yl)-1-(3-methyl-2-oxobutyl)-2-trifluoromethyl-2,3-dihydro-1H-imidazo[1,2-a]-pyrimidin-5-one | R4 = F; p = 0; q = 1; R2 = Me; R3 = CF3 (S) | Chiral 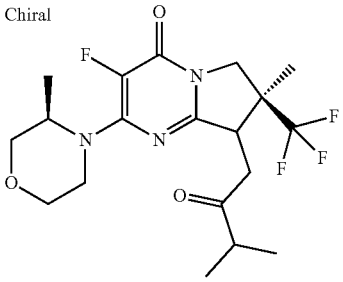 [SMILES: CC(C)C(=O)CC1c2nc(N3CCOC[C@H]3C)c(F)c(=O)n2C[C@@]1(C)C(F)(F)F] | 45 |

Experimental section: Table 2: Examples from 1 to 295, starting intermediates of type F and amount of each example isolated

| EXAMPLE | Example name | Intermediate of type F | Example structure | Amount isolated (mg) |
|---|---|---|---|---|
| EXAMPLE-186 | (S)-6-Fluoro-2-methyl-7-((R)-3-methyl-morpholin-4-yl)-1-[2-oxo-2-(tetrahydro-pyran-4-yl)ethyl]-2-trifluoromethyl-2,3-dihydro-1H-imidazo[1,2-a]-pyrimidin-5-one | R4 = F; p = 0; q = 1; R2 = Me; R3 = CF3 (S) | Chiral 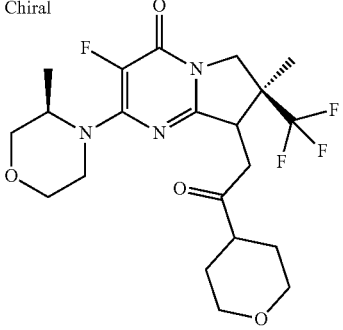 [SMILES: C[C@@H]1COCCN1c1nc2n(c(=O)c1F)C[C@@](C)(C(F)(F)F)C2CC(=O)C1CCOCC1] | 360 |
| EXAMPLE-187 | (S)-1-(2-Cyclopropyl-2-oxoethyl)-6-fluoro-2-methyl-7-((R)-3-methylmorpholin-4-yl)-2-trifluoromethyl-2,3-dihydro-1H-imidazo[1,2-a]-pyrimidin-5-one | R4 = F; p = 0; q = 1; R2 = Me; R3 = CF3 (S) | Chiral 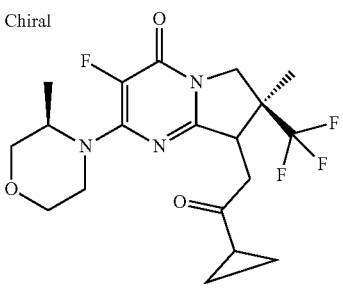 [SMILES: C[C@@H]1COCCN1c1nc2n(c(=O)c1F)C[C@@](C)(C(F)(F)F)C2CC(=O)C1CC1] | 63 |
| EXAMPLE-188 | (S)-2-Methyl-7-((R)-3-methylmorpholin-4-yl)-1-(3-methyl-2-oxo-butyl)-2-trifluoromethyl-2,3-dihydro-1H-imidazo[1,2-a]-pyrimidin-5-one | R4 = H; p = 0; q = 1; R2 = Me; R3 = CF3 (S) | Chiral 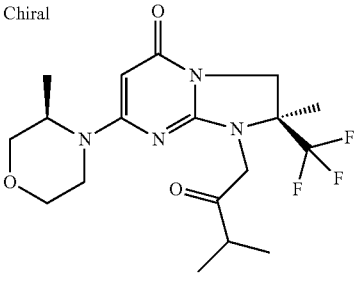 [SMILES: CC(C)C(=O)CN1c2nc(N3CCOC[C@H]3C)cc(=O)n2C[C@@]1(C)C(F)(F)F] | 15 |
| EXAMPLE-189 | (S)-6-Fluoro-2-methyl-7-((R)-3-methyl-morpholin-4-yl)-1-(2-oxo-2-pyridin-3-yl-ethyl)-2-trifluoromethyl-2,3-dihydro-1H-imidazo[1,2-a]-pyrimidin-5-one | R4 = F; p = 0; q = 1; R2 = Me; R3 = CF3 (S) | Chiral 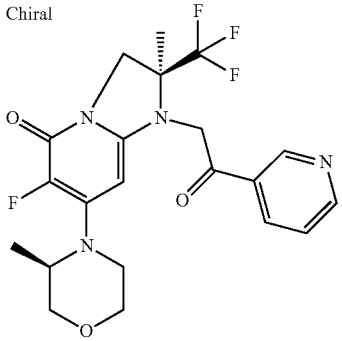 [SMILES: C[C@@H]1COCCN1c1cc2n(c(=O)c1F)C[C@@](C)(C(F)(F)F)N2CC(=O)c1cccnc1] | 172 |

Experimental section: Table 2: Examples from 1 to 295, starting intermediates of type F and amount of each example isolated

| EXAMPLE | Example name | Intermediate of type F | Example structure | Amount isolated (mg) |
|---|---|---|---|---|
| EXAMPLE-190 | (S)-2-Methyl-7-((R)-3-methylmorpholin-4-yl)-1-[2-oxo-2-(tetrahydro-pyran-4-yl)ethyl]-2-trifluoromethyl-2,3-dihydro-1H-imidazo[1,2-a]-pyrimidin-5-one | R4 = H; p = 0; q = 1; R2 = Me; R3 = CF3 (S) | Chiral | 188 |
| EXAMPLE-191 | (S)-9-Benzyl-2-(2-methylmorpholin-4-yl)-8-trifluoromethyl-6,7,8,9-tetrahydro-pyrimido[1,2-a]-pyrimidin-4-one, single stereoisomer | R4 = H; p = 0; q = 2; R2 = H; R3 = CF3 (S) | Chiral | 83 |
| EXAMPLE-192 | (S)-9-Benzyl-2-(2-methylmorpholin-4-yl)-8-trifluoromethyl-6,7,8,9-tetrahydro-pyrimido[1,2-a]-pyrimidin-4-one, single stereoisomer | R4 = H; p = 0; q = 2; R2 = H; R3 = CF3 (S) | Chiral | 70 |
| EXAMPLE-193 | (S)-9-Benzyl-2-(2-fluoromethyl-morpholin-4-yl)-8-trifluoromethyl-6,7,8,9-tetrahydro-pyrimido[1,2-a]-pyrimidin-4-one | R4 = H; p = 0; q = 2; R2 = H; R3 = CF3 (S) | Chiral | 227 |
| EXAMPLE-194 | (S)-9-Benzyl-2-(2-fluoromethyl-morpholin-4-yl)-8-trifluoromethyl-6,7,8,9-tetrahydro-pyrimido[1,2-a]-pyrimidin-4-one, single stereoisomer | R4 = H; p = 0; q = 2; R2 = H; R3 = CF3 (S) | Chiral | 88 |

Experimental section: Table 2: Examples from 1 to 295, starting intermediates of type F and amount of each example isolated

| EXAMPLE | Example name | Intermediate of type F | Example structure | Amount isolated (mg) |
|---|---|---|---|---|
| EXAMPLE-195 | (S)-9-Benzyl-2-(2-fluoromethyl-morpholin-4-yl)-8-trifluoromethyl-6,7,8,9-tetrahydro-pyrimido[1,2-a]-pyrimidin-4-one, single stereoisomer | R4 = H; p = 0; q = 2; R2 = H; R3 = CF3 (S) | Chiral | 89 |
| EXAMPLE-196 | N-Methoxy-N-methyl-2-[(S)-8-((R)-3-methyl-morpholin-4-yl)-6-oxo-2-trifluoromethyl-3,4-dihydro-2H,6H-pyrimido[1,2-a]-pyrimidin-1-yl]-acetamide | R4 = H; p = 0; q = 2; R2 = H; R3 = CF3 (S) | Chiral | 127 |
| EXAMPLE-197 | N-Methoxy-2-[(S)-8-((R)-3-methyl-morpholin-4-yl)-6-oxo-2-trifluoromethyl-3,4-dihydro-2H,6H-pyrimido[1,2-a]-pyrimidin-1-yl]-acetamide | R4 = H; p = 0; q = 2; R2 = H; R3 = CF3 (S) | Chiral | 100 |
| EXAMPLE-198 | (S)-2-((R)-3-Methyl-morpholin-4-yl)-9-pyridin-4-yl-8-trifluoromethyl-6,7,8,9-tetrahydro-pyrimido[1,2-a]-pyrimidin-4-one | R4 = H; p = 0; q = 2; R2 = H; R3 = CF3 (S) | Chiral | 17 |

Experimental section: Table 2: Examples from 1 to 295, starting intermediates of type F and amount of each example isolated

| EXAMPLE | Example name | Intermediate of type F | Example structure | Amount isolated (mg) |
|---|---|---|---|---|
| EXAMPLE-199 | (S)-6-Fluoro-2-methyl-7-((R)-3-methyl-morpholin-4-yl)-1-(2-oxo-2-pyridin-2-yl-ethyl)-2-trifluoromethyl-2,3-dihydro-1H-imidazo[1,2-a]-pyrimidin-5-one | R4 = F; p = 0; q = 1; R2 = Me; R3 = CF3 (S) | Chiral | 1112 |
| EXAMPLE-200 | (S)-9-(2-Hydroxy-2-methylpropyl)-8-methyl-2-((R)-3-methylmorpholin-4-yl)-8-trifluoromethyl-6,7,8,9-tetrahydro-pyrimido[1,2-a]-pyrimidin-4-one | R4 = H; p = 0; q = 2; R2 = Me; R3 = CF3 (S) | Chiral | 62 |
| EXAMPLE-201 | (S)-9-(5-Isopropyl-[1,2,4]oxadiazol-3-yl-methyl)-2-((R)-3-methylmorpholin-4-yl)-8-trifluoromethyl-6,7,8,9-tetrahydro-pyrimido[1,2-a]-pyrimidin-4-one | R4 = H; p = 0; q = 2; R2 = H; R3 = CF3 (S) | Chiral | 103 |
| EXAMPLE-202 | (S)-9-(5-Cyclopropyl-[1,2,4]oxadiazol-3-yl-methyl)-2-((R)-3-methylmorpholin-4-yl)-8-trifluoromethyl-6,7,8,9-tetrahydro-pyrimido[1,2-a]-pyrimidin-4-one | R4 = H; p = 0; q = 2; R2 = H; R3 = CF3 (S) | Chiral | 112 |

Experimental section: Table 2: Examples from 1 to 295, starting intermediates of type F and amount of each example isolated

| EXAMPLE | Example name | Intermediate of type F | Example structure | Amount isolated (mg) |
|---|---|---|---|---|
| EXAMPLE-203 | (S)-9-(5-tert-Butyl-[1,2,4]oxadiazol-3-yl-methyl)-2-((R)-3-methylmorpholin-4-yl)-8-trifluoromethyl-6,7,8,9-tetrahydro-pyrimido[1,2-a]-pyrimidin-4-one | R4 = H; p = 0; q = 2; R2 = H; R3 = CF3 (S) | Chiral | 108 |
| EXAMPLE-204 | (S)-3-Fluoro-9-(2-hydroxyethyl)-2-((R)-3-methylmorpholin-4-yl)-8-trifluoromethyl-6,7,8,9-tetrahydro-pyrimido[1,2-a]-pyrimidin-4-one | R4 = F; p = 0; q = 2; R2 = H; R3 = CF3 (S) | Chiral | 107 |
| EXAMPLE-205 | (S)-9-((S)-2-Hydroxy-propyl)-2-((R)-3-methylmorpholin-4-yl)-8-trifluoromethyl-6,7,8,9-tetrahydro-pyrimido[1,2-a]-pyrimidin-4-one | R4 = H; p = 0; q = 2; R2 = H; R3 = CF3 (S) | Chiral | 114 |
| EXAMPLE-206 | (S)-9-((S)-2-Methoxy-2-phenylethyl)-2-(1R,5S)-8-oxa-3-aza-bicyclo[3.2.1]oct-3-yl-8-trifluoromethyl-6,7,8,9-tetrahydro-pyrimido[1,2-a]-pyrimidin-4-one | R4 = H; p = 0; q = 2; R2 = H; R3 = CF3 (S) | Chiral | 87 |

-continued

Experimental section: Table 2: Examples from 1 to 295, starting intermediates of type F and amount of each example isolated

| EXAMPLE | Example name | Intermediate of type F | Example structure | Amount isolated (mg) |
|---|---|---|---|---|
| EXAMPLE-207 | (S)-6-Fluoro-2-methyl-7-((R)-3-methyl-morpholin-4-yl)-1-(3-methyl-[1,2,4]oxadiazol-5-yl-methyl)-2-trifluoromethyl-2,3-dihydro-1H-imidazo[1,2-a]-pyrimidin-5-one | R4 = F; p = 0; q = 1; R2 = Me; R3 = CF3 (S) | Chiral 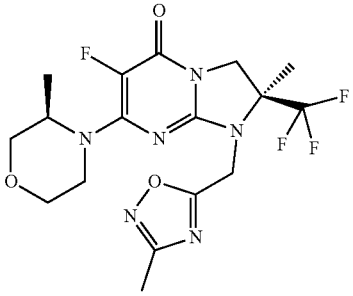 | 47 |
| EXAMPLE-208 | (S)-2-Methyl-7-((R)-3-methylmorpholin-4-yl)-1-(3-methyl-[1,2,4]oxadiazol-5-yl-methyl)-2-trifluoromethyl-2,3-dihydro-1H-imidazo[1,2-a]-pyrimidin-5-one | R4 = F; p = 0; q = 1; R2 = Me; R3 = CF3 (S) | Chiral 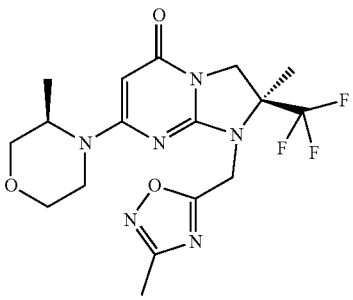 | 147 |
| EXAMPLE-209 | (S)-9-(2-Hydroxy-2-pyridin-3-ylethyl)-2-((R)-3-methyl-morpholin-4-yl)-8-trifluoromethyl-6,7,8,9-tetrahydro-pyrimido[1,2-a]-pyrimidin-4-one, single stereoisomer | R4 = H; p = 0; q = 2; R2 = H; R3 = CF3 (S) | Chiral 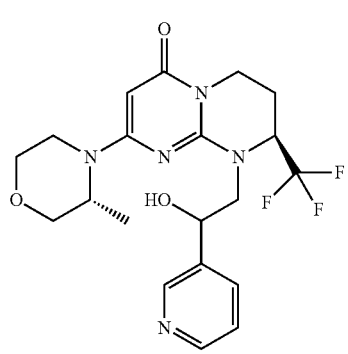 | 44 |
| EXAMPLE-210 | (S)-9-(2-Hydroxy-2-pyridin-3-ylethyl)-2-((R)-3-methyl-morpholin-4-yl)-8-trifluoromethyl-6,7,8,9-tetrahydro-pyrimido[1,2-a]-pyrimidin-4-one, single stereoisomer | R4 = H; p = 0; q = 2; R2 = H; R3 = CF3 (S) | Chiral 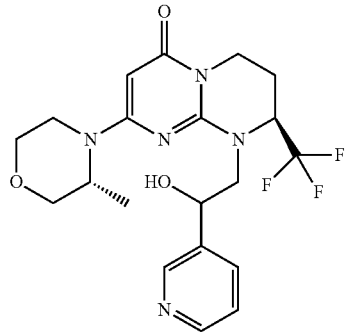 | 67 |

Experimental section: Table 2: Examples from 1 to 295, starting intermediates of type F and amount of each example isolated

| EXAMPLE | Example name | Intermediate of type F | Example structure | Amount isolated (mg) |
|---|---|---|---|---|
| EXAMPLE-211 | (S)-8-Methyl-2-((R)-3-methylmorpholin-4-yl)-9-(5-methyl-[1,2,4]oxadiazol-3-yl-methyl)-8-trifluoromethyl-6,7,8,9-tetrahydro-pyrimido[1,2-a]-pyrimidin-4-one | R4 = H; p = 0; q = 2; R2 = Me; R3 = CF3 (S) | Chiral | 43 |
| EXAMPLE-212 | (S)-9-(2-Hydroxy-2-pyridin-2-ylethyl)-2-((R)-3-methyl-morpholin-4-yl)-8-trifluoromethyl-6,7,8,9-tetrahydro-pyrimido[1,2-a]-pyrimidin-4-one, single stereoisomer | R4 = H; p = 0; q = 2; R2 = H; R3 = CF3 (S) | Chiral | 75 |
| EXAMPLE-213 | (S)-9-(2-Hydroxy-2-pyridin-2-ylethyl)-2-((R)-3-methyl-morpholin-4-yl)-8-trifluoromethyl-6,7,8,9-tetrahydro-pyrimido[1,2-a]-pyrimidin-4-one | R4 = H; p = 0; q = 2; R2 = H; R3 = CF3 (S) | Chiral | 38 |
| EXAMPLE-214 | (S)-9-(2-Difluoromethyl-2H-pyrazol-3-ylmethyl)-8-methyl-2-((R)-3-methylmorpholin-4-yl)-8-trifluoromethyl-6,7,8,9-tetrahydro-pyrimido[1,2-a]-pyrimidin-4-one | R4 = H; p = 0; q = 2; R2 = Me; R3 = CF3 (S) | Chiral | 140 |

Experimental section: Table 2: Examples from 1 to 295, starting intermediates of type F and amount of each example isolated

| EXAMPLE | Example name | Intermediate of type F | Example structure | Amount isolated (mg) |
|---|---|---|---|---|
| EXAMPLE-215 | (S)-9-Isoxazol-3-yl-methyl-8-methyl-2-((R)-3-methyl-morpholin-4-yl)-8-trifluoromethyl-6,7,8,9-tetrahydro-pyrimido[1,2-a]-pyrimidin-4-one | R4 = H; p = 0; q = 2; R2 = Me; R3 = CF3 (S) | Chiral | 35 |
| EXAMPLE-216 | (S)-2-((R)-3-Methyl-morpholin-4-yl)-9-pyridin-4-ylmethyl-8-trifluoromethyl-6,7,8,9-tetrahydro-pyrimido[1,2-a]-pyrimidin-4-one | R4 = H; p = 0; q = 2; R2 = H; R3 = CF3 (S) | Chiral | 43 |
| EXAMPLE-217 | (S)-2-((R)-3-Methyl-morpholin-4-yl)-9-pyridin-3-ylmethyl-8-trifluoromethyl-6,7,8,9-tetrahydro-pyrimido[1,2-a]-pyrimidin-4-one | R4 = H; p = 0; q = 2; R2 = H; R3 = CF3 (S) | Chiral | 110 |
| EXAMPLE-218 | (S)-2-((R)-3-Methyl-morpholin-4-yl)-9-pyridin-2-ylmethyl-8-trifluoromethyl-6,7,8,9-tetrahydro-pyrimido[1,2-a]-pyrimidin-4-one | R4 = H; p = 0; q = 2; R2 = H; R3 = CF3 (S) | Chiral | 110 |

Experimental section: Table 2: Examples from 1 to 295, starting intermediates of type F and amount of each example isolated

| EXAMPLE | Example name | Intermediate of type F | Example structure | Amount isolated (mg) |
|---|---|---|---|---|
| EXAMPLE-219 | (S)-9-[2-(4-Fluoro-phenyl)ethyl]-2-((R)-3-methylmorpholin-4-yl)-8-trifluoromethyl-6,7,8,9-tetrahydro-pyrimido[1,2-a]-pyrimidin-4-one | R4 = H; p = 0; q = 2; R2 = H; R3 = CF3 (S) | Chiral | 40 |
| EXAMPLE-220 | (S)-2-((R)-3-Methyl-morpholin-4-yl)-9-(2-pyridin-2-ylethyl)-8-trifluoromethyl-6,7,8,9-tetrahydro-pyrimido[1,2-a]-pyrimidin-4-one | R4 = H; p = 0; q = 2; R2 = H; R3 = CF3 (S) | Chiral | 6 |
| EXAMPLE-221 | (S)-9-(2-Fluoropyridin-3-ylmethyl)-2-((R)-3-methylmorpholin-4-yl)-8-trifluoromethyl-6,7,8,9-tetrahydro-pyrimido[1,2-a]-pyrimidin-4-one | R4 = H; p = 0; q = 2; R2 = H; R3 = CF3 (S) | Chiral | 110 |
| EXAMPLE-222 | N,N-Dimethyl-2-[(S)-8-((R)-3-methyl-morpholin-4-yl)-6-oxo-2-trifluoromethyl-3,4-dihydro-2H,6H-pyrimido[1,2-a]-pyrimidin-1-yl]-acetamide | R4 = H; p = 0; q = 2; R2 = H; R3 = CF3 (S) | Chiral | 150 |

Experimental section: Table 2: Examples from 1 to 295, starting intermediates of type F and amount of each example isolated

| EXAMPLE | Example name | Intermediate of type F | | Example structure | Amount isolated (mg) |
|---|---|---|---|---|---|
| EXAMPLE-223 | N-Methyl-2-[(S)-8-((R)-3-methylmorpholin-4-yl)-6-oxo-2-trifluoromethyl-3,4-dihydro-2H,6H-pyrimido[1,2-a]-pyrimidin-1-yl]-acetamide | R4 = H; p = 0; q = 2; R2 = H; R3 = CF3 (S) | Chiral | | 90 |
| EXAMPLE-224 | (S)-9-(6-Fluoropyridin-2-ylmethyl)-2-((R)-3-methylmorpholin-4-yl)-8-trifluoromethyl-6,7,8,9-tetrahydro-pyrimido[1,2-a]-pyrimidin-4-one | R4 = H; p = 0; q = 2; R2 = H; R3 = CF3 (S) | Chiral | | 135 |
| EXAMPLE-225 | (S)-9-(2-Isopropoxy-pyridin-4-ylmethyl)-2-((R)-3-methyl-morpholin-4-yl)-8-trifluoromethyl-6,7,8,9-tetrahydro-pyrimido[1,2-a]-pyrimidin-4-one | R4 = H; p = 0; q = 2; R2 = H; R3 = CF3 (S) | Chiral | | 65 |
| EXAMPLE-226 | (S)-9-(3-Isopropyl-[1,2,4]oxadiazol-5-yl-methyl)-2-((R)-3-methylmorpholin-4-yl)-8-trifluoromethyl-6,7,8,9-tetrahydro-pyrimido[1,2-a]-pyrimidin-4-one | R4 = H; p = 0; q = 2; R2 = H; R3 = CF3 (S) | Chiral | | 46 |

Experimental section: Table 2: Examples from 1 to 295, starting intermediates of type F and amount of each example isolated

| EXAMPLE | Example name | Intermediate of type F | Example structure | Amount isolated (mg) |
|---|---|---|---|---|
| EXAMPLE-227 | (S)-9-(3-Cyclopropyl-[1,2,4]oxadiazol-5-yl-methyl)-2-((R)-3-methylmorpholin-4-yl)-8-trifluoromethyl-6,7,8,9-tetrahydro-pyrimido[1,2-a]-pyrimidin-4-one | R4 = H; p = 0; q = 2; R2 = H; R3 = CF3 (S) | Chiral | 130 |
| EXAMPLE-228 | (S)-9-(3-tert-Butyl-[1,2,4]oxadiazol-5-yl-methyl)-2-((R)-3-methylmorpholin-4-yl)-8-trifluoromethyl-6,7,8,9-tetrahydro-pyrimido[1,2-a]-pyrimidin-4-one | R4 = H; p = 0; q = 2; R2 = H; R3 = CF3 (S) | Chiral | 130 |
| EXAMPLE-229 | (S)-9-(6-Isopropoxy-pyridin-3-ylmethyl)-2-((R)-3-methyl-morpholin-4-yl)-8-trifluoromethyl-6,7,8,9-tetrahydro-pyrimido[1,2-a]-pyrimidin-4-one | R4 = H; p = 0; q = 2; R2 = H; R3 = CF3 (S) | Chiral | 165 |

Experimental section: Table 2: Examples from 1 to 295, starting intermediates of type F and amount of each example isolated

| EXAMPLE | Example name | Intermediate of type F | Example structure | Amount isolated (mg) |
|---|---|---|---|---|
| EXAMPLE-230 | (S)-9-(2-Isopropoxy-pyridin-3-ylmethyl)-2-((R)-3-methyl-morpholin-4-yl)-8-trifluoromethyl-6,7,8,9-tetrahydro-pyrimido[1,2-a]-pyrimidin-4-one | R4 = H; p = 0; q = 2; R2 = H; R3 = CF3 (S) | Chiral | 100 |
| EXAMPLE-231 | (S)-2-((R)-3-Methyl-morpholin-4-yl)-9-thiazol-2-ylmethyl-8-trifluoromethyl-6,7,8,9-tetrahydro-pyrimido[1,2-a]-pyrimidin-4-one | R4 = H; p = 0; q = 2; R2 = H; R3 = CF3 (S) | Chiral | 69 |
| EXAMPLE-232 | (S)-3-Fluoro-2-((R)-3-methylmorpholin-4-yl)-9-thiazol-2-ylmethyl-8-trifluoromethyl-6,7,8,9-tetrahydro-pyrimido[1,2-a]-pyrimidin-4-one | R4 = F; p = 0; q = 2; R2 = H; R3 = CF3 (S) | Chiral | 40 |
| EXAMPLE-233 | (S)-2-((R)-3-Methyl-morpholin-4-yl)-9-(2-oxo-2-piperidin-1-yl-ethyl)-8-trifluoromethyl-6,7,8,9-tetrahydro-pyrimido[1,2-a]-pyrimidin-4-one | R4 = H; p = 0; q = 2; R2 = H; R3 = CF3 (S) | Chiral | 153 |

Experimental section: Table 2: Examples from 1 to 295, starting intermediates of type F and amount of each example isolated

| EXAMPLE | Example name | Intermediate of type F | Example structure | Amount isolated (mg) |
|---|---|---|---|---|
| EXAMPLE-234 | (S)-2-((R)-3-Methyl-morpholin-4-yl)-9-(2-morpholin-4-yl-2-oxo-ethyl)-8-trifluoromethyl-6,7,8,9-tetrahydro-pyrimido[1,2-a]-pyrimidin-4-one | R4 = H; p = 0; q = 2; R2 = H; R3 = CF3 (S) | Chiral | 125 |
| EXAMPLE-235 | (S)-3-Fluoro-2-((R)-3-methylmorpholin-4-yl)-9-(2-morpholin-4-yl-2-oxoethyl)-8-trifluoromethyl-6,7,8,9-tetrahydro-pyrimido[1,2-a]-pyrimidin-4-one | R4 = F; p = 0; q = 2; R2 = H; R3 = CF3 (S) | Chiral | 170 |
| EXAMPLE-236 | 2-[(S)-8-((R)-3-Methyl-morpholin-4-yl)-6-oxo-2-trifluoromethyl-3,4-dihydro-2H,6H-pyrimido[1,2-a]-pyrimidin-1-yl]-N-phenyl-acetamide | R4 = H; p = 0; q = 2; R2 = H; R3 = CF3 (S) | Chiral | 136 |

Experimental section: Table 2: Examples from 1 to 295, starting intermediates of type F and amount of each example isolated

| EXAMPLE | Example name | Intermediate of type F | Example structure | Amount isolated (mg) |
|---|---|---|---|---|
| EXAMPLE-237 | (S)-3-Fluoro-2-((R)-3-methylmorpholin-4-yl)-9-(2-oxo-2-piperidin-1-ylethyl)-8-trifluoromethyl-6,7,8,9-tetrahydro-pyrimido[1,2-a]-pyrimidin-4-one | R4 = F; p = 0; q = 2; R2 = H; R3 = CF3 (S) | Chiral | 89 |
| EXAMPLE-238 | (S)-9-Acetyl-2-((R)-3-methylmorpholin-4-yl)-8-trifluoromethyl-6,7,8,9-tetrahydro-pyrimido[1,2-a]-pyrimidin-4-one | R4 = H; p = 0; q = 2; R2 = H; R3 = CF3 (S) | Chiral | 30 |
| EXAMPLE-239 | (S)-8-Methyl-2-((R)-3-methylmorpholin-4-yl)-9-oxazol-2-ylmethyl-8-trifluoromethyl-6,7,8,9-tetrahydro-pyrimido[1,2-a]-pyrimidin-4-one | R4 = H; p = 0; q = 2; R2 = Me; R3 = CF3 (S) | Chiral | 106 |
| EXAMPLE-240 | (S)-2-Methyl-7-((R)-3-methylmorpholin-4-yl)-1-(5-methyl-[1,2,4]oxadiazol-3-ylmethyl)-2-trifluoromethyl-2,3-dihydro-1H-imidazo[1,2-a]-pyrimidin-5-one | R4 = H; p = 0; q = 1; R2 = Me; R3 = CF3 (S) | Chiral | 120 |

Experimental section: Table 2: Examples from 1 to 295, starting intermediates of type F and amount of each example isolated

| EXAMPLE | Example name | Intermediate of type F | Example structure | Amount isolated (mg) |
|---|---|---|---|---|
| EXAMPLE-241 | (S)-9-(2-Cyclopropyl-2-oxoethyl)-2-((R)-3-methylmorpholin-4-yl)-8-trifluoromethyl-6,7,8,9-tetrahydro-pyrimido[1,2-a]-pyrimidin-4-one | R4 = H; p = 0; q = 2; R2 = H; R3 = CF3 (S) | Chiral | 600 |
| EXAMPLE-242 | (S)-2-((R)-3-Methyl-morpholin-4-yl)-9-(2-oxo-2-thiazol-2-yl-ethyl)-8-trifluoromethyl-6,7,8,9-tetrahydro-pyrimido[1,2-a]-pyrimidin-4-one | R4 = H; p = 0; q = 2; R2 = H; R3 = CF3 (S) | Chiral | 55 |
| EXAMPLE-243 | [(S)-8-((R)-3-Methyl-morpholin-4-yl)-6-oxo-2-trifluoromethyl-3,4-dihydro-2H,6H-pyrimido[1,2-a]-pyrimidin-1-yl]acetic acid cyclopentyl ester | R4 = H; p = 0; q = 2; R2 = H; R3 = CF3 (S) | Chiral | 145 |
| EXAMPLE-244 | (S)-9-(2-Cyclopentyl-2-oxoethyl)-2-((R)-3-methylmorpholin-4-yl)-8-trifluoromethyl-6,7,8,9-tetrahydro-pyrimido[1,2-a]-pyrimidin-4-one | R4 = H; p = 0; q = 2; R2 = H; R3 = CF3 (S) | Chiral | 165 |

Experimental section: Table 2: Examples from 1 to 295, starting intermediates of type F and amount of each example isolated

| EXAMPLE | Example name | Intermediate of type F | Example structure | Amount isolated (mg) |
|---|---|---|---|---|
| EXAMPLE-245 | (S)-2-((R)-3-Methyl-morpholin-4-yl)-9-[2-oxo-2-(tetrahydro-pyran-4-yl)ethyl]-8-trifluoromethyl-6,7,8,9-tetrahydro-pyrimido[1,2-a]-pyrimidin-4-one | R4 = H; p = 0; q = 2; R2 = H; R3 = CF3 (S) | Chiral | 200 |
| EXAMPLE-246 | (S)-3-Fluoro-9-(5-isopropyl-[1,2,4]oxadiazol-3-yl-methyl)-2-((R)-3-methylmorpholin-4-yl)-8-trifluoromethyl-6,7,8,9-tetrahydro-pyrimido[1,2-a]-pyrimidin-4-one | R4 = F; p = 0; q = 2; R2 = H; R3 = CF3 (S) | Chiral | 110 |
| EXAMPLE-247 | (S)-9-(5-Cyclopropyl-[1,2,4]oxadiazol-3-yl-methyl)-3-fluoro-2-((R)-3-methyl-morpholin-4-yl)-8-trifluoromethyl-6,7,8,9-tetrahydro-pyrimido[1,2-a]-pyrimidin-4-one | R4 = F; p = 0; q = 2; R2 = H; R3 = CF3 (S) | Chiral | 110 |

Experimental section: Table 2: Examples from 1 to 295, starting intermediates of type F and amount of each example isolated

| EXAMPLE | Example name | Intermediate of type F | Example structure | Amount isolated (mg) |
|---|---|---|---|---|
| EXAMPLE-248 | (S)-3-Fluoro-9-(3-isopropyl-[1,2,4]oxadiazol-5-yl-methyl)-2-((R)-3-methylmorpholin-4-yl)-8-trifluoromethyl-6,7,8,9-tetrahydro-pyrimido[1,2-a]-pyrimidin-4-one | R4 = F; p = 0; q = 2; R2 = H; R3 = CF3 (S) | Chiral | 100 |
| EXAMPLE-249 | (S)-9-(3-Cyclopropyl-[1,2,4]oxadiazol-5-yl-methyl)-3-fluoro-2-((R)-3-methyl-morpholin-4-yl)-8-trifluoromethyl-6,7,8,9-tetrahydro-pyrimido[1,2-a]-pyrimidin-4-one | R4 = F; p = 0; q = 2; R2 = H; R3 = CF3 (S) | Chiral | 125 |
| EXAMPLE-250 | (S)-9-(3-tert-Butyl-[1,2,4]oxadiazol-5-yl-methyl)-3-fluoro-2-((R)-3-methyl-morpholin-4-yl)-8-trifluoromethyl-6,7,8,9-tetrahydro-pyrimido[1,2-a]-pyrimidin-4-one | R4 = F; p = 0; q = 2; R2 = H; R3 = CF3 (S) | Chiral | 100 |

| EXAMPLE | Example name | Intermediate of type F | Example structure | Amount isolated (mg) |
|---|---|---|---|---|
| EXAMPLE-251 | (S)-3-Fluoro-2-((R)-3-methylmorpholin-4-yl)-8-trifluoromethyl-9-(3-trifluoromethyl-[1,2,4]oxadiazol-5-yl-methyl)-6,7,8,9-tetrahydro-pyrimido[1,2-a]-pyrimidin-4-one | R4 = F; p = 0; q = 2; R2 = H; R3 = CF3 (S) | Chiral | 77 |
| EXAMPLE-252 | (S)-8-Methyl-2-((R)-3-methylmorpholin-4-yl)-9-(3-methyl-2-oxo-butyl)-8-trifluoromethyl-6,7,8,9-tetrahydro-pyrimido[1,2-a]-pyrimidin-4-one | R4 = H; p = 0; q = 2; R2 = Me; R3 = CF3 (S) | Chiral | 35 |
| EXAMPLE-253 | (S)-9-[2-(1-Methyl-cyclopentyl)-2-oxo-ethyl]-2-((R)-3-methyl-morpholin-4-yl)-8-trifluoromethyl-6,7,8,9-tetrahydro-pyrimido[1,2-a]-pyrimidin-4-one | R4 = H; p = 0; q = 2; R2 = H; R3 = CF3 (S) | Chiral | 165 |
| EXAMPLE-254 | [(S)-8-((R)-3-Methyl-morpholin-4-yl)-6-oxo-2-trifluoromethyl-3,4-dihydro-2H,6H-pyrimido[1,2-a]-pyrimidin-1-yl]acetic acid isopropyl ester | R4 = H; p = 0; q = 2; R2 = H; R3 = CF3 (S) | Chiral | 103 |

-continued

Experimental section: Table 2: Examples from 1 to 295, starting intermediates of type F and amount of each example isolated

| EXAMPLE | Example name | Intermediate of type F | Example structure | Amount isolated (mg) |
|---|---|---|---|---|
| EXAMPLE-255 | (S)-9-(3,3-Dimethyl-2-oxobutyl)-2-((R)-3-methylmorpholin-4-yl)-8-trifluoromethyl-6,7,8,9-tetrahydro-pyrimido[1,2-a]-pyrimidin-4-one | R4 = H; p = 0; q = 2; R2 = H; R3 = CF3 (S) | Chiral | 144 |
| EXAMPLE-256 | (S)-2-((R)-3-Methyl-morpholin-4-yl)-9-(2-oxopropyl)-8-trifluoromethyl-6,7,8,9-tetrahydro-pyrimido[1,2-a]-pyrimidin-4-one | R4 = H; p = 0; q = 2; R2 = H; R3 = CF3 (S) | Chiral | 129 |
| EXAMPLE-257 | (S)-9-(2-Fluoropyridin-4-ylmethyl)-2-((R)-3-methylmorpholin-4-yl)-8-trifluoromethyl-6,7,8,9-tetrahydro-pyrimido[1,2-a]-pyrimidin-4-one | R4 = H; p = 0; q = 2; R2 = H; R3 = CF3 (S) | Chiral | 150 |
| EXAMPLE-258 | (S)-9-(2-Cyclohexyl-2-oxoethyl)-2-((R)-3-methylmorpholin-4-yl)-8-trifluoromethyl-6,7,8,9-tetrahydro-pyrimido[1,2-a]-pyrimidin-4-one | R4 = H; p = 0; q = 2; R2 = H; R3 = CF3 (S) | Chiral | 114 |

Experimental section: Table 2: Examples from 1 to 295, starting intermediates of type F and amount of each example isolated

| EXAMPLE | Example name | Intermediate of type F | Example structure | Amount isolated (mg) |
|---|---|---|---|---|
| EXAMPLE-259 | (S)-2-((R)-3-methyl-morpholin-4-yl)-9-pyridazin-4-ylmethyl-8-trifluoromethyl-6,7,8,9-tetrahydro-pyrimido[1,2-a]-pyrimidin-4-one | R4 = H; p = 0; q = 2; R2 = H; R3 = CF3 (S) | Chiral | 86 |
| EXAMPLE-260 | [(S)-8-((R)-3-Methyl-morpholin-4-yl)-6-oxo-2-trifluoromethyl-3,4-dihydro-2H,6H-pyrimido[1,2-a]-pyrimidin-1-yl]acetic acid tert-butyl ester | R4 = H; p = 0; q = 2; R2 = H; R3 = CF3 (S) | Chiral | 112 |
| EXAMPLE-261 | 2-{2-[(S)-8-((R)-3-Methylmorpholin-4-yl)-6-oxo-2-trifluoromethyl-3,4-dihydro-2H,6H-pyrimido[1,2-a]-pyrimidin-1-yl]acetyl}-pyrrolidine-1-carboxylic acid tert-butyl ester | R4 = H; p = 0; q = 2; R2 = H; R3 = CF3 (S) | Chiral | 137 |
| EXAMPLE-262 | [(S)-8-((R)-3-Methyl-morpholin-4-yl)-6-oxo-2-trifluoromethyl-3,4-dihydro-2H,6H-pyrimido[1,2-a]-pyrimidin-1-yl]acetic acid methyl ester | R4 = H; p = 0; q = 2; R2 = H; R3 = CF3 (S) | Chiral | 100 |

Experimental section: Table 2: Examples from 1 to 295, starting intermediates of type F and amount of each example isolated

| EXAMPLE | Example name | Intermediate of type F | Example structure | Amount isolated (mg) |
|---|---|---|---|---|
| EXAMPLE-263 | 2-[(S)-8-((R)-3-Methyl-morpholin-4-yl)-6-oxo-2-trifluoromethyl-3,4-dihydro-2H,6H-pyrimido[1,2-a]-pyrimidin-1-yl]-acetamide | R4 = H; p = 0; q = 2; R2 = H; R3 = CF3 (S) | Chiral | 88 |
| EXAMPLE-264 | (S)-2-((R)-3-Methyl-morpholin-4-yl)-9-(4H-[1,2,4]triazol-3-yl-methyl)-8-trifluoromethyl-6,7,8,9-tetrahydro-pyrimido[1,2-a]-pyrimidin-4-one | R4 = H; p = 0; q = 2; R2 = H; R3 = CF3 (S) | Chiral | 100 |
| EXAMPLE-265 | (S)-2-((R)-3-Methyl-morpholin-4-yl)-9-(2-oxo-2-piperidin-4-yl-ethyl)-8-trifluoromethyl-6,7,8,9-tetrahydro-pyrimido[1,2-a]-pyrimidin-4-one | R4 = H; p = 0; q = 2; R2 = H; R3 = CF3 (S) | Chiral | 48 |
| EXAMPLE-266 | (S)-9-(3-Methyl-but-2-enyl)-2-((R)-3-methyl-morpholin-4-yl)-8-trifluoromethyl-6,7,8,9-tetrahydro-pyrimido[1,2-a]-pyrimidin-4-one | R4 = H; p = 0; q = 2; R2 = H; R3 = CF3 (S) | Chiral | 16 |

Experimental section: Table 2: Examples from 1 to 295, starting intermediates of type F and amount of each example isolated

| EXAMPLE | Example name | Intermediate of type F | Example structure | Amount isolated (mg) |
|---|---|---|---|---|
| EXAMPLE-267 | (S)-9-(3-Fluoro-3-methylbutyl)-2-((R)-3-methylmorpholin-4-yl)-8-trifluoromethyl-6,7,8,9-tetrahydro-pyrimido[1,2-a]-pyrimidin-4-one | R4 = H; p = 0; q = 2; R2 = H; R3 = CF3 (S) | Chiral 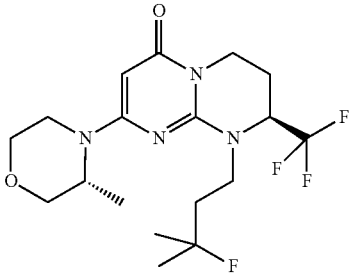 | 11 |
| EXAMPLE-268 | (S)-9-[2-(3-Methyl-isoxazol-4-yl)-2-oxo-ethyl]-2-((R)-3-methyl-morpholin-4-yl)-8-trifluoromethyl-6,7,8,9-tetrahydro-pyrimido[1,2-a]-pyrimidin-4-one | R4 = H; p = 0; q = 2; R2 = H; R3 = CF3 (S) | Chiral 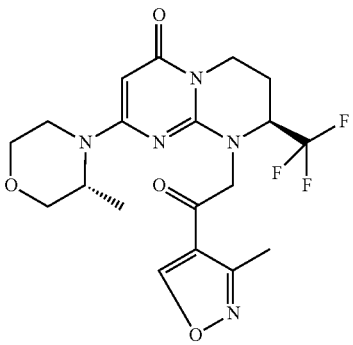 | 30 |
| EXAMPLE-269 | (S)-2-((R)-3-Methyl-morpholin-4-yl)-9-[2-oxo-2-(tetrahydro-furan-3-yl)ethyl]-8-trifluoromethyl-6,7,8,9-tetrahydro-pyrimido[1,2-a]-pyrimidin-4-one | R4 = H; p = 0; q = 2; R2 = H; R3 = CF3 (S) | Chiral 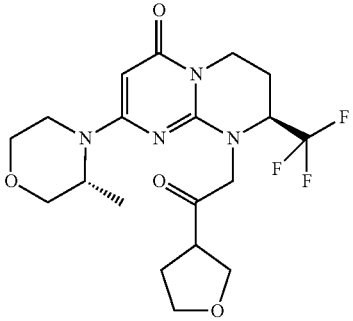 | 57 |
| EXAMPLE-270 | (S)-9-(5-Methyl-[1,2,4]oxadiazol-3-yl-methyl)-2-(8-oxa-3-azabicyclo[3.2.1]oct-3-yl)-8-trifluoromethyl-6,7,8,9-tetrahydro-pyrimido[1,2-a]-pyrimidin-4-one | R4 = H; p = 0; q = 2; R2 = H; R3 = CF3 (S) | Chiral 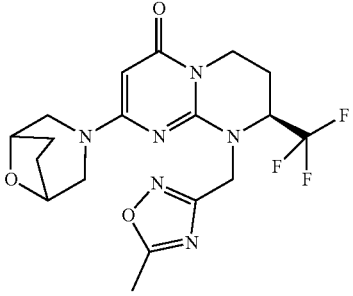 | 133 |

Experimental section: Table 2: Examples from 1 to 295, starting intermediates of type F and amount of each example isolated

| EXAMPLE | Example name | Intermediate of type F | Example structure | Amount isolated (mg) |
|---|---|---|---|---|
| EXAMPLE-271 | (S)-9-(2-Cyclopropyl-2-oxoethyl)-2-(8-oxa-3-azabicyclo[3.2.1]oct-3-yl)-8-trifluoromethyl-6,7,8,9-tetrahydro-pyrimido[1,2-a]-pyrimidin-4-one | R4 = H; p = 0; q = 2; R2 = H; R3 = CF3 (S) | Chiral 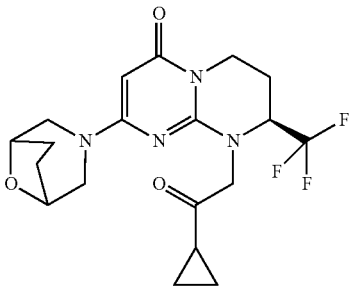 | 197 |
| EXAMPLE-272 | (S)-9-(3-Methyl-2-oxo-butyl)-2-(8-oxa-3-aza-bicyclo[3.2.1]oct-3-yl)-8-trifluoromethyl-6,7,8,9-tetrahydro-pyrimido[1,2-a]-pyrimidin-4-one | R4 = H; p = 0; q = 2; R2 = H; R3 = CF3 (S) | Chiral 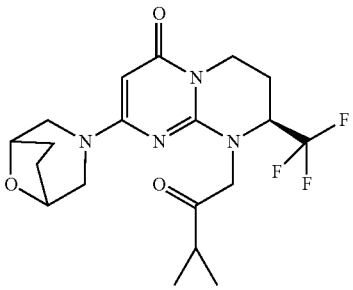 | 200 |
| EXAMPLE-273 | (S)-9-(2-Cyclopropyl-2-oxoethyl)-3-fluoro-2-(8-oxa-3-aza-bicyclo[3.2.1]oct-3-yl)-8-trifluoromethyl-6,7,8,9-tetrahydro-pyrimido[1,2-a]-pyrimidin-4-one | R4 = F; p = 0; q = 2; R2 = H; R3 = CF3 (S) | Chiral 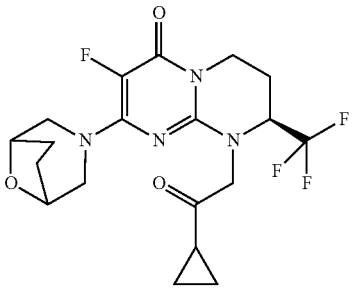 | 200 |
| EXAMPLE-274 | (S)-3-Fluoro-9-(3-methyl-2-oxobutyl)-2-(8-oxa-3-aza-bicyclo[3.2.1]oct-3-yl)-8-trifluoromethyl-6,7,8,9-tetrahydro-pyrimido[1,2-a]-pyrimidin-4-one | R4 = F; p = 0; q = 2; R2 = H; R3 = CF3 (S) | Chiral 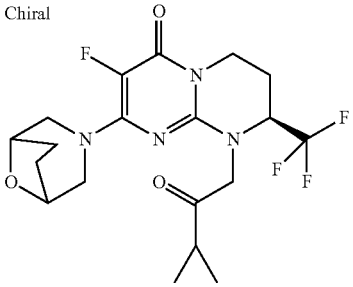 [SMILES: CC(C)C(=O)CN1c2nc(N3CC4CCC(C3)O4)c(F)c(=O)n2CC[C@H]1C(F)(F)F] | 160 |

Experimental section: Table 2: Examples from 1 to 295, starting intermediates of type F and amount of each example isolated

| EXAMPLE | Example name | Intermediate of type F | Example structure | Amount isolated (mg) |
|---|---|---|---|---|
| EXAMPLE-275 | (S)-3-Fluoro-9-(5-methyl-[1,2,4]oxadiazol-3-yl-methyl)-2-(8-oxa-3-azabicyclo[3.2.1]oct-3-yl)-8-trifluoromethyl-6,7,8,9-tetrahydro-pyrimido[1,2-a]-pyrimidin-4-one | R4 = F; p = 0; q = 2; R2 = H; R3 = CF3 (S) | Chiral | 157 |
| EXAMPLE-276 | (S)-2-((R)-3-Methyl-morpholin-4-yl)-9-(4-methyl-2-oxo-pentyl)-8-trifluoromethyl-6,7,8,9-tetrahydro-pyrimido[1,2-a]-pyrimidin-4-one | R4 = H; p = 0; q = 2; R2 = H; R3 = CF3 (S) | Chiral | 106 |
| EXAMPLE-277 | (S)-2-((S)-3-Methyl-morpholin-4-yl)-9-(3-methyl-2-oxobutyl)-8-trifluoromethyl-6,7,8,9-tetrahydro-pyrimido[1,2-a]-pyrimidin-4-one | R4 = H; p = 0; q = 2; R2 = H; R3 = CF3 (S) | Chiral | 245 |
| EXAMPLE-278 | (S)-3-Fluoro-2-((S)-3-methylmorpholin-4-yl)-9-(3-methyl-2-oxo-butyl)-8-trifluoromethyl-6,7,8,9-tetrahydro-pyrimido[1,2-a]-pyrimidin-4-one | R4 = F; p = 0; q = 2; R2 = H; R3 = CF3 (S) | Chiral | 191 |

Experimental section: Table 2: Examples from 1 to 295, starting intermediates of type F and amount of each example isolated

| EXAMPLE | Example name | Intermediate of type F | | Example structure | Amount isolated (mg) |
|---|---|---|---|---|---|
| EXAMPLE-279 | (S)-3-Fluoro-2-((R)-3-methylmorpholin-4-yl)-9-(5-methyl-2-oxo-hexyl)-8-trifluoromethyl-6,7,8,9-tetrahydro-pyrimido[1,2-a]-pyrimidin-4-one | R4 = F; p = 0; q = 2; R2 = H; R3 = CF3 (S) | Chiral | 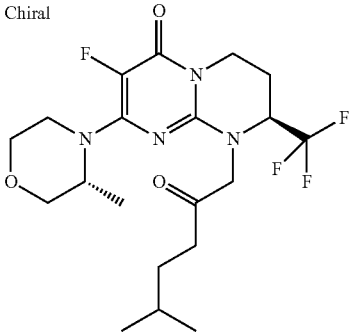 [SMILES: CC(C)CCC(=O)CN1c2nc(N3CCOC[C@H]3C)c(F)c(=O)n2CC[C@H]1C(F)(F)F] | 45 |
| EXAMPLE-280 | (S)-3-Fluoro-2-((R)-3-methylmorpholin-4-yl)-9-(4-methyl-2-oxo-pentyl)-8-trifluoromethyl-6,7,8,9-tetrahydro-pyrimido[1,2-a]-pyrimidin-4-one | R4 = F; p = 0; q = 2; R2 = H; R3 = CF3 (S) | Chiral | 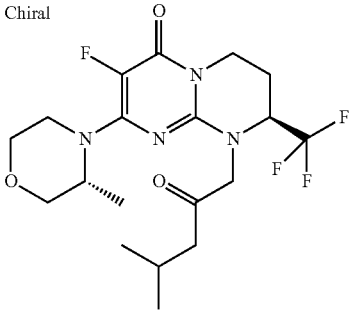 [SMILES: CC(C)CC(=O)CN1c2nc(N3CCOC[C@H]3C)c(F)c(=O)n2CC[C@H]1C(F)(F)F] | 109 |
| EXAMPLE-281 | (S)-9-(3-Ethyl-2-oxo-pentyl)-2-((R)-3-methylmorpholin-4-yl)-8-trifluoromethyl-6,7,8,9-tetrahydro-pyrimido[1,2-a]-pyrimidin-4-one | R4 = H; p = 0; q = 2; R2 = H; R3 = CF3 (S) | Chiral | 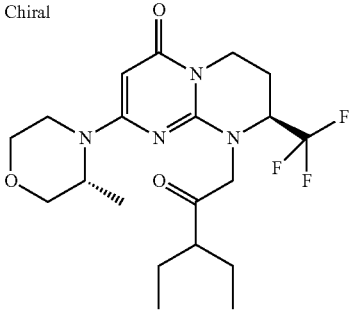 [SMILES: CCC(CC)C(=O)CN1c2nc(N3CCOC[C@H]3C)cc(=O)n2CC[C@H]1C(F)(F)F] | 138 |
| EXAMPLE-282 | (S)-9-(3-Ethyl-2-oxo-pentyl)-3-fluoro-2-((R)-3-methylmorpholin-4-yl)-8-trifluoromethyl-6,7,8,9-tetrahydro-pyrimido[1,2-a]-pyrimidin-4-one | R4 = F; p = 0; q = 2; R2 = H; R3 = CF3 (S) | Chiral | 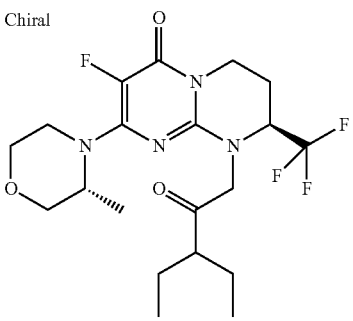 [SMILES: CCC(CC)C(=O)CN1c2nc(N3CCOC[C@H]3C)c(F)c(=O)n2CC[C@H]1C(F)(F)F] | 144 |

Experimental section: Table 2: Examples from 1 to 295, starting intermediates of type F and amount of each example isolated

| EXAMPLE | Example name | Intermediate of type F | | Example structure | Amount isolated (mg) |
|---|---|---|---|---|---|
| EXAMPLE-283 | [(S)-7-Fluoro-8-((R)-3-methylmorpholin-4-yl)-6-oxo-2-trifluoromethyl-3,4-dihydro-2H,6H-pyrimido[1,2-a]-pyrimidin-1-yl]acetic acid methyl ester | R4 = F; p = 0; q = 2; R2 = H; R3 = CF3 (S) | Chiral | | 4320 |
| EXAMPLE-284 | (S)-9-sec-Butyl-2-((R)-3-methylmorpholin-4-yl)-8-trifluoromethyl-6,7,8,9-tetrahydro-pyrimido[1,2-a]-pyrimidin-4-one, single stereoisomer | R4 = H; p = 0; q = 2; R2 = H; R3 = CF3 (S) | Chiral | | 15 |
| EXAMPLE-285 | (S)-9-sec-Butyl-2-((R)-3-methylmorpholin-4-yl)-8-trifluoromethyl-6,7,8,9-tetrahydro-pyrimido[1,2-a]-pyrimidin-4-one, single stereoisomer | R4 = H; p = 0; q = 2; R2 = H; R3 = CF3 (S) | Chiral | | 14 |
| EXAMPLE-286 | (S)-9-(2-Hydroxy-3-methylbutyl)-2-((R)-3-methylmorpholin-4-yl)-8-trifluoromethyl-6,7,8,9-tetrahydro-pyrimido[1,2-a]-pyrimidin-4-one | R4 = H; p = 0; q = 2; R2 = H; R3 = CF3 (S) | Chiral | | 7 |
| EXAMPLE-287 | (S)-9-(2-Hydroxy-3-methylbutyl)-2-((R)-3-methylmorpholin-4-yl)-8-trifluoromethyl-6,7,8,9-tetrahydro-pyrimido[1,2-a]-pyrimidin-4-one | R4 = H; p = 0; q = 2; R2 = H; R3 = CF3 (S) | Chiral | | 150 |

Experimental section: Table 2: Examples from 1 to 295, starting intermediates of type F and amount of each example isolated

| EXAMPLE | Example name | Intermediate of type F | Example structure | Amount isolated (mg) |
|---|---|---|---|---|
| EXAMPLE-288 | (S)-9-(2-Methoxy-3-methylbutyl)-2-((R)-3-methylmorpholin-4-yl)-8-trifluoromethyl-6,7,8,9-tetrahydro-pyrimido[1,2-a]-pyrimidin-4-one, single stereoisomer | R4 = H; p = 0; q = 2; R2 = H; R3 = CF3 (S) | Chiral 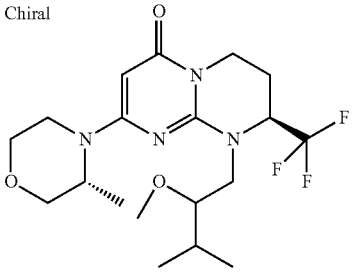 [SMILES: COC(CN1c2nc(N3CCOC[C@H]3C)cc(=O)n2CC[C@H]1C(F)(F)F)C(C)C] | 110 |
| EXAMPLE-289 | (S)-9-(2-Methoxy-3-methylbutyl)-2-((R)-3-methylmorpholin-4-yl)-8-trifluoromethyl-6,7,8,9-tetrahydro-pyrimido[1,2-a]-pyrimidin-4-one single stereoisomer | R4 = H; p = 0; q = 2; R2 = H; R3 = CF3 (S) | Chiral 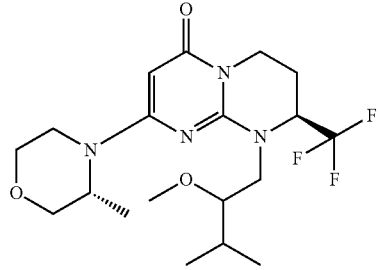 | 14 |
| EXAMPLE-290 | (S)-2-((R)-3-Methyl-morpholin-4-yl)-9-(5-methyl-2-oxo-hexyl)-8-trifluoromethyl-6,7,8,9-tetrahydro-pyrimido[1,2-a]-pyrimidin-4-one | R4 = H; p = 0; q = 2; R2 = H; R3 = CF3 (S) | Chiral 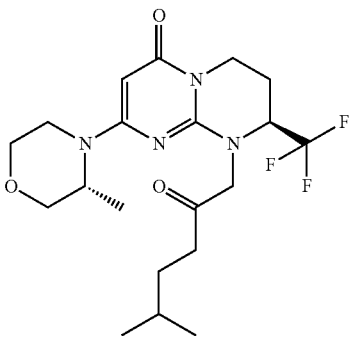 | 172 |
| EXAMPLE-291 | (S)-2-((R)-3-Methyl-morpholin-4-yl)-9-(3-methyl-2-oxo-pentyl)-8-trifluoromethyl-6,7,8,9-tetrahydro-pyrimido[1,2-a]-pyrimidin-4-one | R4 = H; p = 0; q = 2; R2 = H; R3 = CF3 (S) | Chiral 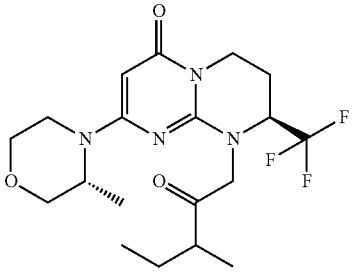 | 150 |

Experimental section: Table 2: Examples from 1 to 295, starting intermediates of type F and amount of each example isolated

| EXAMPLE | Example name | Intermediate of type F | Example structure | Amount isolated (mg) |
|---|---|---|---|---|
| EXAMPLE-292 | (S)-2-((R)-3-Methyl-morpholin-4-yl)-8-trifluoromethyl-9-(3-trifluoromethyl-[1,2,4]oxadiazol-5-yl-methyl)-6,7,8,9-tetrahydro-pyrimido[1,2-a]-pyrimidin-4-one | R4 = H; p = 0; q = 2; R2 = H; R3 = CF3 (S) | Chiral | 80 |
| EXAMPLE-293 | (S)-3-Fluoro-2-((R)-3-methylmorpholin-4-yl)-9-[2-(2-oxa-6-aza-spiro[3.3]hept-6-yl)-2-oxoethyl]-8-trifluoromethyl-6,7,8,9-tetrahydro-pyrimido[1,2-a]-pyrimidin-4-one | R4 = F; p = 0; q = 2; R2 = H; R3 = CF3 (S) | Chiral | 59 |
| EXAMPLE-294 | (S)-3-Fluoro-9-[2-(5-methylisoxazol-3-yl)-2-oxoethyl]-2-((R)-3-methylmorpholin-4-yl)-8-trifluoromethyl-6,7,8,9-tetrahydro-pyrimido[1,2-a]-pyrimidin-4-one | R4 = F; p = 0; q = 2; R2 = H; R3 = CF3 (S) | Chiral | 19 |

Experimental section: Table 2: Examples from 1 to 295, starting intermediates of type F and amount of each example isolated

| EXAMPLE | Example name | Intermediate of type F | Example structure | Amount isolated (mg) |
|---|---|---|---|---|
| EXAMPLE-295 | (S)-9-(2-Fluoro-2-phenylethyl)-2-((R)-3-methylmorpholin-4-yl)-8-trifluoromethyl-6,7,8,9-tetrahydro-pyrimido[1,2-a]-pyrimidin-4-one | R4 = H; p = 0; q = 2; R2 = H; R3 = CF3 (S) | Chiral | 45 |
| EXAMPLE-296 | (S)-3-Fluoro-9-isoxazol-3-ylmethyl-2-((R)-3-methyl-morpholin-4-yl)-8-trifluoromethyl-6,7,8,9-tetrahydro-pyrimido[1,2-a]-pyrimidin-4-one | R4 = F; p = 0; q = 2; R2 = H; R3 = CF3 (S) | Chiral | 100 |
| EXAMPLE-297 | (S)-9-(2-Difluoromethyl-2H-pyrazol-3-ylmethyl)-3-fluoro-2-((R)-3-methyl-morpholin-4-yl)-8-trifluoromethyl-6,7,8,9-tetrahydro-pyrimido[1,2-a]-pyrimidin-4-one | R4 = F; p = 0; q = 2; R2 = H; R3 = CF3 (S) | Chiral | 160 |
| EXAMPLE-298 | 9-Isoxazol-3-ylmethyl-8,8-dimethyl-2-((R)-3-methylmorpholin-4-yl)-6,7,8,9-tetrahydro-pyrimido[1,2-a]-pyrimidin-4-one | R4 = H; p = 0; q = 2; R2 = CH3; R3 = CH3 | Chiral | 27 |

Experimental section: Table 2: Examples from 1 to 295, starting intermediates of type F and amount of each example isolated

| EXAMPLE | Example name | Intermediate of type F | Example structure | Amount isolated (mg) |
|---|---|---|---|---|
| EXAMPLE-299 | (S)-3-Fluoro-9-(3-methylisoxazol-5-yl-methyl)-2-((R)-3-methylmorpholin-4-yl)-8-trifluoromethyl-6,7,8,9-tetrahydro-pyrimido[1,2-a]-pyrimidin-4-one | R4 = F; p = 0; q = 2; R2 = H; R3 = CF3 (S) | Chiral | 67 |
| EXAMPLE-300 | (S)-9-(2-Isopropoxy-ethyl)-2-((R)-3-methyl-morpholin-4-yl)-8-trifluoromethyl-6,7,8,9-tetrahydro-pyrimido[1,2-a]-pyrimidin-4-one | R4 = H; p = 0; q = 2; R2 = H; R3 = CF3 (S) | Chiral | 90 |
| EXAMPLE-301 | (S)-2-((R)-3-Methyl-morpholin-4-yl)-9-pyridin-3-yl-8-trifluoromethyl-6,7,8,9-tetrahydro-pyrimido[1,2-a]-pyrimidin-4-one | R4 = H; p = 0; q = 2; R2 = H; R3 = CF3 (S) | Chiral | 107 |
| EXAMPLE-302 | (S)-9-(6-Cyclopropyl-pyridin-3-yl)-2-((R)-3-methylmorpholin-4-yl)-8-trifluoromethyl-6,7,8,9-tetrahydro-pyrimido[1,2-a]-pyrimidin-4-one | R4 = H; p = 0; q = 2; R2 = H; R3 = CF3 (S) | Chiral | 155 |

Experimental section: Table 2: Examples from 1 to 295, starting intermediates of type F and amount of each example isolated

| EXAMPLE | Example name | Intermediate of type F | | Example structure | Amount isolated (mg) |
|---|---|---|---|---|---|
| EXAMPLE-303 | (S)-2-((R)-3-Methyl-morpholin-4-yl)-9-{2-[2-((R)-3-methyl-morpholin-4-yl)pyridin-4-yl]-2-oxoethyl}-8-trifluoromethyl-6,7,8,9-tetrahydropyrimido[1,2-a]pyrimidin-4-one | R4 = H; p = 0; q = 2; R2 = H; R3 = CF3 (S) | Chiral | | 6.3 |
| EXAMPLE-304 | (S)-9-{2-Cyclopropyl-2-[(Z)-hydroxyimino]-ethyl}-2-((R)-3-methyl-morpholin-4-yl)-8-trifluoromethyl-6,7,8,9-tetrahydropyrimido[1,2-a]pyrimidin-4-one, isomer 1 of undetermined configuration Z or E | R4 = H; p = 0; q = 2; R2 = H; R3 = CF3 (S) | Chiral | | 70.4 |
| EXAMPLE-305 | (S)-9-{2-Cyclopropyl-2-[(E)-hydroxyimino]-ethyl}-2-((R)-3-methyl-morpholin-4-yl)-8-trifluoromethyl-6,7,8,9-tetrahydropyrimido[1,2-a]pyrimidin-4-one, isomer 2 of undetermined configuration Z or E | R4 = H; p = 0; q = 2; R2 = H; R3 = CF3 (S) | Chiral | | 106.9 |
| EXAMPLE-306 | (S)-9-{2-Cyclopropyl-2-[(E)-methoxyimino]-ethyl}-2-((R)-3-methyl-morpholin-4-yl)-8-trifluoromethyl-6,7,8,9-tetrahydropyrimido[1,2-a]pyrimidin-4-one, isomer 1 of undetermined configuration Z or E | R4 = H; p = 0; q = 2; R2 = H; R3 = CF3 (S) | Chiral | | 72 |

Experimental section: Table 2: Examples from 1 to 295, starting intermediates of type F and amount of each example isolated

| EXAMPLE | Example name | Intermediate of type F | Example structure | Amount isolated (mg) |
|---|---|---|---|---|
| EXAMPLE-307 | (S)-9-{2-Cyclopropyl-2-[(Z)-methoxyimino]-ethyl}-2-((R)-3-methyl-morpholin-4-yl)-8-trifluoromethyl-6,7,8,9-tetrahydropyrimido[1,2-a]pyrimidin-4-one, isomer 2 of undetermined configuration Z or E | R4 = H; p = 0; q = 2; R2 = H; R3 = CF3 (S) | Chiral | 48 |
| EXAMPLE-308 | (S)-9-(2-Cyclopropyl-oxetan-2-ylmethyl)-2-((R)-3-methyl-morpholin-4-yl)-8-trifluoromethyl-6,7,8,9-tetrahydropyrimido[1,2-a]pyrimidin-4-one, diastereoisomer 1 of undetermined absolute configuration on the asymmetric carbon of the side chain | R4 = H; p = 0; q = 2; R2 = H; R3 = CF3 (S) | Chiral | 84.5 |
| EXAMPLE-309 | (S)-9-(2-Cyclopropyl-oxetan-2-ylmethyl)-2-((R)-3-methyl-morpholin-4-yl)-8-trifluoromethyl-6,7,8,9-tetrahydropyrimido[1,2-a]pyrimidin-4-one, diastereoisomer 2 of undetermined absolute configuration on the asymmetric carbon of the side chain | R4 = H; p = 0; q = 2; R2 = H; R3 = CF3 (S) | Chiral | 131.4 |
| EXAMPLE-310 | (S)-2-((R)-3-Methyl-morpholin-4-yl)-9-[2-(4-methyl-tetrahydro-pyran-4-yl)-2-oxo-ethyl]-8-trifluoromethyl-6,7,8,9-tetrahydro-pyrimido[1,2-a]-pyrimidin-4-one | R4 = H; p = 0; q = 2; R2 = H; R3 = CF3 (S) | Chiral | 138.5 |

Experimental section: Table 2: Examples from 1 to 295, starting intermediates of type F and amount of each example isolated

| EXAMPLE | Example name | Intermediate of type F | Example structure | Amount isolated (mg) |
|---|---|---|---|---|
| EXAMPLE-311 | (S)-9-[2-(5-Methyl-isoxazol-3-yl)-2-oxo-ethyl]-2-((R)-3-methyl-morpholin-4-yl)-8-trifluoromethyl-6,7,8,9-tetrahydro-pyrimido[1,2-a]-pyrimidin-4-one | R4 = H; p = 0; q = 2; R2 = H; R3 = CF3 (S) | 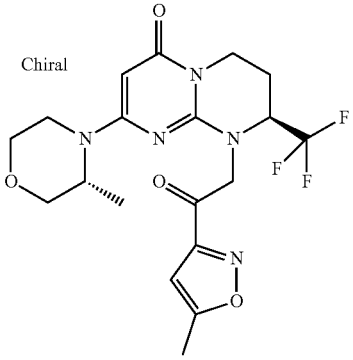 [SMILES: Cc1cc(C(=O)CN2c3nc(N4CCOC[C@H]4C)cc(=O)n3CC[C@H]2C(F)(F)F)no1] | 9 |
| EXAMPLE-312 | (S)-9-(2-Chloro-thiazol-5-ylmethyl)-2-((3R,5R)-3,5-dimethyl-morpholin-4-yl)-8-trifluoromethyl-6,7,8,9-tetrahydro-pyrimido[1,2-a]-pyrimidin-4-one | R4 = H; p = 0; q = 2; R2 = H; R3 = CF3 (S) | 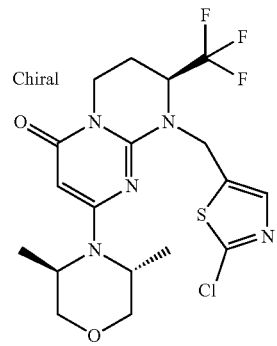 [SMILES: C[C@@H]1COC[C@@H](C)N1c1cc(=O)n2c(n1)N(Cc1cnc(Cl)s1)[C@H](C(F)(F)F)CC2] | 73 |
| EXAMPLE-313 | (S)-2-((3R,5R)-3,5-Dimethylmorpholin-4-yl)-9-isoxazol-3-yl-methyl-8-trifluoromethyl-6,7,8,9-tetrahydropyrimido-[1,2-a]pyrimidin-4-one | R4 = H; p = 0; q = 2; R2 = H; R3 = CF3 (S) | 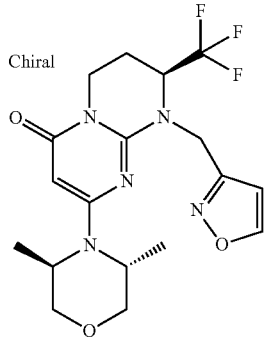 [SMILES: C[C@@H]1COC[C@@H](C)N1c1cc(=O)n2c(n1)N(Cc1ccon1)[C@H](C(F)(F)F)CC2] | 90 |
| EXAMPLE-314 | (S)-3-Fluoro-9-(2-isoxazolidin-2-yl-2-oxoethyl)-2-((R)-3-methylmorpholin-4-yl)-8-trifluoromethyl-6,7,8,9-tetrahydro-pyrimido[1,2-a]-pyrimidin-4-one | R4 = F; p = 0; q = 2; R2 = H; R3 = CF3 (S) | 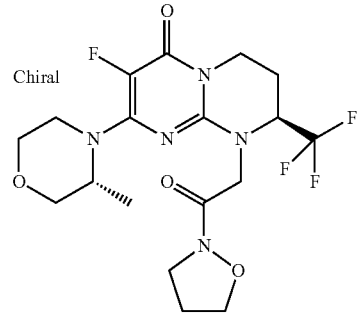 [SMILES: C[C@@H]1COCCN1c1nc2n(c(=O)c1F)CC[C@@H](C(F)(F)F)N2CC(=O)N1CCCO1] | 95 |

Experimental section: Table 2: Examples from 1 to 295, starting intermediates of type F and amount of each example isolated

| EXAMPLE | Example name | Intermediate of type F | Example structure | Amount isolated (mg) |
|---|---|---|---|---|
| EXAMPLE-315 | (S)-9-(2-Hydroxyethyl)-2-((R)-3-methylmorpholin-4-yl)-8-trifluoromethyl-6,7,8,9-tetrahydropyrimido[1,2-a]pyrimidin-4-one | R4 = H; p = 0; q = 2; R2 = H; R3 = CF3 (S) | Chiral | 100 |
| EXAMPLE-316 | (S)-3-Fluoro-2-((R)-3-methylmorpholin-4-yl)-9-[2-(6-oxa-1-azaspiro[3.3]hept-1-yl)-2-oxoethyl]-8-trifluoromethyl-6,7,8,9-tetrahydropyrimido-[1,2-a]pyrimidin-4-one | R4 = F; p = 0; q = 2; R2 = H; R3 = CF3 (S) | Chiral | 72 |
| EXAMPLE-317 | (S)-3-Fluoro-2-((R)-3-methylmorpholin-4-yl)-9-(2-[1,2]oxazinan-2-yl-2-oxoethyl)-8-trifluoromethyl-6,7,8,9-tetrahydropyrimido-[1,2-a]pyrimidin-4-one | R4 = F; p = 0; q = 2; R2 = H; R3 = CF3 (S) | Chiral | 46 |
| EXAMPLE-318 | (S)-2-((R)-3-Methylmorpholin-4-yl)-9-(2-[1,2]oxazinan-2-yl-2-oxoethyl)-8-trifluoromethyl-6,7,8,9-tetrahydropyrimido-[1,2-a]pyrimidin-4-one | R4 = H; p = 0; q = 2; R2 = H; R3 = CF3 (S) | Chiral | 39 |

Experimental section: Table 2: Examples from 1 to 295, starting intermediates of type F and amount of each example isolated

| EXAMPLE | Example name | Intermediate of type F | Example structure | Amount isolated (mg) |
|---|---|---|---|---|
| EXAMPLE-319 | (S)-9-(2-Isoxazolidin-2-yl-2-oxoethyl)-2-((R)-3-methyl-morpholin-4-yl)-8-trifluoromethyl-6,7,8,9-tetrahydropyrimido-[1,2-a]pyrimidin-4-one | R4 = H; p = 0; q = 2; R2 = H; R3 = CF3 (S) | 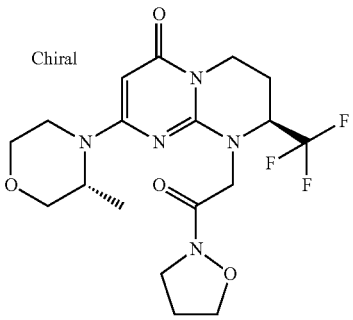 [SMILES: C[C@@H]1COCCN1c1cc(=O)n2c(n1)N(CC(=O)N1CCCO1)[C@H](C(F)(F)F)CC2] | 59 |
| EXAMPLE-320 | (S)-2-(2-Methyl-morpholin-4-yl)-9-(3-methyl-2-oxobutyl)-8-trifluoromethyl-6,7,8,9-tetrahydropyrimido-[1,2-a]pyrimidin-4-one, diastereoisomer 1 of undetermined absolute configuration on the asymmetric carbon of the morpholine | R4 = H; p = 0; q = 2; R2 = H; R3 = CF3 (S) | 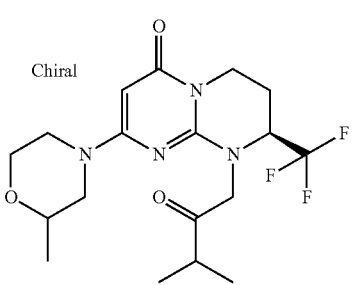 [SMILES: CC1CN(c2cc(=O)n3c(n2)N(CC(=O)C(C)C)[C@H](C(F)(F)F)CC3)CCO1] | 118 |
| EXAMPLE-321 | (S)-9-(2-Cyclopropyl-2-oxoethyl)-3-fluoro-2-((S)-3-methyl-morpholin-4-yl)-8-trifluoromethyl-6,7,8,9-tetrahydropyrimido-[1,2-a]pyrimidin-4-one | R4 = F; p = 0; q = 2; R2 = H; R3 = CF3 (S) | 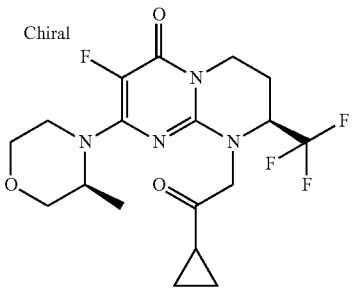 [SMILES: C[C@H]1COCCN1c1nc2n(c(=O)c1F)CC[C@@H](C(F)(F)F)N2CC(=O)C1CC1] | 113 |
| EXAMPLE-322 | (S)-9-(2-Cyclopropyl-2-oxoethyl)-3-fluoro-2-(2-methylmorpholin-4-yl)-8-trifluoromethyl-6,7,8,9-tetrahydro-pyrimido[1,2-a]-pyrimidin-4-one, diastereoisomer 1 of undetermined absolute configuration on the asymmetric carbon of the morpholine | R4 = F; p = 0; q = 2; R2 = H; R3 = CF3 (S) | 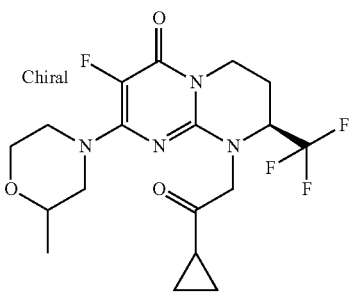 [SMILES: CC1CN(c2nc3n(c(=O)c2F)CC[C@@H](C(F)(F)F)N3CC(=O)C2CC2)CCO1] | 114 |
| EXAMPLE-323 | (S)-9-(2-Fluoro-3-methylbutyl)-2-((R)-3-methylmorpholin-4-yl)-8-trifluoromethyl-6,7,8,9-tetrahydro-pyrimido[1,2-a]-pyrimidin-4-one, diastereoisomer 1 of undetermined absolute configuration on the asymmetric carbon of the 2-fluoro-3-methylbutyl chain | R4 = H; p = 0; q = 2; R2 = H; R3 = CF3 (S) | 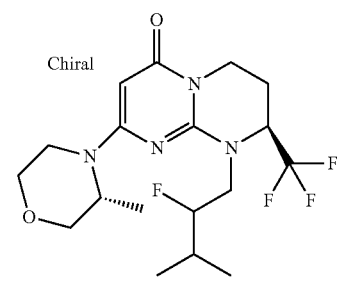 [SMILES: CC(C)C(F)CN1c2nc(N3CCOC[C@H]3C)cc(=O)n2CC[C@H]1C(F)(F)F] | 30 |

Experimental section: Table 2: Examples from 1 to 295, starting intermediates of type F and amount of each example isolated

| EXAMPLE | Example name | Intermediate of type F | Example structure | Amount isolated (mg) |
|---|---|---|---|---|
| EXAMPLE-324 | (S)-9-(2-Fluoro-3-methylbutyl)-2-((R)-3-methylmorpholin-4-yl)-8-trifluoromethyl-6,7,8,9-tetrahydro-pyrimido[1,2-a]-pyrimidin-4-one, diastereoisomer 2 of undetermined absolute configuration on the asymmetric carbon of the 2-fluoro-3-methylbutyl chain | R4 = H; p = 0; q = 2; R2 = H; R3 = CF3 (S) | | 21 |
| EXAMPLE-325 | (S)-9-(2-Cyclopropyl-2-fluoroethyl)-2-((R)-3-methylmorpholin-4-yl)-8-trifluoromethyl-6,7,8,9-tetrahydro-pyrimido[1,2-a]-pyrimidin-4-one, diastereoisomer 1 of undetermined absolute configuration on the asymmetric carbon of the 2-cyclopropyl-2-fluoroethyl chain | R4 = H; p = 0; q = 2; R2 = H; R3 = CF3 (S) | | 73 |
| EXAMPLE-326 | (S)-9-(2-Cyclopropyl-2-fluoroethyl)-2-((R)-3-methylmorpholin-4-yl)-8-trifluoromethyl-6,7,8,9-tetrahydro-pyrimido[1,2-a]-pyrimidin-4-one, diastereoisomer 2 of undetermined absolute configuration on the asymmetric carbon of the 2-cyclopropyl-2-fluoroethyl chain | R4 = H; p = 0; q = 2; R2 = H; R3 = CF3 (S) | | 73 |
| EXAMPLE-327 | (S)-8-Methyl-2-((R)-3-methylmorpholin-4-yl)-9-(2-oxopropyl)-8-trifluoromethyl-6,7,8,9-tetrahydropyrimido-[1,2-a]pyrimidin-4-one | R4 = H; p = 0; q = 2; R2 = Me; R3 = CF3 (S) | | 47 |
| EXAMPLE-328 | (S)-3-Fluoro-9-(2-fluoro-3-methylbutyl)-2-((R)-3-methyl-morpholin-4-yl)-8-trifluoromethyl-6,7,8,9-tetrahydropyrimido-[1,2-a]pyrimidin-4-one, diastereoisomer 1 of undetermined absolute configuration on the asymmetric carbon of the 2-fluoro-3-methylbutyl chain | R4 = F; p = 0; q = 2; R2 = H; R3 = CF3 (S) | | 68 |

Experimental section: Table 2: Examples from 1 to 295, starting intermediates of type F and amount of each example isolated

| EXAMPLE | Example name | Intermediate of type F | Example structure | Amount isolated (mg) |
|---|---|---|---|---|
| EXAMPLE-329 | (S)-3-Fluoro-9-(2-fluoro-3-methylbutyl)-2-((R)-3-methyl-morpholin-4-yl)-8-trifluoromethyl-6,7,8,9-tetrahydropyrimido-[1,2-a]pyrimidin-4-one, diastereoisomer 2 of undetermined absolute configuration on the asymmetric carbon of the 2-fluoro-3-methylbutyl chain | R4 = F; p = 0; q = 2; R2 = H; R3 = CF3 (S) | | 63 |
| EXAMPLE-330 | (S)-2-((R)-3-Methyl-morpholin-4-yl)-9-[2-(1-oxa-6-aza-spiro[3.3]hept-6-yl)-2-oxoethyl]-8-trifluoromethyl-6,7,8,9-tetrahydropyrimido-[1,2-a]pyrimidin-4-one | R4 = H; p = 0; q = 2; R2 = H; R3 = CF3 (S) | | 28 |
| EXAMPLE-331 | (S)-9-(2-Cyclopropyl-2-fluoroethyl)-3-fluoro-2-((R)-3-methyl-morpholin-4-yl)-8-trifluoromethyl-6,7,8,9-tetrahydropyrimido-[1,2-a]pyrimidin-4-one, diastereoisomer 1 of undetermined absolute configuration on the asymmetric carbon of the 2-cyclopropyl-2-fluoroethyl chain | R4 = F; p = 0; q = 2; R2 = H; R3 = CF3 (S) | | 98 |
| EXAMPLE-332 | (S)-9-(2-Cyclopropyl-2-fluoroethyl)-3-fluoro-2-((R)-3-methyl-morpholin-4-yl)-8-trifluoromethyl-6,7,8,9-tetrahydropyrimido-[1,2-a]pyrimidin-4-one, diastereoisomer 2 of undetermined absolute configuration on the asymmetric carbon of the 2-cyclopropyl-2-fluoroethyl chain | R4 = F; p = 0; q = 2; R2 = H; R3 = CF3 (S) | | 96 |

Experimental section: Table 2: Examples from 1 to 295, starting intermediates of type F and amount of each example isolated

| EXAMPLE | Example name | Intermediate of type F | Example structure | Amount isolated (mg) |
|---|---|---|---|---|
| EXAMPLE-333 | (S)-3-Fluoro-2-((R)-3-methylmorpholin-4-yl)-9-[2-(1-oxa-6-aza-spiro[3.3]hept-6-yl)-2-oxoethyl]-8-trifluoromethyl-6,7,8,9-tetrahydropyrimido-[1,2-a]pyrimidin-4-one | R4 = F; p = 0; q = 2; R2 = H; R3 = CF3 (S) | | 12 |

Lengthy table referenced here
US10253043-20190409-T00001
Please refer to the end of the specification for access instructions.

Lengthy table referenced here
US10253043-20190409-T00002
Please refer to the end of the specification for access instructions.

Lengthy table referenced here
US10253043-20190409-T00003
Please refer to the end of the specification for access instructions.

Lengthy table referenced here
US10253043-20190409-T00004
Please refer to the end of the specification for access instructions.

Lengthy table referenced here
US10253043-20190409-T00005
Please refer to the end of the specification for access instructions.

Lengthy table referenced here
US10253043-20190409-T00006
Please refer to the end of the specification for access instructions.

Lengthy table referenced here
US10253043-20190409-T00007
Please refer to the end of the specification for access instructions.

Lengthy table referenced here
US10253043-20190409-T00008
Please refer to the end of the specification for access instructions.

Example 334

Pharamaceutical Composition

Tablets corresponding to the following formula were prepared:

| | |
|---|---|
| Product of Example 42 | 0.2 g |
| Excipient for a tablet with a final weight of | 1 g |
| (details of the excipient: lactose, talc, starch, magnesium stearate). | |

Example 42 is taken by way of example of a pharmaceutical preparation, it being possible for this preparation to be carried out, if desired, with other products in examples in the present application.

Pharmacological section:
Experimental protocols
Study of the phosphorylation of phosphatidylinositol (PI) by Vps34 in vitro This test is based on the detection of the ADP produced during the phosphorylation of PI by Vps34 in the presence of ATP. The ADP is detected by TR-FRET (Time resolved—Fluorescence Resonance Energy transfer) using the Transcreener kit sold by Cisbio (HTRF® Transcreener® ADP, reference 62ADPPEB).

The molecules are diluted 3-fold in pure dimethyl sulfoxide (DMSO, Sigma Fluka 41647), and then diluted, in a second step, in 10% DMSO in water. 2 µl of molecules are added to 96-well plates (Corning Costar 3694), followed by 8 µl of a PI (Sigma P5766) / recombinant Vps34 (Invitrogen PV5126 or produced by Sanofi) mixture in buffer A: 50 mM Hepes, 5 mM $MnCl_2$, 0.1% CHAPS, 2 mM TCEP, pH 7.1. The reaction is initiated with 10 µl of a solution of ATP (Sigma A7699) in buffer A and lasts 1 hour at ambient temperature. The concentrations during the reaction are 1% DMSO, 10 µM ATP, 55 µg/ml PI, approximately 3 nM of Vps34 and between 0.51 nM and 10 µM for the molecules. The amount of enzyme is adapted to each batch so as to form approximately 2 µM of ADP during the reaction. In parallel, a range of ADP and of ATP for calibrating the results is prepared according to the indications of the kit. Controls not containing enzyme (negative control) or not containing molecules (positive control) are also prepared in parallel. The reaction is then blocked and visualized with the transcreener kit using 10 µl of each of the two reagents and according to the indications of the kit. The fluorescence emission is detected on a Rubystar instrument at 620 and 665 nm. The signal ratio is calculated by dividing the 665 nm signal by the 620 nm signal and then multiplying by 10,000. The signal ratios are converted into ADP concentration using the calibration range and according to the instructions of the kit. The percentages of inhibition by the molecules are calculated relative to the positive controls according to the formula (1—signal ratio of the molecule/signal ratio of the positive control)×100. The absolute IC50s (inhibitory concentration which gives 50% inhibition) are calculated according to a 4-parameter logistical model. Two independent experiments make it possible to calculate the mean of the IC50s. The IC50 results, in nM, obtained for the products in examples of the present invention are given in the table below.

Table of pharmacological results obtained by means of the above test

| IC50 activity range in nM | Examples |
|---|---|
| <10 nM | 42, 152, 163, 98, 153, 206, 32, 33, 36, 35, 37, 1, 11, 100, 99, 75, 76, 78, 38, 179, 79, 80, 101, 102, 180, 103, 71, 81, 40, 9, 154, 41, 214, 82, 215, 199, 181, 44, 84, 43, 83, 107, 85, 109, 108, 45, 86, 46, 89, 88, 87, 183, 69, 111, 255, 14, 90, 91, 93, 49, 92, 239, 94, 48, 112, 10, 50, 95, 217, 218, 284, 285, 155, 157, 114, 115, 3, 219, 257, 184, 116, 241, 258, 243, 96, 7, 6, 97, 242, 259, 260, 2, 254, 220, 158, 262, 244, 245, 221, 264, 160, 159, 118, 209, 119, 121, 122, 200, 210, 198, 120, 12, 51, 53, 52, 5, 124, 4, 224, 127, 126, 196, 128, 225, 15, 54, 16, 211, 17, 129, 204, 226, 212, 213, 18, 201, 202, 203, 19, 246, 247, 20, 248, 249, 250, 130, 251, 55, 21, 56, 131, 132, 57, 58, 227, 228, 252, 134, 135, 133, 22, 287, 286, 23, 229, 24, 59, 186, 185, 266, 267, 230, 253, 25, 189, 60, 187, 141, 231, 288, 289, 136, 137, 61, 62, 138, 139, 140, 31, 30, 232, 63, 233, 70, 65, 66, 142, 67, 26, 27, 190, 143, 28, 237, 276, 68, 144, 290, 29, 8, 146, 279, 280, 149, 147, 281, 282, 291, 283, 240, 205, 207, 294, 292, 295, 39, 293, 296, 297, 299, 300, 301, 302, 303, 304, 305, 306, 307, 308, 309, 310, 311, 313, 314, 315, 317, 318, 319, 323, 324, 325, 326, 327, 328, 329, 331, 332, 333 |
| 10-100 nM | 191, 192, 161, 162, 177, 151, 178, 167, 166, 165, 164, 168, 169, 34, 150, 170, 171, 77, 174, 72, 73, 74, 106, 105, 110, 182, 47, 13, 216, 256, 156, 113, 104, 261, 117, 236, 123, 223, 222, 125, 265, 197, 188, 269, 270, 271, 273, 274, 275, 145, 234, 235, 148, 208, 298, 312, 316, 320, 321, 322, 330 |
| >100 nM | 193, 194, 195, 176, 172, 173, 175, 263, 268, 64, 272, 277, 278, 238 |

LENGTHY TABLES

The patent contains a lengthy table section. A copy of the table is available in electronic form from the USPTO web site (http://seqdata.uspto.gov/?pageRequest=docDetail&DocID=US10253043B2). An electronic copy of the table will also be available from the USPTO upon request and payment of the fee set forth in 37 CFR 1.19(b)(3).

The invention claimed is:
1. A compound of formula (I):

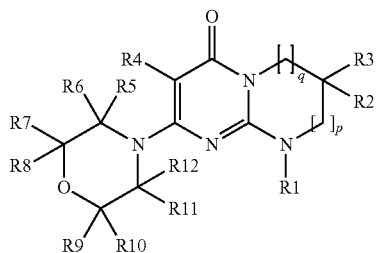

in which:
p and q are the integers such that p =0 and q =2;
R1 is a —(CH$_2$)$_m$—Ra radical with m being the integer 1 and Ra a —CO-cycloalkyl,
R2 and R3, which may be identical or different, are chosen from a hydrogen atom and an alkyl radical optionally substituted with one or more fluorine atoms, it being understood that R2 and R3 are not both CF$_3$ and R2 and R3 are not both hydrogen; or else R2 and R3 form, together with the carbon atom to which they are bonded, a cyclic radical containing from 3 to 6 ring members and optionally one or more other heteroatoms chosen from O, S and —NRz, this cyclic radical being optionally substituted with one or more radicals, which may be identical or different, chosen from halogen atoms and oxo, Rz, —ORz and —NRzRz' radicals; with Rz and Rz', which may be identical or different, being a hydrogen atom or an alkyl, cycloalkyl or heterocycloalkyl radical;
R4 is a hydrogen atom, a fluorine or chlorine atom, a methyl radical or a CN radical;
the morpholine residue is substituted with the radicals R5 to R12, which may be identical or different, chosen from a hydrogen atom and methyl and ethyl radicals optionally substituted with a fluorine atom or a hydroxyl radical, it being understood that at least one of R5 to R12 is not a hydrogen atom,
all the cycloalkyl radicals being optionally substituted with one or more radicals, which may be identical or different, chosen from a fluorine atom and alkyl radicals themselves optionally substituted with one or more fluorine atoms;
all the heterocycloalkyl radicals being optionally substituted with one or more radicals, which may be identical or different, chosen from a fluorine atom and alkyl radicals themselves optionally substituted with one or more fluorine atoms;
all the heterocycloalkyl radicals being, in addition, optionally substituted with a CO$_2$alk radical, where appropriate on a nitrogen atom;
all the alkyl (alk), alkylene and alkoxy radicals above being linear or branched and containing at most 7 carbon atoms,
it being understood that one or more of the hydrogen atoms of said compound of formula (I) can be a deuterium atom;
said compound of formula (I) being in any of the possible racemic, enantiomeric and diastereoisomeric isomer forms, and also the addition salts with inorganic and organic acids or with inorganic and organic bases of said compound of formula (I).

2. The compound of formula (I) as defined in claim 1, in which the morpholine residue is chosen from the following radicals:

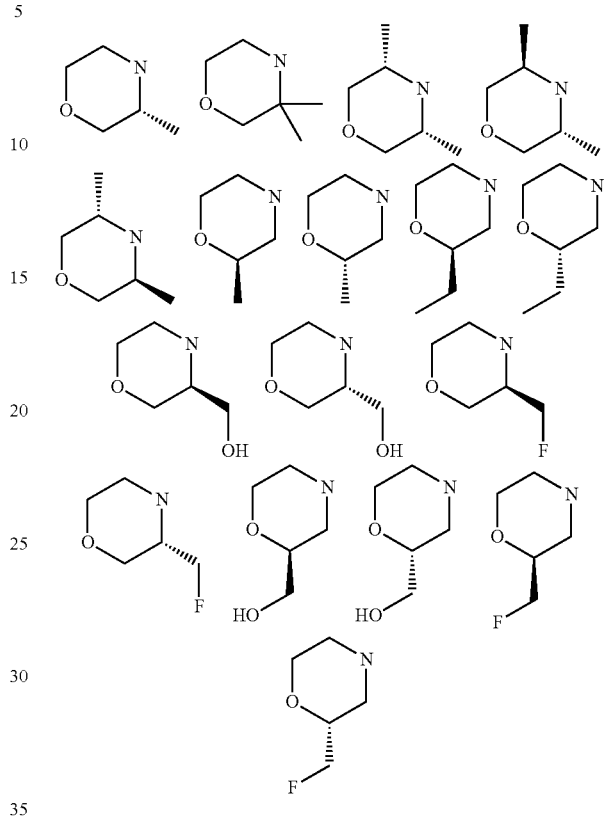

radicals p, q, R1, R2, R3 and R4 having the meanings indicated in claim 1,
said compound of formula (I) being in any of the possible racemic, enantiomeric and diastereoisomeric isomer forms, and also the addition salts with inorganic and organic acids or with inorganic and organic bases of said compound of formula (I).

3. The compound of formula (I) as defined in claim 1, in which:
R1 is a —(CH$_2$)$_m$—Ra radical;
m is the integer 1;
Ra is a —CO-cyclopropyl, —CO-cyclobutyl, —CO-cyclopentyl or —CO-cyclohexyl radical, all optionally substituted with one or more alkyl radicals;
R2 and R3 are such that:
either R2 is a hydrogen atom and R3 is the trifluoromethyl radical CF$_3$;
or R2 is a methyl radical and R3 is the trifluoromethyl radical CF$_3$;
or R2 and R3 are both a methyl radical;
R4 is a hydrogen atom, a fluorine or chlorine atom, a methyl radical or a CN radical;
the morpholine residue is chosen from the following radicals:

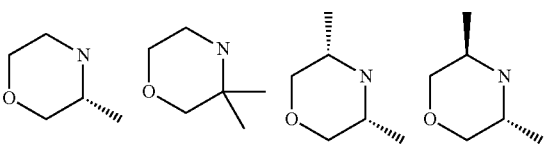

-continued

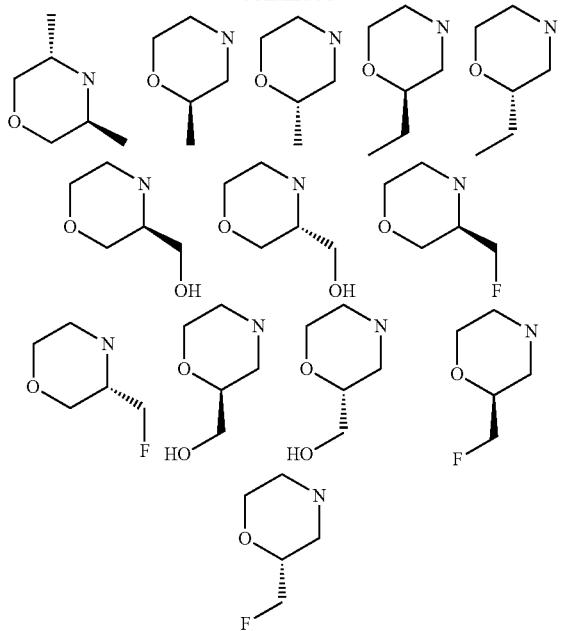

said compound of formula (I) being in any of the possible racemic, enantiomeric and diastereoisomeric isomer forms, and also the addition salts with inorganic and organic acids or with inorganic and organic bases of said compound of formula (I).

4. The compound of formula (I) as defined in claim 1, corresponding to the following formulae:
- (S)-9-(2-Cyclopropyl-2-oxoethyl)-3-fluoro-2-((R)-3-methylmorpholin-4-yl)-8-trifluoromethyl-6,7,8,9-tetrahydropyrimido[1,2-a]pyrimidin-4-one
- (S)-1-(2-Cyclopropyl-2-oxoethyl)-2-methyl-7-((R)-3-methylmorpholin-4- yl)-2-trifluoromethyl-2,3-dihydro-1H-imidazo[1,2-a]pyrimidin-5-one
- (R)-9-(2-Cyclopropyl-2-oxoethyl)-2-((R)-3-methylmorpholin-4-yl)-6-trifluoromethyl-6,7,8,9-tetrahydropyrimido[1,2-a]pyrimidin-4-one
- (R)-9-(2-Cyclopropyl-2-oxoethyl)-3-fluoro-2-((R)-3-methylmorpholin-4- yl)-6-trifluoromethyl -6,7,8,9-tetrahydropyrimido[1,2-a]pyrimidin-4-one
- (S)-1-(2-Cyclopropyl-2-oxoethyl)-6-fluoro-2-methyl-7 ((R)-3-methylmorpholin-4-yl)-2-trifluoromethyl-2,3-dihydro-1H-imidazo[1,2-a]pyrimidin-5-one
- (S)-9-(2-Cyclopropyl-2-oxoethyl)-2-((R)-3-methylmorpholin-4-yl)-8-trifluoromethyl-6,7,8,9-tetrahydropyrimido[1,2-a]pyrimidin-4-one
- (S)-9-(2-Cyclopentyl-2-oxoethyl)-2-((R)-3-methylmorpholin-4-yl)-8-trifluoromethyl-6,7,8,9-tetrahydropyrimido[1,2-a]pyrimidin-4-one
- (S)-9-[2-(1-Methylcyclopentyl)-2-oxoethyl]-2-((R)-3-methylmorpholin-4-yl)-8-trifluoromethyl-6,7,8,9-tetrahydropyrimido[1,2-a]pyrimidin-4-one
- (S)-9-(2-Cyclohexyl-2-oxoethyl)-2-((R)-3-methylmorpholin-4-yl)-8-trifluoromethyl-6,7,8,9-tetrahydropyrimido[1,2-a]pyrimidin-4-one
- (S)-9-(2-Cyclopropyl-2-oxoethyl)-3-fluoro-2-((S)-3-methylmorpholin-4-yl)-8-trifluoromethyl-6,7,8,9-tetrahydropyrimido[1,2-a]pyrimidin-4-one
- (S)-9-(2-Cyclopropyl-2-oxoethyl)-3-fluoro-2-(2-methylmorpholin-4-yl)-8-trifluoromethyl-6,7,8,9-tetrahydropyrimido[1,2-a]pyrimidin-4-one, diastereoisomer 1 of undetermined absolute configuration on the asymmetric carbon of the morpholine and also the addition salts with inorganic and organic acids or with inorganic and organic bases of said compound of formula (I).

5. Pharmaceutical composition comprising at least one compound of formula (I) as defined in claim 1, and also the pharmaceutically acceptable addition salts with inorganic and organic acids or with inorganic and organic bases of said compound of formula (I).

6. Pharmaceutical composition comprising at least one compound of formula (I) as defined in claim 4, and also the pharmaceutically acceptable addition salts with inorganic and organic acids or with inorganic and organic bases of said compound of formula (I).

7. Pharmaceutical compositions containing, as active ingredient, at least one compound of formula (I) as defined in claim 1, or a pharmaceutically acceptable salt of this compound, and a pharmaceutically acceptable carrier.

8. Method of treatment of a disease capable of being modulated by inhibiting the Vps34/PIK3C3 pathway chosen from the following group: blood vessel proliferation disorders, fibrotic disorders, "mesangial" cell proliferation disorders, metabolic disorders, allergies, asthma, thrombosis, nervous system diseases, retinopathy, psoriasis, rheumatoid arthritis, diabetes, muscle degeneration and cancers, comprising administering to a patient a compound of formula (I) as defined in claim 1.

9. Method of treatment of cancers capable of being modulated by inhibiting the Vps34/PIK3C3 pathway, comprising administering to a patient a compound of formula (I) as defined in claim 1.

10. Method of treatment of solid or liquid tumors capable of being modulated by inhibiting the Vps34/PIK3C3 pathway, comprising administering to a patient a compound of formula (I) as defined in claim 1.

11. Method of treatment of cancers resistant to cytotoxic agents capable of being modulated by inhibiting the Vps34/PIK3C3 pathway, comprising administering to a patient a compound of formula (I) as defined in claim 1.

12. Method of treatment of primary tumors and/or of metastases capable of being modulated by inhibiting the Vps34/PIK3C3 pathway, wherein the primary tumor or of metastases is gastric, hepatic, renal, ovarian, colon, prostate or lung (NSCLC and SCLC) cancers, glioblastomas, thyroid, bladder or breast cancers, in melanoma, in lymphoid or myeloid haematopoietic tumours, in sarcomas, in brain, larynx and lymphatic system cancers, bone and pancreatic cancers, and in hamartomas, comprising administering to a patient a compound of formula (I) as defined in claim 1.

13. Method of treatment of lysosomal diseases capable of being modulated by inhibiting the Vps34/PIK3C3 pathway comprising administering to a patient a compound of formula (I) as defined in claim 1.

14. Method of treatment of X-linked myotubular myopathies and Charcot-Marie-Tooth disease, comprising administering to a patient a compound of formula (I) as defined in claim 1.

* * * * *